US010240168B2

(12) United States Patent
Andrei et al.

(10) Patent No.: US 10,240,168 B2
(45) Date of Patent: Mar. 26, 2019

(54) ALTERED HOST CELL PATHWAY FOR IMPROVED ETHANOL PRODUCTION

(71) Applicant: Danisco US Inc., Palo Alto, CA (US)

(72) Inventors: Miasnikov Andrei, Union City, CA (US); Jeffrey W. Munos, San Francisco, CA (US)

(73) Assignee: DANISCO US INC CA (US)

( * ) Notice: Subject to any disclaimer, the term of this patent is extended or adjusted under 35 U.S.C. 154(b) by 0 days.

(21) Appl. No.: 15/126,376

(22) PCT Filed: Mar. 19, 2015

(86) PCT No.: PCT/US2015/021558

§ 371 (c)(1),
(2) Date: Sep. 15, 2016

(87) PCT Pub. No.: WO2015/148272

PCT Pub. Date: Oct. 1, 2015

(65) Prior Publication Data

US 2017/0088861 A1 Mar. 30, 2017

Related U.S. Application Data

(60) Provisional application No. 61/971,745, filed on Mar. 28, 2014.

(51) Int. Cl.

| | |
|---|---|
| ***C12P 7/06*** | (2006.01) |
| ***C12P 7/10*** | (2006.01) |
| ***C12N 9/88*** | (2006.01) |
| ***C12N 9/02*** | (2006.01) |
| ***C12N 9/10*** | (2006.01) |
| ***C12N 15/52*** | (2006.01) |

(52) U.S. Cl.

CPC .............. *C12P 7/10* (2013.01); *C12N 9/0008* (2013.01); *C12N 9/1018* (2013.01); *C12N 9/1029* (2013.01); *C12N 9/88* (2013.01); *C12N 15/52* (2013.01); *C12P 7/06* (2013.01); *C12Y 102/0101* (2013.01); *C12Y 203/01008* (2013.01); *C12Y 401/02009* (2013.01); *Y02E 50/16* (2013.01); *Y02E 50/17* (2013.01)

(58) Field of Classification Search

CPC ..................................... C12N 1/18; C12P 7/06
USPC .................................... 435/161, 194, 254.21
See application file for complete search history.

(56) References Cited

U.S. PATENT DOCUMENTS

| | | | |
|---|---|---|---|
| 7,785,858 B2 | 8/2010 | Kozlov et al. | |
| 8,415,136 B1 | 4/2013 | Gardner et al. | |
| 8,623,622 B2 | 1/2014 | Srience et al. | |
| 2005/0153411 A1 | 7/2005 | Wahlbom et al. | |
| 2007/0190629 A1* | 8/2007 | Wahlbom ................. | C12N 1/18 435/161 |
| 2009/0305363 A1 | 12/2009 | Anthony et al. | |
| 2011/0275130 A1 | 11/2011 | Pronk et al. | |
| 2013/0236942 A1 | 9/2013 | Gardner et al. | |

FOREIGN PATENT DOCUMENTS

| | | |
|---|---|---|
| EP | 2666855 A1 | 11/2013 |
| WO | 2004/085627 A1 | 10/2004 |
| WO | 2009/056984 A1 | 5/2009 |
| WO | 2012/062767 A2 | 5/2012 |
| WO | 2013/076144 A2 | 5/2013 |
| WO | 2013/081456 A2 | 6/2013 |
| WO | 2013/102554 A1 | 7/2013 |
| WO | 2014/081803 A1 | 5/2014 |

OTHER PUBLICATIONS

Wang et al., "Cloning, Sequence, and Disruption of the *Saccharomyces diastaticus* DAR1 Gene Encoding a Glycerol-3-Phosphate Dehydrogenase," J. Bacteriol., 1994, vol. 176, No. 22, pp. 7091-7095.

Walfridsson et al., "Xylose-Metabolizing *Saccharomyces cerevisiae* Strains Overexpressing the TKL1 and TAL1 Genes Encoding the Pentose Phosphate Pathway Enzymes Transketolase and Transaldolase," Appl. Environ. Microbial., 1995, vol. 61, No. 12, pp. 4184-4190.

Suzuki et al., "Overexpression, crystallization and preliminary X-ray analysis of xylulose-5-phosphatelfructose-6-phosphate phosphoketolase from Bifidobacterium breve," Acta Cryst. Section F, 2010, vol. 66, No. 8, pp. 941-943.

Sonderegger et al., "Metabolic engineering of a phosphoketolase pathway for pentose catabolism in *Saccharomyces cerevisiae*," Applied and Environmental Microbiology, 2004, vol. 70, No. 5, pp. 2892-2897.

PCT International Search Report and the Written Opinion of the International Searching Authority for International Application No. PCT/US2015/021558; ISA/EPO; dated Jul. 23, 2015.

Nissen et al., "Anaerobic and aerobic batch cultivations of *Saccharomyces cerevisiae* mutants impaired in glycerol synthesis," Yeast, 2000, vol. 16, pp. 463-474.

Nevoigt et al., "Engineering of Promoter Replacement Cassettes for Fine-Tuning of Gene Expression in *Saccharomyces cerevisiae*," Appl. Environ. Microbial., 2006, vol. 72, No. 8, pp. 5266-5273.

(Continued)

*Primary Examiner* — Tekchand Saidha

(57) ABSTRACT

A recombinant yeast cell, fermentation compositions, and methods of use thereof are provided. The recombinant yeast cell includes at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell.

12 Claims, 16 Drawing Sheets

Specification includes a Sequence Listing.

(56) References Cited

OTHER PUBLICATIONS

Moraes et al., "Development of yeast strains for the efficient utilisation of starch: evaluation of constructs that express-amylase and glucoamylase separately or as bifunctional fusion proteins," Appl. Microbial. Biotechnol., 1995, vol. 43, pp. 1067-1076.
Meile et al., "Characterization of the D-Xylulose 5-Phosphate/D-Fructose 6-Phosphate Phosphoketolase Gene (xfp) from Bifidobacterium lactis," J. Bacteriology, 2001, vol. 183, No. 9, pp. 2929-2936.
Medina et al., "Elimination of Glycerol Production in Anaerobic Cultures of a *Saccharomyces cerevisiae* Strain Engineered To Use Acetic Acid as an Electron Acceptor," Appl. Environ. Microbiol., 2010, vol. 76, No. I, pp. 190-195.
Lengeler et al., Eds., Biology of the Prokaryotes, Blackwell Science, New York, 1999, pp. 299-301.
Kozak et al., "Replacementofthe Saccharomycescerevisiae acetyl-CoAsynthetasesbyalternativepathwaysforcytosolicacetyl-CoAsynthesis," Metabolic Engineering, 2014, vol. 21, pp. 46-59.
Jeong et al., "Cloning and Characterization of a Gene Encoding Phosphoketolase in a Lactobacillus paraplantarum Isolated from Kimchi," J. Microbiol. Biotechnol., 2007, vol. 17, No. 5, pp. 822-829.
Guo et al., "Minimization of glycerol synthesis in industrial ethanol yeast without influencing its fermentation performance," Metabolic Engineering, 2011, vol. 13, pp. 49-59.
Guo et al., "Interruption of glycerol pathway in industrial alcoholic yeasts to improve the ethanol production," Appl. Microbiol. Biotechnol., 2009, vol. 82, pp. 287-292.
Guo et al., "Improving ethanol productivity by modification of glycolytic redox factor generation in glycerol-3-phosphate dehydrogenase mutants of an industrial ethanol yeast", Appl. Microbiol. Biotechnol., 2011, vol. 38, pp. 335-943.
Fleige et al., "Establishment of an alternative phosphoketolase-dependent pathway for fructose catabolism in Ralstania eutropha H16," Appl Microbial Biotechnol., 2011, vol. 91, No. 3, pp. 769-776.
Eriksson et al., "Cloning and characterization of GPD2, a second gene encoding sn-glycerol 3-phosphate dehydrogenase (NAD+) in *Saccharomyces cerevisiae*, and its comparison with GPD1," Mol. Microbiol., 1995, vol. 17, No. 1, pp. 95-107.
Björkqvist et al., "Physiological Response to Anaerobicity of Glycerol-3-Phosphate Dehydrogenase Mutants of *Saccharomyces cerevisiae*," Appl. Environ. Microbiol., 1997, vol. 63, No. 1, pp. 128-132.

* cited by examiner

```
PCR chromosomal DNA of FermaxGold and primer pair:
oURA3_5       GGATGCATATTTAAATAATGTAATTCTATATATGTTAATTACCTTTTTTG
oURA3_Asc_3   GAAGGCGCGCCTTTTTCTTTCCAATTTTTTTTTTTTCGTCATTATAGAAATC
```

ALTERED HOST CELL PATHWAY FOR IMPROVED ETHANOL PRODUCTION

CROSS REFERENCE TO RELATED APPLICATIONS

This application is a U.S. National Phase Application of International Application No. PCT/US2015/021558, filed 19 Mar. 2015, which claims benefit of priority from US provisional application U.S. Ser. No. 61/971,745, filed 28 Mar. 2014 and are incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "NB40628USPCT-SEQ-LIST" created on Sep. 12, 2016, which is 327,680 bytes in size.

FIELD OF THE INVENTION

The invention relates generally to the field of industrial microbiology. The invention relates to recombinant host cells comprising one or more heterologous polynucleotides encoding proteins having phosphoketolase, phosphotransacetylase, and acylating acetaldehyde dehydrogenase activities and that are capable of increased production of ethanol. The invention also includes methods for producing and using the same. In some embodiments, the recombinant cells further comprise one or more modifications in an endogenous gene encoding a polypeptide that converts dihydroxyacetone phosphate to sn-glycerol 3-phosphate.

BACKGROUND

Interest is growing in the use of sustainable and economical biological processes for generating materials of interest. Biological processes hold the promise of renewably using energy from the sun to make such materials. For example, energy from the sun can be stored in plant biomolecules such as the polysaccharides starch and cellulose. By fermentation of the simple sugars arising from breakdown of these polysaccharides, microbes can transfer the sun's energy into molecules of commercial interest to humans, including ethanol. Historically, large-scale polysaccharide breakdown has been accomplished by heat and chemicals, but in the past decades industrially produced starch hydrolytic enzymes have been employed to facilitate this process.

The tools of recombinant DNA technology arising in the 1980's have enabled the creation of transgenic organisms capable of expressing high levels of starch hydrolysis enzymes. In routine use today are alpha amylases, glucoamylases, and pullulanases, produced by recombinant microbes at the scale of tanker trucks per day. However, making biomolecules of interest by this process is lengthy and inherently inefficient. For example, energy is first transferred from the sun to plant polysaccharides, then from these plant polysaccharides to microbes that make starch hydrolysis enzymes, and then the enzymes thus produced are used to facilitate breakdown of additional plant polysaccharides used by yet another microbe to eventually form ethanol. Accordingly, using the same microbe that produces the material of interest to also produce the starch hydrolysis enzymes offers the opportunity for more efficient resource utilization (see for example, U.S. Pat. No. 5,422,267).

Such approaches have recently come to commercial fruition in the form of a glucoamylase-expressing yeast in the fuel ethanol industry. These approaches promise to reduce the use of expensive exogenously added enzymes. However, in this infant industry setting many unmet needs exist. One large need resides in engineering the biochemical pathways of a yeast host to support improved biochemical yield, e.g., ethanol yield.

Another need in the ethanol industry is to improve the levels of ethanol recovered in a yeast fermentation process. Glycerol produced by industrial yeast strains detracts from the potential yield of ethanol recovered. Yeast strains with partially or completely blocked glycerol biosynthesis have been described earlier, e.g., by Wang H-T et al. J. Bacteriol. 176 (22), 709 (1994); Eriksson P et al. Mol. Microbiol. 17 (1), 95, 1995; Björkqvist S et al. Appl. Environ. Microbiol. 63 (1), 128 (1997); Nissen T L et al. Yeast 16, 463 (2000); and Nevoigt E et al. Appl. Environ. Microbiol. 72 (8), 5266 (2006). All of these studies were conducted in haploid laboratory strains of the yeast *Saccharomyces cerevisiae* and are not necessarily directly applicable to industrial diploid/polyploid yeast strains. More recently, some publications report molecular engineering as an approach for industrial yeast strains with disrupted glycerol pathway. (See e.g., Guo Z-p et al. Appl. Microbiol. Biotechnol. 82, 287 (2009); Guo Z-p et al. Appl. Microbiol. Biotechnol. 38, 935 (2011);); Guo Z-p et al. Metabolic Engineering 13, 49 (2011)). However, in reality, these authors work with haploid derivatives of industrial yeast, which has different properties and are not industrial yeast strains themselves. As such, a need still exists for approaches to improve ethanol yield from industrial yeast strains.

SUMMARY

The invention provided herein discloses, inter alia, recombinant cells, compositions of these cells and methods of using these cells to increase production of ethanol.

Accordingly, in one aspect, provided herein is a recombinant cell capable of increased carbon flux through a phosphoketolase utilizing pathway, In other aspects, provided herein are isolated polypeptides with phosphoketolase activity produced by any methods of screening, identifying, and/or detecting disclosed herein.

The present teachings provide recombinant yeast cells, fermentation compositions, and methods of use thereof. The recombinant yeast cells can include at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell.

In general, in one aspect a recombinant yeast cell is envisioned having at least one heterologous nucleic acid encoding one or more polypeptide having i) phosphoketolase activity; ii) phosphotransacetylase activity; and/or iii) acetylating acetaldehyde dehydrogenase activity, wherein the cell does not comprise a heterologous modified xylose reductase gene, and wherein the cell is capable of increased biochemical end product production in a fermentation process when compared to a parent yeast cell.

In one embodiment the yeast cell has a reduced NAD-dependant glycerol phosphate dehydrogenase (GPD) activity when compared to a parent yeast cell. In a related embodiment the yeast cell includes an altered pentose phosphate pathway resulting from one or more heterologously expressed nucleic acid affecting the pentose phosphate pathway.

In one embodiment the recombinant yeast cell produces a biochemical end product and the biochemical end product is ethanol and it is produced at a level at least 0.5% higher to at least 15% higher than that produced in a parent yeast cell. In alternative embodiments, the recombinant yeast produces ethanol a level higher than that produced in a parent yeast cell selected from the group consisting of at least 0.5% higher, at least 1% higher, at least 1.5% higher, at least 2% higher, at least 2.5% higher, at least 3% higher, at least 3.5% higher, at least 4% higher, at least 4.5% higher, at least 5% higher, at least 5.5% higher, at least 6% higher, at least 6.5% higher, at least 7% higher, at least 7.5% higher, at least 8% higher, at least 8.5% higher, at least 9% higher, at least 9.5% higher, at least 10% higher, at least 10.5% higher, at least 11% higher, at least 11.5% higher, at least 12% higher, at least 12.5% higher, at least 13% higher, at least 13.5% higher, at least 14% higher, at least 14.5% higher, and at least 15% higher.

In yet another embodiment the recombinant cell described herein includes a) the phosphoketolase activity is encoded by a nucleic acid comprising SEQ ID NO: 3 or having at least 80%, 85%, 90%, 95%, 98% or 99% identity to SEQ ID NO: 3; b) the phophotransacetylase activity is encoded by a nucleic acid comprising SEQ ID NO: 4 or having at least 80%, 85%, 90%, 95%, 98% or 99% identity to SEQ ID NO: 4; and/or c) the acetylating acetaldehyde dehyrogenase activity is encoded by a nucleic acid comprising SEQ ID NO: 5 or having at least 80%, 85%, 90%, 95%, 98% or 99% identity to SEQ ID NO: 5.

In other embodiments the phosphoketolase activity is encoded by a nucleic acid selected from at least one of the group consisting of a nucleic acid encoding SEQ ID NO: 56, SEQ ID NO: 54, SEQ ID NO: 48, SEQ ID NO: 3, SEQ ID NO: 44, SEQ ID NO: 60, SEQ ID NO: 62, SEQ ID NO: 64, SEQ ID NO:66, SEQ ID NO:72. In a related embodiment the phosphoketolase activity is encoded by a nucleic acid having at least 80%, 85%, 90%, 95%, 98% or 99% identity to at least one of the group consisting of SEQ ID NO: 56, SEQ ID NO: 54, SEQ ID NO: 48, SEQ ID NO: 3, SEQ ID NO: 44, SEQ ID NO: 60, SEQ ID NO: 62, SEQ ID NO: 64, SEQ ID NO:66 or SEQ ID NO:72.

In a further embodiment the acetylating acetaldehyde dehydrogenase activity is encoded by a nucleic acid selected from at least one of the group consisting of a nucleic acid encoding SEQ ID NO: 25, SEQ ID NO: 31, SEQ ID NO: 5, SEQ ID NO: 17, SEQ ID NO: 13, SEQ ID NO: 15, SEQ ID NO: 19, SEQ ID NO: 27, SEQ ID NO: 33. In a related embodiment the acetylating acetaldehyde dehydrogenase activity is encoded by a nucleic acid having at least 80%, 85%, 90%, 95%, 98% or 99% identity to at least one of the group consisting of SEQ ID NO: 25, SEQ ID NO: 31, SEQ ID NO: 5, SEQ ID NO: 17, SEQ ID NO: 13, SEQ ID NO: 15, SEQ ID NO: 19, SEQ ID NO: 27 or SEQ ID NO: 33.

In a particular embodiment the recombinant yeast cell described herein is a recombinant *Saccharomyces cerevisiae.*

In another embodiment the recombinant yeast cell described herein is useful in a fermentation process and the fermentation process can be selected from a number of types of fermentation including, for example, post-liquefaction and saccharification fermentation, simultaneous saccharification and fermentation (SSF) and granular starch hydrolyzing enzyme (GSHE) fermentation.

In another embodiment the recombinant yeast cell produces a biochemical end product selected from a group including an organic acid, an amino acid, an alcohol and ethanol. In a particular embodiment the biochemical end product is ethanol.

In another aspect disclosed herein is a fermentation composition including the recombinant yeast cell of the disclosure, glucose and xylose. In one embodiment the fermentation composition has, for example, a glucose to xylose concentration greater than 1:1. In a different embodiment the glucose to xylose concentration is greater than 5:1. In another embodiment the fermentation composition further includes glucoamylase. In a related embodiment the glucoamylase is expressed by the recombinant yeast cell. The glucoamylase can be, for example, a) encoded by a recombinant gene comprising the amino acid sequence of SEQ ID NO. 11; or b) a recombinant gene having at least 80%, 85%, 90%, 95%, 98% or 99% identity to the amino acid sequence of SEQ ID NO. 11.

In a further embodiment the fermentation composition additionally includes at least one additional recombinant gene, wherein the at least one additional recombinant gene encodes one or more of an enzyme selected from the group including, for example a dehydrogenase, a transketolase, a phosphoketolase, a transladolase, an epimerase, a phytase, a xylanase, a β-glucanase, a phosphatase, a protease, an alpha-amylase, a beta-amylase, a different glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. In a particular embodiment the at least one additional recombinant gene encodes an alpha-amylase, a glucoamylase, a cutinase, a trehalase or combinations thereof. In a specific embodiment, the at least one additional recombinant gene encodes an alpha-amylase.

In another embodiment the fermentation composition further includes an additional yeast species.

In general, in another aspect a method of producing a desired biochemical is provided including use of the recombinant yeast cell or fermentation composition as described herein, in a fermentation process with a feedstock, wherein the desired biochemical is selected from the group consisting of ethanol, butanol, etc. arabinitol, n-butanol, isobutanol, ethanol, glycerol, methanol, ethylene glycol, 1,3-propanediol (propylene glycol), butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, tryptophan, and threonine); a gas (e.g., methane, hydrogen (H2), carbon dioxide ($CO_2$), and carbon monoxide (CO)); isoprene, isoprenoid, sesquiterpene; a ketone (e.g., acetone); an aldehyde (e.g., acetaldehyde, butryladehyde); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); 1-3 propane diol, and polyketide. In a specific embodiment the fermentation employs a feedstock selected from the group including, for example glucose, liquefied starch, granular starch, cellulose, hemicellulose or any combination thereof. In a related aspect of the methods disclosed herein the desired biochemical is ethanol.

BRIEF DESCRIPTION OF THE FIGURES

FIG. 14A shows raw experimental data and FIG. 14B shows the same data corrected for estimated evaporation loss.

DETAILED DESCRIPTION

Figure 1:
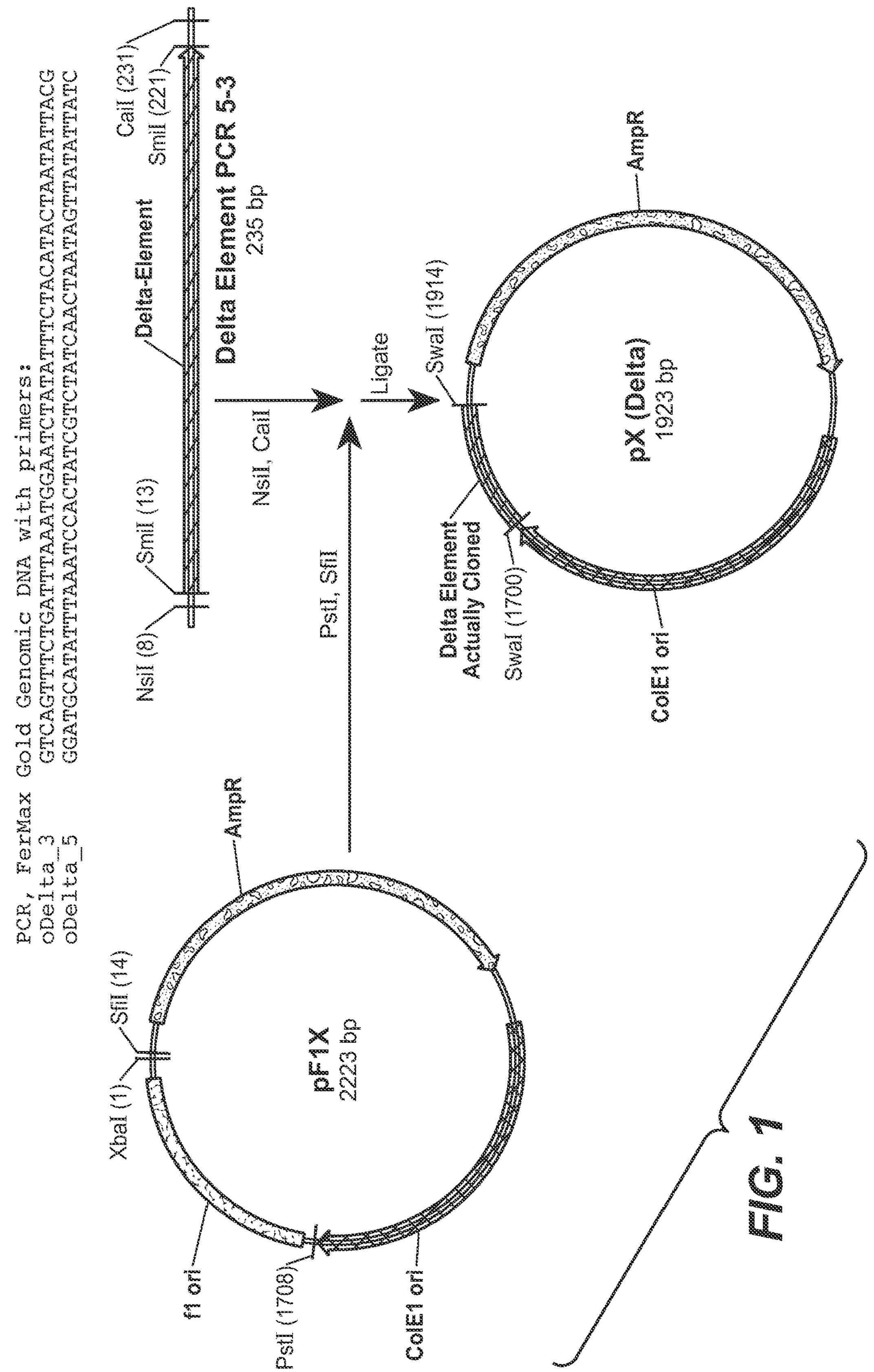
FIG. 1 depicts the construction of plasmid intermediate pX (Delta).
Figure 2:
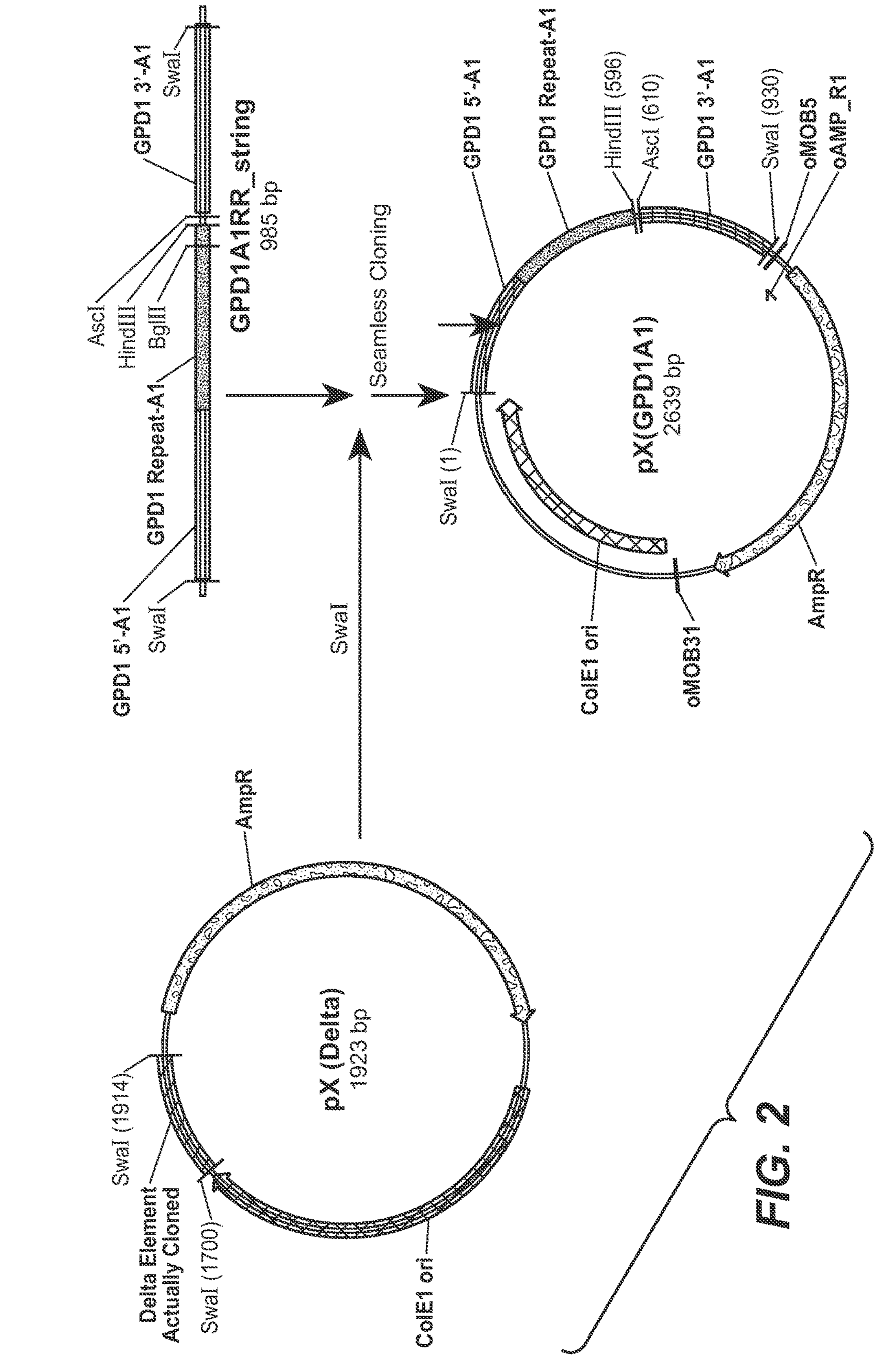
FIG. 2 depicts cloning the synthetic sequence containing GPD1 "flanking" and "repeat" sequence segments into pX (Delta).
Figure 3:
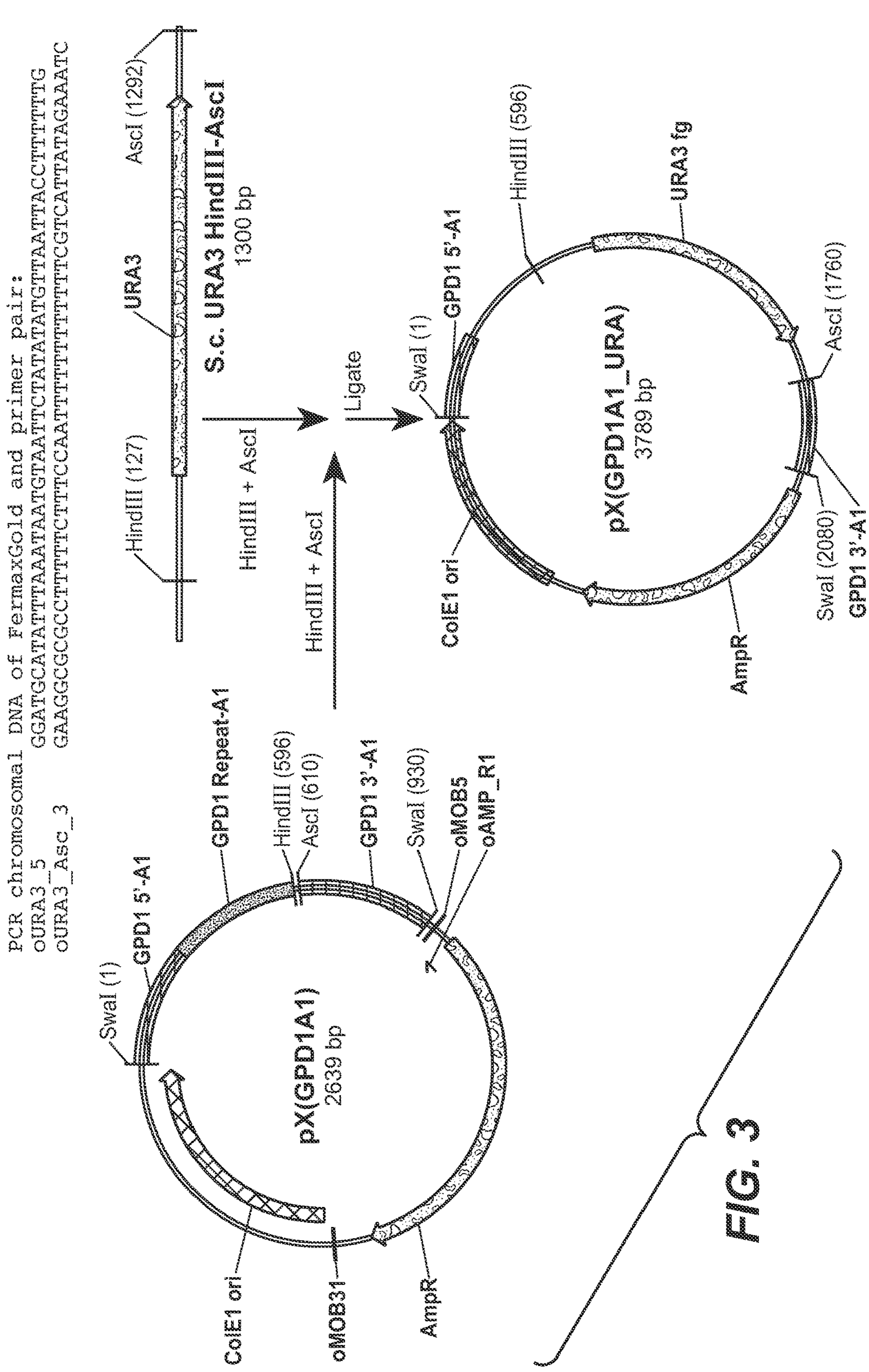
FIG. 3 depicts the final assembly of a disruption cassette for GPD1.
Figure 4:
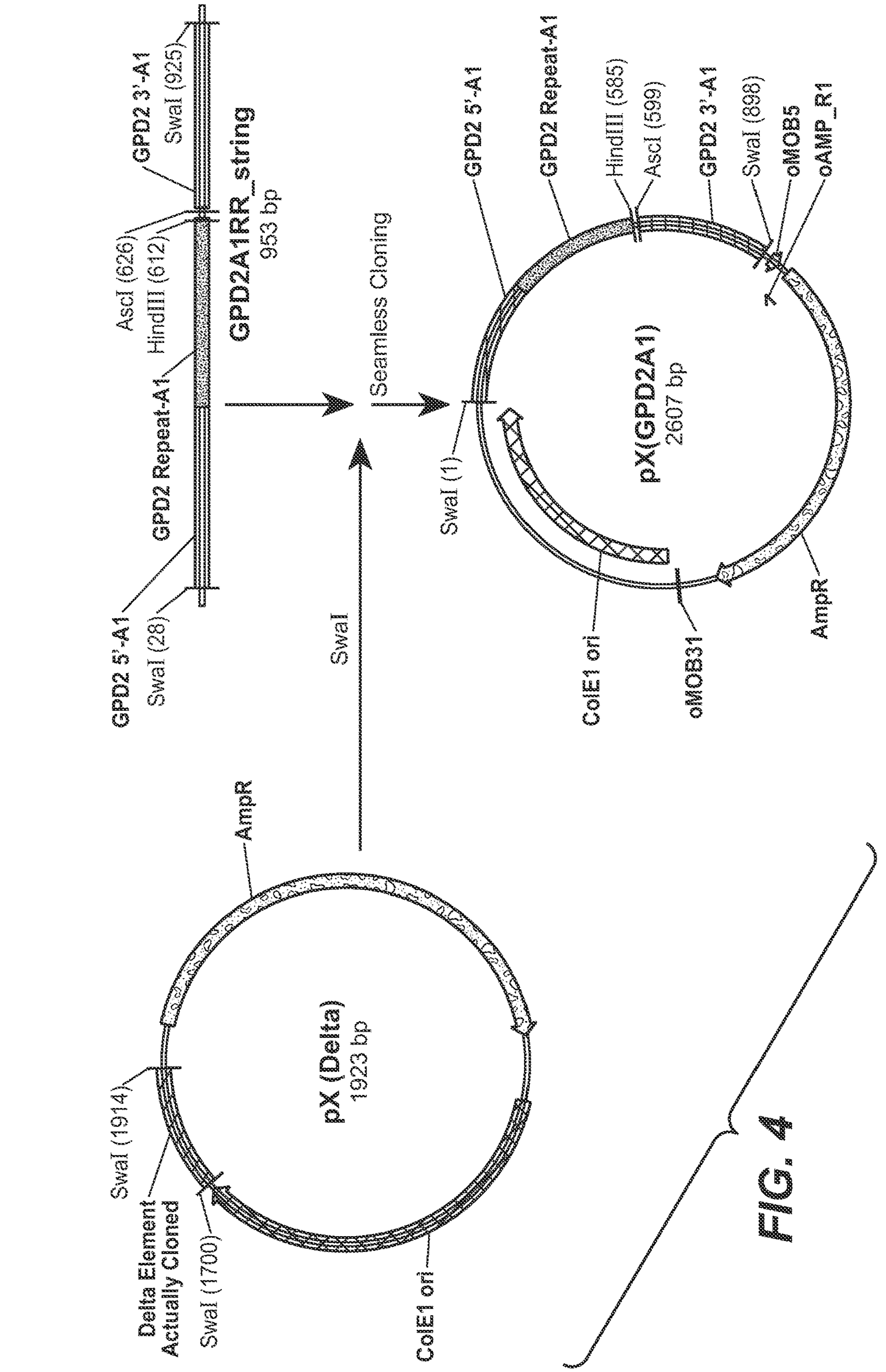
FIG. 4 depicts cloning the synthetic sequence containing GPD2 "flanking" and "repeat" sequence segments into pX (Delta).
Figure 5:
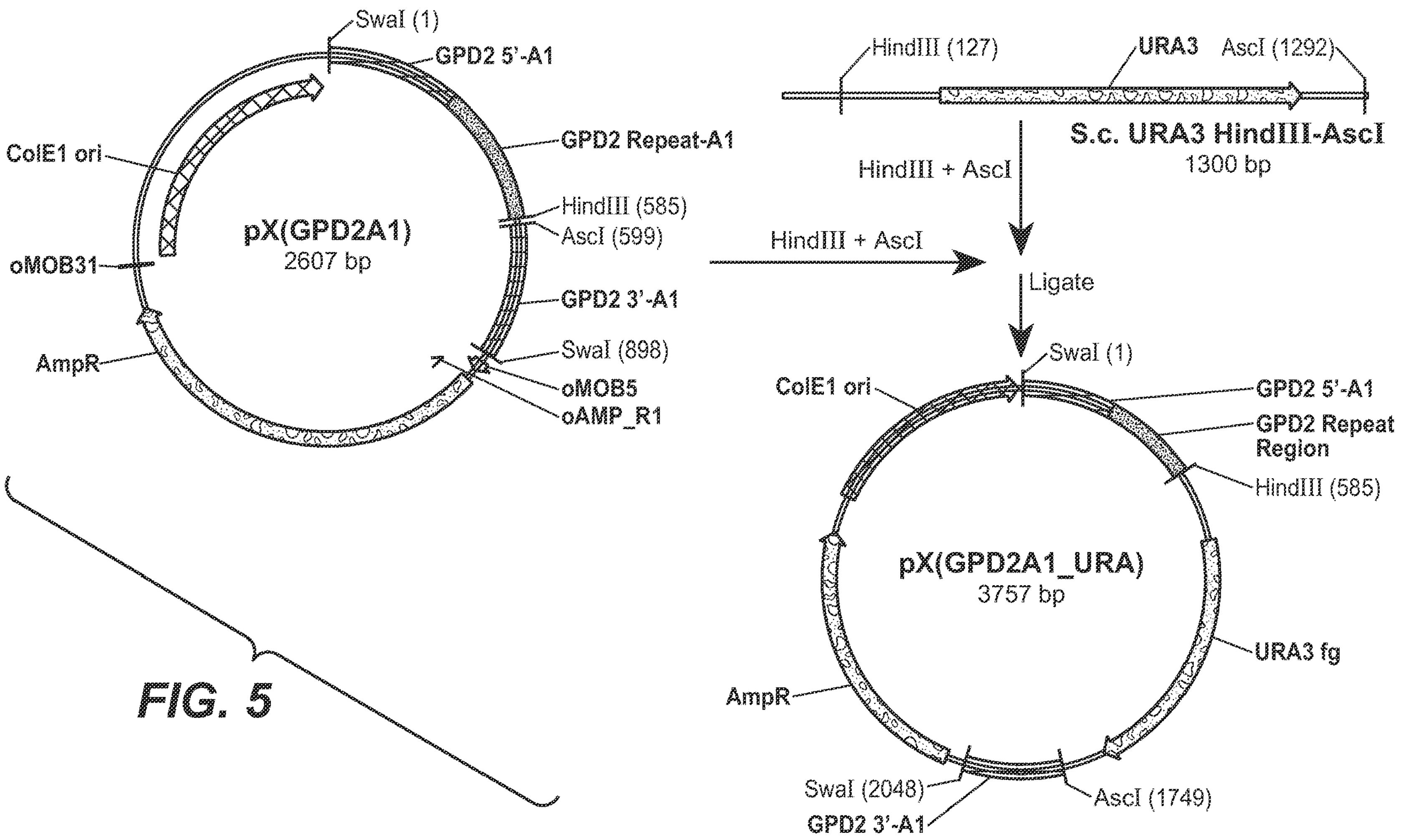
FIG. 5 depicts the final assembly of a disruption cassette for GPD2.

The practice of the present teachings will employ, unless otherwise indicated, conventional techniques of molecular biology (including recombinant techniques), microbiology, cell biology, biochemistry, and animal feed pelleting, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984*; Current Protocols in Molecular Biology* (F. M. Ausubel et al., eds., 1994); *PCR: The Polymerase Chain Reaction* (Mullis et al., eds., 1994); Gene *Transfer and Expression: A Laboratory Manual* (Kriegler, 1990), and *The Alcohol Textbook* (Ingledew et al., eds., Fifth Edition, 2009).

Unless defined otherwise herein, all technical and scientific terms used herein have the same meaning as commonly understood by one of ordinary skill in the art to which the present teachings belong. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present teachings.

Numeric ranges provided herein are inclusive of the numbers defining the range.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

As used herein, the terms "comprises," "comprising," "includes," "including,", "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

The term "polynucleotide" is intended to encompass a singular nucleic acid as well as plural nucleic acids, and refers to a nucleic acid molecule or construct, e.g., messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the phosphoketolase gene from *Bifidobacterium animalis Burkholderia phytofirmans, Lactobacillus buchneri, Bifidobacterium gallicum, Bifidobacterium dentium, Bifidobacterium bifidum*, and/or *Clostridium acetobutylicum* and used to transform yeast, for example, *Saccharomyces cerevisiae* is a heterologous nucleic acid.

A polynucleotide sequence may be referred to as "isolated," in which it has been removed from its native environment. For example, a heterologous polynucleotide encoding a polypeptide or polypeptide fragment having phosphoketolase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA or synthetic DNA.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Endogenous gene" refers to a native gene in its natural location in the genome of an organism. A "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Foreign genes can comprise native genes inserted into a non-native organism, or chimeric genes. In another example, a heterologous gene can be a gene reintroduced into the source organism in a location that is different from that in the unaltered host organism.

As used herein, the term "at least one additional recombinant gene" refers to a nucleic acid encoding a protein that is integrated into the genome of the yeast, in addition to the at least one recombinant gene for hydrolyzing starch. Examples are numerous as will be appreciated by one of skill in the art, and include any of the genes mentioned herein.

The term "parent yeast" or "parent yeast cell" or "parent cell" as used herein, means a yeast, e.g., *Saccharomyces cerevisiae*, to which an alteration is made to produce a recombinant yeast cell or genetically engineered yeast cell of the present disclosure. Suitably the parent yeast may be, for example, a naturally occurring (wild-type) yeast, a laboratory strain of yeast or an industrial yeast strain. In one embodiment the parent yeast is a commercial ethanologen yeast strain suitable for use the fuel ethanol industry.

As used herein, the term "genetically engineered yeast" refers to the targeted modification of at least one nucleotide of a nucleotide sequence resulting in a sequence that does not naturally occur. Such a genetic engineering can be the targeted modification of an endogenous wild type gene, the targeted modification of an endogenous wild type non-coding region, and/or through the insertion of a different organism's gene or non-coding sequence (such different organism's gene or non-coding region itself optionally having been the subject of targeted modification) into the yeast (the use of such a different organism's genetic material aka "recombinant"). Mere genetic changes in a yeast that arise through mutagenesis and screening is not considered by themselves in the present invention to constitute a "genetically engineered yeast". Examples of genes that can constitute a genetically engineered yeast are numerous, and include any of dehydrogenases, transketolases, phosphoketolases, transladolases, epimerases, isomerases, phytases, xylanases, β-glucanases, phosphatases, proteases, amylases (alpha or beta or glucoamylases), pullulanases, isoamylases, cellulases, trehalases, lipases, pectinases, polyesterases, cutinases, oxidases, transferases, reductases, hemicellulases, mannanases, esterases, pectinases, lactases, peroxidases, laccases, and other redox enzymes. Indeed, any enzyme either secreted by the cell or intracellularly expressed can be used according to the present teachings, and non-limiting examples include a phosphoketolase from *Bifidobacterium animalis*, phosphotransacetylase from *Lactobacillus plantarum*, acetaldehyde dehydrogenase from *Salmonella enterica*, xylanase from *Trichoderma reesei* and a variant xylanase from *Trichoderma reesei*, both available from DuPont Industrial Biosciences. Alternatively, the xylanase may be the inherently thermostable xylanase described in EP1222256B1, as well as other xylanases from *Aspergillus niger, Aspergillus kawachii, Aspergillus tubigensis, Bacillus circulans, Bacillus pumilus, Bacillus subtilis, Neocallimastix patriciarum, Penicillium* species, *Streptomyces lividans, Streptomyces thermoviolaceus, Thermomonospora fusca, Trichoderma harzianurn, Trichoderma reesei, Trichoderma viride* or *Fusarium*. Additional enzymes include phytases, such as for example Finase L®, a phytase from *Aspergillus* sp., available from AB Enzymes, Darmstadt, Germany; Phyzyme™ XP, a phytase from *E. Coli*, available from Danisco Animal Nutrition, and other phytases from, for example, the following organisms: *Trichoderma, Penicillium, Fusarium, Buttiauxella, Citrobacter, Enterobacter, Penicillium, Humicola, Bacillus*, and *Peniophora*. An example of a cellulase is Multifect® BGL, a cellulase (beta glucanase), available from DuPont Industrial Biosciences and other cellulases from species such as *Aspergillus, Trichoderma, Penicillium, Humicola, Bacillus, Cellulomonas, Penicillium, Thermomonospore, Clostridium*, and *Hypocrea*. The cellulases and endoglucanases described in US20060193897A1 also may be used. Amylases may be, for example, from species such as *Aspergillus, Trichoderma, Penicillium, Bacillus*, for instance, *B. subtilis, B. stearothermophilus, B. lentus, B. licheniformis, B. coagulans*, and *B. amyloliquefaciens*. Suitable fungal amylases are derived from *Aspergillus*, such as *A. oryzae* and *A. niger*. Proteases may be from *Bacillus amyloliquefaciens, Bacillus lentus, Bacillus subtilis, Bacillus licheniformis, Fusarium* and *Aspergillus* and *Trichoderma* species. In some embodiments, any of the enzymes discussed above may be used, either alone, or in combination with themselves, or others. One of skill in the art will appreciate that various engineering efforts have produced improved enzymes with properties of interest, any of which can be included in a genetically engineered yeast according to the present teachings. For example, in the context of amylases, various swapping and mutation of starch binding modules (SBM) and/or carbohydrate binding modules (CBM) (for cellulose, starch, or otherwise) have generated enzymes of interest that could be placed into the genetically engineered yeast of the present teachings (see for example, U.S. Pat. No. 8,076,109, and EP1687419B1, as well as Machovic, Cell. Mol. Life Sc. 63 (2006) 2710-2724, and Latorre-Garcia, J. biotech, 2005 (3, 019) 167-176). As another example, the *Rhizomucor pusillus* alpha-amylase can be combined with any CBM. Also, the present teachings can employ any of the enzymes disclosed in PCT/US2009/036283, Moraes et al, Appl Microbiol Biotechnol (1995) 43:1067-1076, and Li et al, Protein Expression and Purification 79 (2011) 142-148. In certain embodiments, the microorganism may be genetically modified to produce butanol. It will also be appreciated that in some embodiments the production of butanol by a microorganism, is disclosed, for example, in U.S. Pat. Nos. 7,851,188; 7,993,889; 8,178,328; and 8,206,970; and U.S. Patent Application Publication Nos. 2007/0292927; 2008/0182308; 2008/0274525; 2009/0305363; 2009/0305370; 2011/0250610; 2011/0313206; 2011/0111472; 2012/0258873; and 2013/0071898, the entire contents of each are herein incorporated by reference. In certain embodiments, the microorganism is genetically modified to comprise a butanol biosynthetic pathway or a biosynthetic pathway for a butanol isomer, such as 1-butanol, 2-butanol, or isobutanol. In certain embodiments, at least one, at least two, at least three, at least four, or at least five polypeptides catalyzing substrate to product conversions in the butanol biosynthetic pathway are encoded by heterologous polynucleotides in the microorganism. In certain embodiments, all the polypeptides catalyzing substrate to product conversions of the butanol biosynthetic pathway are encoded by heterologous polynucleotides in the microorganism. It will be appreciated that microorganisms comprising a butanol biosynthetic pathway may further comprise one or more additional genetic modifications as disclosed in U.S. Patent Application Publication No. 2013/0071898, which is herein incorporated by reference in its entirety. Biosynthetic pathways for the production of isobutanol that may be used include those as described by Donaldson et al. in U.S. Pat. No. 7,851,188; U.S. Pat. No. 7,993,388; and International Publication No. WO 2007/050671, which are incorporated herein by reference. Biosynthetic pathways for the production of 1-butanol that may be used include those described in U.S. Patent Application Publication No. 2008/0182308 and WO2007/041269, which are incorporated herein by reference. Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521, all of which are incorporated herein by reference. In some embodiments, the present teachings also contemplate the incorporation of a trehalase into a yeast to generate the genetically modified organism, either alone or with other enzymes of interest. Exemplary trehalases can be found in U.S. Pat. No. 5,312,909 and EP0451896B1.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis.

As used herein, the term "variant" refers to a polypeptide differing from a specifically recited polypeptide of the invention by amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences. By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, the terms "phosphoketolase", "phosphoketolase enzyme" or "phosphoketolase polypeptide" are used interchangeably and refer to a polypeptide that converts xylulose 5-phosphate to glyceraldehyde 3-phosphate and acetyl phosphate and/or converts fructose 6-phosphate to erythrose 4-phosphate and acetyl phosphate. Generally, phosphoketolases act upon ketoses. In certain embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate.

As used herein, the term "mass yield" refers to the mass of the product produced by the recombinant cells divided by the mass of the glucose consumed by the recombinant cells expressed as a percentage.

By "specific productivity," it is meant the mass of the product produced by the recombinant cell divided by the product of the time for production, the cell density, and the volume of the culture.

By "titer," it is meant the mass of the product produced by the recombinant cells divided by the volume of the culture.

As used herein, the term "cell productivity index (CPI)" refers to the mass of the product produced by the recombinant cells divided by the mass of the recombinant cells produced in the culture.

As used herein, the term "an additional yeast species" refers to the existence of another yeast, or more, that is grown to scale along with the genetically engineered yeast and comprises the active dry yeast formulation. Such an additional yeast can itself be a genetically engineered yeast, but need not be.

As used herein, the term "Percent sequence identity" means that a variant has at least a certain percentage of amino acid residues identical to a reference sequence when aligned using the CLUSTAL W algorithm with default parameters. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Deletions are counted as non-identical residues, compared to a reference sequence. Deletions occurring at either terminus are included. For example, a variant with five amino acid deletions of the C-terminus of a mature 617 residue polypeptide would have a percent sequence identity of 99% (612/617 identical residues×100, rounded to the nearest whole number) relative to the mature polypeptide. Such a variant would be encompassed by a variant having "at least 99% sequence identity" to a mature polypeptide.

Exemplary Embodiments

The present teachings provide various embodiments of recombinant yeast cells, fermentation compositions, and methods of use thereof. The recombinant yeast cells can include at least one heterologous nucleic acid encoding one or more polypeptide having phosphoketolase activity; phosphotransacetylase activity; and/or acetylating acetaldehyde dehydrogenase activity, wherein the cell does not include a heterologous modified xylose reductase gene, and wherein the cell is capable of increased biochemical end product production in a fermentation process when compared to a parent yeast cell. The following are additional details and alternatives envisioned.

In some embodiments, the present teachings provide a method of making a desired biochemical comprising including the yeast provided by the present teachings in a fermentation process with a feedstock, wherein the desired biochemical is selected from the group consisting of ethanol, butanol, etc. arabinitol, n-butanol, isobutanol, ethanol, glycerol, methanol, ethylene glycol, 1,3-propanediol (propylene glycol), butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, tryptophan, and threonine); a gas (e.g., methane, hydrogen (H2), carbon dioxide ($CO_2$), and carbon monoxide (CO)); isoprene, isoprenoid, sesquiterpene; a ketone (e.g., acetone); an aldehyde (e.g., acetaldehyde, butryladehyde); an organic acid (e.g., acetic acid, acetonic acid, adipic acid, ascorbic acid, citric acid, 2,5-diketo-Dgluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); 1-3 propane diol, and polyketide. It will be appreciated that the feedstock is not a limitation of the present teachings, and can include for example, glucose, glucose syrups, sucrose, sucrose syrups, liquefact liquifact from starch, granular starch, and various cellulosic feedstocks appropriately treated to liberate fermentable sugars. In some embodiments, the feedstock is selected from the group consisting of glucose, liquefied starch, granular starch, or cellulose.

The present teachings are useful, for example, in fermentation processes. Fermentation post liquefaction and/or saccharification is envisioned. Exemplary fermentation processes include but are not limited to simultaneous saccharification and fermentation (SSF) and granular starch hydrolyzing enzyme (GSHE) fermentation.

The present teachings herein additionally disclose, inter alia, compositions and methods for the production of acetyl coenzyme A-derived metabolites, isoprenoid precursor molecules, isoprene and/or isoprenoids in recombinant cells that have been engineered to express a phosphoketolase polypeptide. The phosphoketolase enzymes of the present teachings can use various substrates, as described in greater detail infra. In certain embodiments, compositions and methods are provided for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate. In other embodiments, provided are compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of fructose 6-phosphate to erythrose 4-phosphate and acetyl phosphate. In still other embodiments, provided are compositions and methods for the production of acetyl coenzyme A-derived metabolites, isoprenoid precursor molecules, isoprene and/or isoprenoids in recombinant cells that have been engineered to express a phosphoketolase polypeptide capable of catalyzing the conversion of sedoheptulose-7-phosphate to ribose-5-phosphate and acetyl phosphate. In still other embodiments, compositions and methods are provided for the production of acetyl coenzyme A-derived metabolites, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Recombinantly expressed phosphoketolase has been used to engineer metabolic pathways in host cells. See U.S. Pat. No. 7,785,858. Sonderegger et al. (Applied and Environmental Microbiology, 2004, 70:5, 2892-97) describe the use of phosphoketolase in *Saccharomyces cerevisiae* for the overproduction of ethanol. Fleige et al. (Appl Microbial Biotechnol., 2011, 91:3, 769-76) describe the expression of a *bifidobacterium* phosphoketolase gene (Meile et al., supra) in a modified *Ralstonia eutropha* strain which restored the capability for the organism to utilize fructose as a sole carbon source for growth.

The present disclosure provides an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms (see, for example, Biology of the Prokaryotes (ed. Lengeler, Drews and Schlegel); Blackwell Science, New York, 1999, p. 299-301; Meile et al., J. of Bacteriology, 2001, 183:9, 2929-36; Jeong et al., J. Microbiol. Biotechnol., 2007, 17:5, 822-829). Phosphoketolase enzymes allow for formation of acetyl-CoA (via acetyl-phosphate) from xylulose 5-phosphate or fructose 6-phosphate rather than through oxidation of pyruvate as in typical metabolism.

Phosphoketolases have been classified into two types based on their substrate preference: xylulose-5-phosphate (X5P) phosphoketolases, which only act on X5P, and X5P/fructose-6-phosphate (F6P) phosphoketolases, which can act on both X5P and F6P (Suzuki et al., Acta Cryst. F66, 2010, 66:8, 941-43). Phosphoketolases catalyze the cleavage of X5P or F6P utilizing inorganic phosphate (Pi) to produce acetyl phosphate (acetyl-P), H2O and glyceraldehyde 3-phosphate or erythrose 4-phosphate.

In another aspect, the invention relates to altered metabolic pathways involving the pentose phosphate pathway (PPP), for example, as a result of one or more heterologously expressed nucleic acids affecting the pentose phosphate pathway. *S. cerevisiae* uses the pentose phosphate pathway to provide cells with intermediates for various anabolic pathways. It is also a major producer of NADPH. The pentose phosphate pathway is composed from an oxidative branch (with enzymes like glucose 6-phosphate 1-dehydrogenase, 6-phosphogluconolactonase or 6-phosphogluconate dehydrogenase) and a non-oxidative branch (with enzymes such as transketolase, transaldolase, ribulose-5-phosphate-epimerase and ribose-5-phosphate isomerase.

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase, ribose-5-phosphate isomerase, expression can be modulated (e.g., increase enzyme activity) to allow more carbon to flux towards fructose 6-phosphate and xylulose 5-phosphate, thereby increasing the eventual production of acetyl CoA and ethanol. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into acetyl-CoA dependent ethanol biosynthetic pathway in comparison to cells that do not have increased expression of transketolase, transaldolase, ribulose-5-phosphate-epimerase and (or) ribose-5-phosphate epimerase.

In any aspects of the invention, provided herein are recombinant cells comprising one or more heterologously expressed nucleic acids encoding phosphoketolase polypeptides as disclosed herein and further engineered to increase the activity of transketolase In any aspects of the invention, provided herein are recombinant cells comprising one or more heterologously expressed nucleic acids encoding phosphoketolase polypeptides as disclosed herein and further engineered to decrease the activity of transketolase. In any aspects of the invention, provided herein are recombinant cells comprising one or more heterologously expressed nucleic acids encoding phosphoketolase polypeptides as disclosed herein and further engineered to increase the activity of transaldolase. In any aspects of the invention, provided herein are recombinant cells comprising one or more heterologously expressed nucleic acids encoding phosphoketolase polypeptides as disclosed herein and further engineered to increase the activity of ribose-5-phosphate isomerase. In any aspects of the invention, provided herein are recombinant cells comprising one or more heterologously expressed nucleic acids encoding phosphoketolase polypeptides as disclosed herein and further engineered to increase the activity of ribulose-5-phosphate 3-epimerase. Activity modulation (e.g., decreased or increased) of glucose 6-phosphate 1-dehydrogenase, 6-phosphogluconolactonase, 6-phosphogluconate dehydrogenase, transketolase, transaldolase, ribulose-5-phosphate-epimerase, ribose-5-phosphate epimerase, ribose-5-phosphate isomerase. In any aspects of the invention, provided herein are recombinant cells comprising one or more heterologously expressed nucleic acids encoding phosphoketolase polypeptides as disclosed herein and further engineered to increase the activity of a glucose 6-phosphate 1-dehydrogenase (zwf) isozyme. In any aspects of the invention, provided herein are recombinant cells comprising one or more heterologously expressed nucleic acids encoding phosphoketolase polypeptides as disclosed herein and further engineered to increase the activity of a transketolase isozyme. In any aspects of the invention, provided herein are recombinant cells comprising one or more heterologously expressed nucleic acids encoding phosphoketolase polypeptides as disclosed herein and further engineered to decrease the activity of a transketolase isozyme. In any aspects of the invention, provided herein are recombinant cells comprising one or more heterologously expressed nucleic acids encoding phosphoketolase polypeptides as disclosed herein and further engineered to increase the activity of a transaldolase isozyme. In any aspects of the invention, provided herein are recombinant cells comprising one or more heterologously expressed nucleic acids encoding phosphoketolase polypeptides as disclosed herein and further engineered to increase the activity of a ribose-5-phosphate isomerase isozyme. In any aspects of the invention, provided herein are recombinant cells comprising one or more heterologously expressed nucleic acids encoding phosphoketolase polypeptides as disclosed herein and further engineered to increase the activity of a ribulose-5-phosphate 3-epimerase isozyme.

In order to direct carbon towards the phosphoketolase enzyme, glucose 6-phosphate 1-dehydrogenase can be modulated (e.g., decrease enzyme activity). In some aspects, the activity of glucose 6-phosphate 1-dehydrogenase (e.g., the endogenous glucose 6-phosphate 1-dehydrogenase gene) can be decreased or attenuated. In certain embodiments, attenuation is achieved by deleting glucose 6-phosphate 1-dehydrogenase. In some aspects, the activity of glucose 6-phosphate 1-dehydrogenase is modulated by decreasing the activity of an endogenous glucose 6-phosphate 1-dehydrogenase. This can be accomplished by replacing the endogenous glucose 6-phosphate 1-dehydrogenase gene promoter with a synthetic constitutively low expressing promoter. In any aspects of the invention, provided herein are recombinant cells comprising one or more heterologously expressed nucleic acids encoding phosphoketolase polypeptides as disclosed herein and further engineered to decrease the activity of glucose 6-phosphate 1-dehydrogenase. Activity modulation (e.g., decreased) of glucose 6-phosphate 1-dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glucose 6-phosphate 1-dehydrogenase isozyme.

In any aspects of the invention, further provided herein are recombinant cells additionally comprising one or more heterologously expressed nucleic acids encoding a variant of the *Trichoderma reseei* glucoamylase gene. In one embodiment the nucleic acid is under control of native *Saccharomyces cerevisiae* FBA1 promoter and transcription terminator. The sequence of this *Trichoderma reseei* glucoamylase gene is shown as SEQ ID NO: 11 herein.

The invention can be further understood by reference to the following examples, which are provided by way of illustration and are not meant to be limiting.

EXAMPLES

Example 1—Construction of Derivatives of Diploid Industrial Yeast Strains with Partially or Completely Deleted Glycerol Biosynthetic Pathway Yeast strain FerMax™ Gold Label Yeast (FG) was purchased from Martrex Inc. This yeast strain is marketed and used for industrial fuel ethanol production. Its growth rate, final ethanol titers and thermotolerance are typical of the yeast strains used by fuel ethanol industry today. To create derivatives of this strain deficient in glycerol production two disruption cassettes specifically targeting GPD1 and GPD2 genes were assembled. These two genes encode two isoenzymes of glycerol-phosphate dehydrogenase, which have similar enzymatic properties but are regulated differently. The deletion cassettes were assembled starting with a minimal-sized derivative of pUC19-plasmid pF1X (described in PCT Publication No. WO 2012/054554; Miasnikov et al.). Each gene disruption cassette contained "5'-flank" and "3'-flank" DNA segments for targeting initial disruption cassette integration into either GPD1 or GPD2 locus of yeast chromosome. Furthermore, downstream of 5'-flank sequence, a "repeat" DNA segment was placed, containing sequence identical to the yeast chromosomal sequence" further downstream from 3'-flank. The detailed description of the disruption vector construction is given by FIGS. 1-5. SEQ ID No 1 provides complete DNA sequence listing of pX(GPD1A1_URA). SEQ ID No. 2 provides complete listing of the DNA sequence of pX(GPD2A1_URA). Tables 1 and 2 specify functional and structural regions within pX(GPD1A1_URA) and pX(GPD2A1_URA).

TABLE 1

Functional and structural elements comprising pX(GPD1A1_URA).

| No | Sequence positions | Functional/Structural element | Origin | Comment |
|---|---|---|---|---|
| 1 | 1-283 | 5'-flanking area yeast GPD1 gene | Synthetic | Synthesized based on yeast strain S288C chromosome IV sequence positions 411198-411480; Sequence ID inGenBank: gi \| 329138864 \| tpg \| BK006938.2 \| |
| 2 | 284-596 | Repeat region downstream of yeast GPD1 gene | Synthetic | Synthesized based on yeast strain S288C chromosome IV sequence positions 412707-413019; Sequence ID in GenBank: gi \| 329138864 \| tpg \| BK006938.2 \| |
| 3 | 597-1758 | Yeast URA3 gene | Yeast FerMax Gold chromosomal DNA | Amplified by PCR, sequence determined experimentally, it is >99% identical to URA3 sequence of S288C chromosome V, 115868-117108; Sequence ID in GenBank: gi \| 329138864 \| tpg \| BK006938.2 \| |
| 4 | 1759-1765 | Creates AscI site | Synthetic | Added for convenience of genet ic engineering |
| 5 | 1766-2079 | 3'-flanking area yeast GPD1 gene | Synthetic | Synthesized based on yeast strain S288C chromosome IV sequence positions 412128-412441; Sequence ID in GenBank: gi \| 329138864 \| tpg \| BK006938.2 \| |
| 6 | 2080-2094 | Added to create a SwaI restriction site | Artificial | Artificial sequence introduced to create SwaI site |
| 7 | 2095-3780 | ColE1 origin of replication and ampicillin resistance gene | pUC19 | A fragment of commonly used laboratory vector pUC19 |
| 8 | 3781-3789 | Added to create a SwaI restriction site | Artificial | Artificial sequence introduced to create SwaI site |

TABLE 2

Functional and structural elements comprising pX(GPD2A1_URA)

| No | Sequence positions | Functional/Structural element | Origin | Comment |
|---|---|---|---|---|
| 1 | 1-287 | 5'-flanking area yeast GPD2 gene | Synthetic | Synthesized based on yeast strain S288C chromosome XV sequence positions 216571-216857; Sequence ID in GenBank: gi \| 329138864 \| tpg \| BK006938.2 \| |
| 2 | 288-583 | Repeat region downstream of yeast GPD2 gene | Synthetic | Synthesized based on yeast strain S288C chromosome XV sequence positions 217956-218252; Sequence ID in GenBank: gi \| 329138864 \| tpg \| BK006938.2 \| |
| 3 | 584-1747 | Yeast URA3 gene | Yeast FerMax Gold chromosomal DNA | Amplified by PCR, sequence determined experimentally, it is >99% identical to URA3 sequence of S288C chromosome V, 115868-117108; Sequence ID in GenBank: gi \| 329138864 \| tpg \| BK006938.2 \| |
| 4 | 1748-1754 | Creates AscI site | Synthetic | Added for convenience of genet ic engineering |
| 5 | 1755-2047 | 3'-flanking area yeast GPD2gene | Synthetic | Synthesized based on yeast strain S288C chromosome XV sequence positions 217632-217924; Sequence ID in GenBank: gi \| 329138864 \| tpg \| BK006938.2 \| |
| 6 | 2048-2062 | Added to create a SwaI restriction site | Artificial | Artificial sequence introduced to create SwaI site |
| 7 | 2063-3748 | ColE1 origin of replication and ampicillin resistance gene | pUC19 | A fragment of commonly used laboratory vector pUC19 |

TABLE 2-continued

Functional and structural elements comprising pX(GPD2A1_URA)

| No | Sequence positions | Functional/Structural element | Origin | Comment |
|---|---|---|---|---|
| 8 | 3749-3757 | Added to create a SwaI restriction site | Artificial | Artificial sequence introduced to create SwaI site |

Figure 6A:
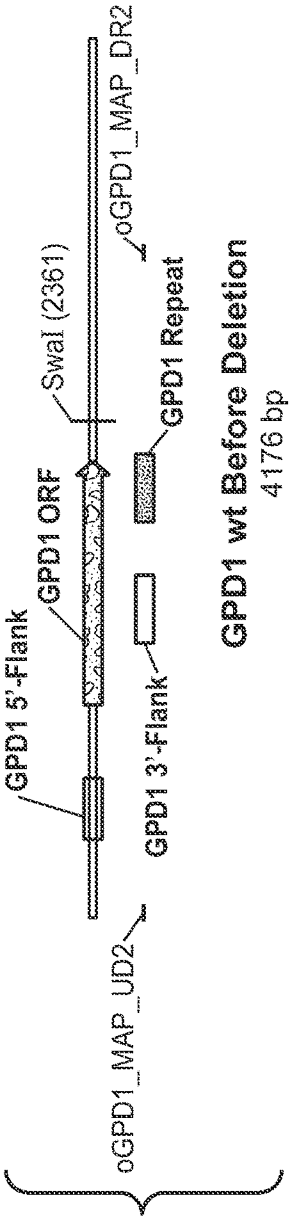
FIGS. 6A, 6B and 6C depict GPD1 chromosomal locus before disruption (FIG. 6A), after disruption with URA3 marker (FIG. 6B), and after excision of URA3 by homologous recombination (FIG. 6C).
Figure 6B:
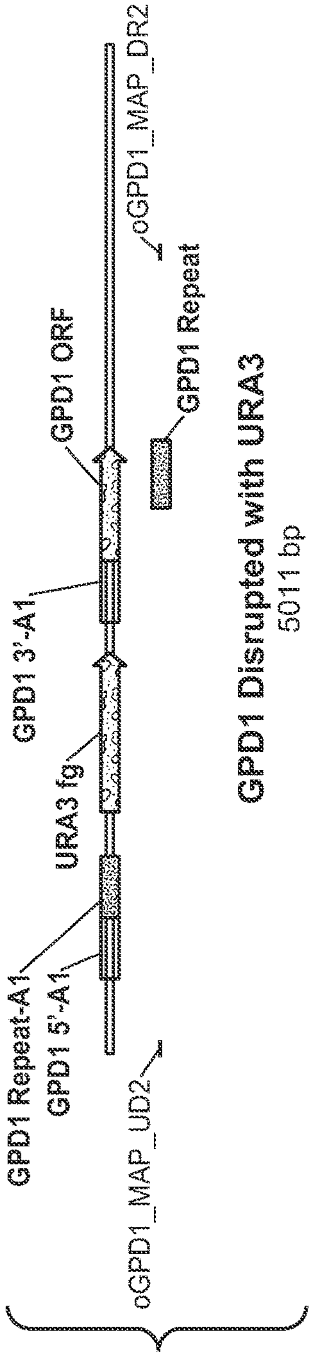
Figure 6C:
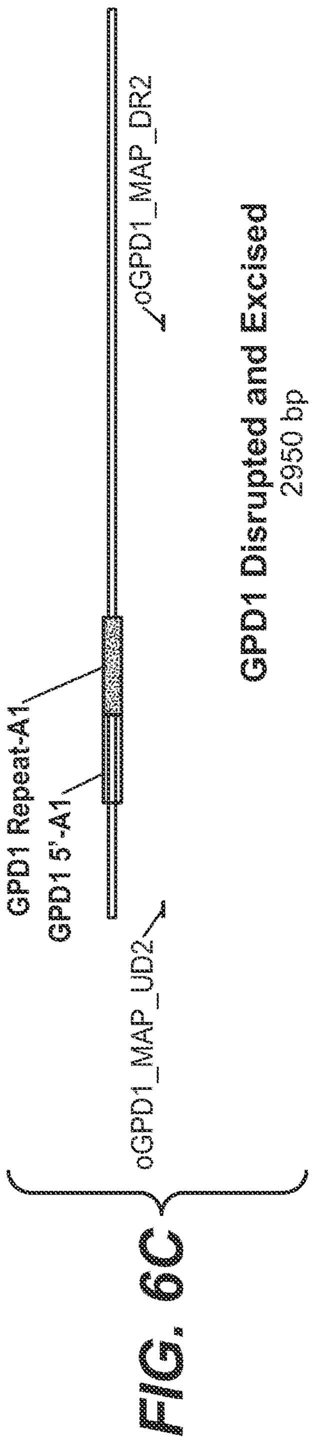

An ura3-derivative of FerMax Gold (strain FG-ura) has been described earlier (Miasnikov et al., U.S. Provisional Application Ser. No. 61/896,869, filed Oct. 29, 2013). This strain was transformed to uracil prototrophy using a purified 2079 bp DNA fragment excised from pX(GPD1A1_URA) with endonuclease SwaI. The transformants were screened by PCR using primers oGPD1_MAP_UD2 and oGPD1_MAP_DR2. The clones containing a single GPD1 allele disrupted by the transforming fragment produced two PCR products: a 3.15 kb product generated by the wild-type allele and a 4.0 kb fragment amplified from the disrupted copy of GPD1(Tables 3 and 4). One strain producing such PCR product mixture was purified by cloning and submitted to a marker excision procedure. Marker excision was done on minimal plates (6.7 g/Yeast nitrogen base w/o amino acids, 20 g/l glucose) supplemented with 100 mg/l of uridine and 1.2 g/l of fluoroorotic acid (FOA). About 24 ura3-clones emerging on FOA plates were purified and again analyzed by PCR using the same primer pair. This time, a clone generating two PCR products: wild-type 3.1 kb fragment and a short, 1.9 kb fragment was selected. The short fragment corresponds to the disrupted GPD1 allele from which the URA3 marker was excised by homologous recombination between the two "repeat" regions. The structure of the GPD1 chromosomal locus during GPD1 gene disruption and marker excision process is illustrated by FIGS. 6A, 6B and 6C. FIG. 6A illustrates GPD1 wt (wild type) before deletion. FIG. 6B illustrates GPD1 disrupted with URA 3. FIG. 6C illustrates the end of the excision process where GPD1 is disrupted and excised. The resulting strain was heterozygous at the GPD1 locus with one wild type allele and one allele with GPD1 gene deletion. Next, the same sequence of manipulations: gene disruption with the SwaI fragment of pX(GPD1A1_URA) and marker excision using FOA (with screening and PCR analysis at each step) was applied to this heterozygous intermediate strain resulting in an isolate with both copies of GPD1 gene disrupted. This strain was named FGG1. The URA3 predecessor of this strain that was not subjected to last marker excision procedure was named FGGlu.

Figures 7A, 7B, 7C:
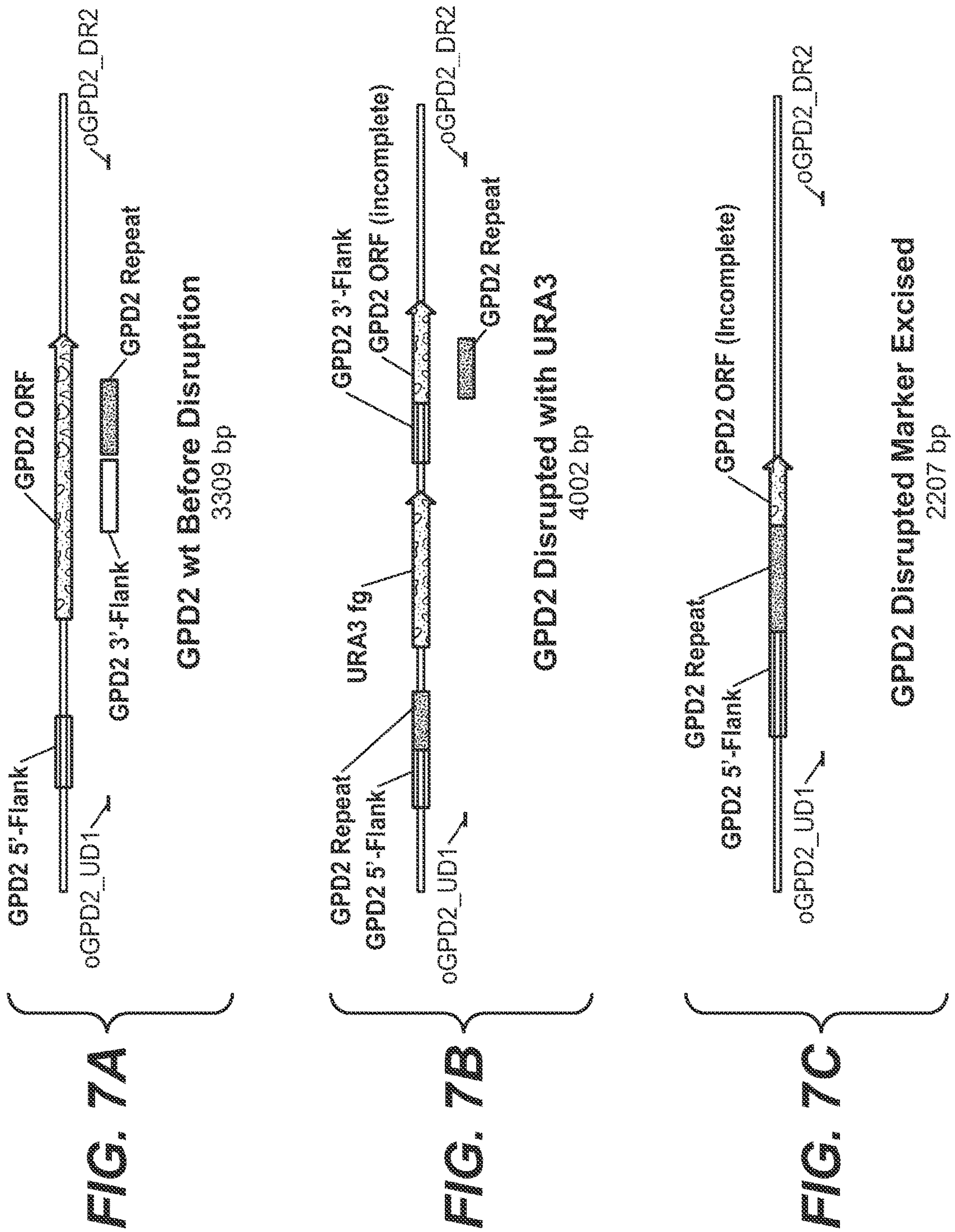
FIGS. 7A, 7B and 7C depict GPD2 chromosomal locus before disruption (FIG. 7A), after disruption with URA3 marker (FIG. 7B), and after excision of URA3 by homologous recombination (FIG. 7C).

Deletion of GPD2 gene from FGG1 was done using exactly the same two-step strategy as used earlier for deletion GPD1 gene and is illustrated in FIGS. 7A, 7B and 7C. FIG. 7A illustrates GPD2 wt (wild type) before deletion. FIG. 7B illustrates GPD2 disrupted with URA 3. FIG. 7C illustrates the end of the excision process where GPD2 is disrupted and excised. The primers used for screening the transformants and FOA-resistant isolates after marker excision are listed in Table 3. The sizes of characteristic PCR fragments obtained by PCR with primer pair oGPD2_DR2+oGPD2_UD1 are given in Table 4. The heterozygous strain with a single deleted GPD2 allele and excised URA3 marker (the other GPD2 allele remains wild-type in this strain) was named FGG2. The strain with both GPD2 alleles deleted was named FGGZ. Similarly to the pair of strains FGG1 and FGGlu, the URA3 predecessors of FGG2 and FGGZ were named FGG2u and FGGZu. Table 5 lists genotypes of the strains with completely or partially blocked glycerol biosynthetic pathway used in this study.

TABLE3

Primers used for mapping deletions of GPD1 and GPD2 genes

| Name | Primer Sequence | SEQ ID NO: |
|---|---|---|
| oGPD1_MAP_DR2 | GAACAATGTCATGACATTGGATGGTGTGCTTGCAGTC | SEQ ID NO: 7 |
| oGDP1_MAP_UD2 | GAGTTATCGTTACTCCGATTATTTTGTACAGCTGATGG | SEQ ID NO: 8 |
| oGPD2_DR2 | CCGTGTATATTAGAACAATGTTCCTTATCGCTGCAC | SEQ ID NO: 9 |
| oGPD2_UD1 | CAGGTAACCGTGCGCGATGAGCTAATCCTGAGCCATC | SEQ ID NO: 10 |

TABLE 4

Characteristic PCR fragment sizes at GPD1 and GPD2 loci during disruption and excision steps (using primer pairs of Table 3, base pairs)

| Modification | GPD1 locus | GPD2 locus |
|---|---|---|
| Wild type | 3152 | 2685 |
| Disrupted with URA3 | 3994 | 3378 |
| After URA3 marker excision | 1929 | 1583 |

TABLE 5

Genotypes of strains with completely or partially blocked glycerol biosynthetic pathway used in this study

| Strain | Genotype |
|---|---|
| FG-ura | Δuro3/Δura3 |
| FGG1u | Δgpd1/Δgpd1 Δura3/URA3 |
| FGG1 | Δgpd1/Δgpd1 Δuro3/Δura3 |
| FGG2u | Δgpd1/Δgpd1 GPD2/Δgpd2 Δura3/URA3 |
| FGG2 | Δgpd1/Δgpd1 GPD2/Δgpd2 Δura3/Δura3 |

TABLE 5-continued

| Genotypes of strains with completely or partially blocked glycerol biosynthetic pathway used in this study | |
|---|---|
| Strain | Genotype |
| FGGZ | Δgpd1/Δgpd1 Δgpd2/Δgpd2 Δura3/URA3 |
| FGGZ | Δgpd1/Δgpd1 Δgpd2/Δgpd2 Δura3/Δura3 |

Figure 8:
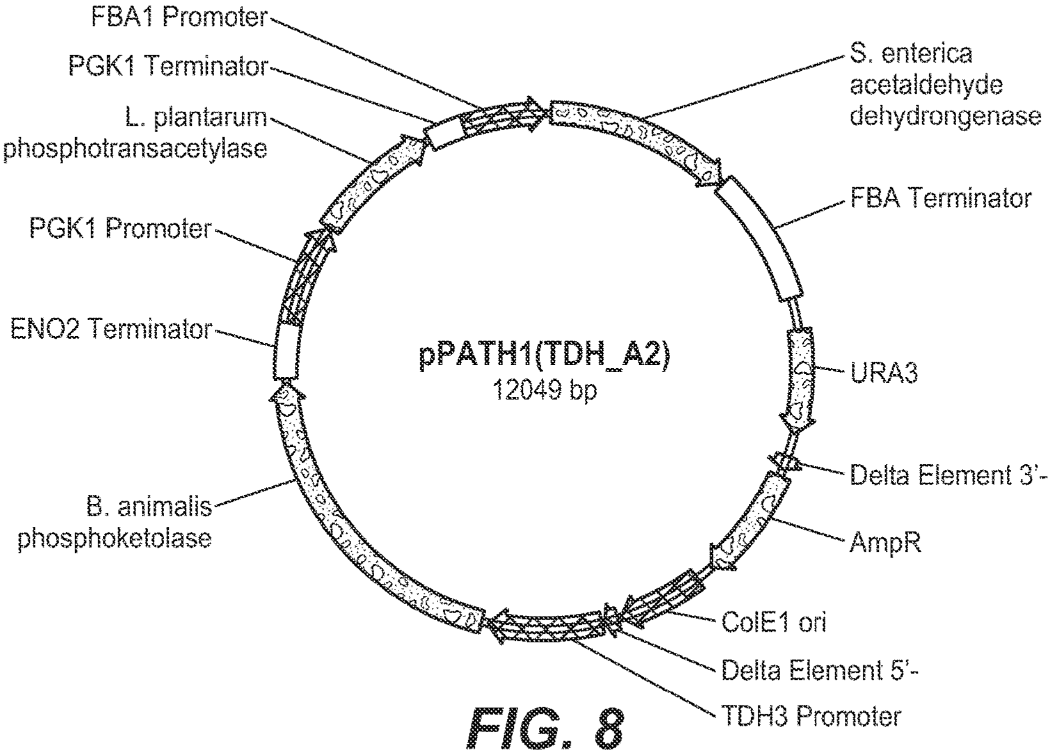
FIG. 8 depicts the structure of recombinant vector pPATH1 (TDH_A2).

Example 2—Construction of a Recombinant Vector pPATH1(TDH_A2) and Transformation of Yeast The genes encoding the three enzymes of the artificial pathway of this invention: phosphoketolase (from *Bifidobacterium animalis*), phosphotransacetylase (*Lactobacillus plantarum*) and acylating acetaldehyde dehydrogenase (*Salmonella enterica*) were synthesized using codons preferred by *Saccharomyces* yeast. The sequences of the three genes are respectively listed below as SEQ ID No 3, SEQ ID No 4 and SEQ ID No 5. These genes were placed under control of the three commonly used strong glycolytic promoters of *S. cerevisiae*: TDH3, PGK1 and FBA1, respectively. DNA fragments comprising promoter and transcription terminator sequences were amplified by PCR from yeast chromosomal DNA templates. The vector was assembled using routine methods of genetic engineering. The structure of pPATH1 (TDH_A2) is illustrated by FIG. 8. Table 6 lists all functional and structural elements comprising pPATH1 (TDH_A2). The DNA sequence listing of this vector is given as SEQ ID No 6.

TABLE 6

Functional and structural elements of vector pPATH1(TDH_A2)

| No | Sequence positions | Functional/Structural element | Origin | Comment |
|---|---|---|---|---|
| 1 | 1-104 | 5'-flank of the yeast -element | *S. cerevisiae* chromosomal DNA | Amplified by PCR |
| 2 | 105-123 | SfiI and SalI restriction sites | Artificial | Introduced for convenience of genetic engineering |
| 3 | 124-1002 | TDH3 promoter | *S. cerevisiae* chromosomal DNA | Amplified by PCR |
| 4 | 1003-1027 | SpeI and EcoRI restriction sites and a sequence for optimal start codon context | Artificial | Introduced for convenience of genetic engineering and improved expression of the downstream coding sequence |
| 5 | 1028-3505 | Encodes *B. animalis* phosphoketolase | Synthetic | Phosphoketolase protein coding sequence optimized for yeast codon bias |
| 6 | 3506-3527 | BamHI and NotI restriction sites | Artificial | Introduced for convenience of genetic engineering |
| 7 | 3528-3547 | ENO2 transcription terminator | *S. cerevisiae* chromosomal DNA | Amplified by PCR |
| 8 | 3954-4700 | PGK1 promoter | *S. cerevisiae* chromosomal DNA | Amplified by PCR |

TABLE 6-continued

Functional and structural elements of vector pPATH1(TDH_A2)

| No | Sequence positions | Functional/Structural element | Origin | Comment |
|---|---|---|---|---|
| 9 | 4701-4710 | SpeI restriction site and a sequence for optimal start codon context | Artificial | Introduced for convenience of genetic engineering and improved expression of the downstream coding sequence |
| 10 | 4711-5688 | Encodes phosphotransacetylase from *L. plantarum* | Synthetic | Phosphotransacetylase protein coding sequence optimized for yeast codon bias |
| 11 | 5689-5704 | BamHI and NotI restriction sites | Artificial | Introduced for convenience of genetic engineering |
| 12 | 5705-5994 | PGK1 transcription terminator | *S. cerevisiae* chromosomal DNA | Amplified by PCR |
| 13 | 5995 | A remnant of e restriction site | Artificial | A remnant of a SalI restriction site earlier appended to FBA1 promoter downstream |
| 14 | 5996-6597 | FBA1 promoter | *S. cerevisiae* chromosomal DNA | Amplified by PCR |
| 15 | 6598-6619 | SpeI and EcoRI restriction sites and a sequence for optimal start codon context | Artificial | Introduced for convenience of genetic engineering and improved expression of the downstream coding sequence |
| 16 | 6220-8023 | Encodes *S. enterica* acylating acetaldehyde dehydrogenase | Synthetic | AADH coding sequence optimized for yeast codon bias |
| 17 | 8024-8042 | BamHI and NotI restriction sites | Artificial | Introduced for convenience of genetic engineering |
| 18 | 8043-9042 | FBA1 transcription terminator | *S. cerevisiae* chromosomal DNA | Amplified by PCR |
| 19 | 9043-9059 | SacI and SacII restriction sites | Artificial | Introduced for convenience of genetic engineering |
| 20 | 9060-10224 | *S. cerevisiae* URA3 gene including native promoter and terminator | *S. cerevisiae* chromosomal DNA | Amplified by PCR |
| 21 | 10225-10231 | Combined with adjacent sequences creates AscI restriction site | Artificial | Introduced for convenience of genetic engineering |
| 22 | 10232-10340 | 3'-flank of the yeast -element | *S. cerevisiae* chromosomal DNA | Amplified by PCR |
| 23 | 10341-12049 | ColE1 and AmpR gene | Plasmid vector pUC19 | Amplified by PCR |

For transformation of yeast vector pPATH1(TDH_A2) was digested with restriction endonuclease SwaI and a 10.3 kb DNA fragment containing the three expression cassettes and URA3 selectable marker gene (but not any of the bacterial vector DNA) was purified by agarose gel electrophoresis. *S. cerevisiae* strains FG-ura, FGG1, FGG2 and FGGZ were transformed with this DNA fragment to uracil prototrophy.

Example 3—Growth and Ethanol Production by Strains Carrying pPATH1(TDH_A2)

Figure 9:
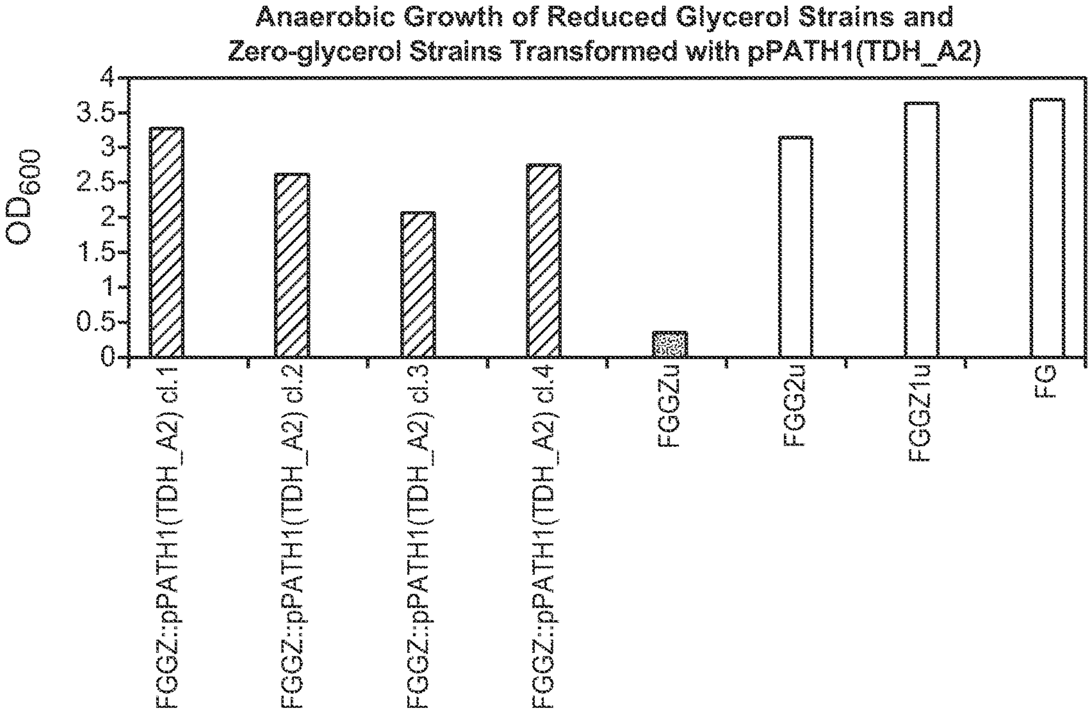
FIG. 9 depicts anaerobic growth values for control and experimental strains including reduced glycerol strains and zero-glycerol strains.
Figure 10A:
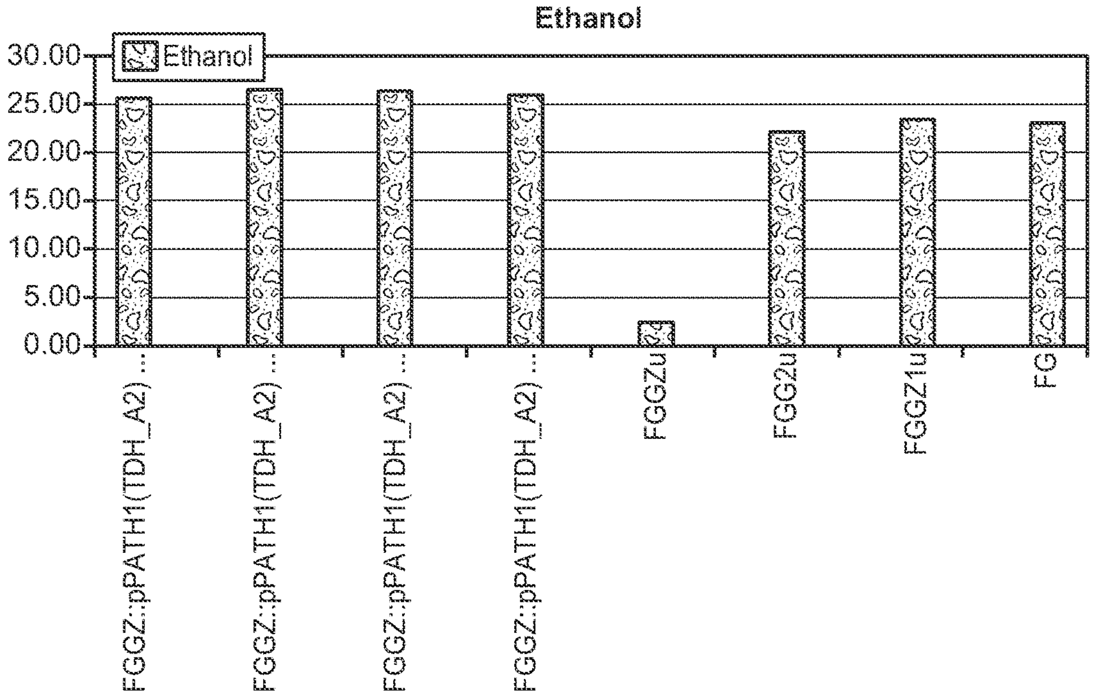
FIGS. 10A and 10B depict ethanol (FIG. 10A) and glycerol (FIG. 10B) production values for anaerobic batch fermentations of control and experimental strains.
Figure 10B:
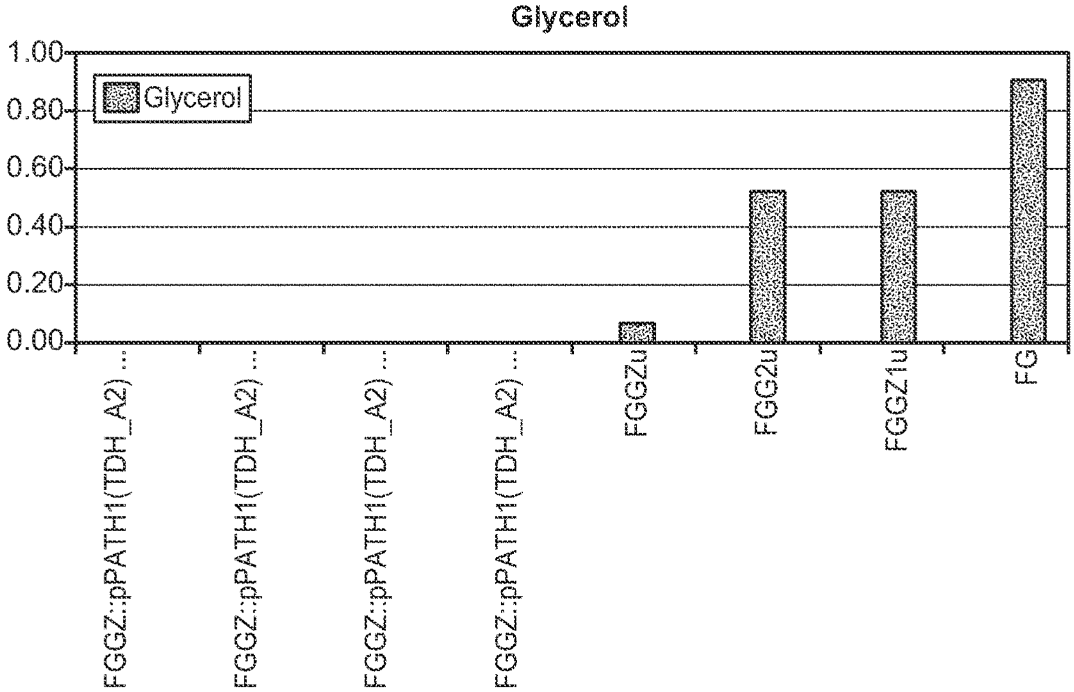

Several transformants of the strain FGGZ with the SwaI fragment of pPATH1(TDH_A2) as well as wild type yeast strain and three control strains with completely or partially blocked glycerol biosynthesis (FGGlu, FGG2u and FGGZu) were grown aerobically overnight in SC6 medium (Yeast Nitrogen Base w/o amino acids ammonium sulfate, 0.2% urea, 6% glucose). These cultures were washed with ice-cold SC6 and used to inoculate 6 ml of the same medium in a 13 mm sterile plastic test tube to initial OD600 of ~0.2. The inoculated cultures were kept on ice until being placed into an anaerobic chamber (<0.1 ppm $O_2$). The cultures were then incubated in vertical position with shaking (500 rpm) at 32° C. for 3 days. At this point the cultures were taken from anaerobic chamber and placed on ice. $OD_{600}$ were measured. An aliquot of supernatant was filtered through a 0.22 μM syringe filter and subjected to HPLC analysis. As shown in FIG. 9 and FIGS. 10A and 10B, the strains with partially deleted glycerol pathway (FGGlu and FGG2u) grow to somewhat lower cell densities and produce equivalent or somewhat lower amount of ethanol than the wild type strain Fermax Gold (FG). Zero-glycerol strain FGGZu does not grow anaerobically (see FIG. 9) and produces only a trace amount of ethanol (See FIG. 10A). However, when a ura3 derivative of this strain (strain FGGZ) is transformed with SwaI fragment of pPATH1(TDH_A2) it recovers the ability to grow anaerobically (see FIG. 9), although biomass yields are reduced relative to the wild type. On the other hand, ethanol yield is consistently higher in the transformants of FGGZ with SwaI fragment of pPATH1(TDH_A2) than in wild type strain (see FIG. 10A). Glycerol production in transformed strains is not detectable (see FIG. 10B). A glycerol signal detected in non-transformed strain FGGZu is likely to be an HPLC artifact, probably caused by the presence of high amount of non-fermented sugar (see FIG. 10B).

Figure 11A:
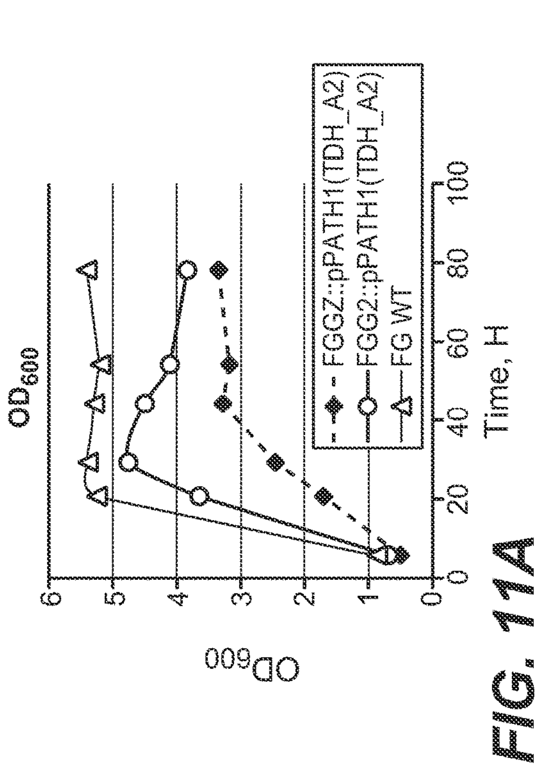
FIGS. 11A, 11B, 11C and 11D depict $OD_{600}$ (FIG. 11A), ethanol (FIG. 11B), glycerol (FIG. 11C) and glucose production (FIG. 11D) values in anaerobic batch fermentations of control and experimental strains.
Figure 11B:
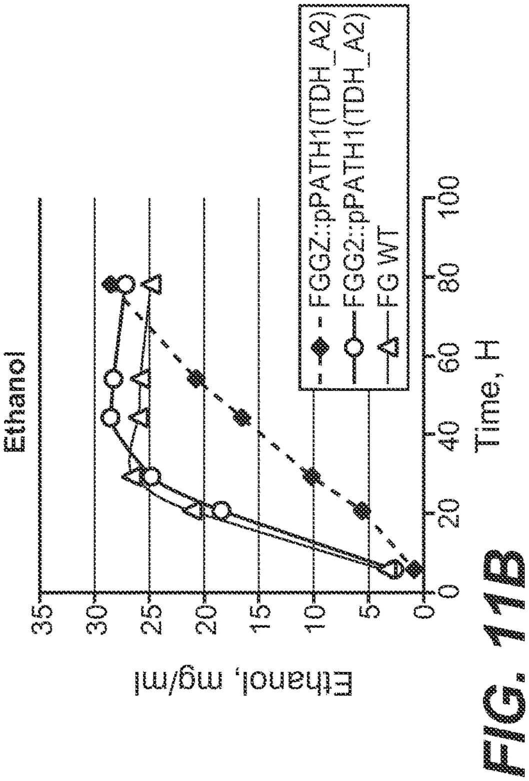
Figure 11C:
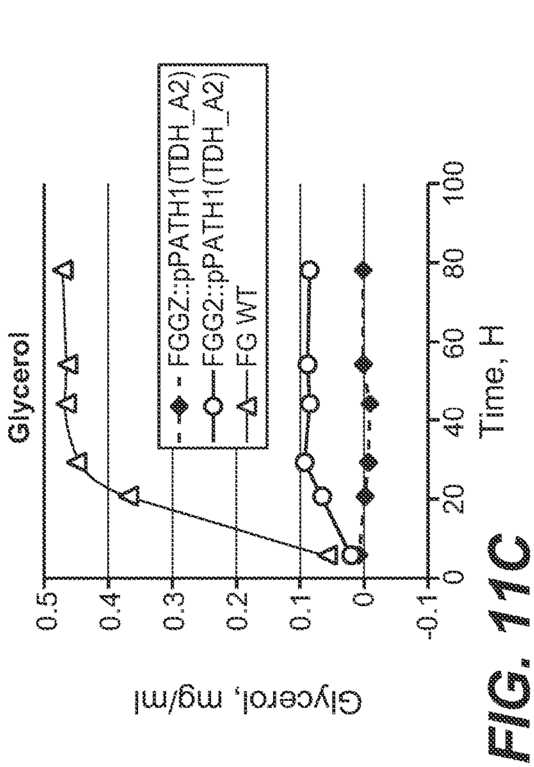
Figure 11D:
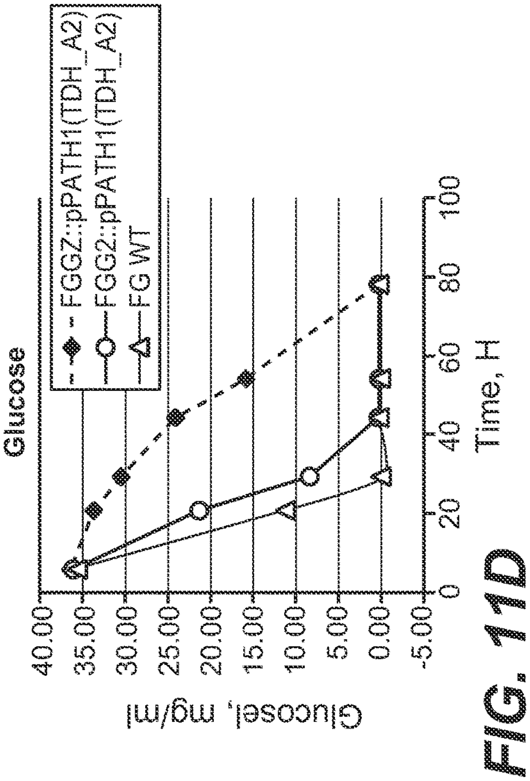
Figure 12:
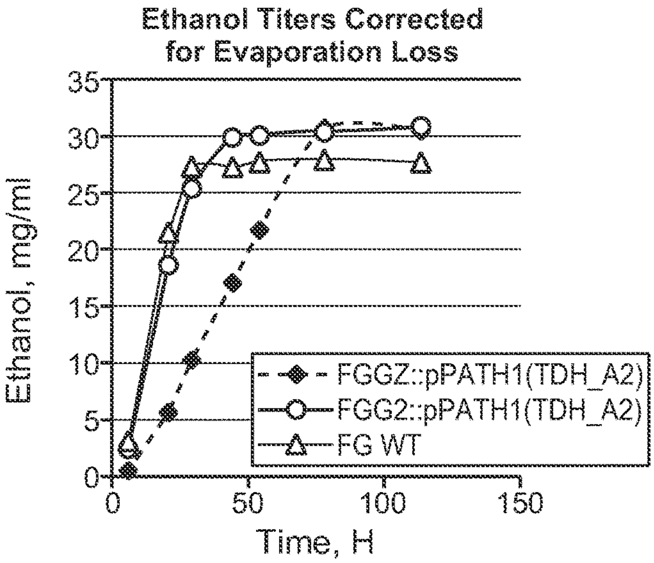
FIG. 12 depicts ethanol production, with correction for calculated evaporation loss, in anaerobic batch fermentations of control and experimental strains, including correction for calculated evaporation loss.

Another experiment was done using a similar setup with the difference that growth and fermentation process was followed kinetically. In this experiment, multiple test tubes were inoculated (to $OD_{600}$=0.5) with each of the strains FGGZ::pPATH1(TDH_A2) cl. 2, FGG2::pPATH1 (TDH_A2) cl. 8 and wild type strain FerMax Gold (FG). The cultures were placed on a shaker in an anaerobic chamber (500 rpm, 32° C.). Individual test tubes were removed from anaerobic chamber at different time points, immediately chilled on ice and analyzed for $OD_{600}$ and extracellular metabolites. The data obtained in this experiment (shown in FIGS. 11A, 11B, 11C and 11D) supports the observations made earlier and allows making several additional conclusions. Firstly, the three strains evaluated in this experiment grow at different rate and reach maximum ethanol titers at different times. In particular, strain FGGZ transformed with the SwaI fragment of pPATH1(TDH_A2) grows much slower than wild type strain FerMax Gold (see FIG. 11A). On the other hand, reduced glycerol strain FGG2 transformed with the same DNA fragment grows at only somewhat slower rate than wild type (see FIG. 11A). As a consequence of differences in growth rate, ethanol concentration in each type of culture reaches its peak at a different time and then slowly decreases due to evaporation (see FIG. 11B). Comparison of the maximum ethanol titers in each culture shows that both strains carrying the triple expression cassette from pPATH1(TDH_A2) produce significantly more ethanol than wild type strain (107% for FGG2::pPATH1(TDH_A2) cl. 8 and 107.5% for FGGZ::pPATH1 (TDH_A2) cl. 2). Assuming that ethanol loss due to evaporation is proportional to ethanol concentration and cultivation time and that no ethanol is produced by wild-type strain after 55 h, ethanol loss under conditions of the experiment was estimated to be 0.00185/h. If the ethanol titer data of FIG. 11B is recalculated to correct for evaporation loss, the improvement in ethanol production by strains FGG2::pPATH1(TDH_A2) cl. 8 and FGGZ::pPATH1 (TDH_A2) cl. 2 relative to the wild type precursor strain FerMax Gold is even higher than estimated based on maximum titer. Both strains produce −110-111% of the ethanol produced by the wild-type strain FerMax Gold (FIG. 12).

Figure 13:
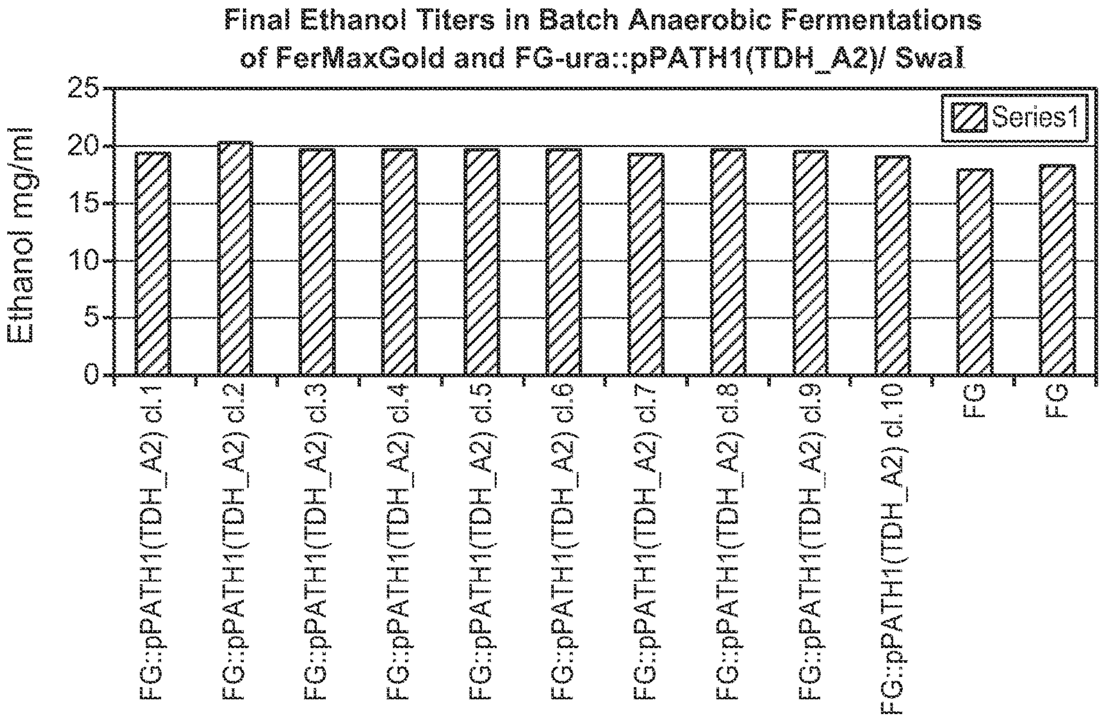
FIG. 13 depicts ethanol production in anaerobic batch fermentations of wild type strain FerMax Gold as well as multiple transformants of FGG1 and FerMax Gold—both transformed with SwaI fragment of pPATH1(TDH_A2).
Figure 14A:
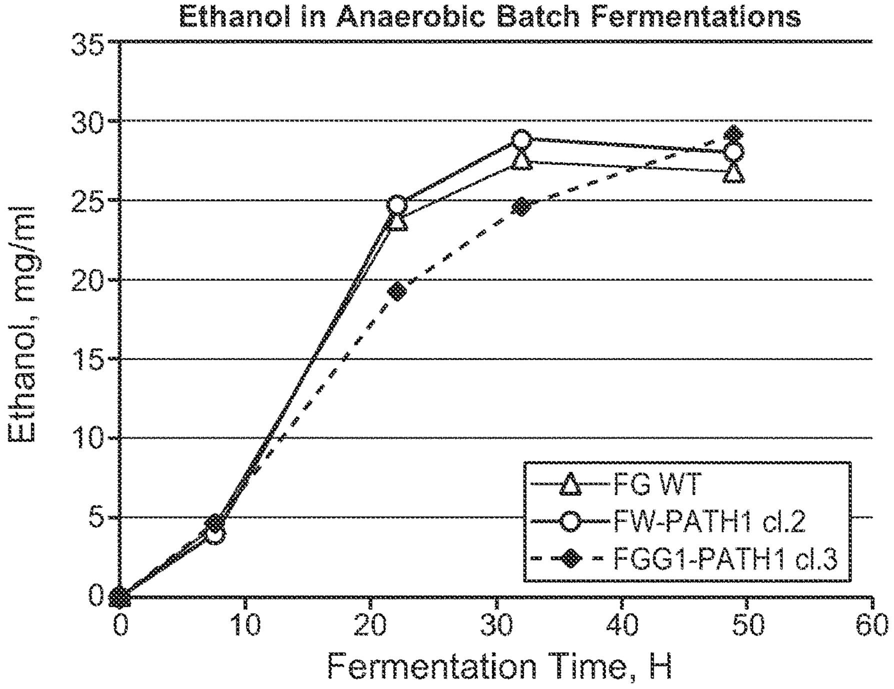
FIGS. 14A and 14B depict time course of ethanol production in anaerobic batch fermentations of wild type strain FerMax Gold and engineered strains: FGG1 transformed with SwaI fragment of pPATH1(TDH_A2) and FerMax Gold transformed with the same DNA.
Figure 14B:
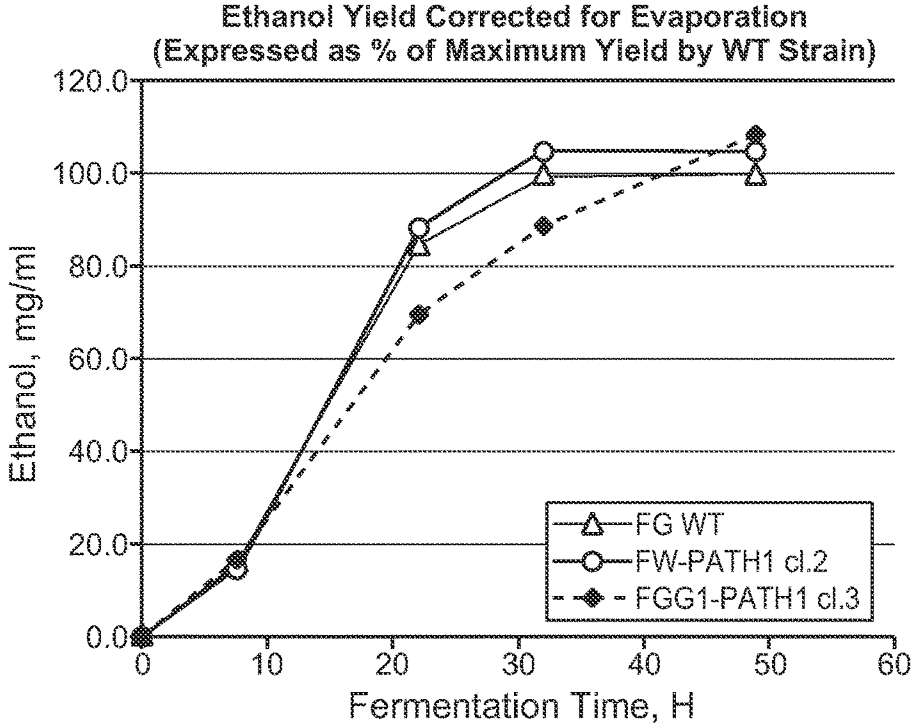

The same large SwaI fragment of pPATH1(TDH_A2) was used to transform strains FGG1 (deleted only for GPD1) and wild-type (with respect to glycerol synthesis) strain FG-ura3. Transformants of both hosts showed significantly improved ethanol yields (FIG. 13) demonstrating that the engineered pathway encoded by pPATH1(TDH_A2) is effective not only in strains with partially or completely reduced glycerol biosynthesis but also strains that are wild type with respect to glycerol biosynthesis. On average FG-ura:: pPATH1(TDH_A2)/SwaI transformants produced 8% more ethanol than wild-type strains FerMax Gold. A time course experiment with selected clones of FG-ura:: pPATH1(TDH_A2)/SwaI and FGG1:: pPATH1(TDH_A2)/ SwaI (FIGS. 14A and 14B) shows that the strain FG-ura:: pPATH1(TDH_A2)/SwaI, which is wild-type with respect to glycerol biosynthetic pathway, ferments glucose at essentially the same rate as wild-type control strain FerMax Gold. At the same time, maximum ethanol yield by FG-ura:: pPATH1(TDH_A2)/SwaI is more than 4% higher than that of wild type control ("FG WT"). The strain lacking GPD1 encoded glycerophosphate dehydrogenase and carrying the recombinant pathway (FGG1:: pPATH1(TDH_A2)/SwaI) ferments at a slower rate but has maximum ethanol yield about 8% higher than that of wild type ethanologen yeast strain ("FG WT").

In conclusion, increased ethanol yields have been observed in every yeast strain transformed with the SwaI fragment of pPATH1(TDH_A2). This DNA fragment carries three expression cassettes producing the enzymes of the phosphoketolase pathway: phosphoketolase, phosphotransacetylase and acylating acetaldehyde dehydrogenase. The yields are highest in strains with reduced glycerol biosynthetic capacity. However, anaerobic glucose fermentation by such strains is slower than fermentation with strains that have native glycerol biosynthetic machinery. Without being limited to a particular theory, slow fermentation rate by the strains expressing phosphoketolase pathway may be caused by the imbalance of metabolites of the lower pentose phosphate pathway: erythrose 4-phosphate, sedoheptulose 7-phosphate, ribulose 5-phosphate, ribose 5-phosphate and xylulose 5-phosphate. Such imbalance may be caused by phosphoketolase reaction that can lead to production of excessive amounts of erythrose 4-phosphate or depletion of the pool of xylulose 5-phosphate. To eliminate this imbalance it would be advantageous to over-produce the enzymes of lower pentose phosphate pathway: transaldolase, transketolase, ribulose 5-phosphate epimerase and ribose 5-phosphate isomerase.

Example 4—Acetaldehyde Dehydrogenases Suitable for Enhanced Ethanol Production in Yeast Genes encoding acetaldehyde dehydrogenases (AADH) from a number of different microorganisms were back-translated using *S. cerevisiae* codon preferences and synthesized by GenScript (GenScript USA Inc. Piscataway, N.J.). Table 7 lists the source organisms, enzyme codes used in screening experiments and SEQ ID numbers for protein and nucleotide sequences.

TABLE 7

Acetaldehyde dehydrogenases evaluated for enhanced ethanol production in yeast.

| Acetaldehyde dehydrogenase code | Source organism | DNA sequence SEQ ID | Protein sequence SEQ ID |
|---|---|---|---|
| A_2 | *Salmonella enterica* | SEQ ID No: 5 | SEQ ID No: 12 |
| A_10 | *Escherichia coli* | SEQ ID No: 13 | SEQ ID No: 14 |
| A_11 | *Citrobacter freundii* | SEQ ID No: 15 | SEQ ID No: 16 |
| A_12 | *Pseudomonas* M1 | SEQ ID No: 17 | SEQ ID No: 18 |
| A_13 | *Morganella morganii* | SEQ ID No: 19 | SEQ ID No: 20 |
| A_14 | *Calditrix abyssii* | SEQ ID No: 21 | SEQ ID No: 22 |
| A_15 | *Marinobacter aquaeoli* | SEQ ID No: 23 | SEQ ID No: 24 |
| A_16 | *Shewanella benthica* | SEQ ID No: 25 | SEQ ID No: 26 |
| A_17 | *Bacillus vireti* | SEQ ID No: 27 | SEQ ID No: 28 |
| A_18 | *Streptococcus massiliensis* | SEQ ID No: 29 | SEQ ID No: 30 |
| A_19 | *Desulfospira joergensenii* | SEQ ID No: 31 | SEQ ID No: 32 |
| A_20 | *Bilophila wadsworthia* | SEQ ID No: 33 | SEQ ID No: 34 |
| A_21 | *Ilyobacter polytropus* | SEQ ID No: 35 | SEQ ID No: 36 |

Each of the synthetic genes was placed between FBA1 promoter and transcription terminator sequences of the vector pPATH1(TDH_A2) replacing the *Salmonella enterica* AADH gene present in the original pPATH1 (TDH_A2). The resulting plasmids were named pPATH1 (TDH_A10), pPATH1(TDH_A11) etc. Large SwaI fragment was excised from each of the eleven new vectors and used to transform the yeast strain FGGZ.

Figure 15A:
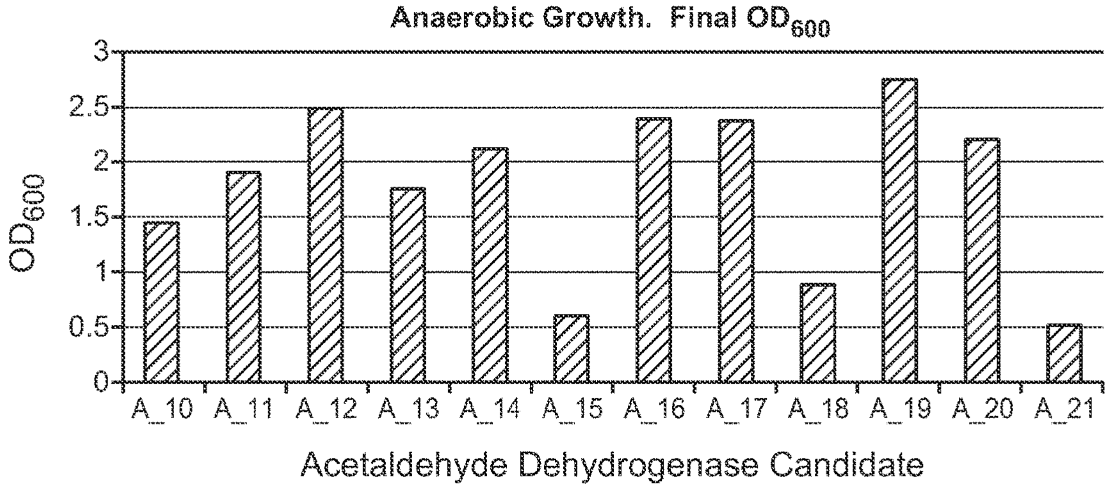
FIG. 15A depicts anaerobic growth by strains obtained by transformation of the strain FGGZ with constructs expressing *B. animalis* phosphoketolase, *L. plantarum* phosphotransacetylase and various acetaldehyde dehydrogenase candidate enzymes.
Figure 15B:
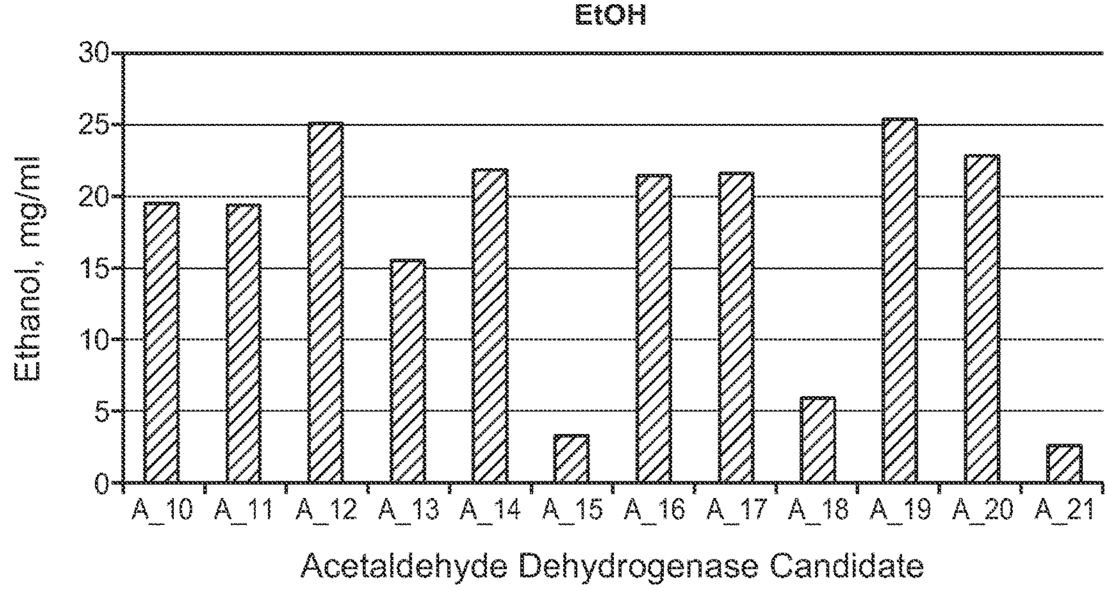
FIG. 15B depicts ethanol production by strains obtained by transformation of the strain FGGZ with constructs expressing *B. animalis* phosphoketolase, *L. plantarum* phosphotransacetylase and various acetaldehyde dehydrogenase candidate enzymes.

The transformants were tested for the restoration of ability to grow anaerobically (FGGZ cannot grow anaerobically because the absence of glycerol production). The total population of transformants was used to inoculate a medium containing 6% glucose, 0.2% urea and 0.67 g/l of Yeast Nitrogen Base without amino acids and ammonium sulfate to initial $OD_{600}$ of 0.3. FIG. 15A shows final $OD_{600}$ values reached by the cultures after 2 days of cultivation under strict anaerobic conditions. The best growth was observed with strains carrying AADH candidates A_12, A_16, A_17 and A_19. The growth of transformants containing AADH candidates A_15 and A_21 was not substantially different from the residual growth of the host strain FGGZ cultivated under the same conditions. Other candidate AADH all rescued anaerobic growth ability of FGGZ to varying degrees. Ethanol production of the various AADH candidates during these fermentations, as shown in FIG. 15B, correlated strongly with the ability to grow anaerobically.

Figure 16:
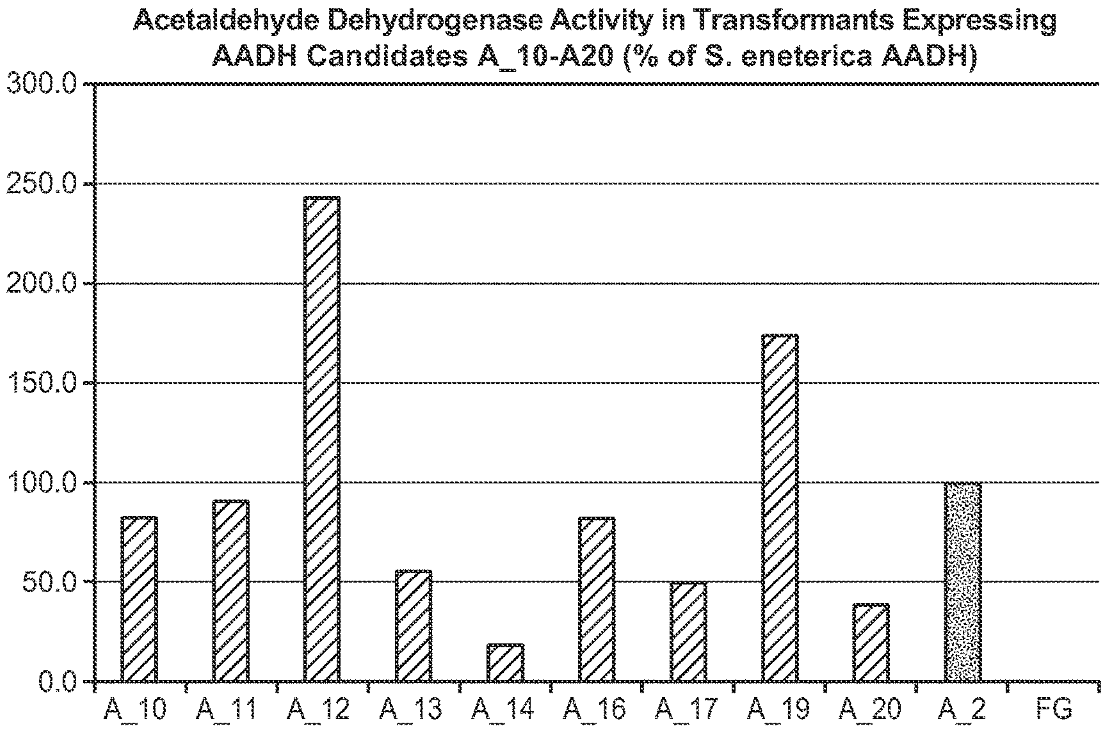
FIG. 16 depicts experimentally determined acetaldehyde dehydrogenase activity in FGGZ transformed with pPATH1 (A_10), pPATH1(A_11), pPATH1(A_12), pPATH1(A_13), pPATH1(A_14), pPATH1(A_16), pPATH1(A_16), pPATH1 (A_17), pPATH1(A_19), pPATH1(A_20), pPATH1(A_2) and the negative control FerMaxGold (FG).

Individual clones of FGGZ yeast transformed with pPATH1(TDH_A10), pPATH1(TDH_A11), pPATH1 (TDH_A12), pPATH1(TDH_A13), pPATH1(TDH_A14), pPATH1(TDH_A16), pPATH1(TDH_A17), pPATH1 (TDH_A19), pPATH1(TDH_A20) were isolated. Two such clones of each type together with two clones of FGGZ transformed with pPATH1(TDH_A2) and wild type Fermax-Gold yeast were grown overnight in 10 ml of YEPPD medium. The cells were collected, washed with water, re-suspended in an Eppendorf tube in 0.5 ml of 100 mM Tris-HCl containing 2 mM phenylmethylsulfonylfluoride (PMSF). Approximately 300 ml of 0.5 mm glass beads were added to each sample. The cells were disrupted by three 40 second pulses of agitation (maximum strength) in a Mini-Beadbeater (model 24; BioSpec Products, Bartlesville, Okla.) with cooling between pulses (approximately 1 min on ice). The cell extracts were cleared by centrifugation (13000 rpm, 10 min) and used to assay AADH activity. The assay was done as follows: 200 ul of 0.2 mM NADH, 0.1 mM AcCoA in 100 mM tris-HCl pH 8.0 was placed in each well of a microtiter plate. $OD_{340}$ followed kinetically using SpectroMax. The value of $\Delta\varepsilon$ $(NADH\text{-}NAD^+)_{340}$ used in calculations was 6200 $M^{-1}$. The protein was measured using Pierce BCA assay kit (Life Technologies, Carlsbad, Calif.). The results of this experiment are shown in FIG. 16. The strongest performers in this screening experiment were AADH candidates A_12 and A_19 while candidates A_10, A_11 and A_16 have been expressed at levels similar or slightly below than that of the originally tested AADH from *S. enterica* (A_2). The ranking of AADH candidates based on measurements of enzymatic activity in yeast transformants generally correlated with the earlier data based on physiological evaluation of the transformed strains (rescue of anaerobic growth capacity and anaerobic ethanol production), however, ranking order was not exactly the same in the two types of evaluations. Using the combined data, AADH candidates A_12 (AADH from *Pseudomonas* M1), A_16 (*Shewanella benthica*) and A_19 (*Desulfospira joergensenii*) were identified as preferred AADH enzymes for practicing the current invention. AADH candidates A_10, A11, A_13, A_17, and A_20 although less efficient according to the screening data are nevertheless also suitable examples for the same purpose.

Example 5—Phosphoketolases Suitable for Enhanced Ethanol Production in Yeast

Genes encoding phosphoketolases (PKL) from a number of different microorganisms were back-translated using *S. cerevisiae* codon preferences and synthesized by GenScript (GenScript USA Inc. Piscataway, N.J.). Table 7 lists the source organisms, enzyme codes used in the screening experiments and SEQ ID numbers for protein and nucleotide sequences Each of the synthetic genes was placed between TDH3 promoter and ENO2 transcription terminator sequences of the vector pPATH1(TDH_A2) replacing the *Bifidobacerium animalis* PKL gene present in the original pPATH1 (TDH_A2). The resulting plasmids were named pPATH1 (TDH_P2_A2), pPATH1(TDH_P3_A2), pPATH1 (TDH_P5_A2) etc. Large SwaI fragment was excised from each of the new vectors and used to transform the yeast strain FGGZ.

Figure 17:
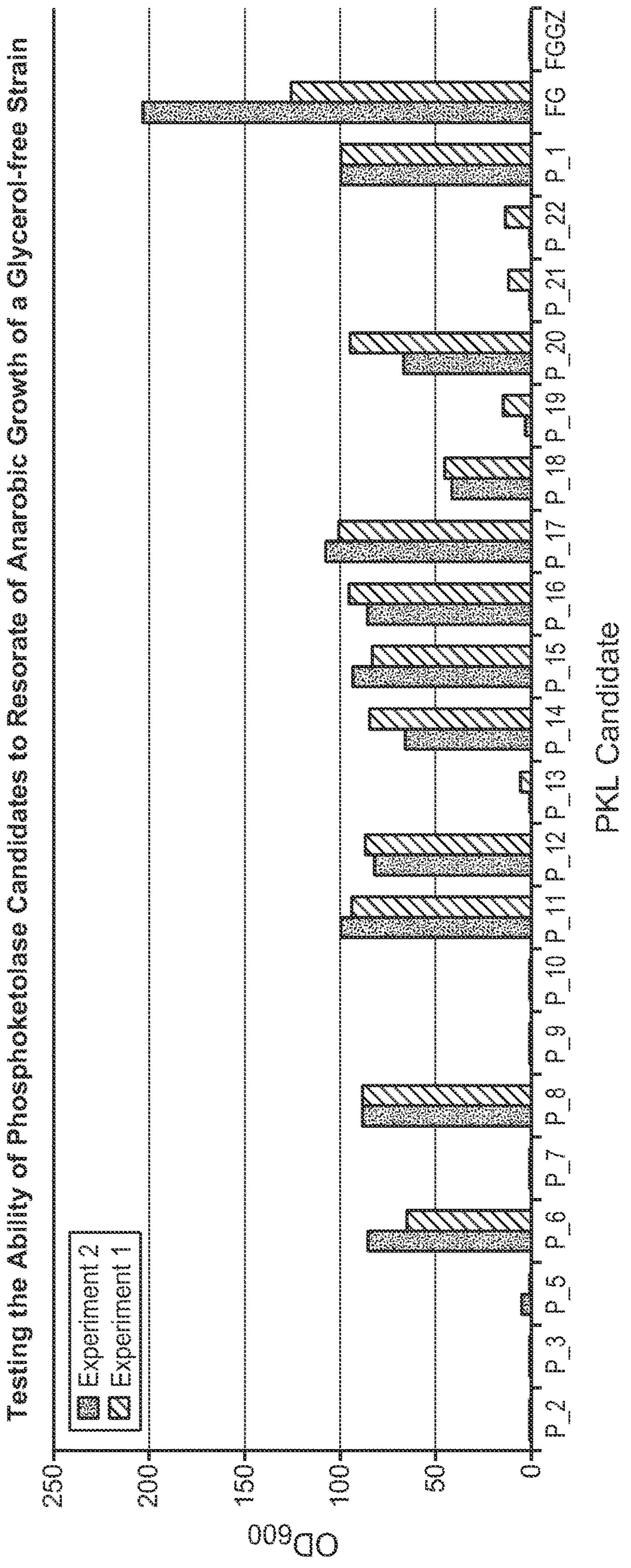
FIG. 17 depicts restoration of the ability of glycerol-free yeast strain FGGZ to grow anaerobically by transformation with recombinant DNA constructs carrying expression cassettes for acetaldehyde dehydrogenase, phosphotransacetylase and various PKL candidates.

The transformants were tested for the restoration of ability to grow anaerobically (FGGZ cannot grow anaerobically because the absence of glycerol production). Four randomly selected transformants of each type were used to inoculate a microtiter plate pre-filled with 250 μl per well of a medium containing 6% glucose, 0.2% urea and 0.67 g/l of Yeast Nitrogen Base without amino acids and ammonium sulfate to initial. The plate was incubated under strict anaerobic conditions with 600 rpm shaking at 32° C. for 48 hours. Final $OD_{600}$ values reached by the cultures were measured and averaged over the four candidate clones of each type. A total of two such experiments were done with well-reproducible results (see FIG. 17).

Figure 18:
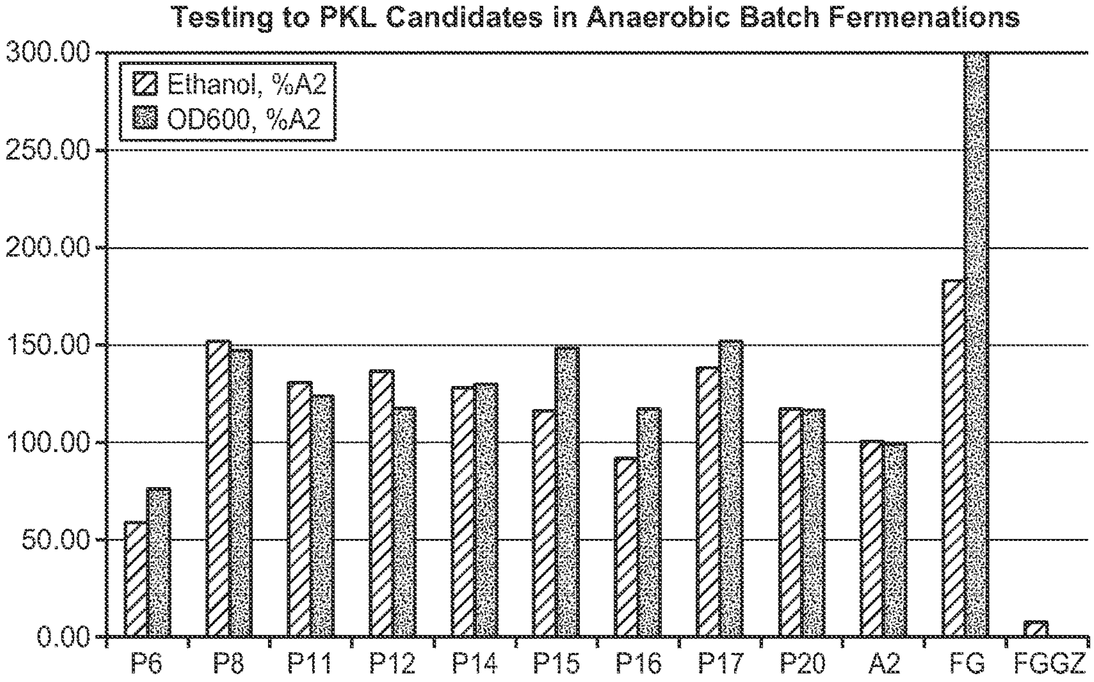
FIG. 18 depicts final OD600 and ethanol titers for transformants of strain FGGZ with recombinant DNA constructs carrying expression cassettes for acetaldehyde dehydrogenase, phosphotransacetylase and various PKL candidates (P_6, P_8, P_11, P_12, P_14, P_15, P_16, P_17, P_20; Table 8) as well as control strains (FGGZ transformed with pPATH1(TDH_A2), FGGZ and wild type FermaxGold, FG).

Clearly, the efficiency of different PKL candidates as components of the three enzyme PKL pathway varied greatly. Half of all the tested candidates failed to restore anaerobic growth ability of FGGZ. Nine preferred candidates from the first round of screening were further tested in batch cultivations. 6 ml aliquots of the same medium were inoculated to initial $OD_{600}$ of 0.2 (using overnight aerobic cultures as the source of inoculum). The tubes were placed (in vertical position) into a shaker located in an anaerobic hood. The cultures were shaken at 600 rpm and 32° C. for two days. Final $OD_{600}$ were measured and ethanol content was analyzed by HPLC. As can be seen from the data shown in FIG. 18, many candidates performed in these tests similarly or better than the original glycerol-free PKL pathway strain (for FGGZ transformed with pPATH1(TDH_A2). Thus, phosphoketolases from *Bifidobacterium asteroides* (P_6), *Clostridium butyricum* (P_8), *Eremococcus coleocola* (P_11), *Gardnerella vaginalis* (P_12), *Kingella kingae* (P_14), *Lactobacillus plantarum* (P_15), *Leuconostoc citreum* (P_16), *Metascardovia criceti* (P_17) and *Scardovia inopinata* (P_20) (see Table 8 for the SEQ ID numbers) were all found suitable for practicing the current invention. The PKL from *C. butyricum* (P_8), *E. coleocola* (P_11) and *G. vaginalis* (P_12) are especially preferable.

TABLE 8

Phosphoketolases evaluated for enhanced ethanol production in yeast.

| Phospho-ketolase | Source organism | DNA sequence SEQ ID No: | Protein sequence SEQ ID No |
|---|---|---|---|
| P_1 | *Bifidobacterium animalis* | SEQ ID No: 3 | SEQ ID No: 37 |
| P_2 | *Schizosaccharomyces pombe* | SEQ ID No: 38 | SEQ ID No: 39 |
| P_3 | *Aspergillus niger* | SEQ ID No: 40 | SEQ ID No: 41 |
| P_5 | *Acidithiobacillus ferrooxidans* | SEQ ID No: 42 | SEQ ID No: 43 |
| P_6 | *Bifidobacterium asteroids* | SEQ ID No: 44 | SEQ ID No: 45 |
| P_7 | *Bifidobacterium catenulatum* | SEQ ID No: 46 | SEQ ID No: 47 |
| P_8 | *Clostridium butyricum* | SEQ ID No: 48 | SEQ ID No: 49 |
| P_9 | *Cryptococcus neoformans* | SEQ ID No: 50 | SEQ ID No: 51 |
| P_10 | *Cyanothece* | SEQ ID No: 52 | SEQ ID No: 53 |
| P_11 | *Eremococcus coleocola* | SEQ ID No: 54 | SEQ ID No: 55 |
| P_12 | *Gardnerella vaginalis* | SEQ ID No: 56 | SEQ ID No: 57 |
| P_13 | *Glaciibacter superstes* | SEQ ID No: 58 | SEQ ID No: 59 |
| P_14 | *Kingella kingae* | SEQ ID No: 60 | SEQ ID No: 61 |
| P_15 | *Lactobacillus plantarum* | SEQ ID No: 62 | SEQ ID No: 63 |
| P_16 | *Leuconostoc citreum* | SEQ ID No: 64 | SEQ ID No: 65 |
| P_17 | *Metascardovia criceti* | SEQ ID No: 66 | SEQ ID No: 67 |
| P_18 | *Oenococcus oeni* | SEQ ID No: 68 | SEQ ID No: 69 |
| P_19 | *Rhodosporidium toruloides* | SEQ ID No: 70 | SEQ ID No: 71 |
| P_20 | *Scardovia inopinata* | SEQ ID No: 72 | SEQ ID No: 73 |
| P_21 | *Schizosaccharomyces japonicus* | SEQ ID No: 74 | SEQ ID No: 75 |
| P_22 | *Trichodermareesei* | SEQ ID No: 76 | SEQ ID No: 77 |

SEQ ID NO: 1

AAATAATAAAAAAAGTAACCCCACTTCTACTTCTACATCGGAAAAACATTCCATTCACATATCGTCTTTGGCCTATC

TTGTTTTGTCCTCGGTAGATCAGGTCAGTACAAACGCAACACGAAAGAACAAAAAAAGAAGAAAACAGAAGGCCAAG

ACAGGGTCAATGAGACTGTTGTCCTCCTACTGTCCCTATGTCTCTGGCCGATCACGCGCCATTGTCCCTCAGAAACA

AATCAAACACCCACACCCCGGGCACCCAAAGTCCCCACCCACACCACCAATAGAGTCTGCTGGTGTTGCTGATTTGA

TCACCACCTGCGCTGGTGGTAGAAACGTCAAGGTTGCTAGGCTAATGGCTACTTCTGGTAAGGACGCCTGGGAATGT

GAAAAGGAGTTGTTGAATGGCCAATCCGCTCAAGGTTTAATTACCTGCAAAGAAGTTCACGAATGGTTGGAAACATG

TGGCTCTGTCGAAGACTTCCCATTATTTGAAGCCGTATACCAAATCGTTTACAACAACTACCCAATGAAGAACCTGC

CGGACATGATTGAAGAATTAGATCTACATGAAGATTAGATTTATTGGAGAAAGATAAGCTTTTCAATTCATCATTTT

TTTTTTATTCTTTTTTTTGATTCCGGTTTCCTTGAAATTTTTTTGATTCGGTAATCTCCGAACAGAAGGAAGAACGA

AGGAAGGAGCACAGACTTAGATTGGTATATATACGCATATGTAGTGTTGAAGAAACATGAAATTGCCCAGTATTCTT

AACCCAACTGCACAGAACAAAAACCTGCAGGAAACGAAGATAAATCATGTCGAAAGCTACATATAAGGAACGTGCTG

CTACTCATCCTAGTCCTGTTGCTGCCAAGCTATTTAATATCATGCACGAAAAGCAAACAAACTTGTGTGCTTCATTG

GATGTTCGTACCACCAAGGAATTACTGGAGTTAGTTGAAGCATTAGGTCCCAAAATTTGTTTACTAAAAACACATGT

GGATATCTTGACTGATTTTTCCATGGAGGGCACAGTTAAGCCGCTAAAGGCATTATCCGCCAAGTACAATTTTTTAC

TCTTCGAAGACAGAAAATTTGCTGACATTGGTAATACAGTCAAATTGCAGTACTCTGCGGGTGTATACAGAATAGCA

GAATGGGCAGACATTACGAATGCACACGGTGTGGTGGGCCCAGGTATTGTTAGCGGTTTGAAGCAGGCGGCAGAAGA

AGTAACAAAGGAACCTAGAGGCCTTTTGATGTTAGCAGAATTGTCATGCAAGGGCTCCCTAGCTACTGGAGAATATA

CTAAGGGTACTGTTGACATTGCGAAGAGCGACAAAGATTTTGTTATCGGCTTTATTGCTCAAAGAGACATGGGTGGA

AGAGATGAAGGTTACGATTGGTTGATTATGACACCCGGTGTGGGTTTAGATGACAAGGGAGACGCATTGGGTCAACA

GTATAGAACCGTGGATGATGTGGTCTCTACAGGATCTGACATTATTATTGTTGGAAGAGGACTATTTGCAAAGGGAA

GGGATGCTAAGGTAGAGGGTGAACGTTACAGAAAAGCAGGCTGGGAAGCATATTTGAGAAGATGCGGCCAGCAAAAC

TAAAAAACTGTATTATAAGTAAATGCATGTATACTAAACTCACAAATTAGAGCTTCAATTTAATTATATCAGTTATT

-continued

ACCCGGGAATCTCGGTCGTAATGATTTTTATAATGACGAAAAAAAAAAAAAAAATTGGAAGAAGGCGCGCCCCCGAC

AATTTGGTTGCTAATCCAGACTTGATTGATTCAGTCAAGGATGTCGACATCATCGTTTTCAACATTCCACATCAATT

TTTGCCCCGTATCTGTAGCCAATTGAAAGGTCATGTTGATTCACACGTCAGAGCTATCTCCTGTCTAAAGGGTTTTG

AAGTTGGTGCTAAAGGTGTCCAATTGCTATCCTCTTACATCACTGAGGAACTAGGTATTCAATGTGGTGCTCTATCT

GGTGCTAACATTGCCACCGAAGTCGCTCAAGAACACTGGTCTGAAACAACAGTTGCTTACCACATTCCAAAGGATTT

AAATCCAAAAATGGCCATGAGACAATAACCCTGATAAATGCTTCAATAATATTGAAAAAGGAAGAGTATGAGTATTC

AACATTTCCGTGTCGCCCTTATTCCCTTTTTTGCGGCATTTTGCCTTCCTGTTTTTGCTCACCCAGAAACGCTGGTG

AAAGTAAAAGATGCTGAAGATCAGTTGGGTGCACGAGTGGGTTACATCGAACTGGATCTCAACAGCGGTAAGATCCT

TGAGAGTTTTCGCCCCGAAGAACGTTTTCCAATGATGAGCACTTTTAAAGTTCTGCTATGTGGCGCGGTATTATCCC

GTATTGACGCCGGGCAAGAGCAACTCGGTCGCCGCATACACTATTCTCAGAATGACTTGGTTGAGTACTCACCAGTC

ACAGAAAAGCATCTTACGGATGGCATGACAGTAAGAGAATTATGCAGTGCTGCCATAACCATGAGTGATAACACTGC

GGCCAACTTACTTCTGACAACGATCGGAGGACCGAAGGAGCTAACCGCTTTTTTGCACAACATGGGGGATCATGTAA

CTCGCCTTGATCGTTGGGAACCGGAGCTGAATGAAGCCATACCAAACGACGAGCGTGACACCACGATGCCTGTAGCA

ATGGCAACAACGTTGCGCAAACTATTAACTGGCGAACTACTTACTCTAGCTTCCCGGCAACAATTAATAGACTGGAT

GGAGGCGGATAAAGTTGCAGGACCACTTCTGCGCTCGGCCCTTCCGGCTGGCTGGTTTATTGCTGATAAATCTGGAG

CCGGTGAGCGTGGGTCTCGCGGTATCATTGCAGCACTGGGGCCAGATGGTAAGCCCTCCCGTATCGTAGTTATCTAC

ACGACGGGGAGTCAGGCAACTATGGATGAACGAAATAGACAGATCGCTGAGATAGGTGCCTCACTGATTAAGCATTG

GTAACTGTCAGACCAAGTTTACTCATATATACTTTAGATTGATTTAAAACTTCATTTTTAATTTAAAAGGATCTAGG

TGAAGATCCTTTTTGATAATCTCATGACCAAAATCCCTTAACGTGAGTTTTCGTTCCACTGAGCGTCAGACCCCGTA

GAAAAGATCAAAGGATCTTCTTGAGATCCTTTTTTTCTGCGCGTAATCTGCTGCTTGCAAACAAAAAAACCACCGCT

ACCAGCGGTGGTTTGTTTGCCGGATCAAGAGCTACCAACTCTTTTTCCGAAGGTAACTGGCTTCAGCAGAGCGCAGA

TACCAAATACTGTCCTTCTAGTGTAGCCGTAGTTAGGCCACCACTTCAAGAACTCTGTAGCACCGCCTACATACCTC

GCTCTGCTAATCCTGTTACCAGTGGCTGCTGCCAGTGGCGATAAGTCGTGTCTTACCGGGTTGGACTCAAGACGATA

GTTACCGGATAAGGCGCAGCGGTCGGGCTGAACGGGGGGTTCGTGCACACAGCCCAGCTTGGAGCGAACGACCTACA

CCGAACTGAGATACCTACAGCGTGAGCTATGAGAAAGCGCCACGCTTCCCGAAGGGAGAAAGGCGGACAGGTATCCG

GTAAGCGGCAGGGTCGGAACAGGAGAGCGCACGAGGGAGCTTCCAGGGGGAAACGCCTGGTATCTTTATAGTCCTGT

CGGGTTTCGCCACCTCTGACTTGAGCGTCGATTTTTGTGATGCTCGTCAGGGGGGCGGAGCCTATGGAAAAACGCCA

GCAACGCTGCATATTT

SEQ ID NO: 2

AAATAAAAACTGGAGCAAGGAATTACCATCACCGTCACCATCACCATCATATCGCCTTAGCCTCTAGCCATAGCCAT

CATGCAAGCGTGTATCTTCTAAGATTCAGTCATCATCATTACCGAGTTTGTTTTCCTTCACATGATGAAGAAGGTTT

GAGTATGCTCGAAACAATAAGACGACGATGGCTCTGCCATTGTTATATTACGCTTTTGCGGCGAGGTGCCGATGGGT

TGCTGAGGGGAAGAGTGTTTAGCTTACGGACCTATTGCCATTGTTATTCCGATTAACGTCAATGTCATCGATGATGT

TGCTGGTATATCCATTGCCGGTGCCTTGAAGAACGTCGTGGCACTTGCATGTGGTTTCGTAGAAGGTATGGGATGGG

GTAACAATGCCTCCGCAGCCATTCAAAGGCTGGGTTTAGGTGAAATTATCAAGTTCGGTAGAATGTTTTTCCCAGAA

TCCAAAGTCGAGACCTACTATCAAGAATCCGCTGGTGTTGCAGATCTGATCACCACCTGCTCAGGCGGTAGAAACGT

CAAGGTTGCCACATACATGGCCAAGACCGGTAAGTCAGCCTTGGAAGCTTTTCAATTCATCATTTTTTTTTTATTCT

TTTTTTTGATTCCGGTTTCCTTGAAATTTTTTTGATTCGGTAATCTCCGAACAGAAGGAAGAACGAAGGAAGGAGCA

CAGACTTAGATTGGTATATATACGCATATGTAGTGTTGAAGAAACATGAAATTGCCCAGTATTCTTAACCCAACTGC

ACAGAACAAAAACCTGCAGGAAACGAAGATAAATCATGTCGAAAGCTACATATAAGGAACGTGCTGCTACTCATCCT

AGTCCTGTTGCTGCCAAGCTATTTAATATCATGCACGAAAAGCAAACAAACTTGTGTGCTTCATTGGATGTTCGTAC

-continued

CACCAAGGAATTACTGGAGTTAGTTGAAGCATTAGGTCCCAAAATTTGTTTACTAAAAACACATGTGGATATCTTGA

CTGATTTTTCCATGGAGGGCACAGTTAAGCCGCTAAAGGCATTATCCGCCAAGTACAATTTTTTACTCTTCGAAGAC

AGAAAATTTGCTGACATTGGTAATACAGTCAAATTGCAGTACTCTGCGGGTGTATACAGAATAGCAGAATGGGCAGA

CATTACGAATGCACACGGTGTGGTGGGCCCAGGTATTGTTAGCGGTTTGAAGCAGGCGGCAGAAGAAGTAACAAAGG

AACCTAGAGGCCTTTTGATGTTAGCAGAATTGTCATGCAAGGGCTCCCTAGCTACTGGAGAATATACTAAGGGTACT

GTTGACATTGCGAAGAGCGACAAAGATTTTGTTATCGGCTTTATTGCTCAAAGAGACATGGGTGGAAGAGATGAAGG

TTACGATTGGTTGATTATGACACCCGGTGTGGGTTTAGATGACAAGGGAGACGCATTGGGTCAACAGTATAGAACCG

TGGATGATGTGGTCTCTACAGGATCTGACATTATTATTGTTGGAAGAGGACTATTTGCAAAGGGAAGGGATGCTAAG

GTAGAGGGTGAACGTTACAGAAAAGCAGGCTGGGAAGCATATTTGAGAAGATGCGGCCAGCAAAACTAAAAAACTGT

ATTATAAGTAAATGCATGTATACTAAACTCACAAATTAGAGCTTCAATTTAATTATATCAGTTATTACCCGGGAATC

TCGGTCGTAATGATTTTTATAATGACGAAAAAAAAAAAATTGGAAAGAAAAAGGCGCGCCCCTTGTTTTCAACATCC

CTCATCAATTTTTACCAAACATAGTCAAACAATTGCAAGGCCACGTGGCCCCTCATGTAAGGGCCATCTCGTGTCTA

AAAGGGTTCGAGTTGGGCTCCAAGGGTGTGCAATTGCTATCCTCCTATGTTACTGATGAGTTAGGAATCCAATGTGG

CGCACTATCTGGTGCAAACTTGGCACCGGAAGTGGCCAAGGAGCATTGGTCCGAAACCACCGTGGCTTACCAACTAC

CAAAGGATTATCAAGGTGATGGCAAGGATGTAGATCATAAGATTTAAATCCAAAAATGGCCATGAGACAATAACCCT

GATAAATGCTTCAATAATATTGAAAAAGGAAGAGTATGAGTATTCAACATTTCCGTGTCGCCCTTATTCCCTTTTTT

GCGGCATTTTGCCTTCCTGTTTTTGCTCACCCAGAAACGCTGGTGAAAGTAAAAGATGCTGAAGATCAGTTGGGTGC

ACGAGTGGGTTACATCGAACTGGATCTCAACAGCGGTAAGATCCTTGAGAGTTTTCGCCCCGAAGAACGTTTTCCAA

TGATGAGCACTTTTAAAGTTCTGCTATGTGGCGCGGTATTATCCCGTATTGACGCCGGGCAAGAGCAACTCGGTCGC

CGCATACACTATTCTCAGAATGACTTGGTTGAGTACTCACCAGTCACAGAAAAGCATCTTACGGATGGCATGACAGT

AAGAGAATTATGCAGTGCTGCCATAACCATGAGTGATAACACTGCGGCCAACTTACTTCTGACAACGATCGGAGGAC

CGAAGGAGCTAACCGCTTTTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTTGCGCAAACTATTAACTGG

CGAACTACTTACTCTAGCTTCCCGGCAACAATTAATAGACTGGATGGAGGCGGATAAAGTTGCAGGACCACTTCTGC

GCTCGGCCCTTCCGGCTGGCTGGTTTATTGCTGATAAATCTGGAGCCGGTGAGCGTGGGTCTCGCGGTATCATTGCA

GCACTGGGGCCAGATGGTAAGCCCTCCCGTATCGTAGTTATCTACACGACGGGGAGTCAGGCAACTATGGATGAACG

AAATAGACAGATCGCTGAGATAGGTGCCTCACTGATTAAGCATTGGTAACTGTCAGACCAAGTTTACTCATATATAC

TTTAGATTGATTTAAAACTTCATTTTTAATTTAAAAGGATCTAGGTGAAGATCCTTTTTGATAATCTCATGACCAAA

ATCCCTTAACGTGAGTTTTCGTTCCACTGAGCGTCAGACCCCGTAGAAAAGATCAAAGGATCTTCTTGAGATCCTTT

TTTTCTGCGCGTAATCTGCTGCTTGCAAACAAAAAAACCACCGCTACCAGCGGTGGTTTGTTTGCCGGATCAAGAGC

TACCAACTCTTTTTCCGAAGGTAACTGGCTTCAGCAGAGCGCAGATACCAAATACTGTCCTTCTAGTGTAGCCGTAG

TTAGGCCACCACTTCAAGAACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGGCGCAGCGGTCGGGCTGAA

CGGGGGGTTCGTGCACACAGCCCAGCTTGGAGCGAACGACCTACACCGAACTGAGATACCTACAGCGTGAGCTATGA

GAAAGCGCCACGCTTCCCGAAGGGAGAAAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGTTTCGCCACCTCTGACTTGAGCGTCGAT

TTTTGTGATGCTCGTCAGGGGGGCGGAGCCTATGGAAAAACGCCAGCAACGCTGCATATTT

SEQ ID NO: 3

ATGACCAACCCAGTCATTGGTACTCCATGGCAAAAATTGGATAGACCAGTTTCCGAAGAAGCCATTGAAGGTATGGA

TAAGTATTGGAGAGTTGCCAACTACATGTCCATTGGTCAAATCTACTTGAGATCCAACCCATTGATGAAGGAACCAT

TCACTAGAGATGATGTCAAGCACAGATTGGTTGGTCATTGGGGTACTACTCCAGGTTTGAATTTTTTGTTGGCCCAC

-continued

ATCAACAGATTGATCGCTGATCATCAACAAAACACCGTTTTCATTATGGGTCCAGGTCATGGTGGTCCAGCTGGTAC

TGCTCAATCTTATATTGATGGTACTTACACCGAATATTACCCAAACATCACTAAGGATGAAGCCGGTTTACAAAAGT

TCTTCAGACAATTTTCTTACCCAGGTGGTATCCCATCTCATTTTGCTCCAGAAACTCCAGGTTCTATTCATGAAGGT

GGTGAATTGGGTTATGCTTTGTCTCATGCTTATGGTGCCATTATGGATAACCCATCTTTGTTCGTTCCATGCATTAT

TGGTGATGGTGAAGCTGAAACTGGTCCATTGGCTACTGGTTGGCAATCTAACAAATTGGTTAACCCAAGAACCGATG

GTATCGTTTTGCCAATCTTGCATTTGAACGGTTACAAGATTGCTAACCCAACCATTTTGGCCAGAATCTCTGATGAA

GAATTGCACGATTTTTTCAGAGGTATGGGTTACCACCCATACGAATTTGTTGCTGGTTTTGATAACGAAGATCACTT

GTCCATCCATAGAAGATTCGCCGAATTATTCGAAACCATCTTCGACGAAATTTGCGATATTAAGGCTGCTGCTCAAA

CTGATGATATGACTAGACCATTTTACCCAATGTTGATCTTCAGAACTCCAAAGGGTTGGACTTGTCCAAAGTTTATC

GATGGTAAAAAGACCGAAGGTTCTTGGAGAGCACATCAAGTTCCATTGGCTTCAGCTAGAGATACTGAAGCTCATTT

CGAAGTTTTGAAGGGTTGGATGGAATCTTACAAGCCTGAAGAATTATTCAACGCCGACGGTTCTATCAAAGAAGATG

TTACTGCTTTTATGCCAAAGGGTGAATTGAGAATTGGTGCTAATCCAAATGCTAACGGTGGTAGAATTAGAGAAGAT

TTGAAGTTGCCAGAATTGGACCAATACGAAATTACCGGTGTCAAAGAATATGGTCATGGTTGGGGTCAAGTTGAAGC

TCCAAGATCTTTGGGTGCTTACTGTAGAGATATCATCAAGAACAACCCAGACTCCTTTAGAGTTTTTGGTCCAGACG

AAACTGCTTCCAATAGATTGAATGCTACTTACGAAGTCACCAAAAAGCAATGGGATAACGGTTATTTGTCTGCCTTG

GTTGACGAAAACATGGCTGTTACTGGTCAAGTTGTTGAACAATTGTCTGAACATCAATGCGAAGGTTTTTTGGAAGC

CTATTTGTTGACTGGTAGACATGGTATTTGGTCCTCTTACGAATCTTTCGTTCACGTTATCGATTCCATGTTGAATC

AACACGCTAAATGGTTGGAAGCTACCGTTAGAGAAATTCCTTGGAGAAAGCCAATCTCCTCTGTTAACTTGTTGGTT

TCTTCACACGTTTGGAGACAAGATCATAACGGTTTCTCTCATCAAGATCCAGGTGTTACTTCTGTCTTGTTGAACAA

AACCTTCAACAACGATCACGTCACCAATATCTACTTTGCTACTGATGCTAACATGTTGTTGGCTATTGCTGAAAAGT

GTTTCAAGTCCACCAACAAGATTAACGCTATTTTCGCTGGTAAACAACCAGCTGCTACTTGGATTACTTTGGATGAA

GTTAGAGCTGAATTGGAAGCTGGTGCTGCTGAATGGAAATGGGCTTCTAATGCTAAGTCTAACGATGAAGTTCAAGT

TGTTTTGGCTGCTGCTGGTGATGTTCCAACTCAAGAAATTATGGCTGCTTCTGATGCTTTGAACAAGATGGGTATTA

AGTTCAAGGTTGTCAACGTCGTTGATTTGATCAAGTTGCAATCCTCCAAAGAAAACGATGAAGCCATGTCTGATGAA

GATTTCGCTGATTTGTTTACCGCTGATAAGCCAGTTTTGTTCGCTTATCATTCTTACGCCCAAGATGTCAGAGGTTT

GATATACGATAGACCAAACCATGATAACTTCACCGTTGTCGGTTACAAAGAACAAGGTTCTACTACTACTCCATTCG

ATATGGTTAGAGTTAACGACATGGATAGATACGCATTGCAAGCTAAGGCTTTGGAATTGATTGATGCTGATAAGTAC

GCCGACAAGATCAACGAATTGAACGAATTTAGAAAGACCGCTTTCCAATTCGCTGTTGATAACGGTTACGATATCCC

AGAATTTACCGATTGGGTTTACCCAGATGTTAAGGTTGACGAAACTTCTATGTTGTCTGCTACTGCTGCTACAGCTG

GTGATAATGAATAA

SEQ ID NO: 4

ATGGACTTGTTCGAATCTTTGGCCCAAAAGATTACTGGTAAGGATCAAACTATCGTTTTCCCAGAAGGTACTGAACC

TAGAATAGTTGGTGCTGCTGCTAGATTGGCTGCTGATGGTTTGGTTAAGCCAATAGTTTTGGGTGCTACTGATAAGG

TTCAAGCTGTTGCTAATGATTTGAACGCTGATTTGACTGGTGTTCAAGTTTTGGATCCAGCTACTTATCCAGCTGAA

GATAAGCAAGCTATGTTGGATGCTTTGGTCGAAAGAAGAAAGGGTAAGAATACTCCAGAACAAGCTGCTAAGATGTT

GGAAGATGAAAACTACTTCGGTACTATGTTGGTCTACATGGGTAAAGCAGATGGTATGGTTTCTGGTGCTATTCATC

CAACTGGTGATACTGTTAGACCAGCCTTGCAAATTATCAAAACTAAGCCAGGTTCCCACAGAATTTCAGGTGCTTTC

ATTATGCAAAAGGGTGAAGAAAGATACGTTTTCGCTGATTGCGCCATTAACATTGATCCAGATGCTGATACTTTGGC

TGAAATTGCTACTCAATCTGCTGCTACTGCTAAAGTTTTCGATATTGATCCAAAGGTCGCCATGTTGTCTTTTTCAA

CAAAAGGTTCTGCTAAGGGTGAAATGGTTACTAAGGTACAAGAAGCTACAGCTAAAGCTCAAGCTGCTGAACCAGAA

TTGGCTATTGATGGTGAATTACAATTCGATGCTGCCTTCGTTGAAAAGGTCGGTTTACAAAAAGCTCCAGGTTCTAA

-continued

AGTTGCTGGTCATGCTAATGTTTTTGTTTTTCCAGAATTGCAATCCGGTAACATCGGTTACAAAATCGCTCAAAGAT

TTGGTCATTTCGAAGCTGTTGGTCCAGTTTTACAAGGTTTGAACAAACCAGTTTCCGACTTGTCTAGAGGTTGTTCT

GAAGAAGATGTTTACAAAGTTGCCATTATTACCGCTGCTCAAGGTTTGGCTTAG

SEQ ID NO: 5

ATGAACCAACAAGACATAGAACAAGTAGTAAAAGCCGTATTATTAAAGATGAAAGACTCCTCTCAACCAGCCTCAAC

CGTACACGAAATGGGTGTTTTTGCCTCTTTGGATGACGCTGTCGCTGCAGCCAAAAGAGCCCAACAAGGTTTGAAGT

CAGTTGCTATGAGACAATTAGCAATCCATGCCATTAGAGAAGCAGGTGAAAAACACGCCAGAGAATTGGCTGAATTA

GCAGTATCCGAAACTGGTATGGGTAGAGTTGATGACAAATTCGCTAAGAATGTCGCTCAAGCAAGAGGTACACCAGG

TGTCGAATGTTTGAGTCCTCAAGTATTAACAGGTGACAATGGTTTGACCTTAATTGAAAACGCCCCATGGGGTGTTG

TCGCTTCTGTTACACCATCAACCAATCCTGCTGCAACTGTTATAAATAACGCAATCTCTTTGATCGCCGCTGGTAAC

TCAGTAGTTTTTGCTCCACATCCTGCAGCCAAAAAGGTTTCCCAAAGAGCAATTACATTGTTAAATCAAGCCGTCGT

AGCTGCAGGTGGTCCAGAAAATTTGTTAGTAACCGTTGCTAACCCTGATATCGAAACTGCACAAAGATTATTCAAGT

ATCCAGGTATCGGTTTGTTAGTTGTCACAGGTGGTGAAGCTGTAGTTGATGCCGCTAGAAAACACACCAATAAGAGA

TTGATTGCAGCCGGTGCAGGTAACCCACCTGTCGTAGTTGATGAAACTGCTGACTTACCAAGAGCTGCACAATCCAT

CGTTAAGGGTGCAAGTTTCGATAACAACATCATCTGCGCTGACGAAAAGGTTTTAATTGTCGTAGATTCTGTCGCTG

ACGAATTGATGAGATTAATGGAAGGTCAACATGCAGTTAAATTGACAGCCGCTCAAGCCGAACAATTGCAACCAGTT

TTGTTGAAAAATATAGATGAACGTGGTAAAGGTACCGTATCAAGAGATTGGGTTGGTAGAGACGCAGGTAAAATTGC

AGCCGCTATAGGTTTGAACGTTCCTGATCAAACTAGATTGTTGTTCGTTGAAACACCAGCTAACCATCCTTTCGCAG

TAACAGAAATGATGATGCCAGTTTTACCTGTTGTCAGAGTTGCTAATGTCGAAGAAGCCATAGCTTTGGCAGTTCAA

TTAGAAGGTGGTTGTCATCACACCGCAGCCATGCACTCCAGAAATATCGATAATATGAACCAAATGGCCAACGCTAT

CGACACTTCTATTTTCGTTAAAAACGGTCCATGCATTGCTGGTTTGGGTTTAGGTGGTGAAGGTTGGACTACAATGA

CCATAACCACTCCTACTGGTGAAGGTGTCACTTCTGCAAGAACATTTGTAAGATTGAGAAGATGTGTCTTAGTAGAT

GCTTTCAGAATTGTTTAG

SEQ ID NO: 6

AAATCCACTATCGTCTATCAACTAATAGTTATATTATCAATATATTATCATATACGGTGTTAAGATGATGACATAAG

TTATGAGAAGCTGTCATCGAGGTTAGAGGCCTTAATGGCCGTCGACATATTTGACCTCTTAACAGGTTCAGACGCGA

CTGCCTCATCAGTAAGACCCGTTGAAAAGAACTTACCTGAAAAAAACGAATATATACTAGCGTTGAATGTTAGCGTC

AACAACAAGAAGTTTAATGACGCGGAGGCCAAGGCAAAAAGATTCCTTGATTACGTAAGGGAGTTAGAATCATTTTG

AATAAAAAACACGCTTTTTCAGTTCGAGTTTATCATTATCAATACTGCCATTTCAAAGAATACGTAAATAATTAATA

GTAGTGATTTTCCTAACTTTATTTAGTCAAAAAATTAGCCTTTTAATTCTGCTGTAACCCGTACATGCCCAAAATAG

GGGGCGGGTTACACAGAATATATAACATCGTAGGTGTCTGGGTGAACAGTTTATTCCTGGCATCCACTAAATATAAT

GGAGCCCGCTTTTTAAGCTGGCATCCAGAAAAAAAAAGAATCCCAGCACCAAAATATTGTTTTCTTCACCAACCATC

AGTTCATAGGTCCATTCTCTTAGCGCAACTACAGAGAACAGGGGCACAAACAGGCAAAAAACGGGCACAACCTCAAT

GGAGTGATGCAACCTGCCTGGAGTAAATGATGACACAAGGCAATTGACCCACGCATGTATCTATCTCATTTTCTTAC

ACCTTCTATTACCTTCTGCTCTCTCTGATTTGGAAAAAGCTGAAAAAAAAGGTTGAAACCAGTTCCCTGAAATTATT

CCCCTACTTGACTAATAAGTATATAAAGACGGTAGGTATTGATTGTAATTCTGTAAATCTATTTCTTAAACTTCTTA

AATTCTACTTTTATAGTTAGTCTTTTTTTTAGTTTTAAAACACCAAGAACTTAGTTTCGAATAAACACACATAAACA

AACTAGTAAGAATTCAAACAACAAAAATGACCAACCCAGTCATTGGTACTCCATGGCAAAAATTGGATAGACCAGTT

TCCGAAGAAGCCATTGAAGGTATGGATAAGTATTGGAGAGTTGCCAACTACATGTCCATTGGTCAAATCTACTTGAG

ATCCAACCCATTGATGAAGGAACCATTCACTAGAGATGATGTCAAGCACAGATTGGTTGGTCATTGGGGTACTACTC

CAGGTTTGAATTTTTTGTTGGCCCACATCAACAGATTGATCGCTGATCATCAACAAAACACCGTTTTCATTATGGGT

-continued

CCAGGTCATGGTGGTCCAGCTGGTACTGCTCAATCTTATATTGATGGTACTTACACCGAATATTACCCAAACATCAC

TAAGGATGAAGCCGGTTTACAAAAGTTCTTCAGACAATTTTCTTACCCAGGTGGTATCCCATCTCATTTTGCTCCAG

AAACTCCAGGTTCTATTCATGAAGGTGGTGAATTGGGTTATGCTTTGTCTCATGCTTATGGTGCCATTATGGATAAC

CCATCTTTGTTCGTTCCATGCATTATTGGTGATGGTGAAGCTGAAACTGGTCCATTGGCTACTGGTTGGCAATCTAA

CAAATTGGTTAACCCAAGAACCGATGGTATCGTTTTGCCAATCTTGCATTTGAACGGTTACAAGATTGCTAACCCAA

CCATTTTGGCCAGAATCTCTGATGAAGAATTGCACGATTTTTTCAGAGGTATGGGTTACCACCCATACGAATTTGTT

GCTGGTTTTGATAACGAAGATCACTTGTCCATCCATAGAAGATTCGCCGAATTATTCGAAACCATCTTCGACGAAAT

TTGCGATATTAAGGCTGCTGCTCAAACTGATGATATGACTAGACCATTTTACCCAATGTTGATCTTCAGAACTCCAA

AGGGTTGGACTTGTCCAAAGTTTATCGATGGTAAAAAGACCGAAGGTTCTTGGAGAGCACATCAAGTTCCATTGGCT

TCAGCTAGAGATACTGAAGCTCATTTCGAAGTTTTGAAGGGTTGGATGGAATCTTACAAGCCTGAAGAATTATTCAA

CGCCGACGGTTCTATCAAAGAAGATGTTACTGCTTTTATGCCAAAGGGTGAATTGAGAATTGGTGCTAATCCAAATG

CTAACGGTGGTAGAATTAGAGAAGATTTGAAGTTGCCAGAATTGGACCAATACGAAATTACCGGTGTCAAAGAATAT

GGTCATGGTTGGGGTCAAGTTGAAGCTCCAAGATCTTTGGGTGCTTACTGTAGAGATATCATCAAGAACAACCCAGA

CTCCTTTAGAGTTTTTGGTCCAGACGAAACTGCTTCCAATAGATTGAATGCTACTTACGAAGTCACCAAAAAGCAAT

GGGATAACGGTTATTTGTCTGCCTTGGTTGACGAAAACATGGCTGTTACTGGTCAAGTTGTTGAACAATTGTCTGAA

CATCAATGCGAAGGTTTTTTGGAAGCCTATTTGTTGACTGGTAGACATGGTATTTGGTCCTCTTACGAATCTTTCGT

TCACGTTATCGATTCCATGTTGAATCAACACGCTAAATGGTTGGAAGCTACCGTTAGAGAAATTCCTTGGAGAAAGC

CAATCTCCTCTGTTAACTTGTTGGTTTCTTCACACGTTTGGAGACAAGATCATAACGGTTTCTCTCATCAAGATCCA

GGTGTTACTTCTGTCTTGTTGAACAAAACCTTCAACAACGATCACGTCACCAATATCTACTTTGCTACTGATGCTAA

CATGTTGTTGGCTATTGCTGAAAAGTGTTTCAAGTCCACCAACAAGATTAACGCTATTTTCGCTGGTAAACAACCAG

CTGCTACTTGGATTACTTTGGATGAAGTTAGAGCTGAATTGGAAGCTGGTGCTGCTGAATGGAAATGGGCTTCTAAT

GCTAAGTCTAACGATGAAGTTCAAGTTGTTTTGGCTGCTGCTGGTGATGTTCCAACTCAAGAAATTATGGCTGCTTC

TGATGCTTTGAACAAGATGGGTATTAAGTTCAAGGTTGTCAACGTCGTTGATTTGATCAAGTTGCAATCCTCCAAAG

AAAACGATGAAGCCATGTCTGATGAAGATTTCGCTGATTTGTTTACCGCTGATAAGCCAGTTTTGTTCGCTTATCAT

TCTTACGCCCAAGATGTCAGAGGTTTGATATACGATAGACCAAACCATGATAACTTCACCGTTGTCGGTTACAAAGA

ACAAGGTTCTACTACTACTCCATTCGATATGGTTAGAGTTAACGACATGGATAGATACGCATTGCAAGCTAAGGCTT

TGGAATTGATTGATGCTGATAAGTACGCCGACAAGATCAACGAATTGAACGAATTTAGAAAGACCGCTTTCCAATTC

GCTGTTGATAACGGTTACGATATCCCAGAATTTACCGATTGGGTTTACCCAGATGTTAAGGTTGACGAAACTTCTAT

GTTGTCTGCTACTGCTGCTACAGCTGGTGATAATGAATAAGGATCCTGATAAGCGGCCGCCGGTGAAAACTTCCACC

ACGGTGACAAGTTGTAAAGTGCTTTTAACTAAGAATTATTAGTCTTTTCTGCTTATTTTTTCATCATAGTTTAGAAC

ACTTTATATTAACGAATAGTTTATGAATCTATTTAGGTTTAAAAATTGATACAGTTTTATAAGTTACTTTTTCAAAG

ACTCGTGCTGTCTATTGCATAATGCACTGGAAGGGGAAAAAAAAGGTGCACACGCGTGGCTTTTTCTTGAATTTGCA

GTTTGAAAAATAACTACATGGATGATAAGAAAACATGGAGTACAGTCACTTTGAGAACCTTCAATCAGCTGGTAACG

TCTTCGTTAATTGGATACTCAAAAAAGATGGATAGCATGAATCACAAGATGGAAGGAAATGCGGGCCACGACCACAG

TGATATGCATATGGGAGATGCTCGACTTCAACTCAAGACGCACAGATATTATAACATCTGCATAATAGGCATTTGCA

AGAATTACTCGTGAGTAAGGAAAGAGTGAGGAACTATCGCATACCTGCATTTAAAGATGCCGATTTGGGCGCGAATC

CTTTATTTTGGCTTCACCCTCATACTATTATCAGGGCCAGAAAAAGGAAGTGTTTCCCTCCTTCTTGAATTGATGTT

ACCCTCATAAAGCACGTGGCCTCTTATCGAGAAAGAAATTACCGTCGCTCGTGATTTGTTTGCAAAAAGAACAAAAC

TGAAAAAACCCAGACACGCTCGACTTCCTGTCTTCCTATTGATTGCAGCTTCCAATTTCGTCACACAACAAGGTCCT

AGCGACGGCTCACAGGTTTTGTAACAAGCAATCGAAGGTTCTGGAATGGCGGGAAAGGGTTTAGTACCACATGCTAT

GATGCCCACTGTGATCTCCAGAGCAAAGTTCGTTCGATCGTACTGTTACTCTCTCTCTTTCAACAGAATTGTCCGA

-continued

ATCGTGTGACAACAACAGCCTGTTCTCACACACTCTTTTCTTCTAACCAAGGGGGTGGTTTAGTTTAGTAGAACCTC

GTGAAACTTACATTTACATATATATAAACTTGCATAAATTGGTCAATGCAAGAAATACATATTTGGTCTTTTCTAAT

TCGTAGTTTTTCAAGTTCTTAGATGCTTTCTTTTTCTCTTTTTTACAGATCATCAAGGAAGTAATTATCTACTTTTT

ACAACTAGTAAAAATGGACTTGTTCGAATCTTTGGCCCAAAAGATTACTGGTAAGGATCAAACTATCGTTTTCCCAG

AAGGTACTGAACCTAGAATAGTTGGTGCTGCTGCTAGATTGGCTGCTGATGGTTTGGTTAAGCCAATAGTTTTGGGT

GCTACTGATAAGGTTCAAGCTGTTGCTAATGATTTGAACGCTGATTTGACTGGTGTTCAAGTTTTGGATCCAGCTAC

TTATCCAGCTGAAGATAAGCAAGCTATGTTGGATGCTTTGGTCGAAAGAAGAAAGGGTAAGAATACTCCAGAACAAG

CTGCTAAGATGTTGGAAGATGAAAACTACTTCGGTACTATGTTGGTCTACATGGGTAAAGCAGATGGTATGGTTTCT

GGTGCTATTCATCCAACTGGTGATACTGTTAGACCAGCCTTGCAAATTATCAAAACTAAGCCAGGTTCCCACAGAAT

TTCAGGTGCTTTCATTATGCAAAAGGGTGAAGAAAGATACGTTTTCGCTGATTGCGCCATTAACATTGATCCAGATG

CTGATACTTTGGCTGAAATTGCTACTCAATCTGCTGCTACTGCTAAAGTTTTCGATATTGATCCAAAGGTCGCCATG

TTGTCTTTTTCAACAAAAGGTTCTGCTAAGGGTGAAATGGTTACTAAGGTACAAGAAGCTACAGCTAAAGCTCAAGC

TGCTGAACCAGAATTGGCTATTGATGGTGAATTACAATTCGATGCTGCCTTCGTTGAAAAGGTCGGTTTACAAAAAG

CTCCAGGTTCTAAAGTTGCTGGTCATGCTAATGTTTTTGTTTTTCCAGAATTGCAATCCGGTAACATCGGTTACAAA

ATCGCTCAAAGATTTGGTCATTTCGAAGCTGTTGGTCCAGTTTTACAAGGTTTGAACAAACCAGTTTCCGACTTGTC

TAGAGGTTGTTCTGAAGAAGATGTTTACAAAGTTGCCATTATTACCGCTGCTCAAGGTTTGGCTTAGGATCCAAGCG

GCCGCCAGGTGTTGCTTTCTTATCCGAAAAGAAATAAATTGAATTGAATTGAAATCGATAGATCAATTTTTTTCTTT

TCTCTTTCCCCATCCTTTACGCTAAAATAATAGTTTATTTTATTTTTTGAATATTTTTTATTTATATACGTATATAT

AGACTATTATTTATCTTTTAATGATTATTAAGATTTTTATTAAAAAAAAATTCGCTCCTCTTTTAATGCCTTTATGC

AGTTTTTTTTTCCCATTCGATATTTCTATGTTCGGGTTCAGCGTATTTTAAGTTTAATAACTCGACGCCTACTTGGC

TTCACATACGTTGCATACGTCGATATAGATAATAATGATAATGACAGCAGGATTATCGTAATACGTAATAGTTGAAA

ATCTCAAAAATGTGTGGGTCATTACGTAAATAATGATAGGAATGGGATTCTTCTATTTTTCCTTTTTCCATTCTAGC

AGCCGTCGGGAAAACGTGGCATCCTCTCTTTCGGGCTCAATTGGAGTCACGCTGCCGTGAGCATCCTCTCTTTCCAT

ATCTAACAACTGAGCACGTAACCAATGGAAAAGCATGAGCTTAGCGTTGCTCCAAAAAAGTATTGGATGGTTAATAC

CATTTGTCTGTTCTCTTCTGACTTTGACTCCTCAAAAAAAAAAAAATCTACAATCAACAGATCGCTTCAATTACGCCC

TCACAAAAACTTTTTTCCTTCTTCTTCGCCCACGTTAAATTTTATCCCTCATGTTGTCTAACGGATTTCTGCACTTG

ATTTATTATAAAAAGACAAAGACATAATACTTCTCTATCAATTTCAGTTATTGTTCTTCCTTGCGTTATTCTTCTGT

TCTTCTTTTTCTTTTGTCATATATAACCATAACCAAGTAATACATATTCAAACTAGTAAGAATTCAAAACAAAAATG

AACCAACAAGACATAGAACAAGTAGTAAAAGCCGTATTATTAAAGATGAAAGACTCCTCTCAACCAGCCTCAACCGT

ACACGAAATGGGTGTTTTTGCCTCTTTGGATGACGCTGTCGCTGCAGCCAAAAGAGCCCAACAAGGTTTGAAGTCAG

TTGCTATGAGACAATTAGCAATCCATGCCATTAGAGAAGCAGGTGAAAAACACGCCAGAGAATTGGCTGAATTAGCA

GTATCCGAAACTGGTATGGGTAGAGTTGATGACAAATTCGCTAAGAATGTCGCTCAAGCAAGAGGTACACCAGGTGT

CGAATGTTTGAGTCCTCAAGTATTAACAGGTGACAATGGTTTGACCTTAATTGAAAACGCCCCATGGGGTGTTGTCG

CTTCTGTTACACCATCAACCAATCCTGCTGCAACTGTTATAAATAACGCAATCTCTTTGATCGCCGCTGGTAACTCA

GTAGTTTTTGCTCCACATCCTGCAGCCAAAAAGGTTTCCCAAAGAGCAATTACATTGTTAAATCAAGCCGTCGTAGC

TGCAGGTGGTCCAGAAAATTTGTTAGTAACCGTTGCTAACCCTGATATCGAAACTGCACAAAGATTATTCAAGTATC

CAGGTATCGGTTTGTTAGTTGTCACAGGTGGTGAAGCTGTAGTTGATGCCGCTAGAAAACACACCAATAAGAGATTG

ATTGCAGCCGGTGCAGGTAACCCACCTGTCGTAGTTGATGAAACTGCTGACTTACCAAGAGCTGCACAATCCATCGT

TAAGGGTGCAAGTTTCGATAACAACATCATCTGCGCTGACGAAAAGGTTTTAATTGTCGTAGATTCTGTCGCTGACG

AATTGATGAGATTAATGGAAGGTCAACATGCAGTTAAATTGACAGCCGCTCAAGCCGAACAATTGCAACCAGTTTTG

-continued

TTGAAAAATATAGATGAACGTGGTAAAGGTACCGTATCAAGAGATTGGGTTGGTAGAGACGCAGGTAAAATTGCAGC

CGCTATAGGTTTGAACGTTCCTGATCAAACTAGATTGTTGTTCGTTGAAACACCAGCTAACCATCCTTTCGCAGTAA

CAGAAATGATGATGCCAGTTTTACCTGTTGTCAGAGTTGCTAATGTCGAAGAAGCCATAGCTTTGGCAGTTCAATTA

GAAGGTGGTTGTCATCACACCGCAGCCATGCACTCCAGAAATATCGATAATATGAACCAAATGGCCAACGCTATCGA

CACTTCTATTTTCGTTAAAAACGGTCCATGCATTGCTGGTTTGGGTTTAGGTGGTGAAGGTTGGACTACAATGACCA

TAACCACTCCTACTGGTGAAGGTGTCACTTCTGCAAGAACATTTGTAAGATTGAGAAGATGTGTCTTAGTAGATGCT

TTCAGAATTGTTTAGGATCCTGATAAGCGGCCGCGTTAATTCAAATTAATTGATATAGTTTTTTAATGAGTATTGAA

TCTGTTTAGAAATAATGGAATATTATTTTTATTTATTTATTTATATTATTGGTCGGCTCTTTTCTTCTGAAGGTCAA

TGACAAAATGATATGAAGGAAATAATGATTTCTAAAATTTTACAACGTAAGATATTTTTACAAAAGCCTAGCTCATC

TTTTGTCATGCACTATTTTACTCACGCTTGAAATTAACGGCCAGTCCACTGCGGAGTCATTTCAAAGTCATCCTAAT

CGATCTATCGTTTTTGATAGCTCATTTTGGAGTTCGCGATTGTCTTCTGTTATTCACAACTGTTTTAATTTTTATTT

CATTCTGGAACTCTTCGAGTTCTTTGTAAAGTCTTTCATAGTAGCTTACTTTATCCTCCAACATATTTAACTTCATG

TCAATTTCGGCTCTTAAATTTTCCACATCATCAAGTTCAACATCATCTTTTAACTTGAATTTATTCTCTAGCTCTTC

CAACCAAGCCTCATTGCTCCTTGATTTACTGGTGAAAAGTGATACACTTTGCGCGCAATCCAGGTCAAAACTTTCCT

GCAAAGAATTCACCAATTTCTCGACATCATAGTACAATTTGTTTTGTTCTCCCATCACAATTTAATATACCTGATGG

ATTCTTATGAAGCGCTGGGTAATGGACGTGTCACTCTACTTCGCCTTTTTCCCTACTCCTTTTAGTACGGAAGACAA

TGCTAATAAATAAGAGGGTAATAATAATATTATTAATCGGCAAAAAAGATTAAACGCCAAGCGTTTAATTATCAGAA

AGCAAACGTCGTACCAATCCTTGAATGCTTCCCAATTGTATATTAAGAGTCATCACAGCAACATATTCTTGTTATTA

AATTAATTATTATTGATTTTTGATATTGTATAAAAAAACCAAATATGTATAAAAAAAGTGAATAAAAAATACCAAGT

ATGGAGAAATATATTAGAAGTCTATACGTTAAACCACCGCGGTGGAGCTCAAGCTTTTCAATTCATCTTTTTTTTTT

TTGTTCTTTTTTTTGATTCCGGTTTCTTTGAAATTTTTTTGATTCGGTAATCTCCGAGCAGAAGGAAGAACGAAGGA

AGGAGCACAGACTTAGATTGGTATATATACGCATATGTGGTGTTGAAGAAACATGAAATTGCCCAGTATTCTTAACC

CAACTGCACAGAACAAAAACCTGCAGGAAACGAAGATAAATCATGTCGAAAGCTACATATAAGGAACGTGCTGCTAC

TCATCCTAGTCCTGTTGCTGCCAAGCTATTTAATATCATGCACGAAAAGCAAACAAACTTGTGTGCTTCATTGGATG

TTCGTACCACCAAGGAATTACTGGAGTTAGTTGAAGCATTAGGTCCCAAAATTTGTTTACTAAAAACACATGTGGAT

ATCTTGACTGATTTTTCCATGGAGGGCACAGTTAAGCCGCTAAAGGCATTATCCGCCAAGTACAATTTTTTACTCTT

CGAAGACAGAAAATTTGCTGACATTGGTAATACAGTCAAATTGCAGTACTCTGCGGGTGTATACAGAATAGCAGAAT

GGGCAGACATTACGAATGCACACGGTGTGGTGGGCCCAGGTATTGTTAGCGGTTTGAAGCAGGCGGCGGAAGAAGTA

ACAAAGGAACCTAGAGGCCTTTTGATGTTAGCAGAATTGTCATGCAAGGGCTCCCTAGCTACTGGAGAATATACTAA

GGGTACTGTTGACATTGCGAAGAGCGACAAAGATTTTGTTATCGGCTTTATTGCTCAAAGAGACATGGGTGGAAGAG

ATGAAGGTTACGATTGGTTGATTATGACACCCGGTGTGGGTTTAGATGACAAGGGAGACGCATTGGGTCAACAGTAT

AGAACCGTGGATGATGTGGTCTCTACAGGATCTGACATTATTATTGTTGGAAGAGGACTATTTGCAAAGGGAAGGGA

TGCTAAGGTAGAGGGTGAACGTTACAGAAAAGCAGGCTGGGAAGCATATTTGAGAAGATGCGGCCAGCAAAACTAAA

AAACTGTATTATAAGTAAATGCATGTATACTAAACTCACAAATTAGAGCTTCAATTTAATTATATCAGTTATTACCC

GGGAATCTCGGTCGTAATGATTTCTATAATGACGAAAAAAAAAAAAAAAAATTGGAAGAAGGCGCGCCGAAGCTGAAG

TGCAAGGATTGATAATGTAATAGGATCAATGAATATAAACATATAAAACGGAATGAGGAATAATCGTAATATTAGTA

TGTAGAAATATAGATTCCATTTAAATCAGAAATGGCCATGAGACAATAACCCTGATAAATGCTTCAATAATATTGAA

AAAGGAAGAGTATGAGTATTCAACATTTCCGTGTCGCCCTTATTCCCTTTTTTGCGGCATTTTGCCTTCCTGTTTTT

GCTCACCCAGAAACGCTGGTGAAAGTAAAAGATGCTGAAGATCAGTTGGGTGCACGAGTGGGTTACATCGAACTGGA

TCTCAACAGCGGTAAGATCCTTGAGAGTTTTCGCCCCGAAGAACGTTTTCCAATGATGAGCACTTTTAAAGTTCTGC

TATGTGGCGCGGTATTATCCCGTATTGACGCCGGGCAAGAGCAACTCGGTCGCCGCATACACTATTCTCAGAATGAC

-continued

TTGGTTGAGTACTCACCAGTCACAGAAAAGCATCTTACGGATGGCATGACAGTAAGAGAATTATGCAGTGCTGCCAT

AACCATGAGTGATAACACTGCGGCCAACTTACTTCTGACAACGATCGGAGGACCGAAGGAGCTAACCGCTTTTTTGC

ACAACATGGGGGATCATGTAACTCGCCTTGATCGTTGGGAACCGGAGCTGAATGAAGCCATACCAAACGACGAGCGT

GACACCACGATGCCTGTAGCAATGGCAACAACGTTGCGCAAACTATTAACTGGCGAACTACTTACTCTAGCTTCCCG

GCAACAATTAATAGACTGGATGGAGGCGGATAAAGTTGCAGGACCACTTCTGCGCTCGGCCCTTCCGGCTGGCTGGT

TTATTGCTGATAAATCTGGAGCCGGTGAGCGTGGGTCTCGCGGTATCATTGCAGCACTGGGGCCAGATGGTAAGCCC

TCCCGTATCGTAGTTATCTACACGACGGGGAGTCAGGCAACTATGGATGAACGAAATAGACAGATCGCTGAGATAGG

TGCCTCACTGATTAAGCATTGGTAACTGTCAGACCAAGTTTACTCATATATACTTTAGATTGATTTAAAACTTCATT

TTTAATTTAAAAGGATCTAGGTGAAGATCCTTTTTGATAATCTCATGACCAAAATCCCTTAACGTGAGTTTTCGTTC

CACTGAGCGTCAGACCCCGTAGAAAAGATCAAAGGATCTTCTTGAGATCCTTTTTTTCTGCGCGTAATCTGCTGCTT

GCAAACAAAAAAACCACCGCTACCAGCGGTGGTTTGTTTGCCGGATCAAGAGCTACCAACTCTTTTTCCGAAGGTAA

CTGGCTTCAGCAGAGCGCAGATACCAAATACTGTCCTTCTAGTGTAGCCGTAGTTAGGCCACCACTTCAAGAACTCT

GTAGCACCGCCTACATACCTCGCTCTGCTAATCCTGTTACCAGTGGCTGCTGCCAGTGGCGATAAGTCGTGTCTTAC

CGGGTTGGACTCAAGACGATAGTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAAAGCGCCACGCTTCCCGAAGGG

AGAAAGGCGGACAGGTATCCGGTAAGCGGCAGGGTCGGAACAGGAGAGCGCACGAGGGAGCTTCCAGGGGGAAACGC

CTGGTATCTTTATAGTCCTGTCGGGTTTCGCCACCTCTGACTTGAGCGTCGATTTTTGTGATGCTCGTCAGGGGGGC

GGAGCCTATGGAAAAACGCCAGCAACGCTGCATATTT

SEQ ID NO: 11

ATGCTACTCCAAGCATTCCTTTTTCTGTTAGCAGGATTTGCTGCCAAAATCTCTGCTAGACCTGGATCTTCAGGCTT

GTCCGACGTCACAAAAAGATCCGTGGATGATTTTATCTCTACAGAAACACCTATTGCACTTAACAATCTCCTGTGTA

ATGTTGGACCAGATGGTTGTAGAGCATTCGGCACAAGTGCAGGCGCTGTTATTGCTTCTCCATCTACAATTGATCCA

GACTATTACTACATGTGGACAAGAGACTCCGCCCTTGTGTTCAAAAACTTGATTGATCGTTTTACAGAAACTTACGA

TGCTGGATTACAAAGACGAATTGAACAATATATCACTGCTCAAGTAACTTTACAAGGATTGAGTAATCCAAGTGGAA

GTTTGGCAGATGGCTCAGGACTAGGAGAGCCAAAGTTTGAACTAACCCTTAAGCCATTCACTGGGAACTGGGGTAGA

CCACAAAGAGATGGTCCTGCTTTGAGAGCAATAGCCTTAATCGGCTACTCAAAATGGTTAATCAACAATAACTACCA

ATCAACAGTTTCAAATGTTATCTGGCCAATTGTTAGGAATGATTTGAACTACGTGGCTCAATACTGGAACCAGACCG

GTTTCGACCTTTGGGAAGAGGTTAATGGCTCTTCCTTTTTCACAGTGGCAAATCAGCATAGAGCTTTGGTTGAAGGA

GCTACTTTAGCGGCCACTCTCGGTCAGTCAGGTTCAGCTTACTCTTCTGTAGCTCCTCAAGTACTTTGTTTTCTACA

GAGATTCTGGGTATCTTCTGGTGGTTACGTTGATTCTAACATTAACACAAATGAAGGGCGTACTGGCAAAGATGTGA

ATAGCGTCCTTACCAGCATCCATACATTCGATCCTAATTTGGGTTGTGATGCCGGGACGTTTCAACCTTGTTCTGAC

AAGGCTTTGAGCAATCTGAAAGTGGTTGTTGATAGTTTCAGAAGCATCTACGGTGTAAACAAGGGTATTCCAGCTGG

TGCTGCCGTGGCTATCGGCAGATATGCAGAAGATGTCTACTATAATGGAAATCCATGGTACTTGGCTACTTTTGCCG

CAGCAGAACAGTTGTACGACGCCATCTACGTTTGGAAAAAGACTGGTAGCATTACTGTTACAGCTACATCCTTAGCA

TTTTTCCAAGAGTTAGTCCCAGGGGTCACAGCAGGCACGTACTCCTCTTCTAGTTCAACCTTTACCAACATCATAAA

CGCTGTCTCCACCTATGCCGACGGTTTTCTATCCGAGGCTGCCAAATACGTTCCTGCAGATGGTTCTCTAGCTGAAC

AATTTGACAGAAATTCAGGTACTCCTCTGTCAGCAGTACACCTCACATGGAGTTACGCATCTTTTCTGACAGCAGCC

GCGAGAAGAGCCGGCATAGTTCCACCAAGTTGGGCCAATTCATCAGCCTCTACAATACCATCTACATGCTCAGGCGC

TTCTGTTGTAGGGAGTTACTCTAGGCCAACCGCTACTTCATTCCCACCTTCCCAAACTCCAAAACCAGGCGTACCTT

CCGGAACACCTTATACCCCACTCCCTTGCGCTACACCAACTTCAGTCGCAGTGACGTTTCACGAATTAGTTTCCACA

CAATTTGGTCACACAGTGAAAGTTGCAGGAAATGCCGCTGCTTTGGGCAATTGGTCAACTTCCGCAGCGGTAGCTTT

-continued

GGACGCTGTTAACTACAGAGATAATCATCCATTGTGGATTGGTACGGTCAACCTAGAAGCTGGTGACGTCGTTGAGT
ATAAGTATATCATAGTTGGTCAAGATGGTTCCGTCACTTGGGAGTCAGATCCTAATCATACTTACACTGTTCCTGCC
GTAGCTTGCGTCACACAAGTTGTGAAGGAAGATACTTGGCAATCTTAA

SEQ ID No: 12

MNQQDIEQVVKAVLLKMKDSSQPASTVHEMGVFASLDDAVAAAKRAQQGLKSVAMRQLAIHAIREAGEKHARELAEL
AVSETGMGRVDDKFAKNVAQARGTPGVECLSPQVLTGDNGLTLIENAPWGVVASVTPSTNPAATVINNAISLIAAGN
SVVFAPHPAAKKVSQRAITLLNQAVVAAGGPENLLVTVANPDIETAQRLFKYPGIGLLVVTGGEAVVDAARKHTNKR
LIAAGAGNPPVVVDETADLPRAAQSIVKGASFDNNIICADEKVLIVVDSVADELMRLMEGQHAVKLTAAQAEQLQPV
LLKNIDERGKGTVSRDWVGRDAGKIAAAIGLNVPDQTRLLFVETPANHPFAVTEMMMPVLPVVRVANVEEAIALAVQ
LEGGCHHTAAMHSRNIDNMNQMANAIDTSIFVKNGPCIAGLGLGGEGWTTMTITTPTGEGVTSARTFVRLRRCVLVD
AFRIV

SEQ ID No: 13

ATGAACCAACAAGACATAGAACAAGTAGTAAAGGCAGTATTATTAAAGATGCAATCCTCTGACACACCACCAGCCGC
AGTACACGAAATGGGTGTATTTGCCTCTTTGGATGACGCTGTTGCTGCAGCCAAAATAGCTCAACAAGGTTTGAAGT
CAGTTGCAATGAGACAATTAGCCATCGCTGCAATTAGAGAAGCTGGTGAAAAACATGCAAGAGATTTGGCCGAATTA
GCTGTCTCCGAAACCGGTATGGGTAGAGTAGAAGACAAATTCGCTAAGAATGTTGCTCAAGCAAGAGGTACTCCAGG
TGTTGAATGTTTGAGTCCTCAAGTCTTAACTGGTGATAACGGTTTGACATTGATCGAAAACGCACCATGGGGTGTTG
TCGCCTCTGTTACTCCATCAACAAATCCTGCCGCTACTGTCATCAATAACGCTATATCTTTGATCGCAGCCGGTAAC
TCAGTTATTTTTGCACCACATCCTGCTGCAAAAAAGGTTTCCCAAAGAGCTATCACATTGTTGAACCAAGCAATCGT
TGCCGCTGGTGGTCCAGAAAATTTGTTAGTCACCGTAGCCAACCCTGATATAGAAACTGCACAAAGATTGTTCAAGT
TCCCTGGTATCGGTTTGTTAGTAGTTACAGGTGGTGAAGCTGTCGTAGAAGCAGCCAGAAAACACACCAATAAGAGA
TTGATTGCTGCAGGTGCTGGTAACCCACCTGTTGTCGTAGATGAAACTGCAGACTTAGCCAGAGCCGCTCAATCCAT
TGTTAAGGGTGCTAGTTTCGATAACAACATAATATGCGCAGACGAAAAGGTATTGATAGTTGTCGATTCTGTTGCTG
ACGAATTGATGAGATTAATGGAAGGTCAACATGCAGTTAAATTGACTGCTGAACAAGCACAACAATTGCAACCAGTT
TTGTTGAAGAACATAGATGAAAGAGGCAAGGGTACAGTCTCAAGAGATTGGGTTGGTAGAGACGCTGGCAAGATTGC
AGCCGCTATAGGTTTAAACGTCCCACAAGAAACTAGATTGTTGTTCGTAGAAACTACAGCCGAACATCCTTTCGCTG
TCACAGAATTGATGATGCCAGTATTACCTGTAGTTAGAGTAGCTAATGTTGCCGATGCTATCGCATTGGCCGTTAAA
TTAGAAGGTGGTTGTCATCACACAGCAGCCATGCACTCCAGAAACATCGAAAACATGAACCAAATGGCTAACGCAAT
CGACACCAGTATTTTTGTTAAGAACGGTCCATGCATAGCTGGTTTGGGTTTAGGTGGTGAAGGTTGGACCACTATGA
CAATCACAACCCCTACCGGTGAAGGTGTTACCTCTGCTAGAACTTTTGTCAGATTGAGAAGATGTGTTTTAGTCGAT
GCATTCAGAATTGTTTAG

SEQ ID No: 14

MNQQDIEQVVKAVLLKMQSSDTPPAAVHEMGVFASLDDAVAAAKIAQQGLKSVAMRQLAIAAIREAGEKHARDLAEL
AVSETGMGRVEDKFAKNVAQARGTPGVECLSPQVLTGDNGLTLIENAPWGVVASVTPSTNPAATVINNAISLIAAGN
SVIFAPHPAAKKVSQRAITLLNQAIVAAGGPENLLVTVANPDIETAQRLFKFPGIGLLVVTGGEAVVEAARKHTNKR
LIAAGAGNPPVVVDETADLARAAQSIVKGASFDNNIICADEKVLIVVDSVADELMRLMEGQHAVKLTAEQAQQLQPV
LLKNIDERGKGTVSRDWVGRDAGKIAAAIGLNVPQETRLLFVETTAEHPFAVTELMMPVLPVVRVANVADAIALAVK
LEGGCHHTAAMHSRNIENMNQMANAIDTSIFVKNGPCIAGLGLGGEGWTTMTITTPTGEGVTSARTFVRLRRCVLVD
AFRIV

SEQ ID No: 15

ATGAACCAACAAGACATAGAACAAGTAGTAAAGGCTGTATTATTAAAAATGAAAGACTCCTCACAACCTGTATCTGC
CGTCCAAGAAATGGGTGTATTTGCATCCTTGGATGACGCCGTTGCTGCAGCCAAATTGGCCCAACAAGGTTTAAAGA

-continued

GTGTTGCAATGAGACAATTGGCCATTACTGCTTTAAGAGAAGCTGGTGAAAAACATGCAAGAGAATTGGCAGAATTA

GCCGTCACTGAAACTGGTATGGGTAGAGTAGAAGATAAATTCGCTAAGAATGTTGCACAAGCCAGAGCTACACCAGG

TGTTGAATGTTTGTCCCCTCAAGTCTTAACAGGTGACAATGGTTTGACCTTAATAGAAAACGCACCATGGGGTGTTG

TCGCCTCTGTTACCCCATCAACTAATCCTGCTGCAACCGTTATCAATAACGCTATCTCTTTGATTGCCGCTGGTAAC

TCAGTAGTTTTTGCACCACATCCTGCAGCCAAAGGTGTTTCTCAAAGAGCTATAACATTGTTGAATCAAGCAGTCGT

AGCTGCAGGTGGTCCAGCCAATTTGTTAGTAACTGTTGCTAACCCTGATATCGAAACAGCACAAAGATTATTCAAGT

ATCCTGGTATTGGTTTGTTAGTTGTTACTGGTGGTGAAGCTGTAGTTGATGCCGCTAGAAAACACACTAATAAGAGA

TTGATAGCAGCCGGTGCTGGTAACCCACCTGTCGTAGTTGATGAAACTGCTGACTTAGCAAGAGCTGCACAATCCAT

TGTTAAGGGTGCTAGTTTTGATAACAACATCATCTGCGCAGACGAAAAGGTATTGATAGTCGTAGATTCCGTTGCTG

ACGAATTGATGAGATTGATGGAAAGTCAACATGCAGTTAAATTGACTACAGCACAAGCCGAACAATTGCAACCAGTA

TTGTTGAAGAACGTTGATGAAAGAGGCAAGGGTACAGTCTCTAGAGATTGGGTTGGTAGAGACGCTGGCAAGATAGC

CGCTGCAATCGGTTTAAACGTCCCAGAACAAACAAGATTGTTGTTCGTTGAAACATCAGCCACCCATCCTTTCGCTG

TCACCGAATTGATGATGCCAGTATTACCTGTTGTCAGAGTTGCTAATGTCGAAGAAGCCATCGAATTGGCTGTTAAA

TTAGAAGGTGGTTGTCATCACACTGCCGCTATGCACTCTAGAAACATCGATAACATGAACAGAATGGCTAACGCAAT

TGACACATCAATATTCGTTAAGAACGGTCCATGCATAGCTGGTTTGGGTTTAGGTGGTGAAGGTTGGACCACTATGA

CCATCACAACCCCTACTGGTGAAGGTGTTACTTCAGCTAGAACATTTGTCAGATTGAGAAGATGTGTCTTAGTAGAT

GCATTCAGAATTGTTTAG

SEQ ID No: 16

MNQQDIEQVVKAVLLKMKDSSQPVSAVQEMGVFASLDDAVAAAKLAQQGLKSVAMRQLAITALREAGEKHARELAEL

AVTETGMGRVEDKFAKNVAQARATPGVECLSPQVLTGDNGLTLIENAPWGVVASVTPSTNPAATVINNAISLIAAGN

SVVFAPHPAAKGVSQRAITLLNQAVVAAGGPANLLVTVANPDIETAQRLFKYPGIGLLVVTGGEAVVDAARKHTNKR

LIAAGAGNPPVVVDETADLARAAQSIVKGASFDNNIICADEKVLIVVDSVADELMRLMESQHAVKLTTAQAEQLQPV

LLKNVDERGKGTVSRDWVGRDAGKIAAAIGLNVPEQTRLLFVETSATHPFAVTELMMPVLPVVRVANVEEAIELAVK

LEGGCHHTAAMHSRNIDNMNRMANAIDTSIFVKNGPCIAGLGLGGEGWTTMTITTPTGEGVTSARTFVRLRRCVLVD

AFRIV

SEQ ID No: 17

ATGGACATCAACCCTAAAGAAATCGAACAAGTCGTAAAAGCCGTATTGGCAAGTATCGGTGCTACATCAACAGCCGC

CGTCGCATCACCAGGTGCCACTTGTGCTCCTGGTGTATTTGTTGAATTAGATGCTGCAGTTGCCGCTGCAGCCCAAG

CACAAAAAGCCTTGAGATCTGTCGCTATGAGAGACAGAGCAATCGCTGCAATTAGAGCCGCTGGTGAAAGACATGCT

CAAGAATTAGCTGAATTGGCAGTTGAAGAAACCGGTATGGGTAGAGTCGCAGATAAAACTGCCAAGAATATTGCCCA

AGCTAGACACACTCCAGGTTCTGAATGCTTACAAGCACAAGTTTTGTCAGGTGACAGAGGTTTAACATTGATCGAAA

ATGCAGCCTGGGGTGTAATTGCTTCCGTTACTCCAAGTACAAACCCTGCTGCAACTGTTATAAACAACGCAATCTCC

ATGATCGCCGCTGGTAACAGTGTTGTCTTTGCTCCACATCCTGCAGCCAAAAGAGTCTCTCAAAGAACAGTATCATT

GTTGAACGAAGCTATGGTCGAAGCAGGTGCCCCAGCTAACTTAATAACTACAGTACAAAGACCTGATATCGAAACCG

CTCAAAGATTGTTCAGATATCCAGGTATTGGTTTGTTAGTAGTTACAGGTGGTGAAGCAGTCGTAGAAGCTGCAAGA

AAACACACCGATAAGAGATTAATAGCCGCTGGTGCTGGTAATCCACCTGTTGTCGTAGATGAAACAGCCGACTTGGC

TAGAGCAGCCAGAGATATAGTTTTCGGTGCATCTTTCGATAACAACATCATCTGTGCTGACGAAAAGGTATTGATCG

TTGTCGATTCAGTTGCAGACGCCTTAAAAGCCGAAATGTTGAAGCATCAAGCTGTTGAATTGTCCGCTGCACAAGGT

CAACAATTGTTACCATTGTTATTGCCTAAAGTTGATGAACAAGGTAGAGGTTCTGTTTCAAGAGATTGGGTCGGTAG

AGACGCCGCTAAGATTGCAGCCGCTATAGGTTTGCAAGTTCCAGAACAAACTAGATTGTTGTTGTTGGAAACAGCAG

CCGATCACCCTTTTGCAATCACAGAAATGATGATGCCAGTTTTGCCTATGGTCAGAGTAGCTAATGTAGACCAAGCT

ATTGCATTAGCCGTTAAATTGGAAGGTGGTTGTCATCACACCGCTGCAATGCATTCCAGAAATTTAGATCACTTGGA

-continued

CAGAATGGCTAACGCAATGGATACTTCTATCTTCGTTAAGAACGGTCCATGCTTAGCTGGTTTGGGTTTCGGTGGTG

AAGGTTGGACCACTATGACAATCACAACCCCTACCGGTGAAGGTGTCACCTCAGCTAGAACTTTCGTAAGATTAAGA

AGATGCGTTATGGTCGATCATTTGAGAATTGTTTAG

SEQ ID No: 18

MDINPKEIEQVVKAVLASIGATSTAAVASPGATCAPGVFVELDAAVAAAAQAQKALRSVAMRDRAIAAIRAAGERHA

QELAELAVEETGMGRVADKTAKNIAQARHTPGSECLQAQVLSGDRGLTLIENAAWGVIASVTPSTNPAATVINNAIS

MIAAGNSVVFAPHPAAKRVSQRTVSLLNEAMVEAGAPANLITTVQRPDIETAQRLFRYPGIGLLVVTGGEAVVEAAR

KHTDKRLIAAGAGNPPVVVDETADLARAARDIVFGASFDNNIICADEKVLIVVDSVADALKAEMLKHQAVELSAAQG

QQLLPLLLPKVDEQGRGSVSRDWVGRDAAKIAAAIGLQVPEQTRLLLLETAADHPFAITEMMMPVLPMVRVANVDQA

IALAVKLEGGCHHTAAMHSRNLDHLDRMANAMDTSIFVKNGPCLAGLGFGGEGWTTMTITTPTGEGVTSARTFVRLR

RCVMVDHLRIV

SEQ ID No: 19

ATGGATCAAAAGGAAATCGAAAATGTAGTCAAAGCCGTATTAGCCTCAATGTCCGCAGGTACTCAACCAGCCGCCGC

CTCCGCCGCACCACAACAAGCTGCAGCCTCCCAAAATAACGGTTTTGGTGTATTCGAAAGTTTGGATGACGCTGTTT

TAGCTGCAAAAGAAGCACAAAAATCCTTGAAGACTGTTGAAATGAGAAATTTATGTATTGGTGCTATCAGAAGAGCC

GCTACCGAACATGCAAGAGAATTGGCTGTTTTAGCAGTCGAAGAAACTGGTATGGGTAGAGTTGAAGATAAATTGGC

TAAGAACTTAGCCCAAGCTAACGGTACTCCAGGTGTAGAATGCTTGAGACCTGAAGTTTTAACAGGTGATCATGGTT

TGACCTTAATAGAAAATGCAGCCTGGGGTGTCATCGCTTCTGTAACTCCATCAACAAACCCTGCTGCAACAGCCATC

AATAACGCTATCTCTATGATTGCTGGTGGTAATTCAGTCATTTTTGCACCACACCCTGCCGCTAAAAAGGTTTCTCA

AAGAACAATCACCATCTTGAATGAAGCTATTGTTGCAGCCGGTGGTCCAAATAACTTGTTAGTCACTGTAGCCAAAC

CTGATATCGAAACAGCTCAAAGATTGTTCAAGTATCCAGGTATAGGTTTGTTAGTTGTCACTGGTGGTGACGCTGTA

GTTGAATCCGCAAGAAAGCATACAAACAAGAGATTGATAGCTGCAGGTGCTGGTAACCCACCTGTCGTAGTTGATGA

AACAGCAGACATCGAAAGAGCCGCTAAAGCCATTGTTCACGGTGCTAGTTTTGATAACAACATCATCTGTGCTGACG

AAAAAGTTTTGATCGCAGTCGATTGCATTGCCGACAAGTTAATCACAGAAATGCAAAGAAACCATGCAGTTTTGTTG

ACCAGAGAACAATCTGAAAAATTAATTCCTGTATTGTTGAAGAACGTTGATGAAACCGGTCACGGTACTGTCTCAAG

AGATTGGGTTGGTAGAGACGCAGCCAAAATAGCTGCAGCCATCGGTATGACTGTTCCAGCAGATACAAGATTGTTAA

TTGCCGAAACCGACTGTAAGCATCCTTTTGCTGTCACTGAATTGATGATGCCAGTATTGCCTATCATAAGAGTAAAG

GATGTTGACCAAGCAATAGATTTGGCCGTTAAGTTAGAAGGTGGTTGTCATCACACTGCTGCAATGCACTCCAACAA

CATCAGTAACTTGAACAGAATGGCAAACGCCATCGATACATCTATCTTCGTTAAGAACGGTCCATGCATAGCTGGTT

TGGGTTTAGGTGGTGAAGGTTGGACTACAATGACCATCACCACTCCTACTGGTGAAGGTGTTACATGTGCAAGAACC

TTTGTCAGATTAAGAAGATGCACTATGGTTGATTCATTCAGAATTGTCTAG

SEQ ID No: 20

MDQKEIENVVKAVLASMSAGTQPAAASAAPQQAAASQNNGFGVFESLDDAVLAAKEAQKSLKTVEMRNLCIGAIRRA

ATEHARELAVLAVEETGMGRVEDKLAKNLAQANGTPGVECLRPEVLTGDHGLTLIENAAWGVIASVTPSTNPAATAI

NNAISMIAGGNSVIFAPHPAAKKVSQRTITILNEAIVAAGGPNNLLVTVAKPDIETAQRLFKYPGIGLLVVTGGDAV

VESARKHTNKRLIAAGAGNPPVVVDETADIERAAKAIVHGASFDNNIICADEKVLIAVDCIADKLITEMQRNHAVLL

TREQSEKLIPVLLKNVDETGHGTVSRDWVGRDAAKIAAAIGMTVPADTRLLIAETDCKHPFAVTELMMPVLPIIRVK

DVDQAIDLAVKLEGGCHHTAAMHSNNISNLNRMANAIDTSIFVKNGPCIAGLGLGGEGWTTMTITTPTGEGVTCART

FVRLRRCTMVDSFRIV

SEQ ID No: 21

ATGCATTTAGACGACAAACAAATCGCACAAATAGTAGAAACCGTATTATCAAGATTAGAAAGAAACGAAAGTAGAAC

AGGTAGAAGTAGACACCCACAAGGTGTCTTTGAAACCTTGGATGAAGCTGTAGAAGCTGCAAGACAAGCACAAAAGA

-continued

AAATTAGAAAATTGGAATTGAGAGCTAAGATCATCCAAGCAATCAGACAAGCCGGTGTTAAACATGCAAGAGAATTG

GCAGAAATGGCCGTTCAAGAAACTGGTATGGGTAGAGTCGAAGATAAGATAGCAAAGAACATCTCTCAAGCCGAAAA

GACCCCAGGTATTGAAGATTTACAACCTTTGGCTTTATCAGGTGACCACGGTTTGACTTTAATCGAAAATGCCGCTT

GGGGTGTTATTGCCTCTGTCACACCATCAACCAACCCTGGTGCTACTGTTATCAATAACTCTATCTCAATGATTGCA

GCCGGTAATGCTGTTGTCTATGCACCACATCCTGCTGCAAAAAAGGTCTCCCAAAGAGCCATTGAAATATTGAACAA

AGCTATTGAAGCCGCTGGTGGTCCAGCAACATTGTTAACTACAGTCGCCGAACCTAGTATCGAAACCGCTCAAAAGT

TATTCGTATATCCAGGTATTGATTTGTTAGTAGTTACTGGTGGTGAAGCTGTCGTAAAAGCAGCCAGAAAGGTTACA

GACAAAAGATTAATGGCTGCAGGTGCAGGTAATCCACCTGTTGTCGTAGATGAAACAGCTGACATTGCAAAAGCCGC

TAGAGATATAGTCTGGGGTGCTTCTTTCGATAATAACATCGTATGTGCAGACGAAAAAGAAATCATTGCCGTTGATG

CCATTGCTGACAGATTGAAGGAAGAAATGAAAAAGCACCAAGCAGTTGAATTAACTCCACAACAAGGTGAAGAATTG

GCTCAAATCATCTTAGAAGATTATCCAGGTCCTAATGCAAGAATAAACAGAAAGTGGGTTGGTAAAGACGCCTACAA

GTTCGCTAGAGAAATAGGTTTGAACGTATCAAAGGAAACAAGATTGTTGTTCGTTGAAGCTGATAAGGACCATCCTT

TCGCACAATTGGAATTAATGATGCCAGTTATCCCTTTGATCAGAGCAGCCGATGCCGACAAAGCTATCGATTTGGCT

ATTGAATTAGAACACGGTTATAGACATACAGCTGCAATGCATTCCAGACACATTGATCATATGGACAGAATGGCTAA

CGAAATCAACACCAGTATCTTCGTTAAAAACGGTCCATGTTTGGCAGGTTTAGGTTTCGGTGGTGAAGGTTGGACTT

CCATGACAATTACCACTCCTACCGGTGAAGGTGTAACTTCCGCTAGAAGTTTTGTTAGATTGAGAAGATGCGTTGTC

GTAGATCATTTCAGAATTGTTTAG

SEQ ID No: 22

MHLDDKQIAQIVETVLSRLERNESRTGRSRHPQGVFETLDEAVEAARQAQKKIRKLELRAKIIQAIRQAGVKHAREL

AEMAVQETGMGRVEDKIAKNISQAEKTPGIEDLQPLALSGDHGLTLIENAAWGVIASVTPSTNPGATVINNSISMIA

AGNAVVYAPHPAAKKVSQRAIEILNKAIEAAGGPATLLTTVAEPSIETAQKLFVYPGIDLLVVTGGEAVVKAARKVT

DKRLMAAGAGNPPVVVDETADIAKAARDIVWGASFDNNIVCADEKEIIAVDAIADRLKEEMKKHQAVELTPQQGEEL

AQIILEDYPGPNARINRKWVGKDAYKFAREIGLNVSKETRLLFVEADKDHPFAQLELMMPVIPLIRAADADKAIDLA

IELEHGYRHTAAMHSRHIDHMDRMANEINTSIFVKNGPCLAGLGFGGEGWTSMTITTPTGEGVTSARSFVRLRRCVV

VDHFRIV

SEQ ID No: 23

ATGCAAACAGACGCCCAACAAATAGAAAGTATCGTTAGAAGAGTCATAGAACAATTACACAGTCCACAAAGAGATGG

TGAAAGTTATGGTGTCTTTAGAACCTTGGATGACGCAGTAGCCGGTGCTCAAGGTGCTTATAAAAAGATAAGAACCA

TGGCTCAAAGAGAAGCAATTATAGCTGCAATCAGAAGAACTGGTAGTGAAAATGTTCAAGCATTGTCTGAATTAGCC

GTCCAAGAAACAGGTTTCGGTAGAGTAGAAGATAAGATCAGAAAGCATAGATTGGTTTTAGACAAAACTCCTGGTAT

CGAAGCTATTGTTCCAATGGCAGTCACAGGTGATCACGGTTTGTCTTTAATTGAAAATGCTCCATGGGGTGTAATAG

CATCCGTTACCCCTAGTACTAACCCATCTGCTACTATCTTGAACAACGCAATCTCAATGATCGCCGCTGGTAATTCA

GTTGTCTTTTCCCCACATCCTGCAGCCAGAGCTGTCTCCCAAAGAACAATCCAATTGATCAACAGAGCCTCTGTTTC

AGCTGGTGGTCCTGCAAACTTAGTCACCTGTGTAGAAGAACCAACAATTGAAGCTGCAACCAGATTGTTTTCATTCC

CTGGTATACAATTGTTAACCATCACTGGTGGTGAAGGTGTAGTTAATGCCGCTAGAAAAGTTACTGATAAGAGATTA

ATCGCAGCCGGTCCAGGTAACCCACCTGTCGTAGTTGATGAAACAGCTGACATTGAAAGAGCTGCAATTTCAATAGT

TCAAGGTGCATCCTTCGATAACAACATCATATGTGTTGACGAAAAGGAAATAATCGCCGTCGAATCCATTGCTACTG

AATTGAAGACAGCTATGTGCAGACATGGTGCCGCTGAAATAAATGCAGATCAAGCAGACGCCGTCGCTAGATTGGTA

TTAGCTGGTTACCCAGGTCCTAACCCACACCCTAAACCAGAATGGGTTGGTAGAGATGCTGAAAAGATTGCAGCCGC

TGCAGGTTTTAGTGTACCTGCAGGTACTAGATTGTTAGTTACAGAAACCGAAAGAGATCATGCATTCGCCACTACAG

AAATGATGTTGCCAGTTATCTCTTTAATAAGAGCTAGAGATGCAGACCAAGCCATTGATTGGGCAGTTGAATTGGAA

GCCGGTAATAGACATACAGCCGCTATGCACTCAAGAAATATCGACAACTTGTCCAGAATGGGTTTAGAAATAAACTG

-continued

TTCTTTGTTCGTTAAAAACGGTCCTTGCTTGGCCGGTTTAGGTGCTGGTGGTGAAGGTTGGACAAGTATGACCATAT

CTACTCCAACAGGTGAAGGTGTAACCAACGCTAGTACTTTCGTTAGAAAGAGAAGATGCACAATGGTTGATTCTTTC

AGAATTGTCTAG

SEQ ID No: 24

MQTDAQQIESIVRRVIEQLHSPQRDGESYGVFRTLDDAVAGAQGAYKKIRTMAQREAIIAAIRRTGSENVQALSELA

VQETGFGRVEDKIRKHRLVLDKTPGIEAIVPMAVTGDHGLSLIENAPWGVIASVTPSTNPSATILNNAISMIAAGNS

VVFSPHPAARAVSQRTIQLINRASVSAGGPANLVTCVEEPTIEAATRLFSFPGIQLLTITGGEGVVNAARKVTDKRL

IAAGPGNPPVVVDETADIERAAISIVQGASFDNNIICVDEKEIIAVESIATELKTAMCRHGAAEINADQADAVARLV

LAGYPGPNPHPKPEWVGRDAEKIAAAAGFSVPAGTRLLVTETERDHAFATTEMMLPVISLIRARDADQAIDWAVELE

AGNRHTAAMHSRNIDNLSRMGLEINCSLFVKNGPCLAGLGAGGEGWTSMTISTPTGEGVTNASTFVRKRRCTMVDSF

RIV

SEQ ID No: 25

ATGGATCAAAAACAAATCGAAGAAATCGTAAAATCAATCGTATTACAATTAAATGACAACCCAGGTATAGCCTCCTC

AGCCAACACCTTGAATCAAAACACATTAACCGAACAGGGTGATTATGGTGTCTTTGAAACTTTGGACGGTGCTGTAG

CTGCAGCCACTGCTGCACAAAAGCAAATTAGAACAGTTGCAATGAGAGATGAAATCATCACAGCCATCAGAAGAATG

ACCAAAAAGCATGCCAGAGAATTATCAGAAATGGCTGTTGAAGAAACAGGTTTCGGTAGAGTCGAAGATAAGATAAA

AAAGCACATCTTGGTCGCTCAAAGAACTCCTGGTACAGAAATTTTATCCCCACAAGCAGTATCCGGTGATAGTGGTT

TCTCTTTGATGGAAAATGCTCCATGGGGTGTCATCGCATCAGTAACCCCTTCCACTAACCCAACTTGTACAGTTATA

AACAACGCTATATCAATGATAGCCGCTGGTAATGCAGTTGTCTTTGCCCCACATCCTGCAGCCAAAAAGGTTTCCCA

ATACACTATCCAATTAGTAAACAAGGCTTCTGAATCAGTTGGTGGTCCTGCATACATATGCACTACAGTAGCCAAAC

CATCTTTGGAAAATGCTCAAGCATTATTCGTTTACCCTGGTATTAGATTGTTAGTAGTTACTGGTGGTGATGCTGTC

GTAGAAGCTGCAAGAGCAGTTACAGACAAAAGATTGATCGCCGCTGGTCCAGGTAACCCACCTGTTGTCGTAGATGA

AACCGCTGACATAGAAAGAGCAGCCATAAGTATCGTAGAAGGTGCTTCTTTCGATAATAACATAGTTTGTGCAACAG

AAAAGGAAATCATTGCTGTCGATTCAATCGCAGACGAATTAAAAGCTGCAATGTGCAGAAATGGTGCCCATTTGTTA

ACTGCTGATCAAGCCGAAGCTGTTGCAAGAGTTGTCTTGAAAGGTTATCCTGGTGACAAGCCATCACCTAACCCAAA

ATGGGTTGGTAGAGATGCTTCCAAGTTAGCCGCTGCAGCCGGTATAGACGTCCCAGCAGAAACAAGATTGTTAATCT

TTGAAGCCGATAAATCTCACGTTTTCGCTGTAGTTGAACAAATGATGCCTATTTTGCCATTAATCAGAGCTGCAAAT

GCCGATCAAGCTATTGACTGGGCTGTTGAATTGGAAAATAAGAACAGACATACAGCCGCTATCCACAGTAAGAACAT

CGATGTTTTGACCAGAATGGCTTACGAAATGGACTGTTCTTTGTTAGCAAAGAACGGTCCTGCCATCGCAGCCATTG

GTGCAGGTGGTGAAGGTTGGACCACTATGACCATTAGTACCCCAACTGGTGAAGGTGTTACTAACGCTTTGACATTC

ACCAGAAAGAGAAGATGCACTGCAGTTGATTCTTTCAGAATTGTCTAG

SEQ ID No: 26

MDQKQIEEIVKSIVLQLNDNPGIASSANTLNQNTLTEQGDYGVFETLDGAVAAATAAQKQIRTVAMRDEIITAIRRM

TKKHARELSEMAVEETGFGRVEDKIKKHILVAQRTPGTEILSPQAVSGDSGFSLMENAPWGVIASVTPSTNPTCTVI

NNAISMIAAGNAVVFAPHPAAKKVSQYTIQLVNKASESVGGPAYICTTVAKPSLENAQALFVYPGIRLLVVTGGDAV

VEAARAVTDKRLIAAGPGNPPVVVDETADIERAAISIVEGASFDNNIVCATEKEIIAVDSIADELKAAMCRNGAHLL

TADQAEAVARVVLKGYPGDKPSPNPKWVGRDASKLAAAAGIDVPAETRLLIFEADKSHVFAVVEQMMPILPLIRAAN

ADQAIDWAVELENKNRHTAAIHSKNIDVLTRMAYEMDCSLLAKNGPAIAAIGAGGEGWTTMTISTPTGEGVTNALTF

TRKRRCTAVDSFRIV

SEQ ID No: 27

ATGCAAATCAACGAAACCGACATAAAGAAAATGGTAGAACAAGTATTAAAACAATTAGGTCAAACAGAAGCTGCTGG

TGCCCCAATCGCTCCACAAAATGATGTTTCTTTAGGTGACGGTGTATTTGCAACTGTTGATGAAGCTGCAGCCGCTG

-continued

CAAGAGTTGCTTGGGAAAAATTGAGAAAGTTGCCTTTAGCATCAAGAAGACAAATGATTGACAATATGAGAGAAGTT

TCCTGTGCCCAAGCTAACGAATTGGCACAATTAGCCGTTGATGAAACAGGTTTAGGTAGAGTCGAAGACAAAGTAGC

TAAGATTTTGTTAGCCGCTAATAAAACACCAGGTGTTGAAGATTTGGTCTCTACCTCATATTCCGGTGATGACGGTT

TGACTTTAGTCGAATACGCTCCTATCGGTGTATTCGGTTCAATTACTCCATCCACAAACCCTGCAGCCACTGTTATA

AATAACAGTATTTCTTTAATCGCTGCAGGTAATACAGTTGTCTATAACCCACATCCTAGTGCTAAGAGAGTTTCTTT

GAAGACTTTGAAGTTGTTAAATCAAGCCATTGTCGCCGCTGGTGGTCCAGAAAATGCTTTGACAAGTGTTGCAGCCC

CTAACTTAGAAACCTCTGCACAAGTTATGAATCACCCAAAAGTCAACGCCTTAGTAGTTACAGGTGGTGGTCCTGTC

GTAAAGGCTGCAATGGCTGTAGGTAAAAAGGTTATCGCCGCTGGTCCAGGTAATCCACCTGTTGTCGTAGATGAAAC

AGCAATTATATCACAAGCAGCCGCTCATATTGTTCAAGGTGCTTCCTTTGATAATAACGTTTTGTGTACCGCAGAAA

AAGAAGTCTTCGTTGTTGATAAGGCAGCCAATGCTTTAAAAGCAGAAATGGTTAAGAACGGTGCTATAGAATTGAAA

GGTTTTCAATTCGAAAAATTGTTAGAAAAGGTATTAGTTAAAAAGAATGATAAATTTTACCCAAACAGAGATTTCAT

TGGCAAGGACGCTAGTGTTATATTGCAAGCTGCAGGTATCCAAGTCTCTCCAAACGTAAAATTGATCATAGCAGAAA

CTACAAAGGATCACCCTTTGGTTATGACTGAAATGTTGATGCCAATCTTACCTATTGTCAGAGTACCAGATGTAGAC

AAAGCTATTGAATTAGCCGTTATAGCTGAAAAGGGTAATAGACATACCGCAATAATGCACTCACAAAACATCACCAA

CTTGACTAAGATGGCACAAGAAATACAAGCCACTATCTTTGTAAAGAACGGTCCATCAGTTGCTGGTTTGGGTTTTG

AATCCGAAGGTTTCACCACTTTAACAATTGCCGGTCCTACCGGTGAAGGTTTGACTTCTGCAAAAACATTTACCAGA

CAAAGAAGATGCGTTTTGGTCGATGGTTTCAGAATAATCTAG

SEQ ID No: 28

MQINETDIKKMVEQVLKQLGQTEAAGAPIAPQNDVSLGDGVFATVDEAAAAARVAWEKLRKLPLASRRQMIDNMREV

SCAQANELAQLAVDETGLGRVEDKVAKILLAANKTPGVEDLVSTSYSGDDGLTLVEYAPIGVFGSITPSTNPAATVI

NNSISLIAAGNTVVYNPHPSAKRVSLKTLKLLNQAIVAAGGPENALTSVAAPNLETSAQVMNHPKVNALVVTGGGPV

VKAAMAVGKKVIAAGPGNPPVVVDETAIISQAAAHIVQGASFDNNVLCTAEKEVFVVDKAANALKAEMVKNGAIELK

GFQFEKLLEKVLVKKNDKFYPNRDFIGKDASVILQAAGIQVSPNVKLIIAETTKDHPLVMTEMLMPILPIVRVPDVD

KAIELAVIAEKGNRHTAIMHSQNITNLTKMAQEIQATIFVKNGPSVAGLGFESEGFTTLTIAGPTGEGLTSAKTFTR

QRRCVLVDGFRII

SEQ ID No: 29

ATGGGTTTATCAGAAATCGAACAATTAGTCAAGCAAATCTTATCAGAAGACATATTAGAAAGTCAAGAATCCGCACA

ATACAGTCAATCCTTGGTTGGTACAAAGGAAATCCAAGGTGATATCTTAGAAGGCAAGGAAACAGAATCTGGTGTCT

TTTCAACCGTAGATCAAGCAGTTCAAGCTGCAAAGATAGCCCAAAAGAAATACTTCGACACTTCTATCGAAAGAAGA

AAAAAGATTATCGCCGCTATAAGATCAAGATTGTTACCAGAAGTTGAAGAAATAGCTAAAAGAGCATTGGAAGAAAC

CGGTATGGGTAACTTCCAAGATAAGATAGCTAAGAACAGATTGGCCTTAGAAGCTACTCCAGGTGTCGAAGATTTGA

TGTATGCAACCAGAGCCTTAACTGGTGACAATGGTTTGACTTTATATGAAATGTGTCCTTACGGTGTTATCGGTGCA

ATTGCCCCATCAACAAACCCTACTGAAACAATCATCAATAACTCCATCAGTATGTTGGCAGCCGGTAACACAATTTA

CTTCGCTCCACATCCTGGTGCAAGAGAAACTACAATCTGGTTGATCAGAAAGATAAACAAGATAGCTAAAGATGCAT

CCGGTATAGACAACTTGATCGTCACCATAGAAAACCCAAGTATACAAGCTGCACAAGAAATGATGGTACACCCAGAT

ATTGCTATATTAGTTGTCACTGGTGGTCCTGGTGTAGTTGCTCAAGCAATGAAATCTGGTAAAAAGGTTATTGGTGC

CGGTGCTGGTAATCCACCTGCAATCGTCGATGAAACTGCCAACATTGAAAAGGCTGGTCAAGATATAGTTGACGGTG

CCTCATTTGACAATAACATTCCTTGTACTGCTGAAAAGAATATAATCGTCGTATCTTCAGTTGCTGAATACTTGATC

TTCAACATGCAAAAGGCAGGTGCCTTCTACGTCAAAGATATCGAAGACATCAAAAAGTTAGAAAACTTGTGCTTGAC

AGAAAAGGGTACCACTAACAAAAAGTATGTTGGTAAGTCTGCTGAAAAAATCTTGACCGATGCAGGTGTTACCTATA

CTGGTCATCCAAGATTAGTAATTGTTGAAGGTTACCCAGATATGCCTTTTGCTGTTGAAGAAATGTTGATGCCAGTT

GTCCCTTTAATTAGAGTCCCTGATTTCGACACTGCCTTGGAAGTAGCTTTGGAATTAGAACATGGTTACAAACACAC

-continued

AGCTACCATTCACTCCCAAAATGTAAGTAGATTAAACAAGGCCGCTAGAGCTATGGAAACATCTATCTTCGTTAAGA

ACGGTCCATCATTCGCAGGTTTGGGTTTAAGAGGTGAAGGTCCAACAACCTTTACTATTGCTACTCCTACAGGTGAA

GGTACTACAACCGCAAGATCCTTTGCCAGAATAAGAAGATGCGTTTTAAGTGATGCATTCATGATCAGATAG

SEQ ID No: 30

MGLSEIEQLVKQILSEDILESQESAQYSQSLVGTKEIQGDILEGKETESGVFSTVDQAVQAAKIAQKKYFDTSIERR

KKIIAAIRSRLLPEVEEIAKRALEETGMGNFQDKIAKNRLALEATPGVEDLMYATRALTGDNGLTLYEMCPYGVIGA

IAPSTNPTETIINNSISMLAAGNTIYFAPHPGARETTIWLIRKINKIAKDASGIDNLIVTIENPSIQAAQEMMVHPD

IAILVVTGGPGVVAQAMKSGKKVIGAGAGNPPAIVDETANIEKAGQDIVDGASFDNNIPCTAEKNIIVVSSVAEYLI

FNMQKAGAFYVKDIEDIKKLENLCLTEKGTTNKKYVGKSAEKILTDAGVTYTGHPRLVIVEGYPDMPFAVEEMLMPV

VPLIRVPDFDTALEVALELEHGYKHTATIHSQNVSRLNKAARAMETSIFVKNGPSFAGLGLRGEGPTTFTIATPTGE

GTTTARSFARIRRCVLSDAFMIR

SEQ ID No: 31

ATGGCTGACGTATTGGAAAAAGACATAGAAGCTATCGTAACAGAAGTATTAAAGAAGATGACATTGCCAACCTCCTC

TCCTAACGGTTCTTCACCTCAAGAAACTTTGTTAGATTCTGACGGTGATTGGGGTGTCTTTCCAGGTTTAGATCAAG

CTGTAGCTGCAGCCTCAGCTGCACAAAAAAGAATACCAACAATAGCTGTTAGAGAACAAGTTGTCAGAATGGTCAGA

AGAGCCGCTAGAGCAAATGCCAGAAGATTAGCCGAAATGGCTGTTGATGAAACCGGTATGGGTAGAGTCGAAGACAA

GGTAAAAAAGAATTTGTTAGTTGCCAACAGAACACCAGGTCCTGAAATTTTGTCTCCTGCAGCCGCTACTGGTGATG

CTGGTTTAACATTGTTTGAAAATGCCCCATGGGGTGTTATTGCTTCTGTCACTCCTTCAACAAACCCAGCAGCCACA

ATCTTCAATAACACCATTTCCATGGTCTCTGGTGGTAATACTGTAGTTTATGCAGTTCATCCAGGTGCCAAGAGAAC

TACATTAGAAACAGTTAAGGTCGTAAACAAGGCAGTCTACGAAGAATTGGGTATAAACAACATAATCACTTGTGTTA

AGGAACCTTCTATCGAAACCGCTCAAAAGTTATTCACTTATCCAGGTATCAACTTGTTAGTTGTTACTGGTGGTGAA

GCAGTAGTTGATGCTGCAAAAAAGATAACTGACAAGAGATTGATCGCCGCTGGTGCTGGTAACCCACCTGTCGTTGT

TGATGACACTGCAGATTTGGCCAGAGCAGCCCAATCTATCTACGATGGTGCTTCATTCGACAACAACATCGTTTGTT

GCGATGAAAAGGAAATCATAGCTTTAGACACAGTTGCAGATAAATTGAAGGACGAATTGAAGAATTGCGGTGCTGTT

GAAATTTCCTTGGACCAAGCTGATGCAATAGCCAGAAAGGTTTTGTTGGATTACCCTGGTTCAAATCCAAGACCTAA

CCCAAAGTGGGTTGGTAGAGATGCTGCAGTTTTGGCTTCTGCCGCTGGTATATCAGTACCAGAAACATGTAGATTGT

TAATCGTTGATGCAGGTACCGACACTGGTTACACCTTTGCCAAAATGGAACAAATGATGCCTTTAATACCAATCTTG

AGAGCAAGAGATTTCAATCAAGCATTGGAATGGGCATTGTTATTGGAAAACGATTGCAGACATTCCGCTGGTTTGCA

CAGTAAGAATATTGACAACATGGATACAATGGCTAAAGCAGTCAATACCTCATTATTCGTAAAGAACGGTCCTCACA

TTGCCGGTTTGGGTGCTGGTGGTGAAGGTTGGACCTCCATGACTATAAGTACACCAACCGGTGAAGGTGTATCCAAT

GCAAGAACTTTCGTTAGATTGAGAAGATGTACATTGGTTGGTAGTTTCAGAATTGCTTAG

SEQ ID No: 32

MADVLEKDIEAIVTEVLKKMTLPTSSPNGSSPQETLLDSDGDWGVFPGLDQAVAAASAAQKRIPTIAVREQVVRMVR

RAARANARRLAEMAVDETGMGRVEDKVKKNLLVANRTPGPEILSPAAATGDAGLTLFENAPWGVIASVTPSTNPAAT

IFNNTISMVSGGNTVVYAVHPGAKRTTLETVKVVNKAVYEELGINNIITCVKEPSIETAQKLFTYPGINLLVVTGGE

AVVDAAKKITDKRLIAAGAGNPPVVVDDTADLARAAQSIYDGASFDNNIVCCDEKEIIALDTVADKLKDELKNCGAV

EISLDQADAIARKVLLDYPGSNPRPNPKWVGRDAAVLASAAGISVPETCRLLIVDAGTDTGYTFAKMEQMMPLIPIL

RARDFNQALEWALLLENDCRHSAGLHSKNIDNMDTMAKAVNTSLFVKNGPHIAGLGAGGEGWTSMTISTPTGEGVSN

ARTFVRLRRCTLVGSFRIA

SEQ ID No: 33

ATGGACGTTAGACAACAAGATGTAGAAAGAATCGTAGTCGAAGTATTAAAGAAAATGATGAGTGACCAACCAACAGC

CGCAGCAACCACAGTTGTCGCTGCATCCGGTTGTGATTGCGGTGACTTTGGTTTGTTCGATAGATTAGAAGACGCTG

-continued

TCCAAGCCGCTGAAGCAGCCCAAAAGAAAATTAGTACAGTAGCAATGAGAGATAAGATAATCGCTGCAATAAGAAAG

GCTGGTTTGGAAAATGCCAAAGCATTTGCAGAAATTGCACATAACGAAACCGGTATGGGTAGAGTCTCTGATAAGAT

CGCTAAGAACATCTTGGTATGCGAAAGAACTCCTGGTACAGAATGCTTATCCCCAATGGCAATTAGTGGTGACATGG

GTTTGACTTTAATAGAAAATGCACCATGGGGTGTAATCGCCTCTGTTACCCCTTCAACTAACCCAACCGCTACTGTT

ATAAATAACGCCATCTCCATGATTGCTGGTGGTAATAGTGTTATCTTTGCTCCACATCCTAACGCTAAGAGAGCATC

TCAAACTGCAATTCAAGTATTGAACAAGGCTATCATCGAAGCAACAGGTGTTGCCAACTTGTTAGTCGCTGTAAAAG

AACCTACCATTGAAGTTGCACAAGAATTATTCTCACACCCAAGAATAAAGTTGTTAGTAGTTACTGGTGGTGAAGCC

GTCGTAGCCCAAGCTAGAAAAGTTGCTACAATGAGATTGATTGCCGCTGGTGCAGGTAATCCACCTGTTGTCGTAGA

TGAAACAGCCAACATTGCTAGAGCAGCCAGATCTATATATGATGGTGCCTCATTCGACAATAACATCATCTGTGCTG

ACGAAAAGGAAATCATCGCAGTTGATTCTATAGCCGACCAATTAAAAGCTGAAATGAAGGCAATTGGTGCCGTTGAA

ATATCATTGGAACAAGCAGATGCCGTCGCTAGAGTTGTCTTAAGAAATTACCCTCAAGTTGAAGGTGGCAAGGCTCC

AAATCCTAACCCAAAATGGGTCGGTAGAGATGCTGCATTGATAGCAAAGGCCGCTGGTATCGATGTTCCAGACTCCT

GCAGATTGTTGATCGTTGATGTCAAGAGAGACATAAACCATGTCTTTGCTAGAGTAGAACAATTGATGCCTGTAATT

CCATTGTTAAGAGCAGCCAACGTTGATGAAGCTATCGAATGGGCATTGATTTTAGAAAGAGGTTTGTCTCATACCGC

TGGTATGCACTCAAGAAATATTGATAACATGGACAAGATGGCAAGAGCCATGAACACTTCATTATTCGTTAAGAACG

GTCCTCACTTGGCTGCATTAGGTGCTGGTGGTGAAGGTTGGACTACAATGACAATTTCCACACCAACCGGTGAAGGT

GTTACCTGTGCTAGAAGTTTTGTCAGATTGAGAAGATGTTGCGTAGTTGATAATTTCAGAATAGTTTAG

SEQ ID No: 34

MDVRQQDVERIVVEVLKKMMSDQPTAAATTVVAASGCDCGDFGLFDRLEDAVQAAEAAQKKISTVAMRDKIIAAIRK

AGLENAKAFAEIAHNETGMGRVSDKIAKNILVCERTPGTECLSPMAISGDMGLTLIENAPWGVIASVTPSTNPTATV

INNAISMIAGGNSVIFAPHPNAKRASQTAIQVLNKAIIEATGVANLLVAVKEPTIEVAQELFSHPRIKLLVVTGGEA

VVAQARKVATMRLIAAGAGNPPVVVDETANIARAARSIYDGASFDNNIICADEKEIIAVDSIADQLKAEMKAIGAVE

ISLEQADAVARVVLRNYPQVEGGKAPNPNPKWVGRDAALIAKAAGIDVPDSCRLLIVDVKRDINHVFARVEQLMPVI

PLLRAANVDEAIEWALILERGLSHTAGMHSRNIDNMDKMARAMNTSLFVKNGPHLAALGAGGEGWTTMTISTPTGEG

VTCARSFVRLRRCCVVDNFRIV

SEQ ID No: 35

ATGAACTTGGATGCTAACAACTTGAACAACATAGTCTCCTTAATAATGAAAGAATTGGACAAAAATAACAACATAGA

TGACACTGGTCAAGGTTGTGGTGGTGAAGAAGGCAAGAACGGTATTTTCTCTTCTATGGACACTGCTGTTTCTAAAG

CCAAGGAAGCTCAAGTAACATTGTTCGCCTCTAAATTGGAATTAAGAGAAAGAATCATCAAGGCTATCAGAGAAGAT

GTTAGAGAAGCTGCAGCCGAATTGGCAGAAATCGCCGTTGAAGAAACCGGTATGGGTAGAGTCGATGACAAGACTTT

GAAGCATTACGTCACTGTAGATAAAACACCAGGTGTTGAAGACTTGAGAGCATTTGCCTATAGTGGTGATAACGGTT

TAACTGTAATGGAATTGTCTCCTTACGGTGTTATTGGTTCTATAACACCATCAACCAATCCTTCCGAAACAATTGTT

TGCAACGCTATCGGTATGATTGCTGCAGGTAATTCAGTTGTCTTTGCCCCACACCCTGGTGCTAAAAAGACATCCTT

AAGAGCAGTTGAAATTTTGAACAAAGCTGTCGCAAGAGCCGGTGGTCCAAACAACTTGGTAGTTACAATCTTCGAAC

CTTCAATCGAAAACACCAACAAGATGGTCAAGAACCCAGATATAAAGATGGTCGTAGCTACCGGTGGTCCTGGTGTT

GTCAAGTCCGTTATGTCCAGTGGTAAAAAGGCTATAGGTGCTGGTGCAGGTAATCCACCTGTTTTGGTCGATGAAAC

TGCAGACATCGAAAAAGCCGCTAAGGATATAGTTAACGGTTGTAGTTTCGACAACAACTTACCATGCATTACCGAAA

AAGAAGTAGTTGCCGTAGATTCTATCACTGACTACTTGATCTTCGAAATGCAAAAGAATGGTGCATACTTGGTTCAA

GATTCAAAGACAATAAAAAAGTTGTGTGAAATGGTCATCAATGACGGTTCACCAAACAGAGCTTATGTAGGTAAAAA

CGCATCCTACATCTTGAAGGATTTAGGTATTGATGTTGGTGACGAAATAAAGGTCATCATTGTAGAAACTGATGCAG

GTCATCCTTTGGCCGTATTAGAAATGTTGATGCCAGTTTTGCCTATAGTAAGAGTTAAGGATGCTTTGGAAGGTATA

AAGGTTTGCAAAAAGTTAGAAGACGGTTTGAGACATACAGCAATGATACACTCTAAGAACATCGATATCTTAACCAA

-continued

GTACGCCAGAGACATGGAAACTACAATCTTGGTTAAAAACGGTCCATCTTATTCAGGTATTGGTGTCGGTGGTGAAG

GTTACACCACTTTTACCATTGCTGGTCCTACTGGTGAAGGTTTAACATCCGCTAAAAGTTTCGCAAGAAATAGAAGA

TGTGCATTAGTTGGTGGTTTGTCTATTAAGTAG

SEQ ID No: 36

MNLDANNLNNIVSLIMKELDKNNNIDDTGQGCGGEEGKNGIFSSMDTAVSKAKEAQVTLFASKLELRERIIKAIRED

VREAAAELAEIAVEETGMGRVDDKTLKHYVTVDKTPGVEDLRAFAYSGDNGLTVMELSPYGVIGSITPSTNPSETIV

CNAIGMIAAGNSVVFAPHPGAKKTSLRAVEILNKAVARAGGPNNLVVTIFEPSIENTNKMVKNPDIKMVVATGGPGV

VKSVMSSGKKAIGAGAGNPPVLVDETADIEKAAKDIVNGCSFDNNLPCITEKEVVAVDSITDYLIFEMQKNGAYLVQ

DSKTIKKLCEMVINDGSPNRAYVGKNASYILKDLGIDVGDEIKVIIVETDAGHPLAVLEMLMPVLPIVRVKDALEGI

KVCKKLEDGLRHTAMIHSKNIDILTKYARDMETTILVKNGPSYSGIGVGGEGYTTFTIAGPTGEGLTSAKSFARNRR

CALVGGLSIK

SEQ ID No: 37

MTNPVIGTPWQKLDRPVSEEAIEGMDKYWRVANYMSIGQIYLRSNPLMKEPFTRDDVKHRLVGHWGTTPGLNFLLAH

INRLIADHQQNTVFIMGPGHGGPAGTAQSYIDGTYTEYYPNITKDEAGLQKFFRQFSYPGGIPSHFAPETPGSIHEG

GELGYALSHAYGAIMDNPSLFVPCIIGDGEAETGPLATGWQSNKLVNPRTDGIVLPILHLNGYKIANPTILARISDE

ELHDFFRGMGYHPYEFVAGFDNEDHLSIHRRFAELFETIFDEICDIKAAAQTDDMTRPFYPMLIFRTPKGWTCPKFI

DGKKTEGSWRAHQVPLASARDTEAHFEVLKGWMESYKPEELFNADGSIKEDVTAFMPKGELRIGANPNANGGRIRED

LKLPELDQYEITGVKEYGHGWGQVEAPRSLGAYCRDIIKNNPDSFRVFGPDETASNRLNATYEVTKKQWDNGYLSAL

VDENMAVTGQVVEQLSEHQCEGFLEAYLLTGRHGIWSSYESFVHVIDSMLNQHAKWLEATVREIPWRKPISSVNLLV

SSHVWRQDHNGFSHQDPGVTSVLLNKTFNNDHVTNIYFATDANMLLAIAEKCFKSTNKINAIFAGKQPAATWITLDE

VRAELEAGAAEWKWASNAKSNDEVQVVLAAAGDVPTQEIMAASDALNKMGIKFKVVNVVDLIKLQSSKENDEAMSDE

DFADLFTADKPVLFAYHSYAQDVRGLIYDRPNHDNFTVVGYKEQGSTTTPFDMVRVNDMDRYALQAKALELIDADKY

ADKINELNEFRKTAFQFAVDNGYDIPEFTDWVYPDVKVDETSMLSATAATAGDNE

SEQ ID No: 38

ATGGCTACTCAAAACGATATCCCTAACTCGACTCCCGAGGATTTAGCGAAACAAGTTGAAATTGCCGAAAAACACCC

CGATCCTCCTGCTATGCCCTCGCGTCTTCCTGACTCTTTAAAAACCCTCGAAGCTAAAATCGACACTTCAAAGATTA

CCGACGAAGAGGTTGCCAATGTCCATCGTTTTCAACGTGCATGTGATTACCTCGCAGCTTCCCTGATTTTCCTTTCC

AACGGTCTCTACACCGGCGGTGACCTAGAGGAAAAAGATATCAAAACTAGACTGCTAGGCCATTGGGGTACTTGTCC

CGGCTTGAGCATCGTTTACTCTCACTGTAATCGTATCATTAATAAATATGATCTCAACATGCTCTTTGTCGTAGGCC

CTGGCCATGGTGCTCCTGCCATTTTATCGGCTCTTTTCCTTGAAGATTCTTTGGGCCCCTTTTACCCTCGATACCAA

TTTACCAAGGAAGGCTTGAACAACCTTATTAACACCTTCTCCCTTCCCGGTGGTTTTCCTTCTCATGTCAACGCCGA

GGTCCCTGGTGCCATTCACGAGGGCGGTGAATTGGGTTATGCGTTGTCCGTCAGTTACGGTGCAGTTCTTGATCGTC

CCGACCTGATTGTAACTTGCGTTGTCGGTGATGGTGAGGCAGAGACCGGCCCCACTGCCACTTCTTGGCATGCTCAT

AAATTCTTGGATCCTGCTGAATCGGGTGCTGTGATTCCTGTTTTGGAACTTAATGGTTACAAGATTTCCGAGCGTAC

CATTTACGGTTGCATGGATGATAGTGAGCTTCTCTCTTTGTTTAGCGGTTTTGGCTATGAAGTTGCCATTGTAAACG

ATACCCCCGACCAAAACAGGGTTATGGCTGCAACTATGGATTGGGCCGTTGAACGCATTCATGACATCCAACATCGC

GCTCGTGTTAACAGAGAAGAAATCAAACCCAGATGGCCCATGATTATCCTTCGTACCCCTAAGGGTAAAGGATGTCC

CAAGTATTTGAATGGCAAATTTTTAGAAGGTACCTTCCGTGCTCACCAAGTTCCTTTGAAATTGGCTCGCACCGATA

CCAACCAGCGCAATCTTCTAAAGGATTGGCTGAACAGCTACAACTGCCAAGACTTCTTAGACGAACATGGACTTCCT

ACTAAGGGCATCACCGAGCATCTTCCGCCTCGTGAGAAGCGCATGGGTCAGCGTCATGAGACATACAATTCTTATCT

ACCTTTGAAGGTACCTGATTGGAAAAAATACGGTGTCAAGAAGGGAGAAACCACTAGTGCCACTTCGGTCGTTGGTC

AATATCTTGATGAACTCCTCGTAACCAACGATTCAACCCTTAGAATTTTCTCACCCGATGAGTTGGAAAGTAATAAA

-continued

TTAGATGGCGCTTTGAAGCACTCATATCGTACCATGCAAACTGATCCAGAGCTCATGGCAAAGCGTGGTCGCGTTAC

CGAAGTCCTTTCAGAGCACCTTTGCCAAGGTTTCATGCAGGGTTATACTTTAACTGGACGTACCGCGATTTTCCCCT

CATATGAAGCCTTTATGACTATTGTTGTTAGTATGCTTGTTCAGTACTCCAAATTTTTGAAGATGGGCTTGGAGACC

GGATGGCATGGAAAATTTGGTAGCTTGAACTATGTTACTTCCAGTACTTGGGCAAGACAAGAGCATAACGGTTTCTC

CCATCAATCACCCAGGTTTATCACCACTATGCTCTCTCTGAAACCTGGTGTTAGCCGCGTATACTTCCCACCGGATG

CCAATTGCTTCTTAGCAACCGTCGCCCGATGCATGAAGTCTGAGAATACTATCAACCTTATGGTTTCTAGTAAAAAT

CCACAACCAGCCTACCTATCTGTTGAAGAGGCCGAACATCATTGCAAGGCCGGTGCTAGTGTTTGGAAGTTTGCTAG

TACAGATAATGGCGAAAATCCTGATGTTGTTATTGCCGGCGTCGGAAATGAGATTATGTTTGAAGTAGTTAAAGCCG

CAGAGATGCTTCAAAATGACATTCCTGAGCTCCGAGTGCGTGTCATTAACGTCACTGACTTGATGGTACTTTCGAGC

TTACATCCCCATGGTATGAATCCTGCGGAATTTGATTCTTTGTTTACCAAAGATCGCCATGTTCATTTCAACTATCA

CGGTTATGTGATGGACTTGAAGGCTCTCTTGTTTGATCGCATACAAGGTACACGGGTCACTATGGAGGGCTATCGAG

AGGAAGGTACTACTACCACTCCTTTTAATATGATGATGTGTAACAATACCTCTCGTTATCATGTTGCAAGAATGGCT

TTGCAACATGCTTTACACAATCCTACCGTGGCCGTTAATTGTAACATGTTGTGTGCCAAATATGCTTGGAAGCTCGA

AGAGATTGAAAATTATATTATGGAAAACAAGGATGATCCTCCTGAAATTTATGCTGCTCCTGTCTTTAAAAATAAGA

CTTCCACATTATAG

SEQ ID No: 39

MATQNDIPNSTPEDLAKQVEIAEKHPDPPAMPSRLPDSLKTLEAKIDTSKITDEEVANVHRFQRACDYLAASLIFLS

NGLYTGGDLEEKDIKTRLLGHWGTCPGLSIVYSHCNRIINKYDLNMLFVVGPGHGAPAILSALFLEDSLGPFYPRYQ

FTKEGLNNLINTFSLPGGFPSHVNAEVPGAIHEGGELGYALSVSYGAVLDRPDLIVTCVVGDGEAETGPTATSWHAH

KFLDPAESGAVIPVLELNGYKISERTIYGCMDDSELLSLFSGFGYEVAIVNDTPDQNRVMAATMDWAVERIHDIQHR

ARVNREEIKPRWPMIILRTPKGKGCPKYLNGKFLEGTFRAHQVPLKLARTDTNQRNLLKDWLNSYNCQDFLDEHGLP

TKGITEHLPPREKRMGQRHETYNSYLPLKVPDWKKYGVKKGETTSATSVVGQYLDELLVTNDSTLRIFSPDELESNK

LDGALKHSYRTMQTDPELMAKRGRVTEVLSEHLCQGFMQGYTLTGRTAIFPSYEAFMTIVVSMLVQYSKFLKMGLET

GWHGKFGSLNYVTSSTWARQEHNGFSHQSPRFITTMLSLKPGVSRVYFPPDANCFLATVARCMKSENTINLMVSSKN

PQPAYLSVEEAEHHCKAGASVWKFASTDNGENPDVVIAGVGNEIMFEVVKAAEMLQNDIPELRVRVINVTDLMVLSS

LHPHGMNPAEFDSLFTKDRHVHFNYHGYVMDLKALLFDRIQGTRVTMEGYREEGTTTTPFNMMMCNNTSRYHVARMA

LQHALHNPTVAVNCNMLCAKYAWKLEEIENYIMENKDDPPEIYAAPVFKNKTSTL

SEQ ID No: 40

ATGCCTGGTGAAGTCATAGAAAGACCTAACCCTGCTCCTAAGCCATCCCACGTTCCTGATTTGGTAGAAAAGTTGAT

TATCCCTGCCCAAAAGACTAAGTTGGAAAAGTCAGATTGTGACGCTTTACATAAATATAGAAGAGCTGCAGCCTACA

TTGCTGCAGGTCACTGGGGTACTTGCCCAGGTTTGATCTTAGTTTACTCTCATTTGAACTACTTAATTAAAAAGCAA

AACTTGGATATGTTATATGTTGTCGGTCCAGGTCACGGTGCCCCTGGTTTGTTAGCTTCATTGTGGTTAGAAGGTTC

CTTGGGTAAATTCTACCCACAATACACAAAGGATAAGGAAGGTTTGCATAATTTGATATCAACCTTCTCTACTTCAG

CAGGTTTACCATCCCATATAAACGCAGAAACTCCTGGTGCCATCCACGAAGGTGGTGAATTGGGTTATGCCTTATCC

GTTAGTTTTGGTGCTGTCATGGACAATCCAGATTTGATTGTTACATGTGTAGTTGGTGACGGTGAAGCTGAAACCGG

TCCTACCGCTACTTCATGGCACGCTATTAAATATATCGATCCAGCCGAATCCGGTGCTGTTTTGCCTATATTGCATG

TCAACGGTTTTAAAATCTCAGAAAGAACCATATTCGGTTGTATGGACAACAGAGAAATAGTTTGCTTGTTTACTGGT

TATGGTTACCAAGTTAGAATTGTCGAAGATTTGGAAGATATCGACAACGATTTGCATTCTGCAATGTCATGGGCCGT

CGAAGAAATTAGAAACATACAAAAAGCCGCTAGAAGTGGTAAACCAATTATGAAACCACAATGGCCTATGATAGTTT

TGAGAACACCAAAGGGTTGGTCTGGTCCTAAAGAATTACATGGTCAATTCATTGAAGGTTCCTTCCATAGTCACCAA

GTTCCATTGCCTAATGCTAAAAAGGATGACGAAGAATTGCAAGCATTACAAAAGTGGTTGTCTTCATACAAGCCAGA

-continued

TGAATTGTTTACTGAATCTGGTGACGTTATCGATGAAATATTGTCCATAATCCCAAGTGATGACAAAAAGTTGGGTA

TGAGACCTGAAGCATACAAAACTCATTTGCCACCTGACTTACCAGATTGGAGACAATTTTGTGTTAAAAAGGGTGAC

CAATTCAGTGCTATGAAGGCAATTGGTTCTTTTATAGATCAAGTATTCGTTAAAAATCCACACACAGTTAGATTGTT

TTCACCTGATGAATTAGAATCTAACAAGTTGTCAGCAGCCTTATCCCATACCGGTAGAAACTTCCAATGGGATGAAT

TTTCTAACGCTAAAGGTGGTAGAGTAATCGAAGTTTTGTCTGAACACTTATGCCAAGGTTTTATGCAAGGTTATACA

TTGACCGGTAGAACAGGTATTTTTCCATCTTACGAATCATTCTTAGGTATCATTCATACCATGATGGTACAATATGC

CAAATTCGCTAAGATGGCAAAAGAAACTGCCTGGCATCACGATGTTTCCAGTATAAATTACATCGAAACTTCTACAT

GGGCTAGACAAGAACATAATGGTTTTAGTCACCAAAACCCATCTTTCATTGGTGCAGTCTTGAAATTAAAGCCTTAT

GCTGCAAGAGTATACTTGCCACCTGATGCTAACACATTTTTGACTACATTGCATCACTGTTTGAAGAGTAAGAATTA

CATAAACTTAATGGTTGGTTCTAAGCAACCAACACCTGTTTACTTAAGTCCAGAAGAAGCTGAATCTCATTGTAGAG

CAGGTGCCTCAATTTTTAAGTTCTGCTCCACCGACGGTGGTTTGAGACCTGATGTCGTATTAGTTGGTATCGGTGTC

GAAGTAATGTTTGAAGTCATAAAAGCCGCTGCAATCTTGAGAGAAAGATGCCCAGAATTAAGAGTAAGAGTTGTCAA

CGTTACTGATTTGTTCATATTAGAAAACGAAGGTGCTCATCCTCACGCATTGAAGCATGAAGCATTCGACAATTTGT

TTACTGAAGATAGATCTATCCATTTCAACTACCACGGTTACGTTAACGAATTGCAAGGTTTGTTATTCGGTAGACCA

AGATTAGACAGAGCTACAATTAAGGGTTATAAAGAAGAAGGTTCAACCACTACACCTTTCGATATGATGTTGGTCAA

CGAAGTATCCAGATACCATGTCGCAAAGGCCGCTGTAACTGGTGGTGCCAGATTCAATGAAAAGGTTAAGTTGAGAC

ATCAAGAATTGTGTTCAGAATTTGATCACAACATCGCTGAAACTAGAAAGTACATAATGAACAACCATCAAGACCCA

GAAGATACATACAATATGCCTTCCTTCAACTAG

SEQ ID No: 41

MPSDSNDQSISAYGAARSTVKGQNLDPEEVRKMDAYFRASMYLCLGMLYLRENVLLKQPLKVEHLKARLLGHWGSDA

GQSFTWIHMNRLIKKYDLDVLFISGPGHGAPGILSQSYLEGVYSEVYPDKSEDERGMQRFFKQFSFPGGIGSHATPE

TPGSLHEGGELGYSISHAFGTVFDHPNLITLTMVGDGEAETGPLATSWHSTKYLNPCTDGAVLPVLHLNGYKINNPT

LLARISHDELSALMKGYGWTPYFVEGSDRETMHQAMAATLEHCVLEIRKFQKKARESKEPFRPHWPMIILRSPKGWS

APREVDGKLLEGFWRAHQIPITDVLTNPSHLQLLESWMKSYKPEELFTHDGRLISELKALAPTGNSRMSANPVGNGG

LLRRPLDLPDFRKYALTSIDPGATIRGSMVNMSHYLRDVVAFNQTNFRVFGPDETESNKLSEIYKAGKKVWLAEYFP

EDNNGGNLSMAGRVMEMLSEHTCEGWLEGYVLSGRHGLLNSYEPFIHIIDSMVNQHCKWIEKCLEVEWRAKVASLNI

LLTATVWRQDHNGFTHQDPGFLDVVANKSPEVVRIYLPPDGNSLLSVMDHCFRSANYVNVIVADKQDHIQFMDMDAA

IAHCTKGVGIWDWASNDQGAEPDVVMAACGDVPTHEALAATALLREHLPQLKVRFVNVVDLFKLMSKIHHPHGMSDR

EWKAIFTADRPIVFNFHSYPWLIHRLTYKRPGQENIHVRGYKEKGNIDTPFELAVRNQTDRYSLAVDAIDHARGLGN

TASGVREKFLNMQLLAKQKAYDDGIDPDYIRNWTWQYPRKKGEGV

SEQ ID No: 42

ATGACCACAGAACACGATGCTGCCTGCGAAGGTGAAAGTATATCCGCTTACGGTACAGCCAGAGCCACAGTCGAAGA

TCAACCATTAAATACTGATGACTTGAGAAAAATCGATGCCTATTGGAGAGCTTCTTTGTACTTATGTTTGGGCATGT

TGTATTTGAGAGATAACCCATTGTTAAGAGACCCATTAAAGCCTGAACATATAAAGCCTAGATTGTTAGGTCACTGG

GGTTCTGATGCTGGTCAATGCTTCACATACATCCATTTCAACAGATTAATTAACAAATATGACTTGAATGCCATATA

CATCTCCGGTCCAGGTCACGGTGCTCCTGCAATATTATCTCAAGCATATTTGGAAGGTACATATTCCGAAACCTACC

CAGATAAAAGTCAAGACATCGCTGGTATGAGAAGATTTTTCAAGCAATTTTCTTTCCCTGGTGGTATTGGTTCACAT

GCTACCCCAGAAACTCCTGGTTCTATACACGAAGGTGGTGAATTGGGTTATTCCGTAAGTCATGCCTTTGGTACTGT

TTACGATAATCCAGACTTAATTGCTTTGGTCATGGTTGGTGACGGTGAAGCTGAAACTGGTCCTTTAGCAACATCTT

GGCATTCAAATAAGTTCTTGAACCCAATCACAGATGGTGCTGTATTGCCTGTTTTGCATTTGAACGGTTACAAGATT

AATAACCCAACCATTTTGGCTAGAATAACTCACGAAGAATTAGAAGCATTGTTTATAGGTTACGGTTACACTCCATA

CTTCGTCGAAGGTTCCGATCCTGCCAGTATGCATCAAGCTATGGCTGCAACAATGGAAAGATGTGTATTGAAAATTA

-continued

GAGAATTTCAAGATAAGGCCAGACACACTGGTACAGCTTTCAGACCAAGATGGCCTATGATTATATTGAGATCCCCA

AAAGGTTGGACTGCTCCTAGAAAGGTTGATGGTCATTATTTGGAAGGTTTTTGGAGAGCACATCAAATTCCAATACC

TGACGTTGTCTCAAATCCAGCACATTTGCAATTGTTAGAATCTTGGATGAGATCATACAGACCTGAAGAATTATTTG

ATGCACAAGGTAGATTGATTCCAGAATTACATGAATTGGCCCCTAAAGGTAAAAGAAGAATGTCCGCAAATCCAGTT

GCCAACGGTGGTTTGTTAAGAAGACCATTAGATATGCCTGACTTTAGAGTTTTCAGTATTGCTGTCCAAGATGCAGG

TGGTACAAGAGCAGACAATGTTCCAACCTTAGGTCATTTCTTGAGAGAAATCACTAGAAGAAACATGCAAAACTTTA

GAATTTTCGGTCCTGATGAAACCCAATCTAACAAATTAGATGCTATCTATGACGTCACTCAAAAAGTATGGTTGGGT

GCATACTTTCCAGAAGATGCCGACGGTGGTGCCTTAGCTTTGTCCGGTAGAGTTATGGAAATGTTGAGTGAACATAC

ATTAGAAGGTTGGTTGGAAGGTTATTTGTTATCTGGTAGACATGGTTTGATTAATTCATACGAAGCCTTTATCCATA

TCATAGATTCTATGTTCAACCAACACGCTAAATGGTTAGAAAAGTGTAACGAATTGCCATGGAGAGCAAAAGTAGCC

TCATTAAATTTGTTGATCACAGGTTTGGTTTGGAGACAAGATCATAACGGTTTTACCCACCAAGATCCAGGTTTCTT

AGACGTAGTTGCTAATAAGTCACCTAACGTCGTAAGAATATATTTGCCACCTGATGCAAATTGTTTGTTATCCGTCA

CCGACCATTGCTTGAGAAGTGTAAACTACATCAACGTTATCGTCGCTGATAAGCAAACTCATTTGCAATACTTGGAT

ATGGACGCCGCTATGGCTCACTGTGCAAAGGGTGCCGGTATTTGGGAATGGGCATCTAATGATATGGGTGAAGAACC

AGACGTTGTCATGGCCTCTTGCGGTGACGTTCCTACTATGGAATCATTAGCAGCCACAGCATTGTTGAGACAACATT

TGCCAGATATCAAGATCAGATTCGTTAACGTAGTTGACTTATTCAAGTTGGTCCCACACACCGAACATCCTCACGGT

ATGACTGATAGAGAATTTGAAGCATTGTTTACTTCTTCTAAGCCAGTTATTTTTAATTTCCATTCATATCCTTGGTT

AATCCACAGATTGACCTACAGAAGACCAGCACAACATCACATACATGTTAGAGGTTACAAGGAAAAGGGTAACATCG

ATACTCCTTTAGAATTGGCTATAAGAAACCAAACAGACAGATTTTCTTTGGCTATTGATGCAATAGACAGAATCCCA

AGATTCTGTGATACAGGTTCAGGTGTTAGAGAAATTTTGTTGAATTTGCAATTCGCATGCAAGAACCATGCCTATGA

ATACGGTGTCGATCCACAAGAAATAACAGACTGGCAATGGCCATTCAGAGATACCCCTTAA

SEQ ID No: 43

MTTEHDAACEGESISAYGTARATVEDQPLNTDDLRKIDAYWRASLYLCLGMLYLRDNPLLRDPLKPEHIKPRLLGHW

GSDAGQCFTYIHFNRLINKYDLNAIYISGPGHGAPAILSQAYLEGTYSETYPDKSQDIAGMRRFFKQFSFPGGIGSH

ATPETPGSIHEGGELGYSVSHAFGTVYDNPDLIALVMVGDGEAETGPLATSWHSNKFLNPITDGAVLPVLHLNGYKI

NNPTILARITHEELEALFIGYGYTPYFVEGSDPASMHQAMAATMERCVLKIREFQDKARHTGTAFRPRWPMIILRSP

KGWTAPRKVDGHYLEGFWRAHQIPIPDVVSNPAHLQLLESWMRSYRPEELFDAQGRLIPELHELAPKGKRRMSANPV

ANGGLLRRPLDMPDFRVFSIAVQDAGGTRADNVPTLGHFLREITRRNMQNFRIFGPDETQSNKLDAIYDVTQKVWLG

AYFPEDADGGALALSGRVMEMLSEHTLEGWLEGYLLSGRHGLINSYEAFIHIIDSMFNQHAKWLEKCNELPWRAKVA

SLNLLITGLVWRQDHNGFTHQDPGFLDVVANKSPNVVRIYLPPDANCLLSVTDHCLRSVNYINVIVADKQTHLQYLD

MDAAMAHCAKGAGIWEWASNDMGEEPDVVMASCGDVPTMESLAATALLRQHLPDIKIRFVNVVDLFKLVPHTEHPHG

MTDREFEALFTSSKPVIFNFHSYPWLIHRLTYRRPAQHHIHVRGYKEKGNIDTPLELAIRNQTDRFSLAIDAIDRIP

RFCDTGSGVREILLNLQFACKNHAYEYGVDPQEITDWQWPFRDTP

SEQ ID No: 44

ATGACAAATCCTGTAATAGGTACTCCTTGGGCAAAGTTAGAAACACCAATAGCCGAAGAAACCATAGAAGCCGTAGA

TAAATACTGGAGAGCTGCAAACTATTTGTCCATAGGTCAAATCTACTTGAGAAGTAATCCATTAATGAAGGAACCTT

TTACAAGAGAAGATGTCAAGCATAGATTAGTAGGTCACTGGGGTACTACACCAGGTTTGAACTTCTTGTTGGGTCAT

ATCAACAGATTGATCGCTGATCACCAACAAAACACTGTTATTATCATGGGTCCAGGTCATGGTGGTCCTGCAGGTAC

CTCCCAAAGTTATTTGGATGGTACTTACTCAGAATACTACCCAAAGATCACAAACGACGAAGCTGGTTTGCAAAAGT

TTTTCAGACAATTTTCCTATCCAGGTGGTATACCTAGTCATTTCGCTCCAGAAACTCCTGGTTCCATCCACGAAGGT

GGTGAATTGGGTTATGCATTATCCCATGCTTACGGTGCAATCATGAATAACCCAAGTTTGTTTGTTCCTTGTATTGT

-continued

CGGTGACGGTGAAGCAGAAACCGGTCCATTAGCCACTGGTTGGCAATCTAACAAATTGGTTAATCCAAGAACCGATG

GTATTGTCTTGCCTATCTTGCATTTGAATGGTTACAAGATTGCTAATCCAACTATCTTGTCTAGAATCTCAGATGAA

GAATTACACGAATACTTCAAGGGTATGGGTTACGAACCTTTTGAATTTGTTGCTGGTTTCGATGACGAAGATCATTT

GTCAATACACAGAAGATTTGCAGATTTGTTAGAAACAGTCTTCGACAAGATCTGCAACATCAAGGCTAGAGCAGAAA

CTGATGACATGACAAGACCATGTTACCCTATGATCATTTTTAGAACACCAAAAGGTTGGACCTGCCCTAAGTTCATA

GATGGTAAAAAGACTGAAGGTTCTTGGAGAGCACATCAAGTTCCATTGACTTCAGCAAGAGACACAGAAGCCCACTT

CCAAATCTTGAAAAATTGGTTAGCTTCTTACAAGCCTGAAGAATTGTTCGATGAAAAGGGTGCATTAAGACCAGAAG

TTACATCATTCATGCCTAAGGGTGACTTAAGAATTGGTGAAAATCCAAACGCTAATGGTGGTAGATTGTTGAAGCCA

TTGGAATTACCTGATATCCATGACTACGAAATAGATGTTAAAAAGCATGGTCACGGTTGGGGTGCCACCGAAGCTAC

TAGAGTATTGGGTTATTACACAAGAGATGTTTTAGCTAAGAATCCAACCGATTTTAGAATTTTCGGTCCTGACGAAA

CTGCATCTAACAGATTAGCCGCTGCATATGAAGTAACAAATAAGCAATGGGATGCAGACTACTTGTCCGAATTAACA

GATGAACATATGGCCCACACCGGTCAAGTTATCGAACAATTAAGTGAACATCAAATGGAAGGTTTCTTGGAAGGTTA

TTTGTTAACTGGTAGACACGGTATTTGGTCTTCATACGAATCTTTCGTTCATGTCATAGATTCAATGATCAATCAAC

ACGCTAAATGGTTGGAAGCAACTGTTAGAGAAATACCATGGAGAAAGCCTATCGCTGGTTTGAACTTGTTAGTAACA

TCTCATGTTTGGAGACAAGATCATAATGGTTTTTCACACCAAGACCCAGGTTTCGTTGATATATTGTTGAACAAAAA

CTTCAACAACGATCATGTTGTCAACATCTATTTCCCTGCCGACGCTAACATGTTGTTGAACGTTGGTGAAAGATGTT

ACAAATCCACAAACTGCATCAATGCAATTTTTGCCGGTAAACAACCAGCCGCTACCTATCAAAGTGTCGATGAAGCA

GCCGCTGAATTGGAAAAAGGTGCAGCCAGATGGGATTGGGCTTCTAATGCAAAGGACGCCGAAGATGCTGACGTTGT

TATTGCTACTGCTGGTGACATACCAACTCAAGAAGCATTGGCTGCTGATGACATGTTGCAAAAATTGGGTGTAAAGG

TTCAATTCGTTAACGTCGTAGATTTGTTGAAGATCCAAGACGCTGAAGAAAACGATCAAGCATTGTCTGACGAAGAG

TTTACTGAATTATTCTCAAAGGATAAGCCAGTCTTGTTTGCATTCCATGCCTATCCTGGTTCAATCTATAGATTGAT

ACATGGTAGACCAAACCACGATAATTTTTCCGTACATGGTTATGAAGAACAAGGTAGTACCACTACACCTTTCGATA

TGGTCAGAGTAAATAACATGGACAGATGGTGTTTAGCCGCTTCTGCCTTGCAATTAGTTGATGCTAATAAGTACACT

GATCAAATAGACAAGTGGACAAAGTTTAGAGATGAAGCCTTTCAATTCGCTGTTGATAAAGGTTATGATCATCCAGA

CTACACCGATTGGGTATGGCCTGATGCTAACAGAGCAGGTCAAGAAACTATTTCTGCCACAGCAGCCACCGCTGGTG

ACAATGAATAA

SEQ ID No: 45

MTNPVIGTPWAKLETPIAEETIEAVDKYWRAANYLSIGQIYLRSNPLMKEPFTREDVKHRLVGHWGTTPGLNFLLGH

INRLIADHQQNTVIIMGPGHGGPAGTSQSYLDGTYSEYYPKITNDEAGLQKFFRQFSYPGGIPSHFAPETPGSIHEG

GELGYALSHAYGAIMNNPSLFVPCIVGDGEAETGPLATGWQSNKLVNPRTDGIVLPILHLNGYKIANPTILSRISDE

ELHEYFKGMGYEPFEFVAGFDDEDHLSIHRRFADLLETVFDKICNIKARAETDDMTRPCYPMIIFRTPKGWTCPKFI

DGKKTEGSWRAHQVPLTSARDTEAHFQILKNWLASYKPEELFDEKGALRPEVTSFMPKGDLRIGENPNANGGRLLKP

LELPDIHDYEIDVKKHGHGWGATEATRVLGYYTRDVLAKNPTDFRIFGPDETASNRLAAAYEVTNKQWDADYLSELT

DEHMAHTGQVIEQLSEHQMEGFLEGYLLTGRHGIWSSYESFVHVIDSMINQHAKWLEATVREIPWRKPIAGLNLLVT

SHVWRQDHNGFSHQDPGFVDILLNKNFNNDHVVNIYFPADANMLLNVGERCYKSTNCINAIFAGKQPAATYQSVDEA

AAELEKGAARWDWASNAKDAEDADVVIATAGDIPTQEALAADDMLQKLGVKVQFVNVVDLLKIQDAEENDQALSDEE

FTELFSKDKPVLFAFHAYPGSIYRLIHGRPNHDNFSVHGYEEQGSTTTPFDMVRVNNMDRWCLAASALQLVDANKYT

DQIDKWTKFRDEAFQFAVDKGYDHPDYTDWVWPDANRAGQETISATAATAGDNE

SEQ ID No: 46

ATGACCTCCCCTGTAATTGGTACCCCATGGAAGAAGTTAAACGCTCCTGTAAGTGAAGAAGCTATTGAAGGTGTCGA

TAAGTATTGGGGTGCTGCAAACTACTTGTCCATCGGTCAAATATATTTGAGAAGTAACCCATTGATGAAAGAACCTT

TCACTAGAGAAGATGTAAAGCATAGATTGGTTGGTCACTGGGGTACTACACCAGGTTTGAACTTTTTAATCGGTCAT

-continued

ATCAACAGATTGATCGCTGATCACAAGCAAAACACCGTTATTATCATGGGTCCAGGTCATGGTGGTCCTGCAGGTAC

TGCCCAATCTTATTTGGATGGTACCTACACTGAAACATTCCCTAAAATAACTAAGGACGAAGCAGGTTTGCAAAAGT

TTTTCAGACAATTTTCCTACCCAGGTGGTATTCCTAGTCATTATGCTCCAGAAACACCTGGTTCAATACACGAAGGT

GGTGAATTGGGTTACGCATTATCCCATGCTTATGGTGCAGTTATGAATAACCCAAGTTTGTTTGTTCCTGCAATTGT

CGGTGACGGTGAAGCCGAAACTGGTCCATTAGCAACAGCCTGGGATTACGACAACATCATTAATCCAAGAACTGATG

GTATCGTTTTGCCTATATTGCACTTAAACGGTTACAAGATCGCTAACCCAACAATCTTGTCTAGAATCTCAGATGAA

GAATTGCATGAATTTTTCCACGGTATGGGTTATGAACCTTACGAATTTGTTGCTAGATTCGATAATGAAGACCATTT

GTCTATTCACAGAAGATTTGCAGAATTGTTCGAAACTGTCTTCGACGAAATCTGTGATATCAAAGCCGCTGCACATA

CCGATGACATGACTAGACCATTCTACCCTATGATAATCTTTAGAACCCCAAAAGGTTGGACTTGCCCTAAGTTCATT

GATGGTAAAAAGACAGAAGGTTCCTGGAGAAGTCATCAAGTACCATTGGCTTCCGCAAGAGATACCGAAGCTCACTT

TGAAGTTTTGACTAACTGGTTGGAATCTTACAACCCTGAAGAATTGTTCGATGAAAACGGTGCTGTAAAACCAGAAG

TTACAGCTTTTATGCCTACCGGTGAATTAAGAATCGGTGCTAATCCAAACGCAAATGGTGGTGTTATTAGAGAAGAA

TTGAATTTGCCTGCCTTAGAAGATTACGAAGTAAAAGAAGTTGCTGAATATGGTCATGGTTGGGGTCAATTGGAAGC

TACTAGAAGATTAGGTGTTTACACAAGAGACATTTTTAAGAACAACCCAGATTCTTTTAGAATATTCGGTCCTGATG

AAACTGCATCAAACAGATTGCAAGCCGCTTACGACGTCACAAATAAGAAATGGGATGCAGGTTATTTGTCTTCACAA

GTAGATGACCATATGGCCGTCACAGGTCAAGTAACCGAACAATTGTCTGAACACCAAATGGAAGGTTTCTTGGAAGC

TTACTTGTTAACTGGTAGACATGGTATCTGGTCCAGTTATGAATCTATTGTCCATGTAAACGATTCAATGTTGAATC

AACACGCAAAATGGTTCGCAGCCACAGTTAGAGAAATTCCATGGAGAAAGCCTATCTCTTCAATGAATTTGTTAGTT

TCCAGTCATGTCTGGAGACAAGACCAAACAGGTTTTTCTCACCAAGATCCAGGTGTCACCTCCGTATTGTTGAGTAG

ATGTTTCAACAACGATAACGTTATAGGTATATACTTTGCTGTCGATTCCGACATGTTGTTAGCCGGTGCTGATAAAT

GCTATCAAAGTAGAAAGGTCATGAATGCCGGTATAGTAGGTAGAGCTCCAGCTGCAACCTGGTTGATCTTAGGTGAA

GCAAGAGCCGAATTGGAAAAAGGTGCCGCTGAATGGGAATGGGCCTCTACTGCTAAGTCAAATGACGAAGCTCAAAT

TGTATTAGCTTCAGCAGGTGACGTTCCTGCACAAGAAATCATGGCAGCCGCTGACAAGTTGAACGAATTGGGTATTA

AGTTTAAAGTTGTCAACGTAGTTGATTTGGTTAAGTTGCAATCTACAAAGGAAAATGACCAAGCTATATCAGATGCA

GACTTCGCCGACTTGTTTACCGAAGATAAGCCAGTCTTATTCGCTTATCATTCTTACGCATCAGACGTTAGAGGTTT

GATCTACGATAGACCAAATCATGATGACTTTAACGTTCACGGTAATCAAGAACAAGGTTCTACCACTACACCTTACG

ACATGGTTAGAGTCAACAACATCGATTCATACGAATTGGTTGCCGAAGCTTTAAGAATGATAGATGCCGACAAGTAC

GCTGATGAAATCAACGAATTGGAAGCTTTTAGACAAGAAGCATTTCAATTCGCCGTTGATAATGGTTATGATCATCC

AGACTACACTGATTGGGTCTATTCTGGTGTCAACACAACCAAGCAAGGTGCAGTCTCAGCCACAGCAGCAACCGCAG

GTGACAACGAATAA

SEQ ID No: 47

MTSPVIGTPWKKLNAPVSEEAIEGVDKYWGAANYLSIGQIYLRSNPLMKEPFTREDVKHRLVGHWGTTPGLNFLIGH

INRLIADHKQNTVIIMGPGHGGPAGTAQSYLDGTYTETFPKITKDEAGLQKFFRQFSYPGGIPSHYAPETPGSIHEG

GELGYALSHAYGAVMNNPSLFVPAIVGDGEAETGPLATAWDYDNIINPRTDGIVLPILHLNGYKIANPTILSRISDE

ELHEFFHGMGYEPYEFVARFDNEDHLSIHRRFAELFETVFDEICDIKAAAHTDDMTRPFYPMIIFRTPKGWTCPKFI

DGKKTEGSWRSHQVPLASARDTEAHFEVLTNWLESYNPEELFDENGAVKPEVTAFMPTGELRIGANPNANGGVIREE

LNLPALEDYEVKEVAEYGHGWGQLEATRRLGVYTRDIFKNNPDSFRIFGPDETASNRLQAAYDVTNKKWDAGYLSSQ

VDDHMAVTGQVTEQLSEHQMEGFLEAYLLTGRHGIWSSYESIVHVNDSMLNQHAKWFAATVREIPWRKPISSMNLLV

SSHVWRQDQTGFSHQDPGVTSVLLSRCFNNDNVIGIYFAVDSDMLLAGADKCYQSRKVMNAGIVGRAPAATWLILGE

ARAELEKGAAEWEWASTAKSNDEAQIVLASAGDVPAQEIMAAADKLNELGIKFKVVNVVDLVKLQSTKENDQAISDA

-continued

DFADLFTEDKPVLFAYHSYASDVRGLIYDRPNHDDFNVHGNQEQGSTTTPYDMVRVNNIDSYELVAEALRMIDADKY

ADEINELEAFRQEAFQFAVDNGYDHPDYTDWVYSGVNTTKQGAVSATAATAGDNE

SEQ ID No: 48

ATGACAAACATCAACTATTCCTCAGAATCATACTTAAAGAAGGTAGACGCTTATTGGAGAGCCACAAACTACATTTC

AGTCGGTCAATTGTATTTGAAGGGTAACCCATTGTTAAGAGAACCATTAAAGCCTGAACATGTTAAAAATGCTGTTT

TTGGTCACTGGGGTACTATAGCTGGTCAAAACTTCATCTACGCACATTTGAATAGAGTTATCAACAAATACGATTTG

TCCATGTTGTACATTAGTGGTCCAGGTCACGGTGGTCAAGTCATGGTATCTAACTCATATTTGGATGGTTCCTATAG

TGAAGTTTACCCTGAAATTACTCAAGACTTGGAAGGTTTATCCAAGTTGTACAAGCAATTTTCTTTCTCAGGTGGTA

TCGGTTCTCATGCTACACCACAAGCACCTGGTTCAATTCACGAAGGTGGTGAATTAGGTTATTCTTTGGTTCATGGT

TTTGGTGCCATCTTAGATAATCCAGACTTGATTGCTACCGTTGTCGTAGGTGACGGTGAAGCCGAAACTGGTCCTTT

AGCTACATCTTGGCAATTGAATAAGTTTATAAACCCAGTTACAGATGGTGTTGTCTTACCTATCTTGTATTTGAATG

GTTTCAAAATCTCAAACCCAACAATTATGGCTAAGATGACCGATGAAGAATTACAAAAGTACTTCGAAGGTTTGGGT

TGGGACCCAATTTTCGTCGAGGGTAATGAACCTGAAGTAATGCATCAATTGATGGCAGAAAAGATGGATGAAGCCAT

AGAAAAGATTTTGACAATCAAAAAGCACGCATTGGAAGAAAATGATATGTCTAGACCAAAGTGGCCTGTTATTTTAA

ACAGAACCCCAAAAGGTTGGACTGGTCCTAAGGAATTGGATGGTAAACCAATTGAAGGTTCCTTTAGAGCCCATCAA

GTTCCAATACCTTTCGATAGTAAGCACATGGAATGTGCTGATGACTTTGTCAAATGGATGAATACCTATGGTCCTGA

AGAATTATTCACTGAAGATGGTAAATTGGTTGAAGAAATCGCAGAAATCATCCCAAAGGGTGACAGAAGAATGTCAT

GCAATCCTGCCACTAACGGTGGTAAAATAATGAAGGGTTTGAGATTGCCAGATTATAGAGAATACGCAATCGACAAT

AAGGAAAAGGGTAAAAACGTTGCCCAAGATATGTTGATATTGGGTAAATACGTCAGAGATGTAATGAAGTTAAACGA

CAAGGAAAGAAACTTTAGAGTCTTCTCTCCAGATGAAGCTGCATCAAACAGATTGTACGCTATGTTCGAAGAAACAA

AGAGACAATGGGTTGGTGAAATTGATGAACCATACGACGAATTTTTAGCACCTGATGGTAGAATTTTAGACTCCATG

TTGAGTGAACATATAGCTGAAGGTGCATTGGAAGCCTATTTGTTAACAGGTAGACATGGTTTTATCCACTCTTACGA

ATCATTCTTAAGAGTAGTTGATTCAATGATCACCCAACATTTCAAGTGGTTGAACCAATGTGAAGATATTCCATGGA

GAGCTGACATCCCTTCCTTGAATTTGATTAATACTTCTCATATCTGGCAACAAGATCATAACGGTTATACACACCAA

GACCCAGGCATGTTAGGTCATTTGGCTGATAAAAATTCTGGTTTAATTCACGAATACTTGCCTGTTGATGCAAACAC

ATTGTTAGTCACCTTCGACAAGTGCATTAGATCTATAAATCAAGTTAACGTCATGACAGCCTCAAAACATCCAAGAC

AACAATGGTTCACCATCGAAGAAGCTGAATATTTGGTAAATAAGGGTTTGGGTATCGTTGATTGGGCATCTACTGAC

AAAAACGGTGAAACAGATATTGTATTTGCAATGGCCGGTGACACCCCAACTTTAGAAGGTTTGGCCGCTGTTCAATT

GTTACATGATTATTTGCCTGACTTGAAGATTAGATTCGTTAACATCGTCGATTTGTTGAAATTGCAATCCCCAGAAG

TTTACGAACATGGTATCAGTGATGAAGAGTTTAATATGATCTTCACCAAGGACAAACCTATCATTTTTGGTTTCCAC

GGTTACGAAAACTTAGTCGATACTTTGTTTTTCAAGAGAGACAACCATAACGTATCTGTTCACGGTTACAGAGATAA

AGGTGAAATAACTACAGGTTTTGACATGAGAGTCATGAACGAATTAGATAGATTCAACTTGGTAAAGGACGCTATCT

ATAATTTGCCACAATTGGGTAACAAAGGTGCACATATCATCCAAGAAATGAACGAAAAGTTGGAAATCCATACTAAG

TTCGTTCACGAAAACGGTATCGATTTGCCTGAAATTGCTAACTGGCAATGGAAGGGTTTGAAATAA

SEQ ID No: 49

MTNINYSSESYLKKVDAYWRATNYISVGQLYLKGNPLLREPLKPEHVKNAVFGHWGTIAGQNFIYAHLNRVINKYDL

SMLYISGPGHGGQVMVSNSYLDGSYSEVYPEITQDLEGLSKLYKQFSFSGGIGSHATPQAPGSIHEGGELGYSLVHG

FGAILDNPDLIATVVVGDGEAETGPLATSWQLNKFINPVTDGVVLPILYLNGFKISNPTIMAKMTDEELQKYFEGLG

WDPIFVEGNEPEVMHQLMAEKMDEAIEKILTIKKHALEENDMSRPKWPVILNRTPKGWTGPKELDGKPIEGSFRAHQ

VPIPFDSKHMECADDFVKWMNTYGPEELFTEDGKLVEEIAEIIPKGDRRMSCNPATNGGKIMKGLRLPDYREYAIDN

KEKGKNVAQDMLILGKYVRDVMKLNDKERNFRVFSPDEAASNRLYAMFEETKRQWVGEIDEPYDEFLAPDGRILDSM

-continued

LSEHIAEGALEAYLLTGRHGFIHSYESFLRVVDSMITQHFKWLNQCEDIPWRADIPSLNLINTSHIWQQDHNGYTHQ

DPGMLGHLADKNSGLIHEYLPVDANTLLVTFDKCIRSINQVNVMTASKHPRQQWFTIEEAEYLVNKGLGIVDWASTD

KNGETDIVFAMAGDTPTLEGLAAVQLLHDYLPDLKIRFVNIVDLLKLQSPEVYEHGISDEEFNMIFTKDKPIIFGFH

GYENLVDTLFFKRDNHNVSVHGYRDKGEITTGFDMRVMNELDRFNLVKDAIYNLPQLGNKGAHIIQEMNEKLEIHTK

FVHENGIDLPEIANWQWKGLK

SEQ ID No: 50

ATGGCAGAAGAAACCTCATCATTAACATCATTCGGTCAAGCAAGATCCACTGTCAAAGACCAACCATTAACTGTAGA

AGAATTAAAAAAAATTGATGCCTATATGAGAGCTTCTTTGTACTTATGTTTGGGCATGTTGTATTTGAGACAAAACC

CATTGTTGAAGGAACCTTTGAAGAAAGAACATTTGAAGGCCAGATTGTTAGGTCACTGGGGTTCCGATGCTGGTCAA

ATCTTTACTTACATCCATATGAACAGATTGATTAAGAAATACGATTTGGACGCTTTGTTCGTTAGTGGTCCAGGTCA

CGGTGCACCTGCCGTCTTATCCCAAAGTTATTTGGAAGGTGTATATACCGAAGTTTACCCAAATATTACTGAAGATG

TCGAGGGTATGAGAAGATTTTTCAAGCAATTTTCCTTCCCTGGTGGTGTTGGTAGTCATGCAACACCAGAAACCCCT

GGTTCTTTACACGAAGGTGGTGAATTGGGTTACTCTATTTCACATGCTTTTGGTACAGTCTTCGATAACCCAAACTT

AATCACTTTGACAATGGTTGGTGACGGTGAATCAGAAACCGGTCCTTTAGCTGCATCCTGGCATAGTACAAAGTTCT

TGAACCCAATCACCGATGGTGCTGTATTGCCTGTTTTGCATTTGAATGGTTACAAGATCAATAACCCAACAGTTTTA

GCTAGAATATCCCACGAAGAAATCGAAGCATTGTTTATTGGTTATGGTTGGAAACCTTACTTCGTTGAAGGTTCTGA

TTTGACCTCAATGCATCAAGCAATGGCCGCTACTTTAGAAAAGGCCGTTTTGGAAATTAAAGCATACCAAAAGCAAG

CCAGAGATTCTGGTAAAGCCTTTAGACCAAGATGGCCTATGATTATATTAAGATCTCCAAAGGGTTGGACTGCACCT

AGAAACGTTTCAGGTCATCACTTGGAAGGTTATTGGAGAGCCCATCAAATTCCATTAGCCGATGTTGCTTCCAATAG

TGAACACTTGAAATTGTTAGAAGACTGGATGAGATCTTACAAGCCAGAAGAATTATTCACAGAAGATGGTAAATTGA

TACCTGAATTAAAGGCATTGCCACCTGCAGGTCAAGCCAGAATGTCTGCCAATCCAGTCTCAAACGGTGGTTTAGTA

AGAAAAGCATTAAACTTGCCTGATTTCAAGGACTACGCTATTAAGGATATAGCACCAGGTGTTACTTTAGCCCCTTC

TATGTCAAATATGGCTTTGTTCGTCAGAGATGTAATTAAAAAGAATCAAACAAACTTCAGATTATTCGGTCCAGACG

AAACCGAATCAAACAAATTGGCAGCCGTTTATGAAGCTGGTAAAAAGGTCTGGATGGGTGAATACTTACCAGAAGAT

ACCGACGGTGGTAATTTGGCTCATGCAGGTAGAGTTATGGAAATTTTGTCCGAACACACTGTCGAAGGTTGGTTAGA

AGGTTATGTATTGTCTGGTAGACATGGTTTGTTAAACTCATACGAACCTTTTATTCATATCATCGATAGTATGGTTA

ACCAACACTGTAAGTGGATAGAAAAGTGCTTAGAAGTCGAATGGAGAGTTAAAGTCTCTTCATTGAACATCTTGTTG

ACCGCAACTGTTTGGAGACAAGATCATAATGGTTTTACTCACCAAGATCCAGGTTTCTTAGACGTTGTCGCTAATAA

GTCTCCTGAAGTAGTTAGAATATATTTGCCACCTGATGGTAATTGTTTGTTATCCGTAATGAACCATTGCTTCGACA

GTAAAAATTACGTTAACGTCGTAGTTGCTGATAAGCAAGACCATTTGCAATACTTGGATATGGAAGCTGCAGTAGCT

CACTGTACAAAAGGTTTAGGTATTTGGGAATGGGCATGCGTTGGTGACCCAAATGAAAACCCTGACTTAGTAATGGC

ATGTTGCGGTGACGTTCCAACTATGGAATCTTTGGCCGCTACAGCTTTGTTGAAGGAATATTTGCCTGAATTGAAGA

TCAGATTCGTTAACGTCGTTGATTTGTTTAAATTGATATCACATGTCGATCATCCACACGGTTTGACCGACAGACAA

TGGGTATCCTACTTCACTGAAGACACACCAATCATCTTTAATTTCCATAGTTACCCTTGGTTAATACACAGATTGAC

ATACAAGAGACCAGGTTCACAAAACATCCATGTTAGAGGTTACAAGGAAAAGGGTAACATAGATACTCCTTTAGAAT

TGGCAATCAGAAATGAAACAGACAGATACTCTTTAGCTATGGATGCAATAGACAGATTGCCACATTTGAAAAATAAG

GGTTCAATGGCTAGAGAAAAAATTGTACGATGCACAAATTAAGGCCAGAGACTGGGCTTTTGAACACGGTATAGATCC

AGAAGACGTTAGAAAATGGAAGTGGCCATACGGTCCTAAAACTGAAGGTATTGCCTCTAAGTTGGGTTTCGGTGGTG

AAAATAAGCAACAAGTTGCTTCCGTCGGTACAAGTGAATAA

SEQ ID No: 51

MAEETSSLTSFGQARSTVKDQPLTVEELKKIDAYMRASLYLCLGMLYLRQNPLLKEPLKKEHLKARLLGHWGSDAGQ

IFTYIHMNRLIKKYDLDALFVSGPGHGAPAVLSQSYLEGVYTEVYPNITEDVEGMRRFFKQFSFPGGVGSHATPETP

-continued

GSLHEGGELGYSISHAFGTVFDNPNLITLTMVGDGESETGPLAASWHSTKFLNPITDGAVLPVLHLNGYKINNPTVL

ARISHEEIEALFIGYGWKPYFVEGSDLTSMHQAMAATLEKAVLEIKAYQKQARDSGKAFRPRWPMIILRSPKGWTAP

RNVSGHHLEGYWRAHQIPLADVASNSEHLKLLEDWMRSYKPEELFTEDGKLIPELKALPPAGQARMSANPVSNGGLV

RKALNLPDFKDYAIKDIAPGVTLAPSMSNMALFVRDVIKKNQTNFRLFGPDETESNKLAAVYEAGKKVWMGEYLPED

TDGGNLAHAGRVMEILSEHTVEGWLEGYVLSGRHGLLNSYEPFIHIIDSMVNQHCKWIEKCLEVEWRVKVSSLNILL

TATVWRQDHNGFTHQDPGFLDVVANKSPEVVRIYLPPDGNCLLSVMNHCFDSKNYVNVVVADKQDHLQYLDMEAAVA

HCTKGLGIWEWACVGDPNENPDLVMACCGDVPTMESLAATALLKEYLPELKIRFVNVVDLFKLISHVDHPHGLTDRQ

WVSYFTEDTPIIFNFHSYPWLIHRLTYKRPGSQNIHVRGYKEKGNIDTPLELAIRNETDRYSLAMDAIDRLPHLKNK

GSMAREKLYDAQIKARDWAFEHGIDPEDVRKWKWPYGPKTEGIASKLGFGGENKQQVASVGTSE

SEQ ID No: 52

ATGGTTGCCACACCTGAAAGACCTACATTAGAACAAACCCCATTATCCGCAGAAGAATTAAGACAAATACAAGCATA

CTGGAGAGCATGTAACTATTTGGCTGTTGGTATGATATATTTGAGAGATAACCCATTGTTGAAAGACCCTTTGACTG

AAGATCATGTTAAGAATAGATTGTTGGGTCACTGGGGTTCTTCACCAGGTTTGTCTTTTATATATATCCATTTGAAC

AGATTAATTAAAAAGTATGGTTTAGATGTTATATACATGGCCGGTCCAGGTCACGGTGCTCCTGGTATTTTGGGTCC

AGTCTACTTAGAAGGTACTTATTCCGAAACATACCCTGACAAAAGTGAAGATGAAGAGGGTATGAAAAAGTTTTTCA

AGCAATTTTCTTTCCCAGGTGGTATTGGTTCACATTGTACCCCAGAAACTCCTGGTTCTATACACGAAGGTGGTGAA

TTGGGTTATTCCTTAAGTCATGCTTACGGTGCTGCATTGGACAATCCTGATTTGATTGTTGCCGCTGTTGTCGGTGA

CGGTGAAGCAGAAACAGGTCCATTGGCCACCGCTTGGCATTCTAATAAGTTTATTAACCCTATTAGAGATGGTGCTG

TTTTGCCAATCTTGCATTTGAATGGTTATAAGATTGCAAACCCAACTATCTTAGCCAGAATTTCCCACGAAGAATTG

GAATATTTGTTTAAAGGTTACGGTTACAAGCCTTACTTTGTTGAAGGTAGTGATCCAGAAGTCATGCATCAAAAGAT

GGCAGCCACATTAGAAACCGCAATAGCCGAAATCAAGCACATTCAACAAGAAGCTAGAACATCAGGTGTCGCAAAAA

GACCAATATGGCCTATGATCGTATTGAGATCTCCTAAGGGTTGGACTGGTCCAGCTTCAGTTGACGGTAAAAAGACA

GAAGATTTCTGGAGATCTCATCAAGTCCCTTTATCAGGCATGCATGGTAATCCAGCACACATTAAAGTATTGGAAGA

CTGGTTAAAGTCCTATACCCCTGAAGAATTGTTCGATGAAAACGGTACTTTAATTCCTGAATTGAAGGAATTAGCTC

CAACTGGTCATCACAGAATGTCAGCAAATCCACATGCCAACGGTGGTTTGTTAAGAAAAGACTTGAAGATGCCTGAT

TTCAGAAATTACGGTGTAGAAGTTGCTAAACCAGGTACTGTCGAAGTTGGTAACACAGCATTGTTGGGTAACTTTTT

AAGAGATGTTATGGCCAACAACATGACAAACTTCAGAGTCTTCGGTCCTGATGAAACCGCCTCTAATAGATTGAACG

CTATCTATGAAATCTCTAAGAAAGTTTGGATGGGTGAAATATTACCAGAAGATGCAGACGGTACTGAAATCACTACA

GATGGTAGAGTTATGGAAATGTTATCAGAACATACATTGCAAGGTTGGTTAGAAGGTTATTTGTTAACAGGTAGACA

TGGTTTCTTTCACACCTACGAAGCATTTGCACATGTAGTTGACTCTATGTTTAATCAACACGCTAAATGGTTGGATA

TTTGTAAGAACGAAGTCCCATGGAGAGCATCAGTATCCAGTTTAAACATCTTGTTATCTTCAACAGTTTGGAGACAA

GATCATAACGGTTTCTCCCACCAAGACCCAGGTTATGTTGATTTGGTCACCAATAAGAGTGCTGACGTCGTAAGAGT

CTACTTTCCACCTGATGCAAATTGTTTGTTATCCGTAGCCAACCATTGCTTGAAAAGTACAGACTACGTTAACGTCA

TCGTATCTGATAAGCAAATCCATTTGCAATACTTAAACATGGACCAAGCCATTAAACACTGCACCAAGGGTATTGGT

ATATGGGATTGGGCTTCTAATGATGACTGTGGTACTGAACCAGACCATCCTGATGTAATAATGGCATCATGCGGTGA

CGTTGCTACCAAAGAAGCATTGGCTGCAACTGCCATATTAAGAGAAGAATTTCCTGACTTGAAAGTTAGATTCATCA

ACGTTGTCGATTTGTTTAAGTTACAATCCGAAATAGAACATCCACACGGTTTGAGTGATAGAGACTTCGATAATTTG

TTTACTAAGGATAAGCCTATCATTTTCAATTTCCATGGTTACCCATGGTTGATTCACAAATTAACCTACAGAAGAAC

TAACCATCACAACTTACATGTTAGAGGTTACAAGGAAAAGGGTAACATCAACACACCTTTGGAATTAGCTATTAATA

ACCAAATCGACAGATTCAATTTGGTTATTGATGTTATAAACAGAGTACCAAAATTAGGTTCTGCCGCTGCATACGTT

-continued

TACGAAAGAATGAAGAACGCAATCATAGAACATAGAGCCTATGCTTACGAACACGGTATCGATAAGCCTGAAATTAA

TAACTGGAAGTGGCCACATTAA

SEQ ID No: 53

MVATPERPTLEQTPLSAEELRQIQAYWRACNYLAVGMIYLRDNPLLKDPLTEDHVKNRLLGHWGSSPGLSFIYIHLN

RLIKKYGLDVIYMAGPGHGAPGILGPVYLEGTYSETYPDKSEDEEGMKKFFKQFSFPGGIGSHCTPETPGSIHEGGE

LGYSLSHAYGAALDNPDLIVAAVVGDGEAETGPLATAWHSNKFINPIRDGAVLPILHLNGYKIANPTILARISHEEL

EYLFKGYGYKPYFVEGSDPEVMHQKMAATLETAIAEIKHIQQEARTSGVAKRPIWPMIVLRSPKGWTGPASVDGKKT

EDFWRSHQVPLSGMHGNPAHIKVLEDWLKSYTPEELFDENGTLIPELKELAPTGHHRMSANPHANGGLLRKDLKMPD

FRNYGVEVAKPGTVEVGNTALLGNFLRDVMANNMTNFRVFGPDETASNRLNAIYEISKKVWMGEILPEDADGTEITT

DGRVMEMLSEHTLQGWLEGYLLTGRHGFFHTYEAFAHVVDSMFNQHAKWLDICKNEVPWRASVSSLNILLSSTVWRQ

DHNGFSHQDPGYVDLVTNKSADVVRVYFPPDANCLLSVANHCLKSTDYVNVIVSDKQIHLQYLNMDQAIKHCTKGIG

IWDWASNDDCGTEPDHPDVIMASCGDVATKEALAATAILREEFPDLKVRFINVVDLFKLQSEIEHPHGLSDRDFDNL

FTKDKPIIFNFHGYPWLIHKLTYRRTNHHNLHVRGYKEKGNINTPLELAINNQIDRFNLVIDVINRVPKLGSAAAYV

YERMKNAIIEHRAYAYEHGIDKPEINNWKWPH

SEQ ID No: 54

ATGACTGTAGACTATAACTCAAAAGAATACTTAACATTGGTCGATAAATGGTGGAGAGCAGCAAACTACTTGTCCGT

TGGTCAAATGTTCTTGAGAGATAACCCATTGTTGCAAGAAGAAGTTACTGCAGACCATGTCAAATTGAATCCTATCG

GTCACTGGGGTACAATTGGTGGTCAAAACTTCTTGTATGCTCATTTGAATAGAATTATAAACAAGTACAATGTTAAC

ATGTTTTACATTGAAGGTCCAGGTCACGGTGGTCAAGTCATGGTAACTAATTCCTACTTGGATGGTAGTTATACTGA

AAGATACCCAGAGTTTACTCAAGACATCGCTGGTATGAAGAAATTGTTTAAAACCTTTTCTTTCCCTGGTGGTATTG

GTTCACATGCTGCACCAGAAACTCCTGGTTCCATGCACGAAGGTGGTGAATTGGGTTATGCTTTAAGTCATGCAACA

GGTGCCATATTGGATAACCCAGACGTTATCGCCGCTACAGTTGTCGGTGACGGTGAAGCAGAAACCGGTCCTTTGGC

AGCCGGTTGGTTTTCCAATGTATTCATAAACCCAGTTAGTGATGGTGCTGTCTTACCTATCTTGTACTTAAATGGTG

GTAAAATTGCTAACCCAACCATCTTGGCAAGAAAGTCAAACGAAGATTTGACTAAGTACTTTGAGGGTATGGGTTGG

AAACCTTACATCGTCGAAGGTACTGATCCAGAACAAGTACATCCTATTATGGCTAAGGTATTGGATGAAGTTATCGA

AGAAATTCAAGCAATACAAGCCGAAGCTAGAAAGGGTAAAGCTGAAGATGCAAAAATGCCACATTGGCCTATGATTT

TATATAGAACCCCAAAAGGTTGGACTGGTCCTGAAGAAGTTGAAGGTAAAACTATTCAAGGTTCTTTTAGAGCACAT

CAAGTCCCAATACCTGTATCAGGTAGAAACATGGAAGATATCGACTTGTTAATCAACTGGTTGAAGTCTTACGGTCC

AGAAGAATTATTCACAGAAAACGGTGAATTGGTTGATGAATTAAAGGAATTTGCCCCAAAGGGTGACCATAGAATGG

CTATGAATCCTTTGACTAATGGTGGTAACCCAAAACCTTTAAATATGCCAAACTGGAAGGATTATGCTTTGGAAATA

GGTACACCTGGTTCTAAAGATGCACAAGACATGATCGAATTTGGTGGTTTCGCCAGAGATATAGTTAAGGAAAACCC

AGAAAACTTTAGAATTTTCGGTCCTGATGAAACAAAGTCTAACAGATTGAACAAGGTTTTCGAAGTCACCAATAGAC

AATGGTTAGAACCAATTTCAGAAAAGTTCGATGAAAACATGTCTGCTTCAGGTAGAGTTATAGACTCTCAATTGTCA

GAACATCAAAACCAAGGTTTCTTGGAAGCATATGTCTTAACAGGTAGACACGGTTTCTTTGCTTCTTACGAATCTTT

CTTTAGAACAGTTGATTCCATGATAACCCAACATTTCAAGTGGATAAGAAAATCTGCCAAGCACTCATGGAGAAAGC

CATATCAAAGTTTGAATTTGATCTCCGCTAGTACAGTTTTTCAACAAGATCATAACGGTTACACCCACCAAGACCCA

GGTTTGTTAACTCATATTGGTGAAAAACACGGTGAATATATGAGAGCTTACTTACCTGCAGATACCAATTCTTTGTT

AGCCGTTATGGACAAGGCTTTTAGATCCGAAAACGTCATTAACTACGTAGTTACTTCTAAGCATCCAAGACCTCAAT

TTTTCACAGCCGATGAAGCTGAAGAATTGGTAAACGAAGGTTTGAAAGTTATAGATTGGGCTTCTACAGTTAAGGAT

AACGAAGAACCAGACGTCGTAATCGCTGCAGCCGGTACCGAACCTAATTTCGAAGCTATCGCTGCAATTTCATATTT

GGTAAAAGCATTTCCAGAATTAAAGATCAGATTCGTTAACGTTGTCGATTTGTTTAGATTGAGATCTCCAGAAATCG

-continued

ACCCTAGAGGTTTGTCAGATGACGAATTTGATGCAATCTTCACCAAAGACAAGCCAGTTTTCTTTGCCTTTCATTCC

TACGAAGGCATGTTGAAGGATATTTTCTTTACTAGACATAACCACAACTTATACGCACACGGTTACAGAGAAAATGG

TGAAATAACTACACCTTTCGATATGAGAGTCTTGAACGAATTAGACAGATTTCATTTGTCAGCACACGTAGCCGATG

TAGTTTATGGTGACAAGGCAAGAGACTACGTCGCCGAAATGAAGGGTAAAGTACAAGAACATAGAGATTACGTTGAA

GAATACGGTGCTGACATGCCAGAAGTTGAAGATTGGAAATGGGAAGACATTAAGTAA

SEQ ID No: 55

MTVDYNSKEYLTLVDKWWRAANYLSVGQMFLRDNPLLQEEVTADHVKLNPIGHWGTIGGQNFLYAHLNRIINKYNVN

MFYIEGPGHGGQVMVTNSYLDGSYTERYPEFTQDIAGMKKLFKTFSFPGGIGSHAAPETPGSMHEGGELGYALSHAT

GAILDNPDVIAATVVGDGEAETGPLAAGWFSNVFINPVSDGAVLPILYLNGGKIANPTILARKSNEDLTKYFEGMGW

KPYIVEGTDPEQVHPIMAKVLDEVIEEIQAIQAEARKGKAEDAKMPHWPMILYRTPKGWTGPEEVEGKTIQGSFRAH

QVPIPVSGRNMEDIDLLINWLKSYGPEELFTENGELVDELKEFAPKGDHRMAMNPLTNGGNPKPLNMPNWKDYALEI

GTPGSKDAQDMIEFGGFARDIVKENPENFRIFGPDETKSNRLNKVFEVTNRQWLEPISEKFDENMSASGRVIDSQLS

EHQNQGFLEAYVLTGRHGFFASYESFFRTVDSMITQHFKWIRKSAKHSWRKPYQSLNLISASTVFQQDHNGYTHQDP

GLLTHIGEKHGEYMRAYLPADTNSLLAVMDKAFRSENVINYVVTSKHPRPQFFTADEAEELVNEGLKVIDWASTVKD

NEEPDVVIAAAGTEPNFEAIAAISYLVKAFPELKIRFVNVVDLFRLRSPEIDPRGLSDDEFDAIFTKDKPVFFAFHS

YEGMLKDIFFTRHNHNLYAHGYRENGEITTPFDMRVLNELDRFHLSAHVADVVYGDKARDYVAEMKGKVQEHRDYVE

EYGADMPEVEDWKWEDIK

SEQ ID No: 56

ATGACCTCCCCTGTAATCGGTACCCCATGGAAAAAGTTAAATGCCCCAGTATCAGAAGCAGCCATAGAAGGTGTAGA

CAAGTATTGGAGAGTTGCTAACTATTTGTCCATTGGTCAAATATACTTGAGAAGTAATCCATTAATGAAGGAACCTT

TTACAAGAGAAGATGTCAAGCATAGATTAGTAGGTCACTGGGGTACTACACCAGGTTTGAACTTCTTAATCGGTCAT

ATCAACAGATTCATTGCAGAACACCAACAAAACACCGTTATTATCATGGGTCCAGGTCATGGTGGTCCTGCCGGTAC

TGCTCAATCCTATTTGGATGGTACCTACACTGAATATTACCCAAAAATTACCAAGGACGAAGCTGGTTTGCAAAAGT

TTTTCAGACAATTCTCTTATCCAGGTGGTATACCTTCACATTTTGCTCCAGAAACTCCTGGTTCAATCCACGAAGGT

GGTGAATTGGGTTATGCATTATCTCATGCATACGGTGCCGTTATGAATAACCCATCATTGTTTGTTCCTGCAATTGT

CGGTGACGGTGAAGCCGAAACCGGTCCATTGGCTACTGGTTGGCAATCAAACAAGTTAGTCAATCCAAGAACTGATG

GTATCGTATTGCCTATATTGCATTTGAATGGTTACAAGATTGCTAATCCAACAATATTGTCCAGAATCAGTGATGAA

GAATTACATGAATTTTTCCACGGTATGGGTTATGAACCTTACGAATTTGTTGCAGGTTTCGATGACGAAGACCATAT

GTCTATACACAGAAGATTTGCCGATATGTTCGAAACTATCTTCGACGAAATCTGTGATATCAAAGCCGAAGCTCAAA

CCAATGATGTTACTAGACCATTCTACCCTATGATCATTTTTAGAACACCAAAGGGTTGGACCTGCCCTAAGTTCATT

GATGGTAAAAAGACAGAAGGTTCCTGGAGAGCCCATCAAGTTCCATTGGCAAGTGCCAGAGATACCGAAGCTCACTT

TGAAGTCTTGAAGAACTGGTTGAAGTCTTACAAGCCTGAAGAATTATTCAATGAAGACGGTTCCATTAAAGAAGATG

TTTTGAGTTTTATGCCACAGGGTGAATTAAGAATTGGTCAAAATCCTAACGCTAATGGTGGTAGAATAAGAGAAGAT

TTGAAATTGCCAAATTTGGATGACTACGAAGTAAAGGAAGTTAAGGAATTTGGTCATGGTTGGGGTCAATTGGAAGC

CACTAGAAGATTAGGTGTTTACACAAGAGACGTCATCAAGAATAACCCAGATTCCTTTAGAATTTTCGGTCCTGATG

AAACTGCTAGTAACAGATTGCAAGCTGCATACGAAGTAACAAATAAGCAATGGGACGCTGGTTACTTGTCCGAATTA

GTTGATGAACATATGGCAGTAACAGGTCAAGTTACCGAACAATTGAGTGAACACCAAATGGAAGGTTTCTTAGAAGC

ATATTTGTTAACAGGTAGACATGGTATCTGGTCTTCATACGAATCTTTTGTCCATGTAATCGATTCAATGTTGAATC

AACACGCAAAGTGGTTAGAAGCCACTGTTAGAGAAATTCCATGGAGAAAACCTATATCCAGTATGAACTTGTTAGTC

TCTTCACATGTATGGAGACAAGACCATAATGGTTTCTCTCACCAAGATCCAGGTGTCACCTCAGTATTGTTGAACAA

AACTTTCAATAACGACCATGTAATCGGTATCTATTTCCCTGTTGATTCTAACATGTTGTTAGCTGTTGGTGAAAAGG

TCTACAAGTCAACAAACATGATCAACGCTATCTTCGCAGGTAAACAACCAGCCGCTACTTGGTTGACATTAGATGAA

-continued

GCAAGAGAAGAATTGGAAAAAGGTGCAGCCGAATGGAAGTGGGCCTCTAATGCTAAAAATAACGACGAAGTACAAGT
TGTCTTGGCTGGTATTGGTGACGTTCCTCAACAAGAATTAATGGCTGCAGCCGACAAATTGAACAAGTTAGGTGTTA
AGTTTAAAGTAGTTAACATCGTCGATTTGTTGAAATTGCAATCTGCAAAGGAAAATAACGAAGCCTTGACTGACGAA
GAGTTTACTGAATTGTTTACTGCTGATAAGCCAGTCTTGTTAGCTTATCATTCTTACGCACACGATGTAAGAGGTTT
AATTTTCGACAGACCAAACCATGATAACTTCAACGTTCACGGTTACAAGGAACAAGGTTCAACCACTACACCTTACG
ATATGGTTAGAGTCAATGATATGGACAGATATGAATTGACAGCTGAAGCATTAAGAATGGTCGATGCTGACAAGTAC
GCAGACGAAATTAAAAAGTTGGAAGATTTCAGATTAGAAGCCTTTCAATTCGCTGTTGATAAAGGTTATGATCATCC
AGACTACACAGACTGGGTATGGCCAGGTGTTAAAACCGATAAGCCTGGTGCAGTTACAGCCACCGCTGCAACTGCTG
GTGACAATGAATAAT

SEQ ID No: 57

MTSPVIGTPWKKLNAPVSEAAIEGVDKYWRVANYLSIGQIYLRSNPLMKEPFTREDVKHRLVGHWGTTPGLNFLIGH
INRFIAEHQQNTVIIMGPGHGGPAGTAQSYLDGTYTEYYPKITKDEAGLQKFFRQFSYPGGIPSHFAPETPGSIHEG
GELGYALSHAYGAVMNNPSLFVPAIVGDGEAETGPLATGWQSNKLVNPRTDGIVLPILHLNGYKIANPTILSRISDE
ELHEFFHGMGYEPYEFVAGFDDEDHMSIHRRFADMFETIFDEICDIKAEAQTNDVTRPFYPMIIFRTPKGWTCPKFI
DGKKTEGSWRAHQVPLASARDTEAHFEVLKNWLKSYKPEELFNEDGSIKEDVLSFMPQGELRIGQNPNANGGRIRED
LKLPNLDDYEVKEVKEFGHGWGQLEATRRLGVYTRDVIKNNPDSFRIFGPDETASNRLQAAYEVTNKQWDAGYLSEL
VDEHMAVTGQVTEQLSEHQMEGFLEAYLLTGRHGIWSSYESFVHVIDSMLNQHAKWLEATVREIPWRKPISSMNLLV
SSHVWRQDHNGFSHQDPGVTSVLLNKTFNNDHVIGIYFPVDSNMLLAVGEKVYKSTNMINAIFAGKQPAATWLTLDE
AREELEKGAAEWKWASNAKNNDEVQVVLAGIGDVPQQELMAAADKLNKLGVKFKVVNIVDLLKLQSAKENNEALTDE
EFTELFTADKPVLLAYHSYAHDVRGLIFDRPNHDNFNVHGYKEQGSTTTPYDMVRVNDMDRYELTAEALRMVDADKY
ADEIKKLEDFRLEAFQFAVDKGYDHPDYTDWVWPGVKTDKPGAVTATAATAGDNE

SEQ ID No: 58

ATGACAGACTCCGCTACAGCCCCAGTTCCTGACAGAAGAGCCACCGCTTTCGCACATAGAGACCCAGCAGAATTAGA
CGATGGTACATTGGCTGCATTAGATGCCTGGTGGAGAACTGCTAACTATTTGTCTGTTGGTCAAATATACTTGTTGG
ATAACCCATTGTTAAGACAACCTTTGGAAAGAGAACAATTAAAGCCAAGATTGTTAGGTCATTGGGGTACTACACCT
GGTTTGAATTTCTTGTACGCTCACTTGAACAGAGTTATCAGAGAAAGAGATTTGTCTACTATCTTCATTACCGGTCC
AGGTCATGGTGGTCCTGGTATGGTCGCAAATGCCTATTTGGATGGTACTTATTCCGAATTATACCCACACGTAGCAA
GAAGTGAAGACGGTATTAGAGAATTGTTTAGACAATTTTCATTCCCAGGTGGTATTCCTTCTCATGCTTCACCAGAA
ACACCTGGTTCCATACACGAAGGTGGTGAATTGGGTTATGCCTTAAGTCATGCTTACGGTGCCGCTTTTGATAATCC
AGGTTTGTTAGTTGCAGCCGTTGTCGGTGACGGTGAAGCCGAAACTGGTCCTTTAGCTACATCCTGGCATAGTAACA
AGTTCTTAGATCCATTAGCTGACGGTGTAGTTTTGCCTATCTTGCACTTAAATGGTTACAAAATCGCAAACCCAACA
GTTTTGGCTAGAATACCAGAACATGAATTGTTATCCTTGATGAGAGGTTATGGTCACACCCCATACTTAGTTAGTGG
TGGTTTTGATGGTGAAGACCCTGCTGCAGTACATAGAAGATTCGCTAAGACCTTGGATACTGTTTTGAACCAAATCG
CAGAAATCAAAGCCTCAGCCGCTGCAGGTACATTGGAAGGTAGACCAGCATGGCCTATGATTATATTAAGAACCCCA
AAAGGTTGGACTTGTCCTGAAGAAATTGATGGTTTGCCAGCTGAAAACTCTTGGAGATCACATCAAGTACCATTAGC
TTCTGCAAGAGATACTCCTGAACACTTGGGTGTTTTAGACGGTTGGTTGAGATCATACAGACCAGAAGAATTATTTG
ATGCCGCTGGTGCACCAATGCCTGTTGCCACAGCTTTGGCACCAGATGGTGAATTAAGAATGTCTGCTAATCCTGTC
GCAAACGGTGGTATTTTGAAGAGAGATTTGGTATTACCAGATTTCAGAGACTATGCTGTTGACGTCCCAGTACCTGG
TGCAACAGTCAATGAAGCCACCAGAGTATTGGGTCAATGGTTAGCTGATGTTATTAGAGCAAACCCAGACACTTTTA
GAATATTCGGTCCTGATGAAACCGCTTCCAATAGATTGGGTGCAGTTTTAGAAGTCACTGATAAACAATGGAACGCT
GAATACTTGCCAACAGACGAACATTTGGCTAGAAGAGGTAGAGTTATTGAAATGTTGAGTGAACACCAATGCCAAGG

-continued

TTGGTTAGAAGGTTATTTGTTAACCGGTAGACATGGTTTGTTTAATACTTACGAAGCATTCGTACATATCGTTGGTT

CTATGTTCAACCAACACGCTAAATGGTTGAAGGTTTCAAAAGAAATCCCATGGAGAAGACCTATTGCATCCTTAAAC

TACTTGTTGACTTCTCATGTTTGGAGACAAGATCATAACGGTTTATCTCACCAAGATCCAGGTTTTATTGACCACGT

CGTAAATAAGAAAGCTGATGTTGTCAGAGTTTATTTGCCTTTCGACGCCAACACCTTGTTGTCTGCTTACGATCATT

GTTTGAGATCAGTTGATTACGTAAACGTAGTTGTCGCAGGTAAACAACCAACTTTTAACTGGTTGTCCATGGATAGA

GCCATCGCTCATATGACCAGAGGTTTAGGTATTTTCGAATGGGCTGGAACTGAAGTTGAAGGTGAAGAACCAGATGT

TGTTTTGGCTTGTGCTGGTGACGTACCTACATTGGAAGTTTTAGCAGCCGCTTCTATTTTGAGACAAGCTATACCAG

ATTTGAAGGTTAGAGTCGTAAACGTTGTTGATTTGATGAGATTAGTCTCTGAAGGTGAACATCCTCACGGCATGTCA

GATAGAGAATATGACGCCGTTTTTACTAAAGATAGACCAGTCATATTCGCTTATCATGGTTACCCTTGGTTGATCCA

CAGATTAACATATAGAAGAAACGGTCATGCTAACTTGCACGTTAGAGGTTACAAAGAAGAAGGTACCACTACAACCC

CATTCGATATGGTCATGTTGAACGATATCGACAGATACCATTTGGTAGTTGATGTCGTAGACAGAGTTCCTGGTTTA

GGTGAAAGATATGCTGGTTTGAGACAAAGAATGTTAGATGCCAGAGTAAGAGCTAGAGCATATACAAGAGAACATGG

TGAAGATATACCAGAAGTTGCAGACTGGACTTGGACAGCCGGTCCTGAAAGACAAGCTAGAGAAGTCAATACCGGTG

TTGGTCAAGTCAATACTGGTGCTGCTGCTACTGGTGGTGACAATGAATCATAA

SEQ ID No: 59

MTDSATAPVPDRRATAFAHRDPAELDDGTLAALDAWWRTANYLSVGQIYLLDNPLLRQPLEREQLKPRLLGHWGTTP

GLNFLYAHLNRVIRERDLSTIFITGPGHGGPGMVANAYLDGTYSELYPHVARSEDGIRELFRQFSFPGGIPSHASPE

TPGSIHEGGELGYALSHAYGAAFDNPGLLVAAVVGDGEAETGPLATSWHSNKFLDPLADGVVLPILHLNGYKIANPT

VLARIPEHELLSLMRGYGHTPYLVSGGFDGEDPAAVHRRFAKTLDTVLNQIAEIKASAAAGTLEGRPAWPMIILRTP

KGWTCPEEIDGLPAENSWRSHQVPLASARDTPEHLGVLDGWLRSYRPEELFDAAGAPMPVATALAPDGELRMSANPV

ANGGILKRDLVLPDFRDYAVDVPVPGATVNEATRVLGQWLADVIRANPDTFRIFGPDETASNRLGAVLEVTDKQWNA

EYLPTDEHLARRGRVIEMLSEHQCQGWLEGYLLTGRHGLFNTYEAFVHIVGSMFNQHAKWLKVSKEIPWRRPIASLN

YLLTSHVWRQDHNGLSHQDPGFIDHVVNKKADVVRVYLPFDANTLLSAYDHCLRSVDYVNVVVAGKQPTFNWLSMDR

AIAHMTRGLGIFEWAGTEVEGEEPDVVLACAGDVPTLEVLAAASILRQAIPDLKVRVVNVVDLMRLVSEGEHPHGMS

DREYDAVFTKDRPVIFAYHGYPWLIHRLTYRRNGHANLHVRGYKEEGTTTTPFDMVMLNDIDRYHLVVDVVDRVPGL

GERYAGLRQRMLDARVRARAYTREHGEDIPEVADWTWTAGPERQAREVNTGVGQVNTGAAATGGDNES

SEQ ID No: 60

ATGACTAATAAGACACAATTTGACACCCCTGAATACTTGGGTAAAGTCGATGCTTGGTGGAGAGCCGCTAACTACAT

TTCCGTCGCTCAAATGTATTTGAAGGATAACCCATTGTTGAAGACACCTTTAGTAGCAAACGACGTTAAAGCCCATC

CAATTGGTCATTGGGGTACTGTTCCTGGTCAAAACTTCATCTATGCTCATTTGAATAGAGCAATCAACAAGTATGAT

GTTGACATGTTCTACATAGAAGGTCCAGGTCACGGTGGTCAAGTCATGGTATCTAATTCATACTTAGATGGTTCTTA

CACTGAAATCTACCCAGATATTACACAAGACACCGCAGGTTTGAAAAAGTTATGCAAGATATTTTCTTTCCCTGGTG

GTATCGCCTCACATGCTGCACCAGAAACACCTGGTTCTATTCACGAAGGTGGTGAATTGGGTTATGCTTTATCACAT

GCCTTTGGTGCTGTTTTGGATAATCCAAACGTTATAGCCGCTGCAGTCATCGGTGACGGTGAAGCAGAAACAGGTCC

TTTGTGCGCCGGTTGGTTTGGTAATACCTTCATAAATCCAGTAAACGATGGTGCTGTTTTACCTATCTTGTACTTAA

ATGGTGGTAAAATACATAACCCAACAATATTGGCAAGAAAAACCGATGAAGAATTAAAGCAATACTTCAACGGTATG

GGTTGGGAACCTATCTTCGTTGATGTCAATAACGTTGACAACTACCATGAAATTATGTCCCAAAAAGTCGATGAAGC

TGTAGAACACATCTTGAGTATTTGGCAAACTGCAAGAACACAAAAGGCAGAAGATGCCACTATGCCACATTGGCCTG

TTTTGGTTGCTAGAATACCAAAAGGTTGGACCGGTCCTAAGACTTGGCACGGTGAACCAATTGAAGGTGGTTTTAGA

GCACATCAAGTTCCAATACCTGCATCTTCACACGATATGGAAACAGCTGGTGAATTGGAAAAGTGGTTAAGATCTTA

TAGACCTGAAGAATTGTTCGATGACAATGGTTGTTTCTTAGACAAGTGGAGAGACATTTCCCCAAAAGGTGCAAAGA

GAATGAGTGTTCATCCTATCACTAATGGTGGTATTAACCCAAAAGCATTGGTCATGCCTGATTGGACACAACACGCC

-continued

TTAGAAATTGGTGTCCCAGGTTCTCAAGATGCTCAAGACATGGTAGAATGCGGTAGATTAATGGCCGATGTTGTCAC

TGCTAACCCAAACAACTTTAGAATTTTCGGTCCTGACGAAACCAAGTCAAACAGATTGAACCAAGTCTTCCAAGTAA

CTAAGAGACAATGGTTAGGTAGAAGAGATGAAGCATATGACGAATGGATTGCACCAGTTGGTAGAGTCATAGATTCC

CAATTGAGTGAACATCAAGCTGAAGGTTTCTTGGAAGGTTATGTTTTAACAGGTAGACACGGTTTCTTTGCTTCTTA

CGAATCATTTTTCAGAGTAGTTGATTCCATGATCACTCAACATTTCAAGTGGTTGAGAAAGTGTAAGACACACGCCG

CTTGGAGAAATGATTATCCATCCTTGAACTTAGTCGCTACCAGTACTGTATTCCAACAAGATCATAACGGTTACACT

CACCAAGACCCTGGTTTGTTAACACATTTGGCCGAAAAGAAACCAGAATTTGTAAGAGAATATTTGCCTGCTGATTC

AAACACCTTAATGGCAGTTATGTCCGAAGCCTTAACTTCTAGAGATAGAATTAATTTGATCGTTTCCAGTAAGCATT

TGAGACCACAATTTTTCAACGCTGAAGAAGCAAAAGAATTGGTTAGAGAAGGTTACAAGGTCATAGATTGGGCTTCC

ACCTGTCATGATGGTGAACCAGACGTCGTAATCGCAGCCGCTGGTACTGAACCTAATATGGAAGCATTGGCAGCCAT

TAGTATCTTGCATAAGCAATTCCCAGAATTAAAGATTAGATTCATAAACGTTGTCGATATATTGAAATTGAGACACC

CATCTATAGACCCTAGAGGTTTGTCAGATGAACAATTTGACGCTTTATTCACTCAAGAAAAGCCAGTAGTTTTCTGT

TTCCATGGTTATGAAGGTATGATTAGAGATTTGTTTTTCCCTAGAGCAAATCATAACGTTAGAATCCACGGTTACAG

AGAAAATGGTGACATTACTACACCATTTGACATGAGAGTTTTATCAGAAATGGATAGATTCCATGTAGCCAAAGACG

CTGCACAAGCTGTTTATGGTGACAAGGCCTCTGAATTTGCTAAAAAGATGGGTGAAACAGTCGCTTTCCATAGATCA

TACATCAGAGAACACGGTACCGATATTCCAGAAGTTGCCGAATGGAAATGGCAACCTTTGGCTAAGTAA

SEQ ID No: 61

MTNKTQFDTPEYLGKVDAWWRAANYISVAQMYLKDNPLLKTPLVANDVKAHPIGHWGTVPGQNFIYAHLNRAINKYD

VDMFYIEGPGHGGQVMVSNSYLDGSYTEIYPDITQDTAGLKKLCKIFSFPGGIASHAAPETPGSIHEGGELGYALSH

AFGAVLDNPNVIAAAVIGDGEAETGPLCAGWFGNTFINPVNDGAVLPILYLNGGKIHNPTILARKTDEELKQYFNGM

GWEPIFVDVNNVDNYHEIMSQKVDEAVEHILSIWQTARTQKAEDATMPHWPVLVARIPKGWTGPKTWHGEPIEGGFR

AHQVPIPASSHDMETAGELEKWLRSYRPEELFDDNGCFLDKWRDISPKGAKRMSVHPITNGGINPKALVMPDWTQHA

LEIGVPGSQDAQDMVECGRLMADVVTANPNNFRIFGPDETKSNRLNQVFQVTKRQWLGRRDEAYDEWIAPVGRVIDS

QLSEHQAEGFLEGYVLTGRHGFFASYESFFRVVDSMITQHFKWLRKCKTHAAWRNDYPSLNLVATSTVFQQDHNGYT

HQDPGLLTHLAEKKPEFVREYLPADSNTLMAVMSEALTSRDRINLIVSSKHLRPQFFNAEEAKELVREGYKVIDWAS

TCHDGEPDVVIAAAGTEPNMEALAAISILHKQFPELKIRFINVVDILKLRHPSIDPRGLSDEQFDALFTQEKPVVFC

FHGYEGMIRDLFFPRANHNVRIHGYRENGDITTPFDMRVLSEMDRFHVAKDAAQAVYGDKASEFAKKMGETVAFHRS

YIREHGTDIPEVAEWKWQPLAK

SEQ ID No: 62

ATGACAACAGATTACTCATCCCCTGCATACTTACAAAAGGTAGACAAATACTGGAGAGCCGCTAACTACTTATCCGT

CGGTCAATTATATTTGAAGGACAACCCATTGTTGCAAAGACCTTTAAAAGCATCTGATGTAAAGGTTCATCCAATAG

GTCACTGGGGTACTATCGCTGGTCAAAACTTCATCTATGCACATTTGAATAGAGTCATTAACAAATACGGTTTGAAG

ATGTTCTACGTAGAAGGTCCTGGTCACGGTGGTCAAGTCATGGTATCTAATTCATACTTGGACGGTACATATACCGA

TATCTATCCAGAAATAACCCAAGATGTTGAGGGTATGCAAAAATTGTTTAAACAATTTTCTTTCCCTGGTGGTGTCG

CTTCACATGCTGCACCAGAAACACCTGGTTCCATTCACGAAGGTGGTGAATTGGGTTATTCCATAAGTCATGGTGTT

GGTGCAATCTTAGATAATCCAGACGAAATTGCCGCTGTTGTCGTAGGTGACGGTGAATCAGAAACTGGTCCTTTGGC

TACATCTTGGCAATCAACCAAGTTTATCAATCCAATTAACGATGGTGCAGTTTTACCTATATTGAATTTGAATGGTT

TTAAAATCTCTAATCCAACTATTTTCGGTAGAACATCAGATGCTAAGATTAAAGAATACTTCGAATCAATGAACTGG

GAACCTATCTTCGTAGAAGGTGACGACCCAGAAAAGGTTCATCCTGCCTTGGCTAAAGCAATGGATGAAGCAGTTGA

AAAGATTAAAGCCATCCAAAAACACGCTAGAGAAAATAACGATGCTACTTTACCAGTCTGGCCTATGATAGTTTTTA

GAGCACCAAAAGGTTGGACAGGTCCTAAGTCCTGGGATGGTGACAAAATCGAAGGTTCTTTTAGAGCACATCAAATT

-continued

CCAATACCTGTTGATCAAAATGACATGGAACACGCCGATGCTTTGGTTGATTGGTTAGAATCCTATCAACCAAAGGA

ATTGTTTAACGAAGATGGTAGTTTAAAGGATGACATAAAGGAAATAATACCAACAGGTGACTCTAGAATGGCAGCCA

ATCCTATAACCAACGGTGGTGTCGATCCAAAAGCATTGAATTTGCCTAACTTCAGAGATTATGCAGTAGACACTTCT

AAGGAAGGTGCCAATGTTAAACAAGATATGATCGTCTGGTCAGATTACTTGAGAGACGTTATTAAAAAGAATCCAGA

CAACTTCAGATTGTTCGGTCCTGATGAAACAATGTCTAACAGATTGTACGGTGTTTTTGAAACTACAAACAGACAAT

GGATGGAAGACATTCATCCAGATTCCGACCAATACGAAGCACCTGCCGGTAGAGTATTGGATGCCCAATTAAGTGAA

CATCAAGCTGAAGGTTGGTTGGAAGGTTATGTTTTAACAGGTAGACACGGTTTGTTTGCATCTTACGAAGCCTTCTT

GAGAGTTGTCGATTCAATGTTGACCCAACATTTCAAGTGGTTGAGAAAGGCTAACGAATTAGATTGGAGAAAGAAAT

ACCCATCCTTAAACATCATAGCTGCAAGTACTGTTTTCCAACAAGACCATAATGGTTACACCCACCAAGATCCTGGT

GCATTGACTCATTTGGCCGAAAAGAAACCAGAATACATTAGAGAATACTTGCCTGCTGACGCAAATACCTTGTTAGC

TGTAGGTGACGTTATTTTTAGATCACAAGAAAAGATCAACTACGTAGTTACTTCTAAACACCCAAGACAACAATGGT

TCTCAATTGAAGAAGCCAAACAATTGGTCGATAATGGTTTAGGTATAATCGACTGGGCTTCCACTGATCAAGGTAGT

GAACCAGATATCGTTTTTGCCGCTGCAGGTACTGAACCTACATTGGAAACCTTAGCCGCTATTCAATTGTTACATGA

TTCTTTCCCAGAAATGAAGATCAGATTCGTTAACGTCGTAGACATCTTGAAGTTAAGATCCCCAGAAAAAGATCCTA

GAGGTTTGAGTGATGCAGAATTTGACCATTACTTCACAAAGGATAAGCCAGTTGTCTTTGCCTTCCACGGTTACGAA

GATTTGGTTAGAGATATTTTCTTTGATAGACATAACCACAACTTATACGTTCATGGTTACAGAGAAAACGGTGACAT

AACCACTCCATTTGATGTTAGAGTCATGAACCAAATGGATAGATTCGACTTGGCCAAGTCTGCTATTGCAGCCCAAC

CTGCTATGGAAAATACTGGTGCTGCATTTGTTCAATCAATGGATAACATGTTAGCTAAACATAACGCATACATTAGA

GACGCAGGTACAGATTTGCCAGAAGTTAACGATTGGCAATGGAAAGGTTTAAAGTAA

SEQ ID No: 63

MTTDYSSPAYLQKVDKYWRAANYLSVGQLYLKDNPLLQRPLKASDVKVHPIGHWGTIAGQNFIYAHLNRVINKYGLK

MFYVEGPGHGGQVMVSNSYLDGTYTDIYPEITQDVEGMQKLFKQFSFPGGVASHAAPETPGSIHEGGELGYSISHGV

GAILDNPDEIAAVVVGDGESETGPLATSWQSTKFINPINDGAVLPILNLNGFKISNPTIFGRTSDAKIKEYFESMNW

EPIFVEGDDPEKVHPALAKAMDEAVEKIKAIQKHARENNDATLPVWPMIVFRAPKGWTGPKSWDGDKIEGSFRAHQI

PIPVDQNDMEHADALVDWLESYQPKELFNEDGSLKDDIKEIIPTGDSRMAANPITNGGVDPKALNLPNFRDYAVDTS

KEGANVKQDMIVWSDYLRDVIKKNPDNFRLFGPDETMSNRLYGVFETTNRQWMEDIHPDSDQYEAPAGRVLDAQLSE

HQAEGWLEGYVLTGRHGLFASYEAFLRVVDSMLTQHFKWLRKANELDWRKKYPSLNIIAASTVFQQDHNGYTHQDPG

ALTHLAEKKPEYIREYLPADANTLLAVGDVIFRSQEKINYVVTSKHPRQQWFSIEEAKQLVDNGLGIIDWASTDQGS

EPDIVFAAAGTEPTLETLAAIQLLHDSFPEMKIRFVNVVDILKLRSPEKDPRGLSDAEFDHYFTKDKPVVFAFHGYE

DLVRDIFFDRHNHNLYVHGYRENGDITTPFDVRVMNQMDRFDLAKSAIAAQPAMENTGAAFVQSMDNMLAKHNAYIR

DAGTDLPEVNDWQWKGLK

SEQ ID No: 64

ATGGCAGACTTCGACTCAAAGGAATACTTAGAATTGGTAGACAAATGGTGGAGAGCAACAAACTACTTATCCGCTGG

TATGATTTTCTTGAAAAGTAATCCATTATTTTCTGTTACAAACACCCCTATTCAAGCTGAAGATGTTAAAGTCAAGC

CAATTGGTCATTGGGGTACTATATCTGGTCAAACATTCTTGTATGCCCACGCTAACAGATTGATTAACAAATACGAT

TTGAATATGTTTTACATAGGTGGTCCAGGTCATGGTGGTCAAGTAATGGTTACTAACGCATACTTAGATGGTGAATA

TACCGAAGACTACCCTGAAATTACTCAAGATTTGGAAGGCATGTCTAGATTGTTTAAAAGATTTTCTTTCCCAGGTG

GTATCGGTTCACATATGACAGCTCAAACCCCTGGTTCTTTGCACGAAGGTGGTGAATTGGGTTATTCCTTAAGTCAT

GCCTTCGGTGCTGTTTTAGATAATCCAGACCAAATTGCATTTGCCGTTGTCGGTGACGGTGAAGCAGAAACCGGTCC

TTCCATGACTTCTTGGCACTCTACAAAATTCTTGAATGCAAAGAACGATGGTGCCGTCTTACCAATCTTGGACTTAA

ATGGTTTCAAAATCTCTAACCCTACAATTTTCTCTAGAATGTCCGATGAAGAAATCACTAAGTTTTTCGAAGGTTTG

GGTTACTCACCAAGATTCATTGAAAACGATGACATCCATGATTATGCTGCATACCACGAATTGGCCGCTAAAGTTTT

-continued

AGATCAAGCTATCGAAGACATTCAAGCTATACAAAAAGATGCAAGAGAAAACGGTAAATACGAAGACGGTACAATTC

CAGCATGGCCTGTCATTATAGCCAGATTGCCAAAGGGTTGGGGTGGTCCTACTCATGATGAAGACGGTAACCCAATC

GAAAATTCTTTTAGAGCACATCAAGTACCATTGCCTTTAGCACAAAATAAGTTGGAAACTTTGTCTCAATTCGAAGA

TTGGATGAACTCTTACAAGCCTGAAGAATTGTTTAATGCAGATGGTTCCTTGAAAGACGAATTAAAGGCTATAGCAC

CAAAAGGTGACAAGAGAATGAGTGCAAATCCTATCGCCAACGGTGGTAGAAGAAGAGGTGAAGAAGCTACTGATTTG

ACATTACCAGACTGGAGACAATTCACAAACGATATAACCAACGAAAACAGAGGTCATGAATTGCCTAAGGTTACTCA

AAACATGGATATGACTACATTGTCTAACTATTTGGAAGAAGTCGCTAAGTTAAACCCAACATCATTCAGAGTATTTG

GTCCTGATGAAACTATGTCAAACAGATTGTGGTCCTTGTTTAATACCACTAACAGACAATGGATGGAAGAAGTAAAA

GAACCAAATGATCAATACGTTGGTCCTGAAGGTAGAATCATTGACAGTCAATTATCTGAACATCAAGCCGAAGGTTG

GTTGGAAGGTTACACTTTGACAGGTAGAGTAGGTATATTCGCTTCATACGAATCCTTTTTGAGAGTAGTTGACACTA

TGGTTACTCAACATTTCAAGTGGTTGAGACACGCTTCTGAACAAGCATGGAGAAACGATTACCCATCCTTGAACTTA

ATTGCCACCAGTACTGCTTTCCAACAAGATCATAATGGTTACACACACCAAGACCCAGGCATGTTGACCCATTTGGC

TGAAAAGAAATCTAACTTCATTAGAGAATATTTGCCTGCAGATGGTAACTCCTTGTTAGCCGTTCAAGACAGAGCTT

TTAGTGAAAGACACAAGGTCAATTTGATAATCGCATCTAAGCAACCAAGACAACAATGGTTCACAGCAGATGAAGCC

GACGAATTGGCTAACGAAGGTTTGAAGATCATCGATTGGGCTTCAACAGCACCATCCGGTGACGTTGACATTACCTT

TGCATCTTCAGGTACAGAACCTACCATAGAAACTTTGGCAGCCTTGTGGTTAATCAATCAAGCATTTCCAGAGGTTA

AGTTTAGATACGTCAACGTCGTAGAATTGTTGAGATTGCAAAAGAAATCTGAATCTCATATGAACGATGAAAGAGAA

TTATCCGACGCCGAGTTTAATAAGTTTTTCCAAGCTGATAAGCCTGTTATCTTCGGTTTTCATGCTTACGAAGACTT

AATCGAATCATTTTTCTTTGAAAGAAAATTCAAGGGTGACGTCTATGTACACGGTTACAGAGAAGATGGTGACATTA

CAACCACTTACGATATGAGAGTTTACTCTAAATTGGACAGATTTCATCAAGCAAAGGAAGCTGCAGAAATCTTAAGT

GCCAATTCTACTATTGATCAAGCCGCTGCAGACACATTCATCGAAAAGATGGATGCCACCTTGGCTAAGCATTTTGA

AGTTACTAGAAATGAAGGTAGAGATATTGAAGAGTTTACTGACTGGAACTGGTCAGCTTTAAAATAA

SEQ ID No: 65

MADFDSKEYLELVDKWWRATNYLSAGMIFLKSNPLFSVTNTPIQAEDVKVKPIGHWGTISGQTFLYAHANRLINKYD

LNMFYIGGPGHGGQVMVTNAYLDGEYTEDYPEITQDLEGMSRLFKRFSFPGGIGSHMTAQTPGSLHEGGELGYSLSH

AFGAVLDNPDQIAFAVVGDGEAETGPSMTSWHSTKFLNAKNDGAVLPILDLNGFKISNPTIFSRMSDEEITKFFEGL

GYSPRFIENDDIHDYAAYHELAAKVLDQAIEDIQAIQKDARENGKYEDGTIPAWPVIIARLPKGWGGPTHDEDGNPI

ENSFRAHQVPLPLAQNKLETLSQFEDWMNSYKPEELFNADGSLKDELKAIAPKGDKRMSANPIANGGRRRGEEATDL

TLPDWRQFTNDITNENRGHELPKVTQNMDMTTLSNYLEEVAKLNPTSFRVFGPDETMSNRLWSLFNTTNRQWMEEVK

EPNDQYVGPEGRIIDSQLSEHQAEGWLEGYTLTGRVGIFASYESFLRVVDTMVTQHFKWLRHASEQAWRNDYPSLNL

IATSTAFQQDHNGYTHQDPGMLTHLAEKKSNFIREYLPADGNSLLAVQDRAFSERHKVNLIIASKQPRQQWFTADEA

DELANEGLKIIDWASTAPSGDVDITFASSGTEPTIETLAALWLINQAFPEVKFRYVNVVELLRLQKKSESHMNDERE

LSDAEFNKFFQADKPVIFGFHAYEDLIESFFFERKFKGDVYVHGYREDGDITTTYDMRVYSKLDRFHQAKEAAEILS

ANSTIDQAAADTFIEKMDATLAKHFEVTRNEGRDIEEFTDWNWSALK

SEQ ID No: 66

ATGACATCCCCAGTTATTGGTACCCCATGGAGAAAGTTGGACGCCCCTGTATCCGAAGAAGCATTAGAAGGTGTAGA

CAAGTATTGGAGAGCTTCCAACTATTTGAGTATAGGTCAAATCTACTTGAGATCAAACCCATTGATGAAGGAACCTT

TCACAAGAGAAGATGTCAAGCATAGATTAGTAGGTCACTGGGGTACTACACCAGGTTTGAACTTTTTAATAGGTCAT

ATCAACAGATTGATCGCAGATCACGGTCAAAACACTGTTATTATCATGGGTCCAGGTCATGGTGGTCCTGCTGGTAC

ATCCCAAAGTTATTTGGACGGTACCTACTCTGAATACTTCCCAGAAATCACAAAGGATGAAGCAGGTTTGCAAAAGT

TTTTCAGACAATTCTCTTACCCAGGTGGTATCCCTTCACATTTTGCACCAGAAACCCCTGGTTCAATTCACGAAGGT

-continued

GGTGAATTGGGTTATGCTTTATCTCATGCCTACGGTGCTGTTATGAATAACCCATCATTATTTGTACCTGCTATTGT

TGGTGACGGTGAAGCTGAAACAGGTCCATTAGCAACCGGTTGGCAATCTAACAAATTGGTTAATCCAAGAACCGATG

GTATAGTCTTGCCTATCTTGCATTTGAACGGTTATAAGATTGCCAATCCAACTATATTGGCTAGAATCTCTGATGAA

GAATTGCATGAATTTTTCCACGGTATGGGTTATGAACCTTACGAATTTGTTGCTGGTTTCGATGACGAAGACGCAAT

GTCAATTCACAGAAGATTTGCTGATTTGTTCGAAACAGTTTTCGACGAAATCTGTGATATCAAGGCTACCGCACAAA

CTAACGATGTTGACAGACCATTCTACCCTATGATCATTTTTAGAACTCCAAAGGGTTGGACATGCCCTAAGTTCATT

GATGGTAAAAAGACAGAAGGTTCTTGGAGATCACATCAAGTACCATTGGCCTCCGCTAGAGATACCGAAGAACACTT

TGAAGTTTTGAAAAATTGGTTGGAAAGTTACAAGCCTGAAGAATTATTCACTGAAGATGGTGCCGTCAGACCAGAAG

TAACAGCTTTTATGCCTGAGGGTGAATTGAGAATAGGTGAAAATCCAAACGCCAATGGTGGTAGAATCAGAGAAGAA

TTGGACTTACCTGCTTTGGAAGATTACGAAGTAACTGAAGTTAAAGAATTTGGTCATGGTTGGGGTCAATTGGAAGC

AACCAGAAAGTTGGGTGAATACACTAGAGACATAATCAAGAGAAACCCAGATTCCTTTAGAATTTTCGGTCCTGATG

AAACCGCTAGTAATAGATTGCAAGCTGCATATGAAGTCACTAACAAACAATGGGACAATGGTTACTTGTCTGAATTA

GTTGATGAACATATGGCAGTTACTGGTCAAGTCACAGAACAATTATCAGAACACCAAATGGAAGGTTTCTTGGAAGC

TTATTTGTTAACAGGTAGACATGGTATTTGGTCTTCATACGAATCCTTCGTCCATGTAATCGATAGTATGTTGAACC

AACACGCTAAATGGTTAGAAGCAACTGTTAGAGAAATCCCATGGAGAAAGCCTATTTCCAGTATGAACTTGTTAGTA

TCTTCACATGTTTGGAGACAAGATCATAATGGTTTTTCCCACCAAGACCCAGGTGTTATCGATATATTGTTGAACAA

AAACTTCAACAACGACCACGTTGTCGGTATCTATTTCCCTGTAGATTCTAACATGTTGTTAGCCGTTTCCGAAAAGG

CTTACAAGAGTACAAACATGATCAACGCAATAATCGCCGGTAAACAACCAGCCGCTACATGGTTGACCTTAGATGAA

GCAAGAGAAGAATTAGCCAAAGGTGCAGCCGAATGGAAGTGGGCTTCTAACGCAGAAGGTGACGACGTTGATATTGT

ATTGGCTTCAGTTGGTGACGTCCCTACTCAAGAATTGATGGCTGCAGCCGACAAATTAAAGGGTTACGGTATAAAAT

ACAAGTTCGTTAACGTAGTTGATTTGTTATCTATCCAAAACGCATCAGAAAATGACCAAGCCTTGTCTGATGAAGAG

TTTACTGAATTGTTTACTGCAGATAAACCAGTCTTGATGGCCTATCATGCATACGCCAGAGAAGTAAGATCCTTAAT

TTGGGACAGACCAAATCATGATAACTTCAATGTTCACGGTTATGAAGAACAAGGTAGTACCACTACACCTTTTGACA

TGGTTAGAGTCAACAACATAGATAGATACGAATTGACTGCTGAAGCATTAAGAGCCGTTGATGCTGACAAATTCGCT

GACGAAATAGAAAAGTTGGAAGCTTTTAGAACTGAAGCATTTCAATTCGCCGTTGATAATGGTTATGATCATCCAGA

CTACACAGATTGGGTCTGGTCTGGTGTCCAAACTGAAAAGCCAGGTGCTGTATCTGCCACTGCTGCCACTGCCGGTG

ACAACGAATAA

SEQ ID No: 67

MTSPVIGTPWRKLDAPVSEEALEGVDKYWRASNYLSIGQIYLRSNPLMKEPFTREDVKHRLVGHWGTTPGLNFLIGH

INRLIADHGQNTVIIMGPGHGGPAGTSQSYLDGTYSEYFPEITKDEAGLQKFFRQFSYPGGIPSHFAPETPGSIHEG

GELGYALSHAYGAVMNNPSLFVPAIVGDGEAETGPLATGWQSNKLVNPRTDGIVLPILHLNGYKIANPTILARISDE

ELHEFFHGMGYEPYEFVAGFDDEDAMSIHRRFADLFETVFDEICDIKATAQTNDVDRPFYPMIIFRTPKGWTCPKFI

DGKKTEGSWRSHQVPLASARDTEEHFEVLKNWLESYKPEELFTEDGAVRPEVTAFMPEGELRIGENPNANGGRIREE

LDLPALEDYEVTEVKEFGHGWGQLEATRKLGEYTRDIIKRNPDSFRIFGPDETASNRLQAAYEVTNKQWDNGYLSEL

VDEHMAVTGQVTEQLSEHQMEGFLEAYLLTGRHGIWSSYESFVHVIDSMLNQHAKWLEATVREIPWRKPISSMNLLV

SSHVWRQDHNGFSHQDPGVIDILLNKNFNNDHVVGIYFPVDSNMLLAVSEKAYKSTNMINAIIAGKQPAATWLTLDE

AREELAKGAAEWKWASNAEGDDVDIVLASVGDVPTQELMAAADKLKGYGIKYKFVNVVDLLSIQNASENDQALSDEE

FTELFTADKPVLMAYHAYAREVRSLIWDRPNHDNFNVHGYEEQGSTTTPFDMVRVNNIDRYELTAEALRAVDADKFA

DEIEKLEAFRTEAFQFAVDNGYDHPDYTDWVWSGVQTEKPGAVSATAATAGDNE

SEQ ID No: 68

ATGACTATCAACTACGATTCAAAAGACTACTTAAAATACGTCGATGCTTACTGGAGAGCCGCTAACTACTTATCCGT

CGGTCAATTGTTCTTGAGAAACAACCCATTGTTGAAGGATGAATTACAATCTAAGGACGTCAAAATCAAGCCAATTG

-continued

GTCATTGGGGTACTGTAGCTCCTCAAAACTTTATCTATGCACACTTGAATAGAGCCATTTTGAAATATGATTTGAAT
ATGTTCTACATTGAAGGTAGTGGTCATGGTGGTCAAGTTATGGTCTCTAACTCATACTTGGATGGTTCTTATACCGA
AACTTACCCAAAAGTTACACAAGATATTCAGGGTATGCAAAGATTGTTTAAACAATTTTCATTCCCTGGTGGTATAG
CTTCCCATGCTGCACCAGAAACCCCTGGTTCTATCCACGAAGGTGGTGAATTGGGTTATTCCATTAGTCATGGTGTT
GGTGCAATATTAGATAATCCAGACGTCATTGCCGCTGTAGAAATAGGTGACGGTGAATCTGAAACAGGTCCTTTGGC
AGCCTCTTGGTTCTCAGATAAATTCATAAACCCAATCCATGACGGTGCTGTTTTACCTATCGTCCAAATTAATGGTT
TTAAGATCTCAAACCCAACAATATTGTCCAGAATGAGTGATAGAGACTTAACCAACTACTACCATGGTATGGGTTGG
GAACCTTTGTTTGTTGAAACTGATGGTTCCGACAACTTCAAAGTTCACGCAGAAATGGCAGATGCCGTTGATAAAGC
CATCGAAAAGATTAAAGCTATCCAAAAGAATGCAAGAAACAACAACGATGACAGTTTGCCAATATGGCCTATGATCG
TTTTAAGAGCACCAAAAGGTTGGACAGGTCCTAAAAAGGATTTGGACGGTAACCCAATCGAAAATTCTTTTAGAGCA
CATCAAGTACCAATTCCTGTTGATGCAAACCATTTGGAACACAAGGATATGTTGATCGACTGGATGAAGAGTTACAA
GCCTGAAGAATTGTTCAACGAAGATGGTTCTTTAAAGGAAATCGTAAAGGTTAACCAACCAAAAGGTCAAAGAAGAA
TGGCTATGAACCCTATAACAAATGGTGGTATCAAGCCAAGAACCTTGAACATGCCTGATATGGAAAGATTTGCATTC
CCTAAAAATTCTTTGAAGAACAATAAGAAACCTGGTATGGATTTGCAAGTTGTCTCCACTTTTATAGCTGAAATTAT
TAAGAAAAATCCAATCAATTTCAGACAATTCGGTCCTGATGAAACTATGTCAAACAGATTGTGGGATGAGTTTAAAG
TAACAAACAGACAATGGATGCAAGCCGTTCATGAACCAAATGATCAATACATGGCTCACAGTGGTAGAATTTTGGAT
GCCCAATTATCTGAACATCAAGCTGAAGGTTGGATGGAAGGTTATGTTTTGACAGGTAGACACGCCTTTTTCGCTTC
ATACGAAGCCTTTACTAGAATCATCGATTCCATGTTGACACAATACTACAAGTGGTTGAGAAAGGCCGTTGAACAAG
ATTGGAGACATGACTATCCAAGTTTAAACGTCATTAATGCATCTCACGCCTTCCAACAAGATCATAATGGTTACACC
CACCAAGACCCAGGCATGTTAACTCATATGGCTGAAAAGGGTCACGAATTTGTTAACGAATTTTTGCCTGCTGATGC
AAACTCATTGTTAGCAGTCATGAATAAGTCTTTGCAAGTAAGAAACAAGATTAATATCATCGTCGCATCAAAGCATC
CAAGAACTCAATGGTTTACAATAGATGAAGCCAAGGAATTGGTAGACAACGGTTTAGGTATTATACCATGGGCTTCC
AATGATGACGGTGTTGAACCTGATGTAGTTTTTGCTGCAGGTGGTACAGAAGCTACCATGGAATCTTTGGCCGCTAT
TTCATTGTTACATGAATCCTTCCCAGAATTAAAGTTTAGATTCATTAACGTTATTGATTTGTTAAAGTTGAGAAAGA
AAGGTGACAATGATGACTATAGAGGTTTGTCAGATTTGGAATTTGACCATTACTTCACTAGAGAAAAACCAGTCGTT
TTCTCTTTCCACGGTTTCGAATCTTTGGCTAGAGATTTGTTTTATGACAGACATAACCACAATGTCATTTTTCATGG
TTACAGAGAAAACGGTGACATAACTACACCTTTTGACATGAGAGTATTGAATCATTTGGATAGATTCCACTTAGCTA
AAGACGCAATTAACGCCACCAAGTATGCTGATGTTGCAGGTCAATTTGACCAAAGAATGGATGACATGTTAGCCAAA
CATACTGCTTACATTTGTGATCAAGGTACCGACTTGCCAGAAGTTACTTCTTGGCAATGGCAAGATATTAAGTAA

SEQ ID No: 69

MTINYDSKDYLKYVDAYWRAANYLSVGQLFLRNNPLLKDELQSKDVKIKPIGHWGTVAPQNFIYAHLNRAILKYDLN
MFYIEGSGHGGQVMVSNSYLDGSYTETYPKVTQDIQGMQRLFKQFSFPGGIASHAAPETPGSIHEGGELGYSISHGV
GAILDNPDVIAAVEIGDGESETGPLAASWFSDKFINPIHDGAVLPIVQINGFKISNPTILSRMSDRDLTNYYHGMGW
EPLFVETDGSDNFKVHAEMADAVDKAIEKIKAIQKNARNNNDDSLPIWPMIVLRAPKGWTGPKKDLDGNPIENSFRA
HQVPIPVDANHLEHKDMLIDWMKSYKPEELFNEDGSLKEIVKVNQPKGQRRMAMNPITNGGIKPRTLNMPDMERFAF
PKNSLKNNKKPGMDLQVVSTFIAEIIKKNPINFRQFGPDETMSNRLWDEFKVTNRQWMQAVHEPNDQYMAHSGRILD
AQLSEHQAEGWMEGYVLTGRHAFFASYEAFTRIIDSMLTQYYKWLRKAVEQDWRHDYPSLNVINASHAFQQDHNGYT
HQDPGMLTHMAEKGHEFVNEFLPADANSLLAVMNKSLQVRNKINIIVASKHPRTQWFTIDEAKELVDNGLGIIPWAS
NDDGVEPDVVFAAGGTEATMESLAAISLLHESFPELKFRFINVIDLLKLRKKGDNDDYRGLSDLEFDHYFTREKPVV
FSFHGFESLARDLFYDRHNHNVIFHGYRENGDITTPFDMRVLNHLDRFHLAKDAINATKYADVAGQFDQRMDDMLAK
HTAYICDQGTDLPEVTSWQWQDIK

-continued

SEQ ID No: 70

ATGGCTGACAACGCCGACGCTCCACCACCTCCAATAGTCCCTTCACAATACGCTCAACATCCAGACGCTCCATTATC

CTCATTACCAGTTCAATTGGACCCTTCTCAATATACAGCTAAATACCCAGCAAAGCATTTGGATGCCATTGTCGCTA

ATTGGAGATTGTCCTGTTATTTGGGTGCTAGTCAAATTTTCTTGCAATCTAACGCAATCTTGTCAAGAAAATTGACT

AAGGATGACGTAAAACCAAGAAGAGCACATACAAATTTGGCTGGTGACATCCAAGGTGGTTTGTCTTTAGCCTACGT

TCACACCCAAGCATTGATCAGAAGAAAAGGTGACGAAGAAGGTGCTGAACCAAAGATGATTTTCGTCACTGGTCCAG

GTCATGGTGCCCCTGCTATATTGTCTCCATTGTACATCGAAGGTGCTATCTCAAAGTTCTACCCACAATACCCTTTG

AACGAACAAGGTTTAGAAAAGTTCGTTAAGTACTTCTCCTGGCCAGGTGGTTTCCCTAGTCATGTCAACGCTGAAAC

ACCAGGTTGCATACACGAAGGTGGTGAATTGGGTTATGCCTTAGGTGTAGCTTACGGTTCCGTTATGGACAGACCTG

AACAAATCAGTGTTGTCGTAGTTGGTGACGGTGAATCTGAAACTGGTCCAACTGCAACAGCCTGGCATTCACACAAA

TGGTTAGATCCTGCAGAATCCGGTGCCGTTTTGCCAATCTTGCATGTCAACGGTTTTAAGATCTCTGAAAGAACTAT

CCCAGGTACAATGGATAACGTTGAATTGTCTTTGTTGTACTCAGGTTACGGTTACCAAGTCAGATTCGTAGAATACA

AAGCTCAAGGTGAAGCACATATGGGTGGTAATGATCCTGCTGACAGAGTTTTGCACGAAGACATGGCTGCAAGTTTA

GATTGGGCATATGGTGAAATAAGAAAAATCCAAAAGGCCGCTAGATCTGGTGGTAAACCAATTGATAAGCCAAGATG

GCCTATGATAATCTTGAGATCACCTAAGGGTTGGACAGGTCCATCTTCAGAACATGGTAAACAATTGTTGAACAACT

TTGCCTCTCACCAAGTTCCATTGCCTGATGCTAAAACTGATGACGAAGCTAACGCATATTTGGAAAGATGGTTGAAG

AGTTACGAAGCTGATAAGTTGTTCGACTTCTCTGAAGATAACTTAAAGAGAGGTACAATCTTCGACCAATTGTTGTA

CGAAGCATTGCCTAAGGATATGGAAAGAAGATTAGGTTTCGTTAAGGAAACTTACAACGGTTACAAGCCATTGGAAT

TAGATGACTGGAAAAAGTACGGTTTTAAAAAGGGTGAAGACGTATCATGTATGAAAGCCATCGCTGGTTACTTAACA

GATGTTATTAAAAGAAACCCTAAGGAGTTTAGAATTTTCAGTCCAGACGAATTGGCTTTAAATAAGTTGGATGGTGT

TTTCTCTGTCACTGAAAGAAACATGCAATGGGACCCAGAAACTGCTCATAAGGGTGGTAGAGTTACAGAAATGTTGT

CTGAACACTCATTGCAAGCATGGTTACAAGGTTATACCTTAACTGGTAGACATGGTGTTTTTCCATCTTACGAAGCA

TTCTTGGGTATTGTCGCCACAATGACCGTACAATATACCAAGTTTATGAAGATGGCATTGGAAACTAATTGGAGAGG

TCCTACCGCCTCTTTAACTTACATCGAAACTTCAACATGGACCAGACAAGAACATAATGGTTACTCCCACCAAAACC

CAGGTTTCGTAAGTACTGTTTTGTCCTTACCTAGTCAATTAGCTAGAGTTTACTTTCCATCAGATGCAAATACATCC

GTAAGTGTTATCGCCCATTGTTTGAGATCCAAAAATTACATAAACTTAATAGTTGGTACAAAGGCTCCAACCCCTGT

CTACTTGTCTGTAGAAGAAGCAGAAAAGACATTGCATTGCAGGTGCCTCTGTTTGGGAAAATTATTCAGTTGATAAGG

GTGTCGATCCAGACGTCGTATTGGTAGGCATCGGTTACGAATTAACAGAAGAAGTTATCCATGCAGCCGCTTTGTTG

AGAAAGGATTTTGGTACTGAATTGAGAGTCAGAGTTGTCAACGTAGTTGATTTGTTAGTATTAGCTCCTAAGGGTGA

CCATCCACACGCCTTGGATGAAGCTGGTTTTAATTCATTATTCCCACCTGGTGTTCCTATCATTTTTAACTACCATG

GTTACGCAGGTCAATTAGCCTCCTTGTTATTCGATAGAAAACACTCCGTTGGTAGAAGTAGAATGAGAATCTTCGCT

TACTCAGAACAAGGTACTACAACCACTCCATTTGCAATGATGTGTTGCAATAACACTGATAGATTCAATTTGGCTGC

TGAAGCATTGGAAATGGTCACATTGAATTTGACAACCCAACATAACATTACCGGTGAAGAAAAGAGACACAGAGTAG

GTTCAGTCGTAGCTAGAGCACATGAAAGAATGTCCTTCTACAAGCACAAAAAGGTTGTCATGATGAGATACGCTGCA

GAAACCCAAAAGGATCATCCAGAAATTGGTGAAGTTGCAACTTTGGCCGAACAATAA

SEQ ID No: 71

MADNADAPPPPIVPSQYAQHPDAPLSSLPVQLDPSQYTAKYPAKHLDAIVANWRLSCYLGASQIFLQSNAILSRKLT

KDDVKPRRAHTNLAGDIQGGLSLAYVHTQALIRRKGDEEGAEPKMIFVTGPGHGAPAILSPLYIEGAISKFYPQYPL

NEQGLEKFVKYFSWPGGFPSHVNAETPGCIHEGGELGYALGVAYGSVMDRPEQISVVVVGDGESETGPTATAWHSHK

WLDPAESGAVLPILHVNGFKISERTIPGTMDNVELSLLYSGYGYQVRFVEYKAQGEAHMGGNDPADRVLHEDMAASL

DWAYGEIRKIQKAARSGGKPIDKPRWPMIILRSPKGWTGPSSEHGKQLLNNFASHQVPLPDAKTDDEANAYLERWLK

-continued

SYEADKLFDFSEDNLKRGTIFDQLLYEALPKDMERRLGFVKETYNGYKPLELDDWKKYGFKKGEDVSCMKAIAGYLT
DVIKRNPKEFRIFSPDELALNKLDGVFSVTERNMQWDPETAHKGGRVTEMLSEHSLQAWLQGYTLTGRHGVFPSYEA
FLGIVATMTVQYTKFMKMALETNWRGPTASLTYIETSTWTRQEHNGYSHQNPGFVSTVLSLPSQLARVYFPSDANTS
VSVIAHCLRSKNYINLIVGTKAPTPVYLSVEEAERHCIAGASVWENYSVDKGVDPDVVLVGIGYELTEEVIHAALL
RKDFGTELRVRVVNVVDLLVLAPKGDHPHALDEAGFNSLFPPGVPIIFNYHGYAGQLASLLFDRKHSVGRSRMRIFA
YSEQGTTTTPFAMMCCNNTDRFNLAAEALEMVTLNLTTQHNITGEEKRHRVGSVVARAHERMSFYKHKKVVMMRYAA
ETQKDHPEIGEVATLAEQ

SEQ ID No: 72

ATGACATCTCCTGTAATTGGTACCCCATGGAAGAAGTTGGATAGACCTGTAACCGACGAAGCATTGGAAGGTGTTGA
TAAGTATTGGAGAGCTGCAAACTATATGTCCATCGGTCAAATATATTTGAGAAGTAATCCATTAATGAAGGAACCTT
TTACAAGAGAAGATGTAAAGCATAGATTGGTTGGTCACTGGGGTACTACACCAGGTTTGAACTTTTTATTCGGTCAT
ATCAACAGATTGATCGCAGATCACCAACAAAACACTGTTTTCATTATGGGTCCAGGTCATGGTGGTCCTGCTGGTAC
TTCTCAATCTTATTTGGATGGTACCTACACTGAATACTACCCAAAGATAACAAACGACGAAGCTGGTTTGCAAAAGT
TTTTCAGACAATTTTCCTACCCAGGTGGTATCCCTAGTCATTACGCACCAGAAACTCCTGGTTCAATTCACGAAGGT
GGTGAATTGGGTTATGCTTTATCTCATGCCTACGGTGCTATCATGAATAACCCATCATTGTTTGTAGCCGCTATTGT
TGGTGACGGTGAAGCTGAAACTGGTCCTTTAGCAACAGGTTGGCAATCTAACAAGTTGGTCAATCCAAGAACAGATG
GTATCGTATTGCCTATATTGCATTTGAATGGTTACAAGATTGCCAATCCAACCATATTGGCTAGAATCTCTGACGAA
GAATTACACGATTTCTTTAGAGGTATGGGTTATAATCCTTACGAATTTGTTGCAGGTTTCGATGACGAAGACCATAT
GTCTATTCACAGAAGATTCGCTGATTTGTTAGAAACTGTATTCGACGAAATCTGTGATATCAAAGCTACTGCACAAA
CAAATGATGTTGACAGACCATTCTACCCTATGATCATATTCAGAACCCCAAAAGGTTGGACTTGCCCTAAGTTTATT
GATGGTAAAAAGACCGAAGGTTCCTGGAGAGCACATCAAGTCCCATTGGCCAGTGCTAGAGATACTGAAGAACACTT
CCAAGTATTGAAGAATTGGTTAGAATCTTACAAGCCTGAAGAATTGTTCGATGAAAAGGGTACATTGAGACCAGAAG
TTACCGAGTTTATGCCTAAGGGTGACTTGAGAATTGGTGCTAATCCAAACGCAAATGGTGGTAGAATCAGAGAAGAT
TTGAAATTGCCTGTTTTGGATGACTACAAAGTCAAGGAAGTAGAAGAATTTGGTCATGGTTGGGGTCAATTGGAAGC
AACTAGAAGATTAGGTGTTTACACAAGAGACATCATTAAGTTAAACCCAGATTCCTTTAGAATATTCGGTCCTGATG
AAACTGCTAGTAATAGATTGCAAGCAGCCTATGAAGTTACAAACAAACAATGGGACAATGGTTACTTGTCTTCATTA
GTCGATGAACATATGGCTGTCACCGGTCAAGTAACTGAACAATTATCAGAACACCAAATGGAAGGTTTTATTGAAGG
TTACGTTTTGACAGGTAGACATGGTATATGGTCCAGTTACGAATCTTTCGTTCATGTCATCGATTCAATGTTGAATC
AACACGCTAAGTGGTTAGAAGCAACTGTTAGAGAAATTCCATGGAGAAAGCCTATATCTTCAGTTAACTTGTTAGTC
TCCAGTCATGTATGGAGACAAGACCATAATGGTTTTTCTCACCAAGATCCAGGTGTTGTCTCAGTTTTGTTGAACAA
AACTTTTAATAACGACCATGTCATTGGTATCTATTTCGCAACCGATGCCAATATGTTGTTAGCCATTGGTGAAAAAG
CATATAAATCTACTAACAAGATAAATGCTATAATCGCAGGTAAACAACCAGCTGCAACCTGGTTGTCATTAGATGAA
GCAAGAGCCGAATTAACTAAAGGTGCCGCTGAATGGAAGTGGGCCTCCACCGCTAAAAATAACGACGAAACTGAAAT
AGTTTTAGCAAGTGTTGGTGACGTCCCAACTCAAGAAATAATGGCAGCCGCTGACAAATTGAAGGGTTACGGTATTA
AGTTTAAAGTAGTTAACGTCGTAGATTTGTTATCTTTACAAAACCCAAAGGAAAACAACGAAGCATTGTCAGACGAA
GAGTTTACTGAATTATTCACCGCCGATAAGCCTGTATTGATGGCATATCATTCCTACGCCAGAGAAGTTAAGGGTTT
GTTGTTCGATAGACCAAACAACGCTAACTTCAATATTCACGGTTATCAAGAACAAGGTTCAACCACTACACCTTTCG
ATATGGTTAGAGTTAACGATATCGACAGATACGAATTGACAGCTGAAGCATTGAGAATGTTAGATGCCGACAAGTAC
GCTGATGACATTAAAAAGTTAGAAGATTTCAGACAAGAAGCATTCCAATATGCCGTTGATAACGGTCATGATCACCC
AGACTACACAGATTGGGTTTGGTCTGGTGTCAAAACCGATAAGCCTGGTGCAGTTACAGCCACCGCAGCCACTGCTG
GTGACAATGAATAA

-continued

SEQ ID No: 73

MTSPVIGTPWKKLDRPVTDEALEGVDKYWRAANYMSIGQIYLRSNPLMKEPFTREDVKHRLVGHWGTTPGLNFLFGH

INRLIADHQQNTVFIMGPGHGGPAGTSQSYLDGTYTEYYPKITNDEAGLQKFFRQFSYPGGIPSHYAPETPGSIHEG

GELGYALSHAYGAIMNNPSLFVAAIVGDGEAETGPLATGWQSNKLVNPRTDGIVLPILHLNGYKIANPTILARISDE

ELHDFFRGMGYNPYEFVAGFDDEDHMSIHRRFADLLETVFDEICDIKATAQTNDVDRPFYPMIIFRTPKGWTCPKFI

DGKKTEGSWRAHQVPLASARDTEEHFQVLKNWLESYKPEELFDEKGTLRPEVTEFMPKGDLRIGANPNANGGRIRED

LKLPVLDDYKVKEVEEFGHGWGQLEATRRLGVYTRDIIKLNPDSFRIFGPDETASNRLQAAYEVTNKQWDNGYLSSL

VDEHMAVTGQVTEQLSEHQMEGFIEGYVLTGRHGIWSSYESFVHVIDSMLNQHAKWLEATVREIPWRKPISSVNLLV

SSHVWRQDHNGFSHQDPGVVSVLLNKTFNNDHVIGIYFATDANMLLAIGEKAYKSTNKINAIIAGKQPAATWLSLDE

ARAELTKGAAEWKWASTAKNNDETEIVLASVGDVPTQEIMAAADKLKGYGIKFKVVNVVDLLSLQNPKENNEALSDE

EFTELFTADKPVLMAYHSYAREVKGLLFDRPNNANFNIHGYQEQGSTTTPFDMVRVNDIDRYELTAEALRMLDADKY

ADDIKKLEDFRQEAFQYAVDNGHDHPDYTDWVWSGVKTDKPGAVTATAATAGDNE

SEQ ID No: 74

ATGAAGTTCGAAGCCACCAAAGAATTTATGAACGAATCCAGAACAGAAGCCGCAAAAGCCGACCCATCACCATTACA

ATCCCACTTACCAGCTACTTTGGATACATTGCAAGTTCATTTGTTGAAAGACTATGTACCTGAAGATGACTTGGTTA

CATTAAAGAATTTCCAAAGAGTATGTAACTACATCGCTGCAGCCATGATTTTCTTGTGCGATAACGTTTTGTTAGAA

AACAAATTAACATCTGACCATATTAAGCCAAGATTGTTAGGTCATTGGGGTACTTGTCCTGCCTTGGCTTTAGCATA

CTCCCATTGCAACAGAATCATCAGTAAGTACAATTTGGATATGTTATTTGTTACTGGTCCAGGTCACGGTGCCCCTG

CTATTTTGGCTGCATTATACATCGAAGGTTCTTTACAAGCATATTACCCACAATACGGTCATAACATGCAAGGTTTG

CACAGATTGATCACCAAATTTTCTGTCACTGGTGGTTTCCCATCACATGTCAATGCCGAAGTACCTGGTGCTATACA

CGAAGGTGGTGAATTGGGTTATGCATTATCTGTATCATACGGTGCCGTTTTGGATAGACCAAATTTGATTGTTGCCT

GTGTTGTCGGTGACGGTGAAGCTGAAACCGGTCCTACTGCCGCTTCTTGGCATTGCCACAAATTCATAGATCCAGCA

GAATCAGGTGCCGTCATACCTATCTTGAATTTGAATGGTTTTAAGATCTCAGAAAGAACAGTATATGGTTGTATGGA

TAGAAGAGAATTGTCTGCTTTGTTTTCTGGTTTCGGTTACCAAGTAGTTTTCGTAGATTACAGAACTGCTGATGACG

TTAATAGAGATATGGCAGCCGCTATGGACTGGTGTGTTGAAATCATACATGAAATACAAGATGCAGCCAGAGCAGGT

ACACCAATAATCAAACCAAGATGGCCTATGATTATATTGCACACCCCAAAGGGTTGGGGTTGCCCTAAAACTTTGCA

TGGTAAACCATTAGAAGGTACTTTTAGAGCACATCAAGTTCCTTTGAAAAATGCTAAGACTGATGCAGAAGAATTGG

GTCAATTAGAAAACTGGTTGAAGTCTTACCATATAGAAGATTTCATCGACAAGTCAAACGGTTTGCCATTAAAGGGT

TTGATTGAACACTTACCACCTAGAGTAAAAAGAATGGGTCAAAAGACTGATGCTAATAACGACTTCCAACCATTATG

TGTTCCTGATTGGAACGACTTTTCTATCGATAGAGGTATTTTGGAATCTGCTACCTCAATTGTTGGTAAATACTTGG

ATAGAGTCTTACAAGCAAACCCAAAGACTTTGAGATTATTTTCCCCTGATGAATTAGCCAGTAACAAATTGGACGGT

GTTTTAGAACATTCAAACAGAACATTGCAAACCGATGCCATATCCGCTTGGAGTAGAGGTAGAGTAACAGAAGTTTT

GTCTGAACATATGTGCCAAGGTTTCATGCAAGGTTATACCTTAACTGGTAGAACCGCTATTTTTCCATCCTACGAAG

CATTCTTGCCTATCATAACTTCTATGACAGTTCAATACACCAAGTTCTTGAAGATGGCATTAGAAACTAAGTGGCAT

GGTAGAGTCGGTTCCTTAAACTACGTAACTACAAGTACATGGGCTAGACAAGAACATAATGGTTTTTCTCACCAATC

ACCAAGATTCATAACCACTATGTTGTCCTTTAAGCCTACATTAACCAGAGTTTATTTCCCACCTGATACAAACTGTT

TCTTGTCTACTATCGCACATTGCTTATCTTCAGACAATGGTGTTAACTTGATGGTCTCCAGTAAAAATCCAGGTCCT

TCCTGGTTAAGTAGAGAAGAAGCTGAAGAACATTGTGTCGCAGGTGCCTCTGTATGGAAGTTCGCATCAACTGATGG

TGGTTTAGATCCAGACGTCGTATTAGTTGGTATCGGTAACGAAATCATGTTCGAAGTCATAGCTGCAGCCTCTATCT

TGGCTCATGATTTGCCAAAATTGAGAATTAGAGTTGTCAACATCACAGATTTGATGATCTTAGCCGACAATCATCCA

CACTCCATGAGTGAAATCGAGTTTAATGCTTTATTCACTCCTAACAGACATGTCCACTTCAATTATCATGGTTACGT

AATGGATTTGCAATCTTTGTTATTTTCAAGAATCGACGCATCTAGAGTTTCAATGGAAGGTTATTGTGAAGAAGGTA

-continued

CAACCACTACACCATTCAATATGATGATTGCAAACAGAACTTCTAGATACCATGTTGCCATGGCTGCAGTCGCTGGT

GCAACATGTAACCCTGAAGTTGCTATGAATTGCCACAAATTGATATCAAACTACAAGCATAGATTGACTCAAATTAA

ACACTATATATACGAAAACGGTGTTGATCCAGAAGGTACTTTTGATATCCCTGACAATTTGACAAAGGGTCAAGTCA

TTTAA

SEQ ID No: 75

MKFEATKEFMNESRTEAAKADPSPLQSHLPATLDTLQVHLLKDYVPEDDLVTLKNFQRVCNYIAAAMIFLCDNVLLE

NKLTSDHIKPRLLGHWGTCPALALAYSHCNRIISKYNLDMLFVTGPGHGAPAILAALYIEGSLQAYYPQYGHNMQGL

HRLITKFSVTGGFPSHVNAEVPGAIHEGGELGYALSVSYGAVLDRPNLIVACVVGDGEAETGPTAASWHCHKFIDPA

ESGAVIPILNLNGFKISERTVYGCMDRRELSALFSGFGYQVVFVDYRTADDVNRDMAAAMDWCVEIIHEIQDAARAG

TPIIKPRWPMIILHTPKGWGCPKTLHGKPLEGTFRAHQVPLKNAKTDAEELGQLENWLKSYHIEDFIDKSNGLPLKG

LIEHLPPRVKRMGQKTDANNDFQPLCVPDWNDFSIDRGILESATSIVGKYLDRVLQANPKTLRLFSPDELASNKLDG

VLEHSNRTLQTDAISAWSRGRVTEVLSEHMCQGFMQGYTLTGRTAIFPSYEAFLPIITSMTVQYTKFLKMALETKWH

GRVGSLNYVTTSTWARQEHNGFSHQSPRFITTMLSFKPTLTRVYFPPDTNCFLSTIAHCLSSDNGVNLMVSSKNPGP

SWLSREEAEEHCVAGASVWKFASTDGGLDPDVVLVGIGNEIMFEVIAAASILAHDLPKLRIRVVNITDLMILADNHP

HSMSEIEFNALFTPNRHVHFNYHGYVMDLQSLLFSRIDASRVSMEGYCEEGTTTTPFNMMIANRTSRYHVAMAAVAG

ATCNPEVAMNCHKLISNYKHRLTQIKHYIYENGVDPEGTFDIPDNLTKGQVI

SEQ ID No: 76

ATGCCAGGTGAAGTCATAGACCAACCAAACCCTCCTCCATTAACATCCCACTTGCCAGATACCATAGAAGAATTAGC

AGTAAAGCCTAGTAAAGCTCCATTGTCTAATTTGGATTTGGTTTCTTTGAGAGAATTTCAAAGAGCTGCATGTTATA

TAGCTTCCGCAATGATCTTCTTAAAGGATAACGTATTGTTGGACAGAGAATTGAGATTTGAAGATGTTAAGCCTAGA

TTGTTAGGTCATTGGGGTACTTGCCCAGGTTTGATATTGATCTGGTCACACTTAAATTTGTTAATTAGAGATTCTTC

ACAAGACATGTTGTTCGTTATAGGTCCTGGTCATGGTGCACCAGCCGCTTTAGCCTGTTTGTGGTTAGAAGGTTCTT

TGGAAAGATTTTACCCTGATAAGTACAGAACAGACAAGGAAGGTTTGCATAATTTGATAACAAAATTTTCTGTTCCA

ACCGGTTTCCCTTCTCATATAAACCCAGAAACTCCTGGTTGTATCCACGAAGGTGGTGAATTGGGTTATGCCTTAGC

TGTCTCATTTGGTGCTGTAATGGATAAGCCTGACTTGATAGTTCCATGCGTTGTCGGTGACGGTGAAGCAGAAACAG

GTCCAACCGCAGCCGCTTGGCATTCAATCAAATACTTAGATCCTGCTGAATCCGGTGCAGTTATCCCAATTTTGCAC

GTCAACGGTTTTAAGATATCTGAAAGAACTATCTTCGGTTGTATGGATAACACAGAATTGGTTTTGTTATTCTCTGG

TTATGGTTACGAAGTTTGCATCGTCGAAAATTTGGATGCTATTGACACTGAATTGCATACAGCCTTATTTTGGGCTT

TGAGTGAAATTAAAAGAATACAAGGTGCAGCCAGATCTGGTAACCCTATTACCAAGCCAAGATGGCCTATGATTATA

TTGAGAACTCCTAAAGGTTGGACCGGTCCAAGAACTGTTGATGACAAGATCATTGAAGGTTCTTTCCATGCACACCA

AGTACCAGTTACAAAAGCCAATAAGGATGAAGGTCATTTGAGAATTTTACAAGATTGGTTGAAGAGTTACGACGTTA

GAGGTTTGTTACCAGATGGTAAACCTTCTGGTGACTTTTTGGACATTTTACCACCTGATCCTCATAAAAGATTAGGT

CAATCTAAGTTGGCTTACGACTGTCATCAACCATTGGATTTGCCTGACTGGAGACCACACTCAGTTGATAAATTTGA

AGAAGCCTCCAGTATGCAACAATCCGGTAAATTCTTGGATGTAGTTGCTAGACAAAACATGAAGACTTTTAGAATTT

TCTCTCCAGATGAATTAGAATCAAATAAGTTATCCGCAGTATTGGATCATTCTTCAAGAAACTTCCAATGGGACCAA

TATTCTAGAGCACAAGGTGGTAGAGTTATAGAAATCTTGTCCGAACACTGTTGCCAAGGTTTCTTGCAAGGTTATAC

TTTGACAGGTAGAACTGCTATTTTTCCTTCTTACGAATCATTCTTAGGTATCATCCATACAATGATGATACAATACT

CCAAATTCAGTAAGATATCTAGAAAATTGCCATGGAGAGGTGACTTGTCTTCTATTAATTACATCGAAACCTCTACT

TGGGCAAGACAAGAACATAATGGTTTTTCACACCAAAACCCATCCTTCATAGGTGCTGTCTTGAATTTGAAAGCAGA

AATCGCCAGAGTATACTTGCCACCTGATGCAAACTGTTTCTTGTCTACTTTGCATCACTGCTTGCAATCCAAAAATT

ACGTCAACTTGATGATAGGTAGTAAGCAACCAACCCCTGTATACTTGTCTGCTGAAGATGCACAAAGACATTGTGAA

-continued

GACGGTGCCAGTATATGGAGATGGGCTTCTACCCATGATGGTGAACACCCTGACGTCGTATTAGTTGGTATCGGTGT

CGAAGTAACTTTTGAAGTCATTAAAGCTGCACAATTGTTATCTAGATTAGCTCCAAATTTGAGAGTTAGAGTTGTCA

ACGTCACAGATTTGTTAGTATTACCTCATGAAAGTCATCACCCACACGCTTTGGACTCTAAAGCATTTGAAGATATG

TTCACATTGGACAAGCCAGTCTGCTTCAATTATCATTCATACGCTACCGAATTACAAGGTTTGTTATTTGGTAGACC

TGCATTGCACAGAATGTCAGTTGAAGGTTATAAAGAAGAAGGTTCCACTACAACCCCATTCGATATGATGTTGGTAA

ACACTGTTTCAAGATTCCATGTTGCCTCCAGAGCTTTGAAGGCCGCTGCAGCCCAAAACGATGAAGTCAAGGAAAAC

TTAAGTGCATTGTTAGCCAAGGTAGATGACGAAATGAAGTCTGTTAAGGATTACATCGAACAATGGGGTAAAGTTGA

CCCAGATGACATCTATGAATTGGATTTCTTGAAGAAAGACTAA

SEQ ID No: 77

MPGEVIDQPNPPPLTSHLPDTIEELAVKPSKAPLSNLDLVSLREFQRAACYIASAMIFLKDNVLLDRELRFEDVKPR

LLGHWGTCPGLILIWSHLNLLIRDSSQDMLFVIGPGHGAPAALACLWLEGSLERFYPDKYRTDKEGLHNLITKFSVP

TGFPSHINPETPGCIHEGGELGYALAVSFGAVMDKPDLIVPCVVGDGEAETGPTAAAWHSIKYLDPAESGAVIPILH

VNGFKISERTIFGCMDNTELVLLFSGYGYEVCIVENLDAIDTELHTALFWALSEIKRIQGAARSGNPITKPRWPMII

LRTPKGWTGPRTVDDKIIEGSFHAHQVPVTKANKDEGHLRILQDWLKSYDVRGLLPDGKPSGDFLDILPPDPHKRLG

QSKLAYDCHQPLDLPDWRPHSVDKFEEASSMQQSGKFLDVVARQNMKTFRIFSPDELESNKLSAVLDHSSRNFQWDQ

YSRAQGGRVIEILSEHCCQGFLQGYTLTGRTAIFPSYESFLGIIHTMMIQYSKFSKISRKLPWRGDLSSINYIETST

WARQEHNGFSHQNPSFIGAVLNLKAEIARVYLPPDANCFLSTLHHCLQSKNYVNLMIGSKQPTPVYLSAEDAQRHCE

DGASIWRWASTHDGEHPDVVLVGIGVEVTFEVIKAAQLLSRLAPNLRVRVVNVTDLLVLPHESHHPHALDSKAFEDM

FTLDKPVCFNYHSYATELQGLLFGRPALHRMSVEGYKEEGSTTTPFDMMLVNTVSRFHVASRALKAAAAQNDEVKEN

LSALLAKVDDEMKSVKDYIEQWGKVDPDDIYELDFLKKD

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed is:

1. A method for producing ethanol from glucose, the method comprising culturing a recombinant yeast cell in a fermentation process employing glucose feedstock, the recombinant yeast cell comprising at least one heterologous nucleic acid encoding polypeptides having:

i) phosphoketolase activity;

ii) phosphotransacetylase activity; and iii) acetylating acetaldehyde dehydrogenase activity, wherein said cell does not comprise a heterologous modified xylose reductase gene, wherein said cell is capable of increased ethanol production from glucose in a fermentation process when compared to the yeast cell without the at least one heterologous nucleic acid, and wherein the polypeptide having phosphoketolase activity has the amino acid of SEQ ID NO: 57, the polypeptide having acetylating dehydrogenase activity has the amino acid of SEQ ID NO: 32, and the polypeptide having phophotransacetylase activity is the phophotransacetylase from *Lactobacillus plantarum.*

2. The method of claim 1, wherein the cell has reduced NAD-dependent glycerol phosphate dehydrogenase (GPD) activity compared to a yeast cell without the at least one heterologous nucleic acid.

3. The method of claim 1, wherein the cell comprises an altered pentose phosphate pathway resulting from one or more heterologously expressed nucleic acids affecting the pentose phosphate pathway.

4. The method of claim 1 wherein the yeast cell is *Saccharomyces cerevisiae.*

5. The method of claim 1, wherein the fermentation process is selected from the group consisting of post-liquefaction and saccharification fermentation, simultaneous saccharification and fermentation (SSF) and granular starch hydrolyzing enzyme (GSHE) fermentation.

6. The method of claim 1, wherein the yeast cell further expresses glucoamylase.

7. The method of claim 6, wherein the glucoamylase is (a) encoded by a recombinant gene comprising the amino acid sequence of SEQ ID NO. 11; or (b) a recombinant gene having at least 80%, 85%, 90%, 95%, 98% or 99% identity to the amino acid sequence of SEQ ID NO. 11.

8. The method according to claim 1 wherein the yeast cell further comprises at least one additional recombinant gene, wherein the at least one additional recombinant gene encodes one or more of an enzyme selected from the group consisting of a dehydrogenase, a transketolase, a phosphoketolase, a transladolase, an epimerase, a phytase, a xylanase, a β-glucanase, a phosphatase, a protease, an alpha-amylase, a beta-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase.

9. The method according claim 8 wherein the at least one additional recombinant gene encodes an alpha-amylase, a glucoamylase, a cutinase, a trehalase or combinations thereof.

10. The method according to claim 8, wherein the at least one additional recombinant gene encodes an alpha-amylase.

11. The method according to claim 1 further comprising an additional yeast species.

12. The method according to claim 1, wherein the polypeptide having phosphoketolase activity is encoded by a nucleic acid having the sequence of SEQ ID NO: 56, the polypeptide having phophotransacetylase activity is encoded by a nucleic acid having the sequence of SEQ ID NO: 4, and the polypeptide having acetylating acetaldehyde dehydrogenase activity is encoded by a nucleic acid having the sequence of SEQ ID NO: 31.

* * * * *

SEQUENCE LISTING

<160> NUMBER OF SEQ ID NOS: 77

<210> SEQ ID NO 1
<211> LENGTH: 3789
<212> TYPE: DNA
<213> ORGANISM: artificial sequence
<220> FEATURE:
<223> OTHER INFORMATION: Constructed Vector

<400> SEQUENCE: 1
aaataataaa aaaagtaacc ccacttctac ttctacatcg gaaaaacatt ccattcacat 60
atcgtctttg gcctatcttg ttttgtcctc ggtagatcag gtcagtacaa acgcaacacg 120
aaagaacaaa aaaagaagaa aacagaaggc caagacaggg tcaatgagac tgttgtcctc 180
ctactgtccc tatgtctctg gccgatcacg cgccattgtc cctcagaaac aaatcaaaca 240
cccacacccc gggcacccaa agtccccacc cacaccacca atagagtctg ctggtgttgc 300
tgatttgatc accacctgcg ctggtggtag aaacgtcaag gttgctaggc taatggctac 360
ttctggtaag gacgcctggg aatgtgaaaa ggagttgttg aatggccaat ccgctcaagg 420
tttaattacc tgcaaagaag ttcacgaatg gttggaaaca tgtggctctg tcgaagactt 480

-continued cccattattt gaagccgtat accaaatcgt ttacaacaac tacccaatga agaacctgcc 540
ggacatgatt gaagaattag atctacatga agattagatt tattggagaa agataagctt 600
ttcaattcat catttttttt ttattctttt ttttgattcc ggtttccttg aaattttttt 660
gattcggtaa tctccgaaca gaaggaagaa cgaaggaagg agcacagact tagattggta 720
tatatacgca tatgtagtgt tgaagaaaca tgaaattgcc cagtattctt aacccaactg 780
cacagaacaa aaacctgcag gaaacgaaga taaatcatgt cgaaagctac atataaggaa 840
cgtgctgcta ctcatcctag tcctgttgct gccaagctat ttaatatcat gcacgaaaag 900
caaacaaact tgtgtgcttc attggatgtt cgtaccacca aggaattact ggagttagtt 960
gaagcattag gtcccaaaat ttgtttacta aaaacacatg tggatatctt gactgatttt 1020
tccatggagg gcacagttaa gccgctaaag gcattatccg ccaagtacaa tttttttactc 1080
ttcgaagaca gaaaatttgc tgacattggt aatacagtca aattgcagta ctctgcgggt 1140
gtatacagaa tagcagaatg ggcagacatt acgaatgcac acggtgtggt gggcccaggt 1200
attgttagcg gtttgaagca ggcggcagaa gaagtaacaa aggaacctag aggccttttg 1260
atgttagcag aattgtcatg caagggctcc ctagctactg gagaatatac taagggtact 1320
gttgacattg cgaagagcga caaagatttt gttatcggct ttattgctca aagagacatg 1380
ggtggaagag atgaaggtta cgattggttg attatgacac ccggtgtggg tttagatgac 1440
aagggagacg cattgggtca acagtataga accgtggatg atgtggtctc tacaggatct 1500
gacattatta ttgttggaag aggactattt gcaaagggaa gggatgctaa ggtagagggt 1560
gaacgttaca gaaaagcagg ctgggaagca tatttgagaa gatgcggcca gcaaaactaa 1620
aaaactgtat tataagtaaa tgcatgtata ctaaactcac aaattagagc ttcaatttaa 1680
ttatatcagt tattacccgg gaatctcggt cgtaatgatt tttataatga cgaaaaaaaa 1740
aaaattggaa agaaaaaggc gcgcccccga caatttggtt gctaatccag acttgattga 1800
ttcagtcaag gatgtcgaca tcatcgtttt caacattcca catcaatttt tgccccgtat 1860
ctgtagccaa ttgaaaggtc atgttgattc acacgtcaga gctatctcct gtctaaaggg 1920
ttttgaagtt ggtgctaaag gtgtccaatt gctatcctct tacatcactg aggaactagg 1980
tattcaatgt ggtgctctat ctggtgctaa cattgccacc gaagtcgctc aagaacactg 2040
gtctgaaaca acagttgctt accacattcc aaaggattta aatccaaaaa tggccatgag 2100
acaataaccc tgataaatgc ttcaataata ttgaaaaagg aagagtatga gtattcaaca 2160
tttccgtgtc gcccttattc ccttttttgc ggcattttgc cttcctgttt ttgctcaccc 2220
agaaacgctg gtgaaagtaa aagatgctga agatcagttg ggtgcacgag tgggttacat 2280
cgaactggat ctcaacagcg gtaagatcct tgagagtttt cgccccgaag aacgttttcc 2340
aatgatgagc acttttaaag ttctgctatg tggcgcggta ttatcccgta ttgacgccgg 2400
gcaagagcaa ctcggtcgcc gcatacacta ttctcagaat gacttggttg agtactcacc 2460
agtcacagaa aagcatctta cggatggcat gacagtaaga gaattatgca gtgctgccat 2520
aaccatgagt gataacactg cggccaactt acttctgaca acgatcggag gaccgaagga 2580
gctaaccgct tttttgcaca acatgggggga tcatgtaact cgccttgatc gttgggaacc 2640
ggagctgaat gaagccatac caaacgacga gcgtgacacc acgatgcctg tagcaatggc 2700
aacaacgttg cgcaaactat taactggcga actacttact ctagcttccc ggcaacaatt 2760
aatagactgg atggaggcgg ataaagttgc aggaccactt ctgcgctcgg cccttccggc 2820
tggctggttt attgctgata aatctggagc cggtgagcgt gggtctcgcg gtatcattgc 2880

-continued

```
agcactgggg ccagatggta agccctcccg tatcgtagtt atctacacga cggggagtca   2940

ggcaactatg gatgaacgaa atagacagat cgctgagata ggtgcctcac tgattaagca   3000

ttggtaactg tcagaccaag tttactcata tatactttag attgatttaa aacttcattt   3060

ttaatttaaa aggatctagg tgaagatcct ttttgataat ctcatgacca aaatccctta   3120

acgtgagttt tcgttccact gagcgtcaga ccccgtagaa aagatcaaag gatcttcttg   3180

agatcctttt tttctgcgcg taatctgctg cttgcaaaca aaaaaaccac cgctaccagc   3240

ggtggtttgt ttgccggatc aagagctacc aactcttttt ccgaaggtaa ctggcttcag   3300

cagagcgcag ataccaaata ctgtccttct agtgtagccg tagttaggcc accacttcaa   3360

gaactctgta gcaccgccta catacctcgc tctgctaatc ctgttaccag tggctgctgc   3420

cagtggcgat aagtcgtgtc ttaccgggtt ggactcaaga cgatagttac cggataaggc   3480

gcagcggtcg ggctgaacgg ggggttcgtg cacacagccc agcttggagc gaacgaccta   3540

caccgaactg agatacctac agcgtgagct atgagaaagc gccacgcttc ccgaagggag   3600

aaaggcggac aggtatccgg taagcggcag ggtcggaaca ggagagcgca cgagggagct   3660

tccaggggga aacgcctggt atctttatag tcctgtcggg tttcgccacc tctgacttga   3720

gcgtcgattt ttgtgatgct cgtcaggggg gcggagccta tggaaaaacg ccagcaacgc   3780

tgcatattt                                                           3789
```

```
<210> SEQ ID NO 2
<211> LENGTH: 3757
<212> TYPE: DNA
<213> ORGANISM: artificial sequence
<220> FEATURE:
<223> OTHER INFORMATION: Constructed Vector

<400> SEQUENCE: 2

aaataaaaac tggagcaagg aattaccatc accgtcacca tcaccatcat atcgccttag     60

cctctagcca tagccatcat gcaagcgtgt atcttctaag attcagtcat catcattacc    120

gagtttgttt tccttcacat gatgaagaag gtttgagtat gctcgaaaca ataagacgac    180

gatggctctg ccattgttat attacgcttt tgcggcgagg tgccgatggg ttgctgaggg    240

gaagagtgtt tagcttacgg acctattgcc attgttattc cgattaacgt caatgtcatc    300

gatgatgttg ctggtatatc cattgccggt gccttgaaga acgtcgtggc acttgcatgt    360

ggtttcgtag aaggtatggg atggggtaac aatgcctccg cagccattca aaggctgggt    420

ttaggtgaaa ttatcaagtt cggtagaatg tttttcccag aatccaaagt cgagacctac    480

tatcaagaat ccgctggtgt tgcagatctg atcaccacct gctcaggcgg tagaaacgtc    540

aaggttgcca catacatggc caagaccggt aagtcagcct tggaagcttt tcaattcatc    600

attttttttt tattcttttt tttgattccg gtttccttga aatttttttg attcggtaat    660

ctccgaacag aaggaagaac gaaggaagga gcacagactt agattggtat atatacgcat    720

atgtagtgtt gaagaaacat gaaattgccc agtattctta acccaactgc acagaacaaa    780

aacctgcagg aaacgaagat aaatcatgtc gaaagctaca tataaggaac gtgctgctac    840

tcatcctagt cctgttgctg ccaagctatt taatatcatg cacgaaaagc aaacaaactt    900

gtgtgcttca ttggatgttc gtaccaccaa ggaattactg gagttagttg aagcattagg    960

tcccaaaatt tgtttactaa aaacacatgt ggatatcttg actgattttt ccatggaggg   1020

cacagttaag ccgctaaagg cattatccgc caagtacaat tttttactct tcgaagacag   1080
```

-continued

```
aaaatttgct gacattggta atacagtcaa attgcagtac tctgcgggtg tatacagaat   1140
agcagaatgg gcagacatta cgaatgcaca cggtgtggtg ggcccaggta ttgttagcgg   1200
tttgaagcag gcggcagaag aagtaacaaa ggaacctaga ggccttttga tgttagcaga   1260
attgtcatgc aagggctccc tagctactgg agaatatact aagggtactg ttgacattgc   1320
gaagagcgac aaagatttg ttatcggctt tattgctcaa agagacatgg gtggaagaga    1380
tgaaggttac gattggttga ttatgacacc cggtgtgggt ttagatgaca agggagacgc   1440
attgggtcaa cagtatagaa ccgtggatga tgtggtctct acaggatctg acattattat   1500
tgttggaaga ggactatttg caaagggaag ggatgctaag gtagagggtg aacgttacag   1560
aaaagcaggc tgggaagcat atttgagaag atgcggccag caaaactaaa aaactgtatt   1620
ataagtaaat gcatgtatac taaactcaca aattagagct tcaatttaat tatatcagtt   1680
attacccggg aatctcggtc gtaatgattt ttataatgac gaaaaaaaaa aaattggaaa   1740
gaaaaaggcg cgccccttgt tttcaacatc cctcatcaat ttttaccaaa catagtcaaa   1800
caattgcaag gccacgtggc ccctcatgta agggccatct cgtgtctaaa agggttcgag   1860
ttgggctcca agggtgtgca attgctatcc tcctatgtta ctgatgagtt aggaatccaa   1920
tgtggcgcac tatctggtgc aaacttggca ccggaagtgg ccaaggagca ttggtccgaa   1980
accaccgtgg cttaccaact accaaaggat tatcaaggtg atggcaagga tgtagatcat   2040
aagatttaaa tccaaaaatg gccatgagac aataaccctg ataaatgctt caataatatt   2100
gaaaaaggaa gagtatgagt attcaacatt tccgtgtcgc ccttattccc ttttttgcgg   2160
cattttgcct tcctgttttt gctcacccag aaacgctggt gaaagtaaaa gatgctgaag   2220
atcagttggg tgcacgagtg ggttacatcg aactggatct caacagcggt aagatccttg   2280
agagttttcg ccccgaagaa cgttttccaa tgatgagcac ttttaaagtt ctgctatgtg   2340
gcgcggtatt atcccgtatt gacgccgggc aagagcaact cggtcgccgc atacactatt   2400
ctcagaatga cttggttgag tactcaccag tcacagaaaa gcatcttacg gatggcatga   2460
cagtaagaga attatgcagt gctgccataa ccatgagtga taacactgcg gccaacttac   2520
ttctgacaac gatcggagga ccgaaggagc taaccgcttt tttgcacaac atgggggatc   2580
atgtaactcg ccttgatcgt tgggaaccgg agctgaatga agccatacca aacgacgagc   2640
gtgacaccac gatgcctgta gcaatggcaa caacgttgcg caaactatta actggcgaac   2700
tacttactct agcttcccgg caacaattaa tagactggat ggaggcggat aaagttgcag   2760
gaccacttct gcgctcggcc cttccggctg gctggtttat tgctgataaa tctggagccg   2820
gtgagcgtgg gtctcgcggt atcattgcag cactggggcc agatggtaag ccctcccgta   2880
tcgtagttat ctacacgacg gggagtcagg caactatgga tgaacgaaat agacagatcg   2940
ctgagatagg tgcctcactg attaagcatt ggtaactgtc agaccaagtt tactcatata   3000
tactttagat tgatttaaaa cttcattttt aatttaaaag gatctaggtg aagatccttt   3060
ttgataatct catgaccaaa atcccttaac gtgagttttc gttccactga gcgtcagacc   3120
ccgtagaaaa gatcaaagga tcttcttgag atcctttttt tctgcgcgta atctgctgct   3180
tgcaaacaaa aaaaccaccg ctaccagcgg tggtttgttt gccggatcaa gagctaccaa   3240
ctctttttcc gaaggtaact ggcttcagca gagcgcagat accaaatact gtccttctag   3300
tgtagccgta gttaggccac cacttcaaga actctgtagc accgcctaca tacctcgctc   3360
tgctaatcct gttaccagtg gctgctgcca gtggcgataa gtcgtgtctt accgggttgg   3420
actcaagacg atagttaccg gataaggcgc agcggtcggg ctgaacgggg ggttcgtgca   3480
```

-continued

```
cacagcccag cttggagcga acgacctaca ccgaactgag atacctacag cgtgagctat   3540

gagaaagcgc cacgcttccc gaagggagaa aggcggacag gtatccggta agcggcaggg   3600

tcggaacagg agagcgcacg agggagcttc caggggggaaa cgcctggtat ctttatagtc   3660

ctgtcgggtt tcgccacctc tgacttgagc gtcgattttt gtgatgctcg tcaggggggc   3720

ggagcctatg gaaaaacgcc agcaacgctg catattt                              3757
```

<210> SEQ ID NO 3
<211> LENGTH: 2478
<212> TYPE: DNA
<213> ORGANISM: Bifidobacterium animalis

<400> SEQUENCE: 3

```
atgaccaacc cagtcattgg tactccatgg caaaaattgg atagaccagt ttccgaagaa     60

gccattgaag gtatggataa gtattggaga gttgccaact acatgtccat tggtcaaatc    120

tacttgagat ccaacccatt gatgaaggaa ccattcacta gagatgatgt caagcacaga    180

ttggttggtc attggggtac tactccaggt ttgaattttt tgttggccca catcaacaga    240

ttgatcgctg atcatcaaca aaacaccgtt ttcattatgg gtccaggtca tggtggtcca    300

gctggtactg ctcaatctta tattgatggt acttacaccg aatattaccc aaacatcact    360

aaggatgaag ccggtttaca aaagttcttc agacaatttt cttacccagg tggtatccca    420

tctcattttg ctccagaaac tccaggttct attcatgaag gtggtgaatt gggttatgct    480

ttgtctcatg cttatggtgc cattatggat aacccatctt tgttcgttcc atgcattatt    540

ggtgatggtg aagctgaaac tggtccattg gctactggtt ggcaatctaa caaattggtt    600

aacccaagaa ccgatggtat cgttttgcca atcttgcatt tgaacggtta caagattgct    660

aacccaacca ttttggccag aatctctgat gaagaattgc acgatttttt cagaggtatg    720

ggttaccacc catacgaatt tgttgctggt tttgataacg aagatcactt gtccatccat    780

agaagattcg ccgaattatt cgaaaccatc ttcgacgaaa tttgcgatat taaggctgct    840

gctcaaactg atgatatgac tagaccattt tacccaatgt tgatcttcag aactccaaag    900

ggttggactt gtccaaagtt tatcgatggt aaaaagaccg aaggttcttg gagagcacat    960

caagttccat tggcttcagc tagagatact gaagctcatt tcgaagtttt gaagggttgg   1020

atggaatctt acaagcctga agaattattc aacgccgacg gttctatcaa agaagatgtt   1080

actgctttta tgccaaaggg tgaattgaga attggtgcta atccaaatgc taacggtggt   1140

agaattagag aagatttgaa gttgccagaa ttggaccaat acgaaattac cggtgtcaaa   1200

gaatatggtc atggttgggg tcaagttgaa gctccaagat ctttgggtgc ttactgtaga   1260

gatatcatca agaacaaccc agactccttt agagtttttg gtccagacga aactgcttcc   1320

aatagattga atgctactta cgaagtcacc aaaaagcaat gggataacgg ttatttgtct   1380

gccttggttg acgaaaacat ggctgttact ggtcaagttg ttgaacaatt gtctgaacat   1440

caatgcgaag gtttttttgga agcctatttg ttgactggta gacatggtat ttggtcctct   1500

tacgaatctt tcgttcacgt tatcgattcc atgttgaatc aacacgctaa atggttggaa   1560

gctaccgtta gagaaattcc ttggagagaaag ccaatctcct ctgttaactt gttggtttct   1620

tcacacgttt ggagacaaga tcataacggt ttctctcatc aagatccagg tgttacttct   1680

gtcttgttga acaaaacctt caacaacgat cacgtcacca atatctactt tgctactgat   1740

gctaacatgt tgttggctat tgctgaaaag tgtttcaagt ccaccaacaa gattaacgct   1800
```

-continued

```
attttcgctg gtaaacaacc agctgctact tggattactt tggatgaagt tagagctgaa   1860

ttggaagctg gtgctgctga atggaaatgg gcttctaatg ctaagtctaa cgatgaagtt   1920

caagttgttt tggctgctgc tggtgatgtt ccaactcaag aaattatggc tgcttctgat   1980

gctttgaaca agatgggtat taagttcaag gttgtcaacg tcgttgattt gatcaagttg   2040

caatcctcca aagaaaacga tgaagccatg tctgatgaag atttcgctga tttgtttacc   2100

gctgataagc cagttttgtt cgcttatcat tcttacgccc aagatgtcag aggtttgata   2160

tacgatagac caaaccatga taacttcacc gttgtcggtt acaaagaaca aggttctact   2220

actactccat tcgatatggt tagagttaac gacatggata gatacgcatt gcaagctaag   2280

gctttggaat tgattgatgc tgataagtac gccgacaaga tcaacgaatt gaacgaattt   2340

agaaagaccg ctttccaatt cgctgttgat aacggttacg atatcccaga atttaccgat   2400

tgggtttacc cagatgttaa ggttgacgaa acttctatgt tgtctgctac tgctgctaca   2460

gctggtgata atgaataa                                                 2478
```

<210> SEQ ID NO 4
<211> LENGTH: 978
<212> TYPE: DNA
<213> ORGANISM: Lactobacillus plantarum

<400> SEQUENCE: 4

```
atggacttgt tcgaatcttt ggcccaaaag attactggta aggatcaaac tatcgttttc     60

ccagaaggta ctgaacctag aatagttggt gctgctgcta gattggctgc tgatggtttg    120

gttaagccaa tagttttggg tgctactgat aaggttcaag ctgttgctaa tgatttgaac    180

gctgatttga ctggtgttca agttttggat ccagctactt atccagctga agataagcaa    240

gctatgttgg atgctttggt cgaaagaaga aagggtaaga atactccaga acaagctgct    300

aagatgttgg aagatgaaaa ctacttcggt actatgttgg tctacatggg taaagcagat    360

ggtatggttt ctggtgctat tcatccaact ggtgatactg ttagaccagc cttgcaaatt    420

atcaaaacta agccaggttc ccacagaatt tcaggtgctt tcattatgca aaagggtgaa    480

gaaagatacg ttttcgctga ttgcgccatt aacattgatc cagatgctga tactttggct    540

gaaattgcta ctcaatctgc tgctactgct aaagttttcg atattgatcc aaaggtcgcc    600

atgttgtctt tttcaacaaa aggttctgct aagggtgaaa tggttactaa ggtacaagaa    660

gctacagcta aagctcaagc tgctgaacca gaattggcta ttgatggtga attacaattc    720

gatgctgcct tcgttgaaaa ggtcggttta caaaaagctc caggttctaa agttgctggt    780

catgctaatg tttttgtttt tccagaattg caatccggta acatcggtta caaaatcgct    840

caaagatttg gtcatttcga agctgttggt ccagttttac aaggtttgaa caaaccagtt    900

tccgacttgt ctagaggttg ttctgaagaa gatgtttaca aagttgccat tattaccgct    960

gctcaaggtt tggcttag                                                  978
```

<210> SEQ ID NO 5
<211> LENGTH: 1404
<212> TYPE: DNA
<213> ORGANISM: Salmonella enterica

<400> SEQUENCE: 5

```
atgaaccaac aagacataga acaagtagta aaagccgtat tattaaagat gaaagactcc     60

tctcaaccag cctcaaccgt acacgaaatg ggtgtttttg cctctttgga tgacgctgtc    120

gctgcagcca aaagagccca acaaggtttg aagtcagttg ctatgagaca attagcaatc    180
```

```
catgccatta gagaagcagg tgaaaaacac gccagagaat tggctgaatt agcagtatcc    240
gaaactggta tgggtagagt tgatgacaaa ttcgctaaga atgtcgctca agcaagaggt    300
acaccaggtg tcgaatgttt gagtcctcaa gtattaacag gtgacaatgg tttgacctta    360
attgaaaacg ccccatgggg tgttgtcgct tctgttacac catcaaccaa tcctgctgca    420
actgttataa ataacgcaat ctctttgatc gccgctggta actcagtagt ttttgctcca    480
catcctgcag ccaaaaaggt ttcccaaaga gcaattacat tgttaaatca agccgtcgta    540
gctgcaggtg gtccagaaaa tttgttagta accgttgcta accctgatat cgaaactgca    600
caaagattat tcaagtatcc aggtatcggt ttgttagttg tcacaggtgg tgaagctgta    660
gttgatgccg ctagaaaaca caccaataag agattgattg cagccggtgc aggtaaccca    720
cctgtcgtag ttgatgaaac tgctgactta ccaagagctg cacaatccat cgttaagggt    780
gcaagtttcg ataacaacat catctgcgct gacgaaaagg ttttaattgt cgtagattct    840
gtcgctgacg aattgatgag attaatggaa ggtcaacatg cagttaaatt gacagccgct    900
caagccgaac aattgcaacc agttttgttg aaaaatatag atgaacgtgg taaaggtacc    960
gtatcaagag attgggttgg tagagacgca ggtaaaattg cagccgctat aggtttgaac   1020
gttcctgatc aaactagatt gttgttcgtt gaaacaccag ctaaccatcc tttcgcagta   1080
acagaaatga tgatgccagt tttacctgtt gtcagagttg ctaatgtcga agaagccata   1140
gctttggcag ttcaattaga aggtggttgt catcacaccg cagccatgca ctccagaaat   1200
atcgataata tgaaccaaat ggccaacgct atcgacactt ctattttcgt taaaaacggt   1260
ccatgcattg ctggtttggg tttaggtggt gaaggttgga ctacaatgac cataaccact   1320
cctactggtg aaggtgtcac ttctgcaaga acatttgtaa gattgagaag atgtgtctta   1380
gtagatgctt tcagaattgt ttag                                          1404
```

```
<210> SEQ ID NO 6
<211> LENGTH: 12049
<212> TYPE: DNA
<213> ORGANISM: artificial sequence
<220> FEATURE:
<223> OTHER INFORMATION: Constructed Vector

<400> SEQUENCE: 6

aaatccacta tcgtctatca actaatagtt atattatcaa tatattatca tatacggtgt      60
taagatgatg acataagtta tgagaagctg tcatcgaggt tagaggcctt aatggccgtc     120
gacatatttg acctcttaac aggttcagac gcgactgcct catcagtaag acccgttgaa     180
aagaacttac ctgaaaaaaa cgaatatata ctagcgttga atgttagcgt caacaacaag     240
aagtttaatg acgcggaggc caaggcaaaa agattccttg attacgtaag ggagttagaa     300
tcattttgaa taaaaaacac gctttttcag ttcgagttta tcattatcaa tactgccatt     360
tcaaagaata cgtaaataat taatagtagt gatttcccta actttattta gtcaaaaaat     420
tagcctttta attctgctgt aacccgtaca tgcccaaaat agggggcggg ttacacagaa     480
tatataacat cgtaggtgtc tgggtgaaca gtttattcct ggcatccact aaatataatg     540
gagcccgctt tttaagctgg catccagaaa aaaaaagaat cccagcacca aaatattgtt     600
ttcttcacca accatcagtt cataggtcca ttctcttagc gcaactacag agaacagggg     660
cacaaacagg caaaaaacgg gcacaacctc aatggagtga tgcaacctgc ctggagtaaa     720
tgatgacaca aggcaattga cccacgcatg tatctatctc attttcttac accttctatt     780
```

-continued

```
accttctgct ctctctgatt tggaaaaagc tgaaaaaaaa ggttgaaacc agttccctga    840
aattattccc ctacttgact aataagtata taaagacggt aggtattgat tgtaattctg    900
taaatctatt tcttaaactt cttaaattct acttttatag ttagtctttt ttttagtttt    960
aaaacaccaa gaacttagtt tcgaataaac acacataaac aaactagtaa gaattcaaac   1020
aacaaaaatg accaacccag tcattggtac tccatggcaa aaattggata gaccagtttc   1080
cgaagaagcc attgaaggta tggataagta ttggagagtt gccaactaca tgtccattgg   1140
tcaaatctac ttgagatcca acccattgat gaaggaacca ttcactagag atgatgtcaa   1200
gcacagattg gttggtcatt ggggtactac tccaggtttg aattttttgt tggcccacat   1260
caacagattg atcgctgatc atcaacaaaa caccgttttc attatgggtc caggtcatgg   1320
tggtccagct ggtactgctc aatcttatat tgatggtact tacaccgaat attacccaaa   1380
catcactaag gatgaagccg gtttacaaaa gttcttcaga caattttctt acccaggtgg   1440
tatcccatct catttgctc cagaaactcc aggttctatt catgaaggtg gtgaattggg    1500
ttatgctttg tctcatgctt atggtgccat tatggataac ccatctttgt tcgttccatg   1560
cattattggt gatggtgaag ctgaaactgg tccattggct actggttggc aatctaacaa   1620
attggttaac ccaagaaccg atggtatcgt tttgccaatc ttgcatttga acggttacaa   1680
gattgctaac ccaaccattt tggccagaat ctctgatgaa gaattgcacg atttttcag    1740
aggtatgggt taccacccat acgaatttgt tgctggtttt gataacgaag atcacttgtc   1800
catccataga agattcgccg aattattcga aaccatcttc gacgaaattt gcgatattaa   1860
ggctgctgct caaactgatg atatgactag accattttac ccaatgttga tcttcagaac   1920
tccaaagggt tggacttgtc caaagtttat cgatggtaaa aagaccgaag gttcttggag   1980
agcacatcaa gttccattgg cttcagctag agatactgaa gctcatttcg aagttttgaa   2040
gggttggatg gaatcttaca agcctgaaga attattcaac gccgacggtt ctatcaaaga   2100
agatgttact gcttttatgc caaagggtga attgagaatt ggtgctaatc caaatgctaa   2160
cggtggtaga attagagaag atttgaagtt gccagaattg gaccaatacg aaattaccgg   2220
tgtcaaagaa tatggtcatg gttggggtca agttgaagct ccaagatctt tgggtgctta   2280
ctgtagagat atcatcaaga acaacccaga ctcctttaga gtttttggtc cagacgaaac   2340
tgcttccaat agattgaatg ctacttacga agtcaccaaa aagcaatggg ataacggtta   2400
tttgtctgcc ttggttgacg aaaacatggc tgttactggt caagttgttg aacaattgtc   2460
tgaacatcaa tgcgaaggtt ttttggaagc ctatttgttg actggtagac atggtatttg   2520
gtcctcttac gaatctttcg ttcacgttat cgattccatg ttgaatcaac acgctaaatg   2580
gttggaagct accgttagag aaattccttg gagaaagcca atctcctctg ttaacttgtt   2640
ggtttcttca cacgtttgga gacaagatca taacggtttc tctcatcaag atccaggtgt   2700
tacttctgtc ttgttgaaca aaaccttcaa caacgatcac gtcaccaata tctactttgc   2760
tactgatgct aacatgttgt tggctattgc tgaaaagtgt ttcaagtcca ccaacaagat   2820
taacgctatt ttcgctggta aacaaccagc tgctacttgg attactttgg atgaagttag   2880
agctgaattg gaagctggtg ctgctgaatg gaaatgggct tctaatgcta agtctaacga   2940
tgaagttcaa gttgttttgg ctgctgctgg tgatgttcca actcaagaaa ttatggctgc   3000
ttctgatgct ttgaacaaga tgggtattaa gttcaaggtt gtcaacgtcg ttgatttgat   3060
caagttgcaa tcctccaaag aaaacgatga agccatgtct gatgaagatt tcgctgattt   3120
gtttaccgct gataagccag ttttgttcgc ttatcattct tacgcccaag atgtcagagg   3180
```

tttgatatac gatagaccaa accatgataa cttcaccgtt gtcggttaca aagaacaagg 3240
ttctactact actccattcg atatggttag agttaacgac atggatagat acgcattgca 3300
agctaaggct ttggaattga ttgatgctga taagtacgcc gacaagatca acgaattgaa 3360
cgaatttaga aagaccgctt tccaattcgc tgttgataac ggttacgata tcccagaatt 3420
taccgattgg gtttacccag atgttaaggt tgacgaaact tctatgttgt ctgctactgc 3480
tgctacagct ggtgataatg aataaggatc ctgataagcg gccgccggtg aaaacttcca 3540
ccacggtgac aagttgtaaa gtgcttttaa ctaagaatta ttagtctttt ctgcttattt 3600
tttcatcata gtttagaaca ctttatatta acgaatagtt tatgaatcta tttaggttta 3660
aaaattgata cagttttata agttactttt tcaaagactc gtgctgtcta ttgcataatg 3720
cactggaagg ggaaaaaaaa ggtgcacacg cgtggctttt tcttgaattt gcagtttgaa 3780
aaataactac atggatgata agaaaacatg gagtacagtc actttgagaa ccttcaatca 3840
gctggtaacg tcttcgttaa ttggatactc aaaaaagatg gatagcatga atcacaagat 3900
ggaaggaaat gcgggccacg accacagtga tatgcatatg ggagatgctc gacttcaact 3960
caagacgcac agatattata acatctgcat aataggcatt tgcaagaatt actcgtgagt 4020
aaggaaagag tgaggaacta tcgcatacct gcatttaaag atgccgattt gggcgcgaat 4080
cctttatttt ggcttcaccc tcatactatt atcagggcca gaaaaaggaa gtgtttccct 4140
ccttcttgaa ttgatgttac cctcataaag cacgtggcct cttatcgaga aagaaattac 4200
cgtcgctcgt gatttgtttg caaaaagaac aaaactgaaa aaacccagac acgctcgact 4260
tcctgtcttc ctattgattg cagcttccaa tttcgtcaca caacaaggtc ctagcgacgg 4320
ctcacaggtt ttgtaacaag caatcgaagg ttctggaatg gcgggaaagg gtttagtacc 4380
acatgctatg atgcccactg tgatctccag agcaaagttc gttcgatcgt actgttactc 4440
tctctctttc aaacagaatt gtccgaatcg tgtgacaaca acagcctgtt ctcacacact 4500
cttttcttct aaccaagggg gtggtttagt ttagtagaac ctcgtgaaac ttacatttac 4560
atatatataa acttgcataa attggtcaat gcaagaaata catatttggt cttttctaat 4620
tcgtagtttt tcaagttctt agatgctttc tttttctctt ttttacagat catcaaggaa 4680
gtaattatct actttttaca actagtaaaa atggacttgt tcgaatcttt ggcccaaaag 4740
attactggta aggatcaaac tatcgttttc ccagaaggta ctgaacctag aatagttggt 4800
gctgctgcta gattggctgc tgatggtttg gttaagccaa tagttttggg tgctactgat 4860
aaggttcaag ctgttgctaa tgatttgaac gctgatttga ctggtgttca agttttggat 4920
ccagctactt atccagctga agataagcaa gctatgttgg atgctttggt cgaaagaaga 4980
aagggtaaga atactccaga acaagctgct aagatgttgg aagatgaaaa ctacttcggt 5040
actatgttgg tctacatggg taaagcagat ggtatggttt ctggtgctat tcatccaact 5100
ggtgatactg ttagaccagc cttgcaaatt atcaaaacta agccaggttc ccacagaatt 5160
tcaggtgctt tcattatgca aaagggtgaa gaaagatacg ttttcgctga ttgcgccatt 5220
aacattgatc cagatgctga tactttggct gaaattgcta ctcaatctgc tgctactgct 5280
aaagttttcg atattgatcc aaaggtcgcc atgttgtctt tttcaacaaa aggttctgct 5340
aagggtgaaa tggttactaa ggtacaagaa gctacagcta aagctcaagc tgctgaacca 5400
gaattggcta ttgatggtga attacaattc gatgctgcct tcgttgaaaa ggtcggttta 5460
caaaaagctc caggttctaa agttgctggt catgctaatg tttttgtttt tccagaattg 5520

-continued caatccggta acatcggtta caaaatcgct caaagatttg gtcatttcga agctgttggt 5580
ccagttttac aaggtttgaa caaaccagtt tccgacttgt ctagaggttg ttctgaagaa 5640
gatgtttaca aagttgccat tattaccgct gctcaaggtt tggcttagga tccaagcggc 5700
cgccaggtgt tgctttctta tccgaaaaga aataaattga attgaattga aatcgataga 5760
tcaatttttt tcttttctct ttccccatcc tttacgctaa aataatagtt tattttattt 5820
tttgaatatt ttttatttat atacgtatat atagactatt atttatcttt taatgattat 5880
taagattttt attaaaaaaa aattcgctcc tcttttaatg cctttatgca gttttttttt 5940
cccattcgat atttctatgt tcgggttcag cgtattttaa gtttaataac tcgacgccta 6000
cttggcttca catacgttgc atacgtcgat atagataata atgataatga cagcaggatt 6060
atcgtaatac gtaatagttg aaaatctcaa aaatgtgtgg gtcattacgt aaataatgat 6120
aggaatggga ttcttctatt tttccttttt ccattctagc agccgtcggg aaaacgtggc 6180
atcctctctt tcgggctcaa ttggagtcac gctgccgtga gcatcctctc tttccatatc 6240
taacaactga gcacgtaacc aatggaaaag catgagctta gcgttgctcc aaaaaagtat 6300
tggatggtta ataccatttg tctgttctct tctgactttg actcctcaaa aaaaaaaaat 6360
ctacaatcaa cagatcgctt caattacgcc ctcacaaaaa ctttttttcct tcttcttcgc 6420 ccacgttaaa ttttatccct catgttgtct aacggatttc tgcacttgat ttattataaa 6480
aagacaaaga cataatactt ctctatcaat ttcagttatt gttcttcctt gcgttattct 6540
tctgttcttc tttttctttt gtcatatata accataacca agtaatacat attcaaacta 6600
gtaagaattc aaaacaaaaa tgaaccaaca agacatagaa caagtagtaa aagccgtatt 6660
attaaagatg aaagactcct ctcaaccagc ctcaaccgta cacgaaatgg gtgtttttgc 6720
ctctttggat gacgctgtcg ctgcagccaa aagagcccaa caaggtttga agtcagttgc 6780
tatgagacaa ttagcaatcc atgccattag agaagcaggt gaaaaacacg ccagagaatt 6840
ggctgaatta gcagtatccg aaactggtat gggtagagtt gatgacaaat tcgctaagaa 6900
tgtcgctcaa gcaagaggta caccaggtgt cgaatgtttg agtcctcaag tattaacagg 6960
tgacaatggt ttgaccttaa ttgaaaacgc cccatggggt gttgtcgctt ctgttacacc 7020
atcaaccaat cctgctgcaa ctgttataaa taacgcaatc tctttgatcg ccgctggtaa 7080
ctcagtagtt tttgctccac atcctgcagc caaaaaggtt tcccaaagag caattacatt 7140
gttaaatcaa gccgtcgtag ctgcaggtgg tccagaaaat ttgttagtaa ccgttgctaa 7200
ccctgatatc gaaactgcac aaagattatt caagtatcca ggtatcggtt tgttagttgt 7260
cacaggtggt gaagctgtag ttgatgccgc tagaaaacac accaataaga gattgattgc 7320
agccggtgca ggtaacccac ctgtcgtagt tgatgaaact gctgacttac caagagctgc 7380
acaatccatc gttaagggtg caagtttcga taacaacatc atctgcgctg acgaaaaggt 7440
tttaattgtc gtagattctg tcgctgacga attgatgaga ttaatggaag gtcaacatgc 7500
agttaaattg acagccgctc aagccgaaca attgcaacca gttttgttga aaaatataga 7560
tgaacgtggt aaaggtaccg tatcaagaga ttgggttggt agagacgcag gtaaaattgc 7620
agccgctata ggtttgaacg ttcctgatca aactagattg ttgttcgttg aaacaccagc 7680
taaccatcct ttcgcagtaa cagaaatgat gatgccagtt ttacctgttg tcagagttgc 7740
taatgtcgaa gaagccatag ctttggcagt tcaattagaa ggtggttgtc atcacaccgc 7800
agccatgcac tccagaaata tcgataatat gaaccaaatg gccaacgcta tcgacacttc 7860
tattttcgtt aaaaacggtc catgcattgc tggtttgggt ttaggtggtg aaggttggac 7920

-continued

```
tacaatgacc ataaccactc ctactggtga aggtgtcact tctgcaagaa catttgtaag   7980
attgagaaga tgtgtcttag tagatgcttt cagaattgtt taggatcctg ataagcggcc   8040
gcgttaattc aaattaattg atatagtttt ttaatgagta ttgaatctgt ttagaaataa   8100
tggaatatta tttttattta tttatttata ttattggtcg gctcttttct tctgaaggtc   8160
aatgacaaaa tgatatgaag gaaataatga tttctaaaat tttacaacgt aagatatttt   8220
tacaaaagcc tagctcatct tttgtcatgc actattttac tcacgcttga aattaacggc   8280
cagtccactg cggagtcatt tcaaagtcat cctaatcgat ctatcgtttt tgatagctca   8340
ttttggagtt cgcgattgtc ttctgttatt cacaactgtt ttaattttta tttcattctg   8400
gaactcttcg agttctttgt aaagtctttc atagtagctt actttatcct ccaacatatt   8460
taacttcatg tcaatttcgg ctcttaaatt ttccacatca tcaagttcaa catcatcttt   8520
taacttgaat ttattctcta gctcttccaa ccaagcctca ttgctccttg atttactggt   8580
gaaaagtgat acactttgcg cgcaatccag gtcaaaactt tcctgcaaag aattcaccaa   8640
tttctcgaca tcatagtaca atttgttttg ttctcccatc acaatttaat atacctgatg   8700
gattcttatg aagcgctggg taatggacgt gtcactctac ttcgcctttt tccctactcc   8760
ttttagtacg gaagacaatg ctaataaata agagggtaat aataatatta ttaatcggca   8820
aaaaagatta aacgccaagc gtttaattat cagaaagcaa acgtcgtacc aatccttgaa   8880
tgcttcccaa ttgtatatta agagtcatca cagcaacata ttcttgttat taaattaatt   8940
attattgatt tttgatattg tataaaaaaa ccaaatatgt ataaaaaaag tgaataaaaa   9000
ataccaagta tggagaaata tattagaagt ctatacgtta aaccaccgcg gtggagctca   9060
agcttttcaa ttcatctttt tttttttgt tcttttttt gattccggtt tctttgaaat   9120
tttttgatt cggtaatctc cgagcagaag gaagaacgaa ggaaggagca cagacttaga   9180
ttggtatata tacgcatatg tggtgttgaa gaaacatgaa attgcccagt attcttaacc   9240
caactgcaca gaacaaaaac ctgcaggaaa cgaagataaa tcatgtcgaa agctacatat   9300
aaggaacgtg ctgctactca tcctagtcct gttgctgcca agctatttaa tatcatgcac   9360
gaaaagcaaa caaacttgtg tgcttcattg gatgttcgta ccaccaagga attactggag   9420
ttagttgaag cattaggtcc caaaatttgt ttactaaaaa cacatgtgga tatcttgact   9480
gatttttcca tggagggcac agttaagccg ctaaaggcat tatccgccaa gtacaatttt   9540
ttactcttcg aagacagaaa atttgctgac attggtaata cagtcaaatt gcagtactct   9600
gcgggtgtat acagaatagc agaatgggca gacattacga atgcacacgg tgtggtgggc   9660
ccaggtattg ttagcggttt gaagcaggcg gcggaagaag taacaaagga acctagaggc   9720
cttttgatgt tagcagaatt gtcatgcaag ggctccctag ctactggaga atatactaag   9780
ggtactgttg acattgcgaa gagcgacaaa gattttgtta tcggctttat tgctcaaaga   9840
gacatgggtg gaagagatga aggttacgat tggttgatta tgacacccgg tgtgggttta   9900
gatgacaagg gagacgcatt gggtcaacag tatagaaccg tggatgatgt ggtctctaca   9960
ggatctgaca ttattattgt tggaagagga ctatttgcaa agggaaggga tgctaaggta  10020
gagggtgaac gttacagaaa agcaggctgg gaagcatatt tgagaagatg cggccagcaa  10080
aactaaaaaa ctgtattata agtaaatgca tgtatactaa actcacaaat tagagcttca  10140
atttaattat atcagttatt acccgggaat ctcggtcgta atgatttcta taatgacgaa  10200
aaaaaaaaaa ttggaaagaa aaaggcgcgc cgaagctgaa gtgcaaggat tgataatgta  10260
```

-continued

```
ataggatcaa tgaatataaa catataaaac ggaatgagga ataatcgtaa tattagtatg  10320

tagaaatata gattccattt aaatcagaaa tggccatgag acaataaccc tgataaatgc  10380

ttcaataata ttgaaaaagg aagagtatga gtattcaaca tttccgtgtc gcccttattc  10440

ccttttttgc ggcattttgc cttcctgttt ttgctcaccc agaaacgctg gtgaaagtaa  10500

aagatgctga agatcagttg ggtgcacgag tgggttacat cgaactggat ctcaacagcg  10560

gtaagatcct tgagagtttt cgccccgaag aacgttttcc aatgatgagc acttttaaag  10620

ttctgctatg tggcgcggta ttatcccgta ttgacgccgg gcaagagcaa ctcggtcgcc  10680

gcatacacta ttctcagaat gacttggttg agtactcacc agtcacagaa aagcatctta  10740

cggatggcat gacagtaaga gaattatgca gtgctgccat aaccatgagt gataacactg  10800

cggccaactt acttctgaca acgatcggag gaccgaagga gctaaccgct tttttgcaca  10860

acatggggga tcatgtaact cgccttgatc gttgggaacc ggagctgaat gaagccatac  10920

caaacgacga gcgtgacacc acgatgcctg tagcaatggc aacaacgttg cgcaaactat  10980

taactggcga actacttact ctagcttccc ggcaacaatt aatagactgg atggaggcgg  11040

ataaagttgc aggaccactt ctgcgctcgg cccttccggc tggctggttt attgctgata  11100

aatctggagc cggtgagcgt gggtctcgcg gtatcattgc agcactgggg ccagatggta  11160

agccctcccg tatcgtagtt atctacacga cggggagtca ggcaactatg gatgaacgaa  11220

atagacagat cgctgagata ggtgcctcac tgattaagca ttggtaactg tcagaccaag  11280

tttactcata tatactttag attgatttaa aacttcattt ttaatttaaa aggatctagg  11340

tgaagatcct ttttgataat ctcatgacca aaatccctta acgtgagttt tcgttccact  11400

gagcgtcaga ccccgtagaa aagatcaaag gatcttcttg agatcctttt tttctgcgcg  11460

taatctgctg cttgcaaaca aaaaaaccac cgctaccagc ggtggtttgt ttgccggatc  11520

aagagctacc aactcttttt ccgaaggtaa ctggcttcag cagagcgcag ataccaaata  11580

ctgtccttct agtgtagccg tagttaggcc accacttcaa gaactctgta gcaccgccta  11640

catacctcgc tctgctaatc ctgttaccag tggctgctgc cagtggcgat aagtcgtgtc  11700

ttaccgggtt ggactcaaga cgatagttac cggataaggc gcagcggtcg ggctgaacgg  11760

ggggttcgtg cacacagccc agcttggagc gaacgaccta caccgaactg agatacctac  11820

agcgtgagct atgagaaagc gccacgcttc ccgaagggag aaaggcggac aggtatccgg  11880

taagcggcag ggtcggaaca ggagagcgca cgagggagct tccaggggga aacgcctggt  11940

atctttatag tcctgtcggg tttcgccacc tctgacttga gcgtcgattt ttgtgatgct  12000

cgtcaggggg gcggagccta tggaaaaacg ccagcaacgc tgcatattt              12049
```

<210> SEQ ID NO 7
<211> LENGTH: 37
<212> TYPE: DNA
<213> ORGANISM: artificial sequence
<220> FEATURE:
<223> OTHER INFORMATION: Primer

<400> SEQUENCE: 7

```
gaacaatgtc atgacattgg atggtgtgct tgcagtc                            37
```

<210> SEQ ID NO 8
<211> LENGTH: 38
<212> TYPE: DNA
<213> ORGANISM: artificial sequence
<220> FEATURE:
<223> OTHER INFORMATION: Primer

<400> SEQUENCE: 8
gagttatcgt tactccgatt attttgtaca gctgatgg 38

<210> SEQ ID NO 9
<211> LENGTH: 36
<212> TYPE: DNA
<213> ORGANISM: artificial sequence
<220> FEATURE:
<223> OTHER INFORMATION: Primer

<400> SEQUENCE: 9
ccgtgtatat tagaacaatg ttccttatcg ctgcac 36

<210> SEQ ID NO 10
<211> LENGTH: 37
<212> TYPE: DNA
<213> ORGANISM: artificial sequence
<220> FEATURE:
<223> OTHER INFORMATION: Primer

<400> SEQUENCE: 10
caggtaaccg tgcgcgatga gctaatcctg agccatc 37

<210> SEQ ID NO 11
<211> LENGTH: 1896
<212> TYPE: DNA
<213> ORGANISM: Trichoderma reseii

<400> SEQUENCE: 11
atgctactcc aagcattcct ttttctgtta gcaggatttg ctgccaaaat ctctgctaga 60
cctggatctt caggcttgtc cgacgtcaca aaaagatccg tggatgattt tatctctaca 120
gaaacaccta ttgcacttaa caatctcctg tgtaatgttg gaccagatgg ttgtagagca 180
ttcggcacaa gtgcaggcgc tgttattgct tctccatcta caattgatcc agactattac 240
tacatgtgga caagagactc cgcccttgtg ttcaaaaact tgattgatcg ttttacagaa 300
acttacgatg ctggattaca aagacgaatt gaacaatata tcactgctca agtaacttta 360
caaggattga gtaatccaag tggaagtttg gcagatggct caggactagg agagccaaag 420
tttgaactaa cccttaagcc attcactggg aactggggta gaccacaaag agatggtcct 480
gctttgagag caatagcctt aatcggctac tcaaaatggt taatcaacaa taactaccaa 540
tcaacagttt caaatgttat ctggccaatt gttaggaatg atttgaacta cgtggctcaa 600
tactggaacc agaccggttt cgacctttgg gaagaggtta atggctcttc ctttttcaca 660
gtggcaaatc agcatagagc tttggttgaa ggagctactt tagcggccac tctcggtcag 720
tcaggttcag cttactcttc tgtagctcct caagtacttt gttttctaca gagattctgg 780
gtatcttctg gtggttacgt tgattctaac attaacacaa atgaagggcg tactggcaaa 840
gatgtgaata gcgtccttac cagcatccat acattcgatc ctaatttggg ttgtgatgcc 900
gggacgtttc aaccttgttc tgacaaggct ttgagcaatc tgaaagtggt tgttgatagt 960
ttcagaagca tctacggtgt aaacaagggt attccagctg gtgctgccgt ggctatcggc 1020
agatatgcag aagatgtcta ctataatgga aatccatggt acttggctac ttttgccgca 1080
gcagaacagt tgtacgacgc catctacgtt tggaaaaaga ctggtagcat tactgttaca 1140
gctacatcct tagcattttt ccaagagtta gtcccagggg tcacagcagg cacgtactcc 1200
tcttctagtt caacctttac caacatcata aacgctgtct ccacctatgc cgacggtttt 1260

```
ctatccgagg ctgccaaata cgttcctgca gatggttctc tagctgaaca atttgacaga   1320

aattcaggta ctcctctgtc agcagtacac ctcacatgga gttacgcatc ttttctgaca   1380

gcagccgcga gaagagccgg catagttcca ccaagttggg ccaattcatc agcctctaca   1440

ataccatcta catgctcagg cgcttctgtt gtagggagtt actctaggcc aaccgctact   1500

tcattcccac cttcccaaac tccaaaacca ggcgtacctt ccggaacacc ttataccccca  1560

ctcccttgcg ctacaccaac ttcagtcgca gtgacgtttc acgaattagt ttccacacaa   1620

tttggtcaca cagtgaaagt tgcaggaaat gccgctgctt tgggcaattg gtcaacttcc   1680

gcagcggtag ctttggacgc tgttaactac agagataatc atccattgtg gattggtacg   1740

gtcaacctag aagctggtga cgtcgttgag tataagtata tcatagttgg tcaagatggt   1800

tccgtcactt gggagtcaga tcctaatcat acttacactg ttcctgccgt agcttgcgtc   1860

acacaagttg tgaaggaaga tacttggcaa tcttaa                             1896


<210> SEQ ID NO 12
<211> LENGTH: 467
<212> TYPE: PRT
<213> ORGANISM: Salmonella enterica

<400> SEQUENCE: 12

Met Asn Gln Gln Asp Ile Glu Gln Val Val Lys Ala Val Leu Leu Lys
1               5                   10                  15

Met Lys Asp Ser Ser Gln Pro Ala Ser Thr Val His Glu Met Gly Val
            20                  25                  30

Phe Ala Ser Leu Asp Asp Ala Val Ala Ala Ala Lys Arg Ala Gln Gln
        35                  40                  45

Gly Leu Lys Ser Val Ala Met Arg Gln Leu Ala Ile His Ala Ile Arg
    50                  55                  60

Glu Ala Gly Glu Lys His Ala Arg Glu Leu Ala Glu Leu Ala Val Ser
65                  70                  75                  80

Glu Thr Gly Met Gly Arg Val Asp Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Val Phe Ala Pro
145                 150                 155                 160

His Pro Ala Ala Lys Lys Val Ser Gln Arg Ala Ile Thr Leu Leu Asn
                165                 170                 175

Gln Ala Val Val Ala Ala Gly Gly Pro Glu Asn Leu Leu Val Thr Val
            180                 185                 190

Ala Asn Pro Asp Ile Glu Thr Ala Gln Arg Leu Phe Lys Tyr Pro Gly
        195                 200                 205

Ile Gly Leu Leu Val Val Thr Gly Gly Glu Ala Val Val Asp Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Pro Arg Ala Ala Gln Ser
                245                 250                 255

Ile Val Lys Gly Ala Ser Phe Asp Asn Asn Ile Ile Cys Ala Asp Glu
```

```
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Ala Gln Ala Glu Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Asp Gln Thr Arg Leu Leu Phe Val Glu Thr
            340                 345                 350

Pro Ala Asn His Pro Phe Ala Val Thr Glu Met Met Met Pro Val Leu
        355                 360                 365

Pro Val Val Arg Val Ala Asn Val Glu Glu Ala Ile Ala Leu Ala Val
    370                 375                 380

Gln Leu Glu Gly Gly Cys His His Thr Ala Ala Met His Ser Arg Asn
385                 390                 395                 400

Ile Asp Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465
```

<210> SEQ ID NO 13
<211> LENGTH: 1404
<212> TYPE: DNA
<213> ORGANISM: Escherichia coli

<400> SEQUENCE: 13

```
atgaaccaac aagacataga acaagtagta aaggcagtat tattaaagat gcaatcctct      60

gacacaccac cagccgcagt acacgaaatg ggtgtatttg cctctttgga tgacgctgtt     120

gctgcagcca aaatagctca acaaggtttg aagtcagttg caatgagaca attagccatc     180

gctgcaatta gagaagctgg tgaaaaacat gcaagagatt tggccgaatt agctgtctcc     240

gaaaccggta tgggtagagt agaagacaaa ttcgctaaga atgttgctca agcaagaggt     300

actccaggtg ttgaatgttt gagtcctcaa gtcttaactg gtgataacgg tttgacattg     360

atcgaaaacg caccatgggg tgttgtcgcc tctgttactc catcaacaaa tcctgccgct     420

actgtcatca ataacgctat atctttgatc gcagccggta actcagttat ttttgcacca     480

catcctgctg caaaaaaggt ttcccaaaga gctatcacat tgttgaacca agcaatcgtt     540

gccgctggtg gtccagaaaa tttgttagtc accgtagcca accctgatat agaaactgca     600

caaagattgt tcaagttccc tggtatcggt ttgttagtag ttacaggtgg tgaagctgtc     660

gtagaagcag ccagaaaaca caccaataag agattgattg ctgcaggtgc tggtaaccca     720

cctgttgtcg tagatgaaac tgcagactta gccagagccg ctcaatccat tgttaagggt     780

gctagtttcg ataacaacat aatatgcgca gacgaaaagg tattgatagt tgtcgattct     840

gttgctgacg aattgatgag attaatggaa ggtcaacatg cagttaaatt gactgctgaa     900
```

```
caagcacaac aattgcaacc agttttgttg aagaacatag atgaaagagg caagggtaca    960

gtctcaagag attgggttgg tagagacgct ggcaagattg cagccgctat aggtttaaac   1020

gtcccacaag aaactagatt gttgttcgta gaaactacag ccgaacatcc tttcgctgtc   1080

acagaattga tgatgccagt attacctgta gttagagtag ctaatgttgc cgatgctatc   1140

gcattggccg ttaaattaga aggtggttgt catcacacag cagccatgca ctccagaaac   1200

atcgaaaaca tgaaccaaat ggctaacgca atcgacacca gtatttttgt taagaacggt   1260

ccatgcatag ctggtttggg tttaggtggt gaaggttgga ccactatgac aatcacaacc   1320

cctaccggtg aaggtgttac ctctgctaga acttttgtca gattgagaag atgtgtttta   1380

gtcgatgcat tcagaattgt ttag                                          1404


<210> SEQ ID NO 14
<211> LENGTH: 467
<212> TYPE: PRT
<213> ORGANISM: Escherichia coli

<400> SEQUENCE: 14

Met Asn Gln Gln Asp Ile Glu Gln Val Val Lys Ala Val Leu Leu Lys
1               5                   10                  15

Met Gln Ser Ser Asp Thr Pro Pro Ala Ala Val His Glu Met Gly Val
            20                  25                  30

Phe Ala Ser Leu Asp Asp Ala Val Ala Ala Ala Lys Ile Ala Gln Gln
        35                  40                  45

Gly Leu Lys Ser Val Ala Met Arg Gln Leu Ala Ile Ala Ala Ile Arg
    50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285
```

-continued

```
Met Glu Gly Gln His Ala Val Lys Leu Thr Ala Glu Gln Ala Gln Gln
    290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Gln Glu Thr Arg Leu Leu Phe Val Glu Thr
            340                 345                 350

Thr Ala Glu His Pro Phe Ala Val Thr Glu Leu Met Met Pro Val Leu
        355                 360                 365

Pro Val Val Arg Val Ala Asn Val Ala Asp Ala Ile Ala Leu Ala Val
    370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465


<210> SEQ ID NO 15
<211> LENGTH: 1404
<212> TYPE: DNA
<213> ORGANISM: Citrobacter freundii

<400> SEQUENCE: 15

atgaaccaac aagacataga acaagtagta aaggctgtat tattaaaaat gaaagactcc     60

tcacaacctg tatctgccgt ccaagaaatg ggtgtatttg catccttgga tgacgccgtt    120

gctgcagcca aattggccca acaaggttta aagagtgttg caatgagaca attggccatt    180

actgctttaa gagaagctgg tgaaaaacat gcaagagaat tggcagaatt agccgtcact    240

gaaactggta tgggtagagt agaagataaa ttcgctaaga atgttgcaca agccagagct    300

acaccaggtg ttgaatgttt gtcccctcaa gtcttaacag gtgacaatgg tttgacctta    360

atagaaaacg caccatgggg tgttgtcgcc tctgttaccc catcaactaa tcctgctgca    420

accgttatca ataacgctat ctctttgatt gccgctggta actcagtagt ttttgcacca    480

catcctgcag ccaaaggtgt ttctcaaaga gctataacat tgttgaatca agcagtcgta    540

gctgcaggtg gtccagccaa tttgttagta actgttgcta accctgatat cgaaacagca    600

caaagattat tcaagtatcc tggtattggt ttgttagttg ttactggtgg tgaagctgta    660

gttgatgccg ctagaaaaca cactaataag agattgatag cagccggtgc tggtaaccca    720

cctgtcgtag ttgatgaaac tgctgactta gcaagagctg cacaatccat tgttaagggt    780

gctagttttg ataacaacat catctgcgca gacgaaaagg tattgatagt cgtagattcc    840

gttgctgacg aattgatgag attgatggaa agtcaacatg cagttaaatt gactacagca    900

caagccgaac aattgcaacc agtattgttg aagaacgttg atgaaagagg caagggtaca    960

gtctctagag attgggttgg tagagacgct ggcaagatag ccgctgcaat cggtttaaac   1020
```

-continued

```
gtcccagaac aaacaagatt gttgttcgtt gaaacatcag ccacccatcc tttcgctgtc   1080

accgaattga tgatgccagt attacctgtt gtcagagttg ctaatgtcga agaagccatc   1140

gaattggctg ttaaattaga aggtggttgt catcacactg ccgctatgca ctctagaaac   1200

atcgataaca tgaacagaat ggctaacgca attgacacat caatattcgt taagaacggt   1260

ccatgcatag ctggtttggg tttaggtggt gaaggttgga ccactatgac catcacaacc   1320

cctactggtg aaggtgttac ttcagctaga acatttgtca gattgagaag atgtgtctta   1380

gtagatgcat tcagaattgt ttag                                          1404
```

<210> SEQ ID NO 16
<211> LENGTH: 467
<212> TYPE: PRT
<213> ORGANISM: Citrobacter freundii

<400> SEQUENCE: 16

```
Met Asn Gln Gln Asp Ile Glu Gln Val Val Lys Ala Val Leu Leu Lys
1               5                   10                  15

Met Lys Asp Ser Ser Gln Pro Val Ser Ala Val Gln Glu Met Gly Val
            20                  25                  30

Phe Ala Ser Leu Asp Asp Ala Val Ala Ala Ala Lys Leu Ala Gln Gln
        35                  40                  45

Gly Leu Lys Ser Val Ala Met Arg Gln Leu Ala Ile Thr Ala Leu Arg
    50                  55                  60

Glu Ala Gly Glu Lys His Ala Arg Glu Leu Ala Glu Leu Ala Val Thr
65                  70                  75                  80

Glu Thr Gly Met Gly Arg Val Glu Asp Lys Phe Ala Lys Asn Val Ala
                85                  90                  95

Gln Ala Arg Ala Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
        115                 120                 125

Val Ala Ser Val Thr Pro Ser Thr Asn Pro Ala Ala Thr Val Ile Asn
    130                 135                 140

Asn Ala Ile Ser Leu Ile Ala Ala Gly Asn Ser Val Val Phe Ala Pro
145                 150                 155                 160

His Pro Ala Ala Lys Gly Val Ser Gln Arg Ala Ile Thr Leu Leu Asn
                165                 170                 175

Gln Ala Val Val Ala Ala Gly Gly Pro Ala Asn Leu Leu Val Thr Val
            180                 185                 190

Ala Asn Pro Asp Ile Glu Thr Ala Gln Arg Leu Phe Lys Tyr Pro Gly
        195                 200                 205

Ile Gly Leu Leu Val Val Thr Gly Gly Glu Ala Val Val Asp Ala Ala
    210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
                245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Ser Gln His Ala Val Lys Leu Thr Thr Ala Gln Ala Glu Gln
    290                 295                 300
```

-continued

```
Leu Gln Pro Val Leu Leu Lys Asn Val Asp Glu Arg Gly Lys Gly Thr
305                 310                 315                 320

Val Ser Arg Asp Trp Val Gly Arg Asp Ala Gly Lys Ile Ala Ala Ala
                325                 330                 335

Ile Gly Leu Asn Val Pro Glu Gln Thr Arg Leu Leu Phe Val Glu Thr
            340                 345                 350

Ser Ala Thr His Pro Phe Ala Val Thr Glu Leu Met Met Pro Val Leu
        355                 360                 365

Pro Val Val Arg Val Ala Asn Val Glu Glu Ala Ile Glu Leu Ala Val
    370                 375                 380

Lys Leu Glu Gly Gly Cys His His Thr Ala Ala Met His Ser Arg Asn
385                 390                 395                 400

Ile Asp Asn Met Asn Arg Met Ala Asn Ala Ile Asp Thr Ser Ile Phe
                405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465


<210> SEQ ID NO 17
<211> LENGTH: 1422
<212> TYPE: DNA
<213> ORGANISM: Pseudomonas M1

<400> SEQUENCE: 17

atggacatca accctaaaga aatcgaacaa gtcgtaaaag ccgtattggc aagtatcggt     60

gctacatcaa cagccgccgt cgcatcacca ggtgccactt gtgctcctgg tgtatttgtt    120

gaattagatg ctgcagttgc cgctgcagcc caagcacaaa aagccttgag atctgtcgct    180

atgagagaca gagcaatcgc tgcaattaga gccgctggtg aaagacatgc tcaagaatta    240

gctgaattgg cagttgaaga aaccggtatg ggtagagtcg cagataaaac tgccaagaat    300

attgcccaag ctagacacac tccaggttct gaatgcttac aagcacaagt tttgtcaggt    360

gacagaggtt taacattgat cgaaaatgca gcctggggtg taattgcttc cgttactcca    420

agtacaaacc ctgctgcaac tgttataaac aacgcaatct ccatgatcgc cgctggtaac    480

agtgttgtct ttgctccaca tcctgcagcc aaaagagtct ctcaaagaac agtatcattg    540

ttgaacgaag ctatggtcga agcaggtgcc ccagctaact taataactac agtacaaaga    600

cctgatatcg aaaccgctca aagattgttc agatatccag gtattggttt gttagtagtt    660

acaggtggtg aagcagtcgt agaagctgca agaaaacaca ccgataagag attaatagcc    720

gctggtgctg gtaatccacc tgttgtcgta gatgaaacag ccgacttggc tagagcagcc    780

agagatatag ttttcggtgc atctttcgat aacaacatca tctgtgctga cgaaaaggta    840

ttgatcgttg tcgattcagt tgcagacgcc ttaaaagccg aaatgttgaa gcatcaagct    900

gttgaattgt ccgctgcaca aggtcaacaa ttgttaccat tgttattgcc taaagttgat    960

gaacaaggta gaggttctgt ttcaagagat tgggtcggta gagacgccgc taagattgca   1020

gccgctatag gtttgcaagt tccagaacaa actagattgt tgttgttgga aacagcagcc   1080

gatcaccctt ttgcaatcac agaaatgatg atgccagttt tgcctatggt cagagtagct   1140
```

-continued

```
aatgtagacc aagctattgc attagccgtt aaattggaag gtggttgtca tcacaccgct   1200

gcaatgcatt ccagaaattt agatcacttg gacagaatgg ctaacgcaat ggatacttct   1260

atcttcgtta agaacggtcc atgcttagct ggtttgggtt tcggtggtga aggttggacc   1320

actatgacaa tcacaacccc taccggtgaa ggtgtcacct cagctagaac tttcgtaaga   1380

ttaagaagat gcgttatggt cgatcatttg agaattgttt ag                      1422


<210> SEQ ID NO 18
<211> LENGTH: 473
<212> TYPE: PRT
<213> ORGANISM: Pseudomonas M1

<400> SEQUENCE: 18

Met Asp Ile Asn Pro Lys Glu Ile Glu Gln Val Val Lys Ala Val Leu
1               5                   10                  15

Ala Ser Ile Gly Ala Thr Ser Thr Ala Ala Val Ala Ser Pro Gly Ala
            20                  25                  30

Thr Cys Ala Pro Gly Val Phe Val Glu Leu Asp Ala Ala Val Ala Ala
        35                  40                  45

Ala Ala Gln Ala Gln Lys Ala Leu Arg Ser Val Ala Met Arg Asp Arg
    50                  55                  60

Ala Ile Ala Ala Ile Arg Ala Ala Gly Glu Arg His Ala Gln Glu Leu
65                  70                  75                  80

Ala Glu Leu Ala Val Glu Glu Thr Gly Met Gly Arg Val Ala Asp Lys
                85                  90                  95

Thr Ala Lys Asn Ile Ala Gln Ala Arg His Thr Pro Gly Ser Glu Cys
            100                 105                 110

Leu Gln Ala Gln Val Leu Ser Gly Asp Arg Gly Leu Thr Leu Ile Glu
        115                 120                 125

Asn Ala Ala Trp Gly Val Ile Ala Ser Val Thr Pro Ser Thr Asn Pro
    130                 135                 140

Ala Ala Thr Val Ile Asn Asn Ala Ile Ser Met Ile Ala Ala Gly Asn
145                 150                 155                 160

Ser Val Val Phe Ala Pro His Pro Ala Ala Lys Arg Val Ser Gln Arg
                165                 170                 175

Thr Val Ser Leu Leu Asn Glu Ala Met Val Glu Ala Gly Ala Pro Ala
            180                 185                 190

Asn Leu Ile Thr Thr Val Gln Arg Pro Asp Ile Glu Thr Ala Gln Arg
        195                 200                 205

Leu Phe Arg Tyr Pro Gly Ile Gly Leu Leu Val Val Thr Gly Gly Glu
    210                 215                 220

Ala Val Val Glu Ala Ala Arg Lys His Thr Asp Lys Arg Leu Ile Ala
225                 230                 235                 240

Ala Gly Ala Gly Asn Pro Pro Val Val Val Asp Glu Thr Ala Asp Leu
                245                 250                 255

Ala Arg Ala Ala Arg Asp Ile Val Phe Gly Ala Ser Phe Asp Asn Asn
            260                 265                 270

Ile Ile Cys Ala Asp Glu Lys Val Leu Ile Val Val Asp Ser Val Ala
        275                 280                 285

Asp Ala Leu Lys Ala Glu Met Leu Lys His Gln Ala Val Glu Leu Ser
    290                 295                 300

Ala Ala Gln Gly Gln Gln Leu Leu Pro Leu Leu Leu Pro Lys Val Asp
305                 310                 315                 320

Glu Gln Gly Arg Gly Ser Val Ser Arg Asp Trp Val Gly Arg Asp Ala
```

```
                325                 330                 335

Ala Lys Ile Ala Ala Ala Ile Gly Leu Gln Val Pro Glu Gln Thr Arg
            340                 345                 350

Leu Leu Leu Leu Glu Thr Ala Ala Asp His Pro Phe Ala Ile Thr Glu
        355                 360                 365

Met Met Met Pro Val Leu Pro Met Val Arg Val Ala Asn Val Asp Gln
    370                 375                 380

Ala Ile Ala Leu Ala Val Lys Leu Glu Gly Gly Cys His His Thr Ala
385                 390                 395                 400

Ala Met His Ser Arg Asn Leu Asp His Leu Asp Arg Met Ala Asn Ala
                405                 410                 415

Met Asp Thr Ser Ile Phe Val Lys Asn Gly Pro Cys Leu Ala Gly Leu
            420                 425                 430

Gly Phe Gly Gly Glu Gly Trp Thr Thr Met Thr Ile Thr Thr Pro Thr
        435                 440                 445

Gly Glu Gly Val Thr Ser Ala Arg Thr Phe Val Arg Leu Arg Arg Cys
    450                 455                 460

Val Met Val Asp His Leu Arg Ile Val
465                 470
```

<210> SEQ ID NO 19
<211> LENGTH: 1437
<212> TYPE: DNA
<213> ORGANISM: Morganella morganii

<400> SEQUENCE: 19

```
atggatcaaa aggaaatcga aaatgtagtc aaagccgtat tagcctcaat gtccgcaggt     60

actcaaccag ccgccgcctc cgccgcacca caacaagctg cagcctccca aaataacggt    120

tttggtgtat tcgaaagttt ggatgacgct gttttagctg caaaagaagc acaaaaaatcc   180

ttgaagactg ttgaaatgag aaatttatgt attggtgcta tcagaagagc cgctaccgaa    240

catgcaagag aattggctgt tttagcagtc gaagaaactg gtatgggtag agttgaagat    300

aaattggcta agaacttagc ccaagctaac ggtactccag gtgtagaatg cttgagacct    360

gaagttttaa caggtgatca tggtttgacc ttaatagaaa atgcagcctg gggtgtcatc    420

gcttctgtaa ctccatcaac aaaccctgct gcaacagcca tcaataacgc tatctctatg    480

attgctggtg gtaattcagt catttttgca ccacaccctg ccgctaaaaa ggtttctcaa    540

agaacaatca ccatcttgaa tgaagctatt gttgcagccg gtggtccaaa taacttgtta    600

gtcactgtag ccaaacctga tatcgaaaca gctcaaagat tgttcaagta tccaggtata    660

ggtttgttag ttgtcactgg tggtgacgct gtagttgaat ccgcaagaaa gcatacaaac    720

aagagattga tagctgcagg tgctggtaac ccacctgtcg tagttgatga aacagcagac    780

atcgaaagag ccgctaaagc cattgttcac ggtgctagtt ttgataacaa catcatctgt    840

gctgacgaaa aagttttgat cgcagtcgat tgcattgccg acaagttaat cacagaaatg    900

caaagaaacc atgcagtttt gttgaccaga gaacaatctg aaaaattaat tcctgtattg    960

ttgaagaacg ttgatgaaac cggtcacggt actgtctcaa gagattgggt tggtagagac   1020

gcagccaaaa tagctgcagc catcggtatg actgttccag cagatacaag attgttaatt   1080

gccgaaaccg actgtaagca tccttttgct gtcactgaat tgatgatgcc agtattgcct   1140

atcataagag taaaggatgt tgaccaagca atagatttgg ccgttaagtt agaaggtggt   1200

tgtcatcaca ctgctgcaat gcactccaac aacatcagta acttgaacag aatggcaaac   1260
```

```
gccatcgata catctatctt cgttaagaac ggtccatgca tagctggttt gggtttaggt   1320

ggtgaaggtt ggactacaat gaccatcacc actcctactg gtgaaggtgt tacatgtgca   1380

agaacctttg tcagattaag aagatgcact atggttgatt cattcagaat tgtctag      1437


<210> SEQ ID NO 20
<211> LENGTH: 478
<212> TYPE: PRT
<213> ORGANISM: Morganella morganii

<400> SEQUENCE: 20

Met Asp Gln Lys Glu Ile Glu Asn Val Val Lys Ala Val Leu Ala Ser
1               5                   10                  15

Met Ser Ala Gly Thr Gln Pro Ala Ala Ala Ser Ala Ala Pro Gln Gln
            20                  25                  30

Ala Ala Ala Ser Gln Asn Asn Gly Phe Gly Val Phe Glu Ser Leu Asp
        35                  40                  45

Asp Ala Val Leu Ala Ala Lys Glu Ala Gln Lys Ser Leu Lys Thr Val
    50                  55                  60

Glu Met Arg Asn Leu Cys Ile Gly Ala Ile Arg Arg Ala Ala Thr Glu
65                  70                  75                  80

His Ala Arg Glu Leu Ala Val Leu Ala Val Glu Glu Thr Gly Met Gly
                85                  90                  95

Arg Val Glu Asp Lys Leu Ala Lys Asn Leu Ala Gln Ala Asn Gly Thr
            100                 105                 110

Pro Gly Val Glu Cys Leu Arg Pro Glu Val Leu Thr Gly Asp His Gly
        115                 120                 125

Leu Thr Leu Ile Glu Asn Ala Ala Trp Gly Val Ile Ala Ser Val Thr
    130                 135                 140

Pro Ser Thr Asn Pro Ala Ala Thr Ala Ile Asn Asn Ala Ile Ser Met
145                 150                 155                 160

Ile Ala Gly Gly Asn Ser Val Ile Phe Ala Pro His Pro Ala Ala Lys
                165                 170                 175

Lys Val Ser Gln Arg Thr Ile Thr Ile Leu Asn Glu Ala Ile Val Ala
            180                 185                 190

Ala Gly Gly Pro Asn Asn Leu Leu Val Thr Val Ala Lys Pro Asp Ile
        195                 200                 205

Glu Thr Ala Gln Arg Leu Phe Lys Tyr Pro Gly Ile Gly Leu Leu Val
    210                 215                 220

Val Thr Gly Gly Asp Ala Val Val Glu Ser Ala Arg Lys His Thr Asn
225                 230                 235                 240

Lys Arg Leu Ile Ala Ala Gly Ala Gly Asn Pro Pro Val Val Val Asp
                245                 250                 255

Glu Thr Ala Asp Ile Glu Arg Ala Ala Lys Ala Ile Val His Gly Ala
            260                 265                 270

Ser Phe Asp Asn Asn Ile Ile Cys Ala Asp Glu Lys Val Leu Ile Ala
        275                 280                 285

Val Asp Cys Ile Ala Asp Lys Leu Ile Thr Glu Met Gln Arg Asn His
    290                 295                 300

Ala Val Leu Leu Thr Arg Glu Gln Ser Glu Lys Leu Ile Pro Val Leu
305                 310                 315                 320

Leu Lys Asn Val Asp Glu Thr Gly His Gly Thr Val Ser Arg Asp Trp
                325                 330                 335

Val Gly Arg Asp Ala Ala Lys Ile Ala Ala Ala Ile Gly Met Thr Val
            340                 345                 350
```

```
Pro Ala Asp Thr Arg Leu Leu Ile Ala Glu Thr Asp Cys Lys His Pro
        355                 360                 365

Phe Ala Val Thr Glu Leu Met Met Pro Val Leu Pro Ile Ile Arg Val
    370                 375                 380

Lys Asp Val Asp Gln Ala Ile Asp Leu Ala Val Lys Leu Glu Gly Gly
385                 390                 395                 400

Cys His His Thr Ala Ala Met His Ser Asn Asn Ile Ser Asn Leu Asn
                405                 410                 415

Arg Met Ala Asn Ala Ile Asp Thr Ser Ile Phe Val Lys Asn Gly Pro
            420                 425                 430

Cys Ile Ala Gly Leu Gly Leu Gly Gly Glu Gly Trp Thr Thr Met Thr
        435                 440                 445

Ile Thr Thr Pro Thr Gly Glu Gly Val Thr Cys Ala Arg Thr Phe Val
    450                 455                 460

Arg Leu Arg Arg Cys Thr Met Val Asp Ser Phe Arg Ile Val
465                 470                 475


<210> SEQ ID NO 21
<211> LENGTH: 1410
<212> TYPE: DNA
<213> ORGANISM: Calditrix abyssii

<400> SEQUENCE: 21

atgcatttag acgacaaaca aatcgcacaa atagtagaaa ccgtattatc aagattagaa      60

agaaacgaaa gtagaacagg tagaagtaga cacccacaag gtgtctttga aaccttggat     120

gaagctgtag aagctgcaag acaagcacaa aagaaaatta gaaaattgga attgagagct     180

aagatcatcc aagcaatcag acaagccggt gttaaacatg caagagaatt ggcagaaatg     240

gccgttcaag aaactggtat gggtagagtc gaagataaga tagcaaagaa catctctcaa     300

gccgaaaaga ccccaggtat tgaagattta caacctttgg ctttatcagg tgaccacggt     360

ttgactttaa tcgaaaatgc cgcttggggt gttattgcct ctgtcacacc atcaaccaac     420

cctggtgcta ctgttatcaa taactctatc tcaatgattg cagccggtaa tgctgttgtc     480

tatgcaccac atcctgctgc aaaaaaggtc tcccaaagag ccattgaaat attgaacaaa     540

gctattgaag ccgctggtgg tccagcaaca ttgttaacta cagtcgccga acctagtatc     600

gaaaccgctc aaaagttatt cgtatatcca ggtattgatt tgttagtagt tactggtggt     660

gaagctgtcg taaaagcagc cagaaaggtt acagacaaaa gattaatggc tgcaggtgca     720

ggtaatccac ctgttgtcgt agatgaaaca gctgacattg caaaagccgc tagagatata     780

gtctggggtg cttctttcga taataacatc gtatgtgcag acgaaaaaga aatcattgcc     840

gttgatgcca ttgctgacag attgaaggaa gaaatgaaaa agcaccaagc agttgaatta     900

actccacaac aaggtgaaga attggctcaa atcatcttag aagattatcc aggtcctaat     960

gcaagaataa acagaaagtg ggttggtaaa gacgcctaca agttcgctag agaaataggt    1020

ttgaacgtat caaaggaaac aagattgttg ttcgttgaag ctgataagga ccatcctttc    1080

gcacaattgg aattaatgat gccagttatc cctttgatca gagcagccga tgccgacaaa    1140

gctatcgatt tggctattga attagaacac ggttatagac atacagctgc aatgcattcc    1200

agacacattg atcatatgga cagaatggct aacgaaatca acaccagtat cttcgttaaa    1260

aacggtccat gtttggcagg tttaggtttc ggtggtgaag gttggacttc catgacaatt    1320

accactccta ccggtgaagg tgtaacttcc gctagaagtt ttgttagatt gagaagatgc    1380
```

```
gttgtcgtag atcatttcag aattgtttag                                    1410


<210> SEQ ID NO 22
<211> LENGTH: 469
<212> TYPE: PRT
<213> ORGANISM: Calditrix abyssii

<400> SEQUENCE: 22

Met His Leu Asp Asp Lys Gln Ile Ala Gln Ile Val Glu Thr Val Leu
1               5                   10                  15

Ser Arg Leu Glu Arg Asn Glu Ser Arg Thr Gly Arg Ser Arg His Pro
            20                  25                  30

Gln Gly Val Phe Glu Thr Leu Asp Glu Ala Val Glu Ala Ala Arg Gln
        35                  40                  45

Ala Gln Lys Lys Ile Arg Lys Leu Glu Leu Arg Ala Lys Ile Ile Gln
    50                  55                  60

Ala Ile Arg Gln Ala Gly Val Lys His Ala Arg Glu Leu Ala Glu Met
65                  70                  75                  80

Ala Val Gln Glu Thr Gly Met Gly Arg Val Glu Asp Lys Ile Ala Lys
                85                  90                  95

Asn Ile Ser Gln Ala Glu Lys Thr Pro Gly Ile Glu Asp Leu Gln Pro
            100                 105                 110

Leu Ala Leu Ser Gly Asp His Gly Leu Thr Leu Ile Glu Asn Ala Ala
        115                 120                 125

Trp Gly Val Ile Ala Ser Val Thr Pro Ser Thr Asn Pro Gly Ala Thr
    130                 135                 140

Val Ile Asn Asn Ser Ile Ser Met Ile Ala Ala Gly Asn Ala Val Val
145                 150                 155                 160

Tyr Ala Pro His Pro Ala Ala Lys Lys Val Ser Gln Arg Ala Ile Glu
                165                 170                 175

Ile Leu Asn Lys Ala Ile Glu Ala Ala Gly Gly Pro Ala Thr Leu Leu
            180                 185                 190

Thr Thr Val Ala Glu Pro Ser Ile Glu Thr Ala Gln Lys Leu Phe Val
        195                 200                 205

Tyr Pro Gly Ile Asp Leu Leu Val Val Thr Gly Gly Glu Ala Val Val
    210                 215                 220

Lys Ala Ala Arg Lys Val Thr Asp Lys Arg Leu Met Ala Ala Gly Ala
225                 230                 235                 240

Gly Asn Pro Pro Val Val Val Asp Glu Thr Ala Asp Ile Ala Lys Ala
                245                 250                 255

Ala Arg Asp Ile Val Trp Gly Ala Ser Phe Asp Asn Asn Ile Val Cys
            260                 265                 270

Ala Asp Glu Lys Glu Ile Ile Ala Val Asp Ala Ile Ala Asp Arg Leu
        275                 280                 285

Lys Glu Glu Met Lys Lys His Gln Ala Val Glu Leu Thr Pro Gln Gln
    290                 295                 300

Gly Glu Glu Leu Ala Gln Ile Ile Leu Glu Asp Tyr Pro Gly Pro Asn
305                 310                 315                 320

Ala Arg Ile Asn Arg Lys Trp Val Gly Lys Asp Ala Tyr Lys Phe Ala
                325                 330                 335

Arg Glu Ile Gly Leu Asn Val Ser Lys Glu Thr Arg Leu Leu Phe Val
            340                 345                 350

Glu Ala Asp Lys Asp His Pro Phe Ala Gln Leu Glu Leu Met Met Pro
        355                 360                 365
```

```
Val Ile Pro Leu Ile Arg Ala Ala Asp Ala Asp Lys Ala Ile Asp Leu
    370                 375                 380

Ala Ile Glu Leu Glu His Gly Tyr Arg His Thr Ala Ala Met His Ser
385                 390                 395                 400

Arg His Ile Asp His Met Asp Arg Met Ala Asn Glu Ile Asn Thr Ser
                405                 410                 415

Ile Phe Val Lys Asn Gly Pro Cys Leu Ala Gly Leu Gly Phe Gly Gly
            420                 425                 430

Glu Gly Trp Thr Ser Met Thr Ile Thr Thr Pro Thr Gly Glu Gly Val
        435                 440                 445

Thr Ser Ala Arg Ser Phe Val Arg Leu Arg Arg Cys Val Val Val Asp
    450                 455                 460

His Phe Arg Ile Val
465


<210> SEQ ID NO 23
<211> LENGTH: 1398
<212> TYPE: DNA
<213> ORGANISM: Marinobacter aquaeoli

<400> SEQUENCE: 23

atgcaaacag acgcccaaca aatagaaagt atcgttagaa gagtcataga acaattacac      60

agtccacaaa gagatggtga aagttatggt gtctttagaa ccttggatga cgcagtagcc     120

ggtgctcaag gtgcttataa aaagataaga accatggctc aaagagaagc aattatagct     180

gcaatcagaa gaactggtag tgaaaatgtt caagcattgt ctgaattagc cgtccaagaa     240

acaggtttcg gtagagtaga agataagatc agaaagcata gattggtttt agacaaaact     300

cctggtatcg aagctattgt tccaatggca gtcacaggtg atcacggttt gtctttaatt     360

gaaaatgctc catggggtgt aatagcatcc gttacccccta gtactaaccc atctgctact     420

atcttgaaca acgcaatctc aatgatcgcc gctggtaatt cagttgtctt ttccccacat     480

cctgcagcca gagctgtctc ccaaagaaca atccaattga tcaacagagc ctctgtttca     540

gctggtggtc ctgcaaactt agtcacctgt gtagaagaac caacaattga agctgcaacc     600

agattgtttt cattccctgg tatacaattg ttaaccatca ctggtggtga aggtgtagtt     660

aatgccgcta gaaaagttac tgataagaga ttaatcgcag ccggtccagg taacccacct     720

gtcgtagttg atgaaacagc tgacattgaa agagctgcaa tttcaatagt tcaaggtgca     780

tccttcgata acaacatcat atgtgttgac gaaaaggaaa taatcgccgt cgaatccatt     840

gctactgaat tgaagacagc tatgtgcaga catggtgccg ctgaaataaa tgcagatcaa     900

gcagacgccg tcgctagatt ggtattagct ggttacccag gtcctaaccc acaccctaaa     960

ccagaatggg ttggtagaga tgctgaaaag attgcagccg ctgcaggttt tagtgtacct    1020

gcaggtacta gattgttagt tacagaaacc gaaagagatc atgcattcgc cactacagaa    1080

atgatgttgc cagttatctc tttaataaga gctagagatg cagaccaagc cattgattgg    1140

gcagttgaat tggaagccgg taatagacat acagccgcta tgcactcaag aaatatcgac    1200

aacttgtcca gaatgggttt agaaataaac tgttctttgt tcgttaaaaa cggtccttgc    1260

ttggccggtt taggtgctgg tggtgaaggt tggacaagta tgaccatatc tactccaaca    1320

ggtgaaggtg taaccaacgc tagtactttc gttagaaaga gaagatgcac aatggttgat    1380

tctttcagaa ttgtctag                                                  1398


<210> SEQ ID NO 24
```

<211> LENGTH: 465
<212> TYPE: PRT
<213> ORGANISM: Marinobacter aquaeoli

<400> SEQUENCE: 24

```
Met Gln Thr Asp Ala Gln Gln Ile Glu Ser Ile Val Arg Arg Val Ile
1               5                   10                  15

Glu Gln Leu His Ser Pro Gln Arg Asp Gly Glu Ser Tyr Gly Val Phe
            20                  25                  30

Arg Thr Leu Asp Asp Ala Val Ala Gly Ala Gln Gly Ala Tyr Lys Lys
        35                  40                  45

Ile Arg Thr Met Ala Gln Arg Glu Ala Ile Ile Ala Ala Ile Arg Arg
    50                  55                  60

Thr Gly Ser Glu Asn Val Gln Ala Leu Ser Glu Leu Ala Val Gln Glu
65                  70                  75                  80

Thr Gly Phe Gly Arg Val Glu Asp Lys Ile Arg Lys His Arg Leu Val
                85                  90                  95

Leu Asp Lys Thr Pro Gly Ile Glu Ala Ile Val Pro Met Ala Val Thr
            100                 105                 110

Gly Asp His Gly Leu Ser Leu Ile Glu Asn Ala Pro Trp Gly Val Ile
        115                 120                 125

Ala Ser Val Thr Pro Ser Thr Asn Pro Ser Ala Thr Ile Leu Asn Asn
    130                 135                 140

Ala Ile Ser Met Ile Ala Ala Gly Asn Ser Val Val Phe Ser Pro His
145                 150                 155                 160

Pro Ala Ala Arg Ala Val Ser Gln Arg Thr Ile Gln Leu Ile Asn Arg
                165                 170                 175

Ala Ser Val Ser Ala Gly Gly Pro Ala Asn Leu Val Thr Cys Val Glu
            180                 185                 190

Glu Pro Thr Ile Glu Ala Ala Thr Arg Leu Phe Ser Phe Pro Gly Ile
        195                 200                 205

Gln Leu Leu Thr Ile Thr Gly Gly Glu Gly Val Val Asn Ala Ala Arg
    210                 215                 220

Lys Val Thr Asp Lys Arg Leu Ile Ala Ala Gly Pro Gly Asn Pro Pro
225                 230                 235                 240

Val Val Val Asp Glu Thr Ala Asp Ile Glu Arg Ala Ala Ile Ser Ile
                245                 250                 255

Val Gln Gly Ala Ser Phe Asp Asn Asn Ile Ile Cys Val Asp Glu Lys
            260                 265                 270

Glu Ile Ile Ala Val Glu Ser Ile Ala Thr Glu Leu Lys Thr Ala Met
        275                 280                 285

Cys Arg His Gly Ala Ala Glu Ile Asn Ala Asp Gln Ala Asp Ala Val
    290                 295                 300

Ala Arg Leu Val Leu Ala Gly Tyr Pro Gly Pro Asn Pro His Pro Lys
305                 310                 315                 320

Pro Glu Trp Val Gly Arg Asp Ala Glu Lys Ile Ala Ala Ala Ala Gly
                325                 330                 335

Phe Ser Val Pro Ala Gly Thr Arg Leu Leu Val Thr Glu Thr Glu Arg
            340                 345                 350

Asp His Ala Phe Ala Thr Thr Glu Met Met Leu Pro Val Ile Ser Leu
        355                 360                 365

Ile Arg Ala Arg Asp Ala Asp Gln Ala Ile Asp Trp Ala Val Glu Leu
    370                 375                 380

Glu Ala Gly Asn Arg His Thr Ala Ala Met His Ser Arg Asn Ile Asp
```

-continued

```
385                 390                 395                 400

Asn Leu Ser Arg Met Gly Leu Glu Ile Asn Cys Ser Leu Phe Val Lys
                405                 410                 415

Asn Gly Pro Cys Leu Ala Gly Leu Gly Ala Gly Gly Glu Gly Trp Thr
            420                 425                 430

Ser Met Thr Ile Ser Thr Pro Thr Gly Glu Gly Val Thr Asn Ala Ser
        435                 440                 445

Thr Phe Val Arg Lys Arg Arg Cys Thr Met Val Asp Ser Phe Arg Ile
    450                 455                 460

Val
465
```

<210> SEQ ID NO 25
<211> LENGTH: 1434
<212> TYPE: DNA
<213> ORGANISM: Shewanella benthica

<400> SEQUENCE: 25

```
atggatcaaa aacaaatcga agaaatcgta aaatcaatcg tattacaatt aaatgacaac     60

ccaggtatag cctcctcagc caacaccttg aatcaaaaca cattaaccga acagggtgat    120

tatggtgtct ttgaaacttt ggacggtgct gtagctgcag ccactgctgc acaaaagcaa    180

attagaacag ttgcaatgag agatgaaatc atcacagcca tcagaagaat gaccaaaaag    240

catgccagag aattatcaga aatggctgtt gaagaaacag gtttcggtag agtcgaagat    300

aagataaaaa agcacatctt ggtcgctcaa agaactcctg gtacagaaat tttatcccca    360

caagcagtat ccggtgatag tggtttctct ttgatggaaa atgctccatg ggtgtcatc    420

gcatcagtaa ccccttccac taacccaact tgtacagtta taaacaacgc tatatcaatg    480

atagccgctg gtaatgcagt tgtctttgcc ccacatcctg cagccaaaaa ggtttcccaa    540

tacactatcc aattagtaaa caaggcttct gaatcagttg gtggtcctgc atacatatgc    600

actacagtag ccaaaccatc tttggaaaat gctcaagcat tattcgttta ccctggtatt    660

agattgttag tagttactgg tggtgatgct gtcgtagaag ctgcaagagc agttacagac    720

aaaagattga tcgccgctgg tccaggtaac ccacctgttg tcgtagatga aaccgctgac    780

atagaaagag cagccataag tatcgtagaa ggtgcttctt tcgataataa catagtttgt    840

gcaacagaaa aggaaatcat tgctgtcgat tcaatcgcag acgaattaaa agctgcaatg    900

tgcagaaatg gtgcccattt gttaactgct gatcaagccg aagctgttgc aagagttgtc    960

ttgaaaggtt atcctggtga caagccatca cctaacccaa aatgggttgg tagagatgct   1020

tccaagttag ccgctgcagc cggtatagac gtcccagcag aaacaagatt gttaatcttt   1080

gaagccgata aatctcacgt tttcgctgta gttgaacaaa tgatgcctat tttgccatta   1140

atcagagctg caaatgccga tcaagctatt gactgggctg ttgaattgga aaataagaac   1200

agacatacag ccgctatcca cagtaagaac atcgatgttt tgaccagaat ggcttacgaa   1260

atggactgtt ctttgttagc aaagaacggt cctgccatcg cagccattgg tgcaggtggt   1320

gaaggttgga ccactatgac cattagtacc ccaactggtg aaggtgttac taacgctttg   1380

acattcacca gaaagagaag atgcactgca gttgattctt tcagaattgt ctag          1434
```

<210> SEQ ID NO 26
<211> LENGTH: 477
<212> TYPE: PRT
<213> ORGANISM: Shewanella benthica

<400> SEQUENCE: 26

Met Asp Gln Lys Gln Ile Glu Glu Ile Val Lys Ser Ile Val Leu Gln
1 5 10 15

Leu Asn Asp Asn Pro Gly Ile Ala Ser Ser Ala Asn Thr Leu Asn Gln
20 25 30

Asn Thr Leu Thr Glu Gln Gly Asp Tyr Gly Val Phe Glu Thr Leu Asp
35 40 45

Gly Ala Val Ala Ala Ala Thr Ala Ala Gln Lys Gln Ile Arg Thr Val
50 55 60

Ala Met Arg Asp Glu Ile Ile Thr Ala Ile Arg Arg Met Thr Lys Lys
65 70 75 80

His Ala Arg Glu Leu Ser Glu Met Ala Val Glu Glu Thr Gly Phe Gly
85 90 95

Arg Val Glu Asp Lys Ile Lys Lys His Ile Leu Val Ala Gln Arg Thr
100 105 110

Pro Gly Thr Glu Ile Leu Ser Pro Gln Ala Val Ser Gly Asp Ser Gly
115 120 125

Phe Ser Leu Met Glu Asn Ala Pro Trp Gly Val Ile Ala Ser Val Thr
130 135 140

Pro Ser Thr Asn Pro Thr Cys Thr Val Ile Asn Asn Ala Ile Ser Met
145 150 155 160

Ile Ala Ala Gly Asn Ala Val Val Phe Ala Pro His Pro Ala Ala Lys
165 170 175

Lys Val Ser Gln Tyr Thr Ile Gln Leu Val Asn Lys Ala Ser Glu Ser
180 185 190

Val Gly Gly Pro Ala Tyr Ile Cys Thr Thr Val Ala Lys Pro Ser Leu
195 200 205

Glu Asn Ala Gln Ala Leu Phe Val Tyr Pro Gly Ile Arg Leu Leu Val
210 215 220

Val Thr Gly Gly Asp Ala Val Val Glu Ala Ala Arg Ala Val Thr Asp
225 230 235 240

Lys Arg Leu Ile Ala Ala Gly Pro Gly Asn Pro Pro Val Val Val Asp
245 250 255

Glu Thr Ala Asp Ile Glu Arg Ala Ala Ile Ser Ile Val Glu Gly Ala
260 265 270

Ser Phe Asp Asn Asn Ile Val Cys Ala Thr Glu Lys Glu Ile Ile Ala
275 280 285

Val Asp Ser Ile Ala Asp Glu Leu Lys Ala Ala Met Cys Arg Asn Gly
290 295 300

Ala His Leu Leu Thr Ala Asp Gln Ala Glu Ala Val Ala Arg Val Val
305 310 315 320

Leu Lys Gly Tyr Pro Gly Asp Lys Pro Ser Pro Asn Pro Lys Trp Val
325 330 335

Gly Arg Asp Ala Ser Lys Leu Ala Ala Ala Ala Gly Ile Asp Val Pro
340 345 350

Ala Glu Thr Arg Leu Leu Ile Phe Glu Ala Asp Lys Ser His Val Phe
355 360 365

Ala Val Val Glu Gln Met Met Pro Ile Leu Pro Leu Ile Arg Ala Ala
370 375 380

Asn Ala Asp Gln Ala Ile Asp Trp Ala Val Glu Leu Glu Asn Lys Asn
385 390 395 400

Arg His Thr Ala Ala Ile His Ser Lys Asn Ile Asp Val Leu Thr Arg
405 410 415

```
Met Ala Tyr Glu Met Asp Cys Ser Leu Leu Ala Lys Asn Gly Pro Ala
            420                 425                 430

Ile Ala Ala Ile Gly Ala Gly Gly Glu Gly Trp Thr Thr Met Thr Ile
        435                 440                 445

Ser Thr Pro Thr Gly Glu Gly Val Thr Asn Ala Leu Thr Phe Thr Arg
    450                 455                 460

Lys Arg Arg Cys Thr Ala Val Asp Ser Phe Arg Ile Val
465                 470                 475


<210> SEQ ID NO 27
<211> LENGTH: 1428
<212> TYPE: DNA
<213> ORGANISM: Bacillus vireti

<400> SEQUENCE: 27

atgcaaatca acgaaaccga cataaagaaa atggtagaac aagtattaaa acaattaggt      60

caaacagaag ctgctggtgc cccaatcgct ccacaaaatg atgtttcttt aggtgacggt     120

gtatttgcaa ctgttgatga agctgcagcc gctgcaagag ttgcttggga aaaattgaga     180

aagttgcctt tagcatcaag aagacaaatg attgacaata tgagagaagt ttcctgtgcc     240

caagctaacg aattggcaca attagccgtt gatgaaacag gtttaggtag agtcgaagac     300

aaagtagcta agattttgtt agccgctaat aaaacaccag gtgttgaaga tttggtctct     360

acctcatatt ccggtgatga cggtttgact ttagtcgaat acgctcctat cggtgtattc     420

ggttcaatta ctccatccac aaaccctgca gccactgtta taaataacag tatttcttta     480

atcgctgcag gtaatacagt tgtctataac ccacatccta gtgctaagag agtttctttg     540

aagactttga agttgttaaa tcaagccatt gtcgccgctg gtggtccaga aaatgctttg     600

acaagtgttg cagcccctaa cttagaaacc tctgcacaag ttatgaatca cccaaaagtc     660

aacgccttag tagttacagg tggtggtcct gtcgtaaagg ctgcaatggc tgtaggtaaa     720

aaggttatcg ccgctggtcc aggtaatcca cctgttgtcg tagatgaaac agcaattata     780

tcacaagcag ccgctcatat tgttcaaggt gcttcctttg ataataacgt tttgtgtacc     840

gcagaaaaag aagtcttcgt tgttgataag gcagccaatg ctttaaaagc agaaatggtt     900

aagaacggtg ctatagaatt gaaaggtttt caattcgaaa aattgttaga aaaggtatta     960

gttaaaaaga atgataaatt ttacccaaac agagatttca ttggcaagga cgctagtgtt    1020

atattgcaag ctgcaggtat ccaagtctct ccaaacgtaa aattgatcat agcagaaact    1080

acaaaggatc accctttggt tatgactgaa atgttgatgc caatcttacc tattgtcaga    1140

gtaccagatg tagacaaagc tattgaatta gccgttatag ctgaaaaggg taatagacat    1200

accgcaataa tgcactcaca aaacatcacc aacttgacta agatggcaca agaaatacaa    1260

gccactatct ttgtaaagaa cggtccatca gttgctggtt tgggttttga atccgaaggt    1320

ttcaccactt taacaattgc cggtcctacc ggtgaaggtt tgacttctgc aaaaacattt    1380

accagacaaa gaagatgcgt tttggtcgat ggtttcagaa taatctag                 1428


<210> SEQ ID NO 28
<211> LENGTH: 475
<212> TYPE: PRT
<213> ORGANISM: Bacillus vireti

<400> SEQUENCE: 28

Met Gln Ile Asn Glu Thr Asp Ile Lys Lys Met Val Glu Gln Val Leu
1               5                   10                  15
```

-continued

```
Lys Gln Leu Gly Gln Thr Glu Ala Ala Gly Ala Pro Ile Ala Pro Gln
            20                  25                  30

Asn Asp Val Ser Leu Gly Asp Gly Val Phe Ala Thr Val Asp Glu Ala
        35                  40                  45

Ala Ala Ala Ala Arg Val Ala Trp Glu Lys Leu Arg Lys Leu Pro Leu
    50                  55                  60

Ala Ser Arg Arg Gln Met Ile Asp Asn Met Arg Glu Val Ser Cys Ala
65                  70                  75                  80

Gln Ala Asn Glu Leu Ala Gln Leu Ala Val Asp Glu Thr Gly Leu Gly
                85                  90                  95

Arg Val Glu Asp Lys Val Ala Lys Ile Leu Leu Ala Ala Asn Lys Thr
            100                 105                 110

Pro Gly Val Glu Asp Leu Val Ser Thr Ser Tyr Ser Gly Asp Asp Gly
        115                 120                 125

Leu Thr Leu Val Glu Tyr Ala Pro Ile Gly Val Phe Gly Ser Ile Thr
    130                 135                 140

Pro Ser Thr Asn Pro Ala Ala Thr Val Ile Asn Asn Ser Ile Ser Leu
145                 150                 155                 160

Ile Ala Ala Gly Asn Thr Val Val Tyr Asn Pro His Pro Ser Ala Lys
                165                 170                 175

Arg Val Ser Leu Lys Thr Leu Lys Leu Leu Asn Gln Ala Ile Val Ala
            180                 185                 190

Ala Gly Gly Pro Glu Asn Ala Leu Thr Ser Val Ala Ala Pro Asn Leu
        195                 200                 205

Glu Thr Ser Ala Gln Val Met Asn His Pro Lys Val Asn Ala Leu Val
    210                 215                 220

Val Thr Gly Gly Gly Pro Val Val Lys Ala Ala Met Ala Val Gly Lys
225                 230                 235                 240

Lys Val Ile Ala Ala Gly Pro Gly Asn Pro Pro Val Val Val Asp Glu
                245                 250                 255

Thr Ala Ile Ile Ser Gln Ala Ala Ala His Ile Val Gln Gly Ala Ser
            260                 265                 270

Phe Asp Asn Asn Val Leu Cys Thr Ala Glu Lys Glu Val Phe Val Val
        275                 280                 285

Asp Lys Ala Ala Asn Ala Leu Lys Ala Glu Met Val Lys Asn Gly Ala
    290                 295                 300

Ile Glu Leu Lys Gly Phe Gln Phe Glu Lys Leu Leu Glu Lys Val Leu
305                 310                 315                 320

Val Lys Lys Asn Asp Lys Phe Tyr Pro Asn Arg Asp Phe Ile Gly Lys
                325                 330                 335

Asp Ala Ser Val Ile Leu Gln Ala Ala Gly Ile Gln Val Ser Pro Asn
            340                 345                 350

Val Lys Leu Ile Ile Ala Glu Thr Thr Lys Asp His Pro Leu Val Met
        355                 360                 365

Thr Glu Met Leu Met Pro Ile Leu Pro Ile Val Arg Val Pro Asp Val
    370                 375                 380

Asp Lys Ala Ile Glu Leu Ala Val Ile Ala Glu Lys Gly Asn Arg His
385                 390                 395                 400

Thr Ala Ile Met His Ser Gln Asn Ile Thr Asn Leu Thr Lys Met Ala
                405                 410                 415

Gln Glu Ile Gln Ala Thr Ile Phe Val Lys Asn Gly Pro Ser Val Ala
            420                 425                 430
```

```
Gly Leu Gly Phe Glu Ser Glu Gly Phe Thr Thr Leu Thr Ile Ala Gly
        435                 440                 445

Pro Thr Gly Glu Gly Leu Thr Ser Ala Lys Thr Phe Thr Arg Gln Arg
    450                 455                 460

Arg Cys Val Leu Val Asp Gly Phe Arg Ile Ile
465                 470                 475


<210> SEQ ID NO 29
<211> LENGTH: 1458
<212> TYPE: DNA
<213> ORGANISM: Streptococcus massiliensis

<400> SEQUENCE: 29

atgggtttat cagaaatcga acaattagtc aagcaaatct tatcagaaga catattagaa      60

agtcaagaat ccgcacaata cagtcaatcc ttggttggta caaaggaaat ccaaggtgat     120

atcttagaag gcaaggaaac agaatctggt gtcttttcaa ccgtagatca agcagttcaa     180

gctgcaaaga tagcccaaaa gaaatacttc gacacttcta tcgaaagaag aaaaaagatt     240

atcgccgcta taagatcaag attgttacca gaagttgaag aaatagctaa aagagcattg     300

gaagaaaccg gtatgggtaa cttccaagat aagatagcta agaacagatt ggccttagaa     360

gctactccag gtgtcgaaga tttgatgtat gcaaccagag ccttaactgg tgacaatggt     420

ttgactttat atgaaatgtg tccttacggt gttatcggtg caattgcccc atcaacaaac     480

cctactgaaa caatcatcaa taactccatc agtatgttgg cagccggtaa cacaatttac     540

ttcgctccac atcctggtgc aagagaaact acaatctggt tgatcagaaa gataaacaag     600

atagctaaag atgcatccgg tatagacaac ttgatcgtca ccatagaaaa cccaagtata     660

caagctgcac aagaaatgat ggtacaccca gatattgcta tattagttgt cactggtggt     720

cctggtgtag ttgctcaagc aatgaaatct ggtaaaaagg ttattggtgc cggtgctggt     780

aatccacctg caatcgtcga tgaaactgcc aacattgaaa aggctggtca agatatagtt     840

gacggtgcct catttgacaa taacattcct tgtactgctg aaaagaatat aatcgtcgta     900

tcttcagttg ctgaatactt gatcttcaac atgcaaaagg caggtgcctt ctacgtcaaa     960

gatatcgaag acatcaaaaa gttagaaaac ttgtgcttga cagaaaaggg taccactaac    1020

aaaaagtatg ttggtaagtc tgctgaaaaa atcttgaccg atgcaggtgt tacctatact    1080

ggtcatccaa gattagtaat tgttgaaggt tacccagata tgccttttgc tgttgaagaa    1140

atgttgatgc cagttgtccc tttaattaga gtccctgatt tcgacactgc cttggaagta    1200

gctttggaat tagaacatgg ttacaaacac acagctacca ttcactccca aaatgtaagt    1260

agattaaaca aggccgctag agctatggaa acatctatct tcgttaagaa cggtccatca    1320

ttcgcaggtt tgggtttaag aggtgaaggt ccaacaacct ttactattgc tactcctaca    1380

ggtgaaggta ctacaaccgc aagatccttt gccagaataa gaagatgcgt tttaagtgat    1440

gcattcatga tcagatag                                                  1458


<210> SEQ ID NO 30
<211> LENGTH: 485
<212> TYPE: PRT
<213> ORGANISM: Streptococcus massiliensis

<400> SEQUENCE: 30

Met Gly Leu Ser Glu Ile Glu Gln Leu Val Lys Gln Ile Leu Ser Glu
1               5                   10                  15

Asp Ile Leu Glu Ser Gln Glu Ser Ala Gln Tyr Ser Gln Ser Leu Val
```

-continued

```
            20                  25                  30

Gly Thr Lys Glu Ile Gln Gly Asp Ile Leu Glu Gly Lys Glu Thr Glu
        35                  40                  45

Ser Gly Val Phe Ser Thr Val Asp Gln Ala Val Gln Ala Ala Lys Ile
    50                  55                  60

Ala Gln Lys Lys Tyr Phe Asp Thr Ser Ile Glu Arg Arg Lys Lys Ile
65                  70                  75                  80

Ile Ala Ala Ile Arg Ser Arg Leu Leu Pro Glu Val Glu Glu Ile Ala
                85                  90                  95

Lys Arg Ala Leu Glu Glu Thr Gly Met Gly Asn Phe Gln Asp Lys Ile
            100                 105                 110

Ala Lys Asn Arg Leu Ala Leu Glu Ala Thr Pro Gly Val Glu Asp Leu
        115                 120                 125

Met Tyr Ala Thr Arg Ala Leu Thr Gly Asp Asn Gly Leu Thr Leu Tyr
    130                 135                 140

Glu Met Cys Pro Tyr Gly Val Ile Gly Ala Ile Ala Pro Ser Thr Asn
145                 150                 155                 160

Pro Thr Glu Thr Ile Ile Asn Asn Ser Ile Ser Met Leu Ala Ala Gly
                165                 170                 175

Asn Thr Ile Tyr Phe Ala Pro His Pro Gly Ala Arg Glu Thr Thr Ile
            180                 185                 190

Trp Leu Ile Arg Lys Ile Asn Lys Ile Ala Lys Asp Ala Ser Gly Ile
        195                 200                 205

Asp Asn Leu Ile Val Thr Ile Glu Asn Pro Ser Ile Gln Ala Ala Gln
    210                 215                 220

Glu Met Met Val His Pro Asp Ile Ala Ile Leu Val Val Thr Gly Gly
225                 230                 235                 240

Pro Gly Val Val Ala Gln Ala Met Lys Ser Gly Lys Lys Val Ile Gly
                245                 250                 255

Ala Gly Ala Gly Asn Pro Pro Ala Ile Val Asp Glu Thr Ala Asn Ile
            260                 265                 270

Glu Lys Ala Gly Gln Asp Ile Val Asp Gly Ala Ser Phe Asp Asn Asn
        275                 280                 285

Ile Pro Cys Thr Ala Glu Lys Asn Ile Ile Val Val Ser Ser Val Ala
    290                 295                 300

Glu Tyr Leu Ile Phe Asn Met Gln Lys Ala Gly Ala Phe Tyr Val Lys
305                 310                 315                 320

Asp Ile Glu Asp Ile Lys Lys Leu Glu Asn Leu Cys Leu Thr Glu Lys
                325                 330                 335

Gly Thr Thr Asn Lys Lys Tyr Val Gly Lys Ser Ala Glu Lys Ile Leu
            340                 345                 350

Thr Asp Ala Gly Val Thr Tyr Thr Gly His Pro Arg Leu Val Ile Val
        355                 360                 365

Glu Gly Tyr Pro Asp Met Pro Phe Ala Val Glu Glu Met Leu Met Pro
    370                 375                 380

Val Val Pro Leu Ile Arg Val Pro Asp Phe Asp Thr Ala Leu Glu Val
385                 390                 395                 400

Ala Leu Glu Leu Glu His Gly Tyr Lys His Thr Ala Thr Ile His Ser
                405                 410                 415

Gln Asn Val Ser Arg Leu Asn Lys Ala Ala Arg Ala Met Glu Thr Ser
            420                 425                 430

Ile Phe Val Lys Asn Gly Pro Ser Phe Ala Gly Leu Gly Leu Arg Gly
        435                 440                 445
```

-continued

```
Glu Gly Pro Thr Thr Phe Thr Ile Ala Thr Pro Thr Gly Glu Gly Thr
    450                 455                 460

Thr Thr Ala Arg Ser Phe Ala Arg Ile Arg Arg Cys Val Leu Ser Asp
465                 470                 475                 480

Ala Phe Met Ile Arg
                485
```

<210> SEQ ID NO 31
<211> LENGTH: 1446
<212> TYPE: DNA
<213> ORGANISM: Desulfospira joergensenii

<400> SEQUENCE: 31

```
atggctgacg tattggaaaa agacatagaa gctatcgtaa cagaagtatt aaagaagatg      60

acattgccaa cctcctctcc taacggttct tcacctcaag aaactttgtt agattctgac     120

ggtgattggg gtgtctttcc aggtttagat caagctgtag ctgcagcctc agctgcacaa     180

aaaagaatac caacaatagc tgttagagaa caagttgtca gaatggtcag aagagccgct     240

agagcaaatg ccagaagatt agccgaaatg gctgttgatg aaaccggtat gggtagagtc     300

gaagacaagg taaaaaagaa tttgttagtt gccaacagaa caccaggtcc tgaaattttg     360

tctcctgcag ccgctactgg tgatgctggt ttaacattgt ttgaaaatgc cccatggggt     420

gttattgctt ctgtcactcc ttcaacaaac ccagcagcca caatcttcaa taacaccatt     480

tccatggtct ctggtggtaa tactgtagtt tatgcagttc atccaggtgc caagagaact     540

acattagaaa cagttaaggt cgtaaacaag gcagtctacg aagaattggg tataaacaac     600

ataatcactt gtgttaagga accttctatc gaaaccgctc aaaagttatt cacttatcca     660

ggtatcaact tgttagttgt tactggtggt gaagcagtag ttgatgctgc aaaaaagata     720

actgacaaga gattgatcgc cgctggtgct ggtaacccac ctgtcgttgt tgatgacact     780

gcagatttgg ccagagcagc ccaatctatc tacgatggtg cttcattcga caacaacatc     840

gtttgttgcg atgaaaagga aatcatagct ttagacacag ttgcagataa attgaaggac     900

gaattgaaga attgcggtgc tgttgaaatt tccttggacc aagctgatgc aatagccaga     960

aaggttttgt tggattaccc tggttcaaat ccaagaccta acccaaagtg ggttggtaga    1020

gatgctgcag ttttggcttc tgccgctggt atatcagtac cagaaacatg tagattgtta    1080

atcgttgatg caggtaccga cactggttac acctttgcca aaatggaaca aatgatgcct    1140

ttaataccaa tcttgagagc aagagatttc aatcaagcat tggaatgggc attgttattg    1200

gaaaacgatt gcagacattc cgctggtttg cacagtaaga atattgacaa catggataca    1260

atggctaaag cagtcaatac ctcattattc gtaaagaacg gtcctcacat tgccggtttg    1320

ggtgctggtg gtgaaggttg gacctccatg actataagta caccaaccgg tgaaggtgta    1380

tccaatgcaa gaactttcgt tagattgaga agatgtacat tggttggtag tttcagaatt    1440

gcttag                                                               1446
```

<210> SEQ ID NO 32
<211> LENGTH: 481
<212> TYPE: PRT
<213> ORGANISM: Desulfospira joergensenii

<400> SEQUENCE: 32

```
Met Ala Asp Val Leu Glu Lys Asp Ile Glu Ala Ile Val Thr Glu Val
1               5                   10                  15
```

-continued

```
Leu Lys Lys Met Thr Leu Pro Thr Ser Ser Pro Asn Gly Ser Ser Pro
            20                  25                  30

Gln Glu Thr Leu Leu Asp Ser Asp Gly Asp Trp Gly Val Phe Pro Gly
        35                  40                  45

Leu Asp Gln Ala Val Ala Ala Ala Ser Ala Ala Gln Lys Arg Ile Pro
    50                  55                  60

Thr Ile Ala Val Arg Glu Gln Val Val Arg Met Val Arg Arg Ala Ala
65                  70                  75                  80

Arg Ala Asn Ala Arg Arg Leu Ala Glu Met Ala Val Asp Glu Thr Gly
                85                  90                  95

Met Gly Arg Val Glu Asp Lys Val Lys Lys Asn Leu Leu Val Ala Asn
            100                 105                 110

Arg Thr Pro Gly Pro Glu Ile Leu Ser Pro Ala Ala Ala Thr Gly Asp
        115                 120                 125

Ala Gly Leu Thr Leu Phe Glu Asn Ala Pro Trp Gly Val Ile Ala Ser
    130                 135                 140

Val Thr Pro Ser Thr Asn Pro Ala Ala Thr Ile Phe Asn Asn Thr Ile
145                 150                 155                 160

Ser Met Val Ser Gly Gly Asn Thr Val Val Tyr Ala Val His Pro Gly
                165                 170                 175

Ala Lys Arg Thr Thr Leu Glu Thr Val Lys Val Val Asn Lys Ala Val
            180                 185                 190

Tyr Glu Glu Leu Gly Ile Asn Asn Ile Ile Thr Cys Val Lys Glu Pro
        195                 200                 205

Ser Ile Glu Thr Ala Gln Lys Leu Phe Thr Tyr Pro Gly Ile Asn Leu
    210                 215                 220

Leu Val Val Thr Gly Gly Glu Ala Val Val Asp Ala Ala Lys Lys Ile
225                 230                 235                 240

Thr Asp Lys Arg Leu Ile Ala Ala Gly Ala Gly Asn Pro Pro Val Val
                245                 250                 255

Val Asp Asp Thr Ala Asp Leu Ala Arg Ala Ala Gln Ser Ile Tyr Asp
            260                 265                 270

Gly Ala Ser Phe Asp Asn Asn Ile Val Cys Cys Asp Glu Lys Glu Ile
        275                 280                 285

Ile Ala Leu Asp Thr Val Ala Asp Lys Leu Lys Asp Glu Leu Lys Asn
    290                 295                 300

Cys Gly Ala Val Glu Ile Ser Leu Asp Gln Ala Asp Ala Ile Ala Arg
305                 310                 315                 320

Lys Val Leu Leu Asp Tyr Pro Gly Ser Asn Pro Arg Pro Asn Pro Lys
                325                 330                 335

Trp Val Gly Arg Asp Ala Ala Val Leu Ala Ser Ala Ala Gly Ile Ser
            340                 345                 350

Val Pro Glu Thr Cys Arg Leu Leu Ile Val Asp Ala Gly Thr Asp Thr
        355                 360                 365

Gly Tyr Thr Phe Ala Lys Met Glu Gln Met Met Pro Leu Ile Pro Ile
    370                 375                 380

Leu Arg Ala Arg Asp Phe Asn Gln Ala Leu Glu Trp Ala Leu Leu Leu
385                 390                 395                 400

Glu Asn Asp Cys Arg His Ser Ala Gly Leu His Ser Lys Asn Ile Asp
                405                 410                 415

Asn Met Asp Thr Met Ala Lys Ala Val Asn Thr Ser Leu Phe Val Lys
            420                 425                 430

Asn Gly Pro His Ile Ala Gly Leu Gly Ala Gly Gly Glu Gly Trp Thr
```

```
        435                 440                 445

Ser Met Thr Ile Ser Thr Pro Thr Gly Glu Gly Val Ser Asn Ala Arg
    450                 455                 460

Thr Phe Val Arg Leu Arg Arg Cys Thr Leu Val Gly Ser Phe Arg Ile
465                 470                 475                 480

Ala


<210> SEQ ID NO 33
<211> LENGTH: 1455
<212> TYPE: DNA
<213> ORGANISM: Bilophila wadsworthia

<400> SEQUENCE: 33

atggacgtta gacaacaaga tgtagaaaga atcgtagtcg aagtattaaa gaaaatgatg      60

agtgaccaac caacagccgc agcaaccaca gttgtcgctg catccggttg tgattgcggt     120

gactttggtt tgttcgatag attagaagac gctgtccaag ccgctgaagc agcccaaaag     180

aaaattagta cagtagcaat gagagataag ataatcgctg caataagaaa ggctggtttg     240

gaaaatgcca aagcatttgc agaaattgca cataacgaaa ccggtatggg tagagtctct     300

gataagatcg ctaagaacat cttggtatgc gaaagaactc ctggtacaga atgcttatcc     360

ccaatggcaa ttagtggtga catgggtttg actttaatag aaaatgcacc atggggtgta     420

atcgcctctg ttaccccttc aactaaccca accgctactg ttataaataa cgccatctcc     480

atgattgctg gtggtaatag tgttatcttt gctccacatc ctaacgctaa gagagcatct     540

caaactgcaa ttcaagtatt gaacaaggct atcatcgaag caacaggtgt tgccaacttg     600

ttagtcgctg taaaagaacc taccattgaa gttgcacaag aattattctc acacccaaga     660

ataaagttgt tagtagttac tggtggtgaa gccgtcgtag cccaagctag aaaagttgct     720

acaatgagat tgattgccgc tggtgcaggt aatccacctg ttgtcgtaga tgaaacagcc     780

aacattgcta gagcagccag atctatatat gatggtgcct cattcgacaa taacatcatc     840

tgtgctgacg aaaaggaaat catcgcagtt gattctatag ccgaccaatt aaaagctgaa     900

atgaaggcaa ttggtgccgt tgaaatatca ttggaacaag cagatgccgt cgctagagtt     960

gtcttaagaa attaccctca agttgaaggt ggcaaggctc caaatcctaa cccaaaatgg    1020

gtcggtagag atgctgcatt gatagcaaag gccgctggta tcgatgttcc agactcctgc    1080

agattgttga tcgttgatgt caagagagac ataaaccatg tctttgctag agtagaacaa    1140

ttgatgcctg taattccatt gttaagagca gccaacgttg atgaagctat cgaatgggca    1200

ttgattttag aaagaggttt gtctcatacc gctggtatgc actcaagaaa tattgataac    1260

atggacaaga tggcaagagc catgaacact tcattattcg ttaagaacgg tcctcacttg    1320

gctgcattag gtgctggtgg tgaaggttgg actacaatga caatttccac accaaccggt    1380

gaaggtgtta cctgtgctag aagttttgtc agattgagaa gatgttgcgt agttgataat    1440

ttcagaatag tttag                                                     1455


<210> SEQ ID NO 34
<211> LENGTH: 484
<212> TYPE: PRT
<213> ORGANISM: Bilophila wadsworthia

<400> SEQUENCE: 34

Met Asp Val Arg Gln Gln Asp Val Glu Arg Ile Val Val Glu Val Leu
1               5                   10                  15
```

-continued

```
Lys Lys Met Met Ser Asp Gln Pro Thr Ala Ala Ala Thr Thr Val Val
            20                  25                  30

Ala Ala Ser Gly Cys Asp Cys Gly Asp Phe Gly Leu Phe Asp Arg Leu
        35                  40                  45

Glu Asp Ala Val Gln Ala Ala Glu Ala Ala Gln Lys Lys Ile Ser Thr
    50                  55                  60

Val Ala Met Arg Asp Lys Ile Ile Ala Ala Ile Arg Lys Ala Gly Leu
65                  70                  75                  80

Glu Asn Ala Lys Ala Phe Ala Glu Ile Ala His Asn Glu Thr Gly Met
                85                  90                  95

Gly Arg Val Ser Asp Lys Ile Ala Lys Asn Ile Leu Val Cys Glu Arg
            100                 105                 110

Thr Pro Gly Thr Glu Cys Leu Ser Pro Met Ala Ile Ser Gly Asp Met
        115                 120                 125

Gly Leu Thr Leu Ile Glu Asn Ala Pro Trp Gly Val Ile Ala Ser Val
    130                 135                 140

Thr Pro Ser Thr Asn Pro Thr Ala Thr Val Ile Asn Asn Ala Ile Ser
145                 150                 155                 160

Met Ile Ala Gly Gly Asn Ser Val Ile Phe Ala Pro His Pro Asn Ala
                165                 170                 175

Lys Arg Ala Ser Gln Thr Ala Ile Gln Val Leu Asn Lys Ala Ile Ile
            180                 185                 190

Glu Ala Thr Gly Val Ala Asn Leu Leu Val Ala Val Lys Glu Pro Thr
        195                 200                 205

Ile Glu Val Ala Gln Glu Leu Phe Ser His Pro Arg Ile Lys Leu Leu
    210                 215                 220

Val Val Thr Gly Gly Glu Ala Val Val Ala Gln Ala Arg Lys Val Ala
225                 230                 235                 240

Thr Met Arg Leu Ile Ala Ala Gly Ala Gly Asn Pro Pro Val Val Val
                245                 250                 255

Asp Glu Thr Ala Asn Ile Ala Arg Ala Ala Arg Ser Ile Tyr Asp Gly
            260                 265                 270

Ala Ser Phe Asp Asn Asn Ile Ile Cys Ala Asp Glu Lys Glu Ile Ile
        275                 280                 285

Ala Val Asp Ser Ile Ala Asp Gln Leu Lys Ala Glu Met Lys Ala Ile
    290                 295                 300

Gly Ala Val Glu Ile Ser Leu Glu Gln Ala Asp Ala Val Ala Arg Val
305                 310                 315                 320

Val Leu Arg Asn Tyr Pro Gln Val Glu Gly Gly Lys Ala Pro Asn Pro
                325                 330                 335

Asn Pro Lys Trp Val Gly Arg Asp Ala Ala Leu Ile Ala Lys Ala Ala
            340                 345                 350

Gly Ile Asp Val Pro Asp Ser Cys Arg Leu Leu Ile Val Asp Val Lys
        355                 360                 365

Arg Asp Ile Asn His Val Phe Ala Arg Val Glu Gln Leu Met Pro Val
    370                 375                 380

Ile Pro Leu Leu Arg Ala Ala Asn Val Asp Glu Ala Ile Glu Trp Ala
385                 390                 395                 400

Leu Ile Leu Glu Arg Gly Leu Ser His Thr Ala Gly Met His Ser Arg
                405                 410                 415

Asn Ile Asp Asn Met Asp Lys Met Ala Arg Ala Met Asn Thr Ser Leu
            420                 425                 430

Phe Val Lys Asn Gly Pro His Leu Ala Ala Leu Gly Ala Gly Gly Glu
```

```
        435                 440                 445

Gly Trp Thr Thr Met Thr Ile Ser Thr Pro Thr Gly Glu Gly Val Thr
    450                 455                 460

Cys Ala Arg Ser Phe Val Arg Leu Arg Arg Cys Cys Val Val Asp Asn
465                 470                 475                 480

Phe Arg Ile Val
```

<210> SEQ ID NO 35
<211> LENGTH: 1419
<212> TYPE: DNA
<213> ORGANISM: Ilyobacter polytropus

<400> SEQUENCE: 35

```
atgaacttgg atgctaacaa cttgaacaac atagtctcct taataatgaa agaattggac      60
aaaaataaca acatagatga cactggtcaa ggttgtggtg gtgaagaagg caagaacggt     120
attttctctt ctatggacac tgctgtttct aaagccaagg aagctcaagt aacattgttc     180
gcctctaaat tggaattaag agaaagaatc atcaaggcta tcagagaaga tgttagagaa     240
gctgcagccg aattggcaga aatcgccgtt gaagaaaccg gtatgggtag agtcgatgac     300
aagactttga agcattacgt cactgtagat aaaacaccag gtgttgaaga cttgagagca     360
tttgcctata gtggtgataa cggtttaact gtaatggaat tgtctcctta cggtgttatt     420
ggttctataa caccatcaac caatccttcc gaaacaattg tttgcaacgc tatcggtatg     480
attgctgcag gtaattcagt tgtctttgcc ccacaccctg gtgctaaaaa gacatcctta     540
agagcagttg aaattttgaa caaagctgtc gcaagagccg gtggtccaaa caacttggta     600
gttacaatct tcgaaccttc aatcgaaaac accaacaaga tggtcaagaa cccagatata     660
aagatggtcg tagctaccgg tggtcctggt gttgtcaagt ccgttatgtc cagtggtaaa     720
aaggctatag gtgctggtgc aggtaatcca cctgttttgg tcgatgaaac tgcagacatc     780
gaaaaagccg ctaaggatat agttaacggt tgtagtttcg acaacaactt accatgcatt     840
accgaaaaag aagtagttgc cgtagattct atcactgact acttgatctt cgaaatgcaa     900
aagaatggtg catacttggt tcaagattca aagacaataa aaaagttgtg tgaaatggtc     960
atcaatgacg gttcaccaaa cagagcttat gtaggtaaaa acgcatccta catcttgaag    1020
gatttaggta ttgatgttgg tgacgaaata aaggtcatca ttgtagaaac tgatgcaggt    1080
catcctttgg ccgtattaga aatgttgatg ccagttttgc ctatagtaag agttaaggat    1140
gctttggaag gtataaaggt ttgcaaaaag ttagaagacg gtttgagaca tacagcaatg    1200
atacactcta agaacatcga tatcttaacc aagtacgcca gagacatgga aactacaatc    1260
ttggttaaaa acggtccatc ttattcaggt attggtgtcg gtggtgaagg ttacaccact    1320
tttaccattg ctggtcctac tggtgaaggt ttaacatccg ctaaaagttt cgcaagaaat    1380
agaagatgtg cattagttgg tggtttgtct attaagtag                           1419
```

<210> SEQ ID NO 36
<211> LENGTH: 472
<212> TYPE: PRT
<213> ORGANISM: Ilyobacter polytropus

<400> SEQUENCE: 36

```
Met Asn Leu Asp Ala Asn Asn Leu Asn Asn Ile Val Ser Leu Ile Met
1               5                   10                  15

Lys Glu Leu Asp Lys Asn Asn Asn Ile Asp Asp Thr Gly Gln Gly Cys
            20                  25                  30
```

-continued

```
Gly Gly Glu Glu Gly Lys Asn Gly Ile Phe Ser Ser Met Asp Thr Ala
        35                  40                  45

Val Ser Lys Ala Lys Glu Ala Gln Val Thr Leu Phe Ala Ser Lys Leu
    50                  55                  60

Glu Leu Arg Glu Arg Ile Ile Lys Ala Ile Arg Glu Asp Val Arg Glu
65                  70                  75                  80

Ala Ala Ala Glu Leu Ala Glu Ile Ala Val Glu Glu Thr Gly Met Gly
                85                  90                  95

Arg Val Asp Asp Lys Thr Leu Lys His Tyr Val Thr Val Asp Lys Thr
            100                 105                 110

Pro Gly Val Glu Asp Leu Arg Ala Phe Ala Tyr Ser Gly Asp Asn Gly
        115                 120                 125

Leu Thr Val Met Glu Leu Ser Pro Tyr Gly Val Ile Gly Ser Ile Thr
    130                 135                 140

Pro Ser Thr Asn Pro Ser Glu Thr Ile Val Cys Asn Ala Ile Gly Met
145                 150                 155                 160

Ile Ala Ala Gly Asn Ser Val Val Phe Ala Pro His Pro Gly Ala Lys
                165                 170                 175

Lys Thr Ser Leu Arg Ala Val Glu Ile Leu Asn Lys Ala Val Ala Arg
            180                 185                 190

Ala Gly Gly Pro Asn Asn Leu Val Val Thr Ile Phe Glu Pro Ser Ile
        195                 200                 205

Glu Asn Thr Asn Lys Met Val Lys Asn Pro Asp Ile Lys Met Val Val
    210                 215                 220

Ala Thr Gly Gly Pro Gly Val Val Lys Ser Val Met Ser Ser Gly Lys
225                 230                 235                 240

Lys Ala Ile Gly Ala Gly Ala Gly Asn Pro Pro Val Leu Val Asp Glu
                245                 250                 255

Thr Ala Asp Ile Glu Lys Ala Ala Lys Asp Ile Val Asn Gly Cys Ser
            260                 265                 270

Phe Asp Asn Asn Leu Pro Cys Ile Thr Glu Lys Glu Val Val Ala Val
        275                 280                 285

Asp Ser Ile Thr Asp Tyr Leu Ile Phe Glu Met Gln Lys Asn Gly Ala
    290                 295                 300

Tyr Leu Val Gln Asp Ser Lys Thr Ile Lys Lys Leu Cys Glu Met Val
305                 310                 315                 320

Ile Asn Asp Gly Ser Pro Asn Arg Ala Tyr Val Gly Lys Asn Ala Ser
                325                 330                 335

Tyr Ile Leu Lys Asp Leu Gly Ile Asp Val Gly Asp Glu Ile Lys Val
            340                 345                 350

Ile Ile Val Glu Thr Asp Ala Gly His Pro Leu Ala Val Leu Glu Met
        355                 360                 365

Leu Met Pro Val Leu Pro Ile Val Arg Val Lys Asp Ala Leu Glu Gly
    370                 375                 380

Ile Lys Val Cys Lys Lys Leu Glu Asp Gly Leu Arg His Thr Ala Met
385                 390                 395                 400

Ile His Ser Lys Asn Ile Asp Ile Leu Thr Lys Tyr Ala Arg Asp Met
                405                 410                 415

Glu Thr Thr Ile Leu Val Lys Asn Gly Pro Ser Tyr Ser Gly Ile Gly
            420                 425                 430

Val Gly Gly Glu Gly Tyr Thr Thr Phe Thr Ile Ala Gly Pro Thr Gly
        435                 440                 445
```

-continued

```
Glu Gly Leu Thr Ser Ala Lys Ser Phe Ala Arg Asn Arg Arg Cys Ala
    450                 455                 460

Leu Val Gly Gly Leu Ser Ile Lys
465                 470


<210> SEQ ID NO 37
<211> LENGTH: 825
<212> TYPE: PRT
<213> ORGANISM: Bifidobacterium animalis

<400> SEQUENCE: 37

Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285

Pro Phe Tyr Pro Met Leu Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Ala His Phe Glu Val
                325                 330                 335

Leu Lys Gly Trp Met Glu Ser Tyr Lys Pro Glu Glu Leu Phe Asn Ala
            340                 345                 350
```

```
Asp Gly Ser Ile Lys Glu Asp Val Thr Ala Phe Met Pro Lys Gly Glu
        355                 360                 365

Leu Arg Ile Gly Ala Asn Pro Asn Ala Asn Gly Gly Arg Ile Arg Glu
    370                 375                 380

Asp Leu Lys Leu Pro Glu Leu Asp Gln Tyr Glu Ile Thr Gly Val Lys
385                 390                 395                 400

Glu Tyr Gly His Gly Trp Gly Gln Val Glu Ala Pro Arg Ser Leu Gly
                405                 410                 415

Ala Tyr Cys Arg Asp Ile Ile Lys Asn Asn Pro Asp Ser Phe Arg Val
            420                 425                 430

Phe Gly Pro Asp Glu Thr Ala Ser Asn Arg Leu Asn Ala Thr Tyr Glu
        435                 440                 445

Val Thr Lys Lys Gln Trp Asp Asn Gly Tyr Leu Ser Ala Leu Val Asp
    450                 455                 460

Glu Asn Met Ala Val Thr Gly Gln Val Val Glu Gln Leu Ser Glu His
465                 470                 475                 480

Gln Cys Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Thr Asn Ile Tyr
                565                 570                 575

Phe Ala Thr Asp Ala Asn Met Leu Leu Ala Ile Ala Glu Lys Cys Phe
            580                 585                 590

Lys Ser Thr Asn Lys Ile Asn Ala Ile Phe Ala Gly Lys Gln Pro Ala
        595                 600                 605

Ala Thr Trp Ile Thr Leu Asp Glu Val Arg Ala Glu Leu Glu Ala Gly
    610                 615                 620

Ala Ala Glu Trp Lys Trp Ala Ser Asn Ala Lys Ser Asn Asp Glu Val
625                 630                 635                 640

Gln Val Val Leu Ala Ala Ala Gly Asp Val Pro Thr Gln Glu Ile Met
                645                 650                 655

Ala Ala Ser Asp Ala Leu Asn Lys Met Gly Ile Lys Phe Lys Val Val
            660                 665                 670

Asn Val Val Asp Leu Ile Lys Leu Gln Ser Ser Lys Glu Asn Asp Glu
        675                 680                 685

Ala Met Ser Asp Glu Asp Phe Ala Asp Leu Phe Thr Ala Asp Lys Pro
    690                 695                 700

Val Leu Phe Ala Tyr His Ser Tyr Ala Gln Asp Val Arg Gly Leu Ile
705                 710                 715                 720

Tyr Asp Arg Pro Asn His Asp Asn Phe Thr Val Val Gly Tyr Lys Glu
                725                 730                 735

Gln Gly Ser Thr Thr Thr Pro Phe Asp Met Val Arg Val Asn Asp Met
            740                 745                 750

Asp Arg Tyr Ala Leu Gln Ala Lys Ala Leu Glu Leu Ile Asp Ala Asp
        755                 760                 765
```

-continued

```
Lys Tyr Ala Asp Lys Ile Asn Glu Leu Asn Glu Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Ser Met Leu Ser Ala
                805                 810                 815

Thr Ala Ala Thr Ala Gly Asp Asn Glu
            820                 825


<210> SEQ ID NO 38
<211> LENGTH: 2478
<212> TYPE: DNA
<213> ORGANISM: Schizosaccharomyces_pombe

<400> SEQUENCE: 38

atggctactc aaaacgatat ccctaactcg actcccgagg atttagcgaa acaagttgaa      60

attgccgaaa aacaccccga tcctcctgct atgccctcgc gtcttcctga ctctttaaaa     120

accctcgaag ctaaaatcga cacttcaaag attaccgacg aagaggttgc caatgtccat     180

cgttttcaac gtgcatgtga ttacctcgca gcttccctga ttttcctttc caacggtctc     240

tacaccggcg gtgacctaga ggaaaaagat atcaaaaacta gactgctagg ccattggggt     300

acttgtcccg gcttgagcat cgtttactct cactgtaatc gtatcattaa taaatatgat     360

ctcaacatgc tctttgtcgt aggccctggc catggtgctc ctgccatttt atcggctctt     420

ttccttgaag attctttggg ccccttttac cctcgatacc aatttaccaa ggaaggcttg     480

aacaacctta ttaacacctt ctcccttccc ggtggttttc cttctcatgt caacgccgag     540

gtccctggtg ccattcacga gggcggtgaa ttgggttatg cgttgtccgt cagttacggt     600

gcagttcttg atcgtcccga cctgattgta acttgcgttg tcggtgatgg tgaggcagag     660

accggcccca ctgccacttc ttggcatgct cataaattct tggatcctgc tgaatcgggt     720

gctgtgattc ctgttttgga acttaatggt tacaagattt ccgagcgtac catttacggt     780

tgcatggatg atagtgagct tctctctttg tttagcggtt ttggctatga agttgccatt     840

gtaaacgata cccccgacca aaacagggtt atggctgcaa ctatggattg ggccgttgaa     900

cgcattcatg acatccaaca tcgcgctcgt gttaacagag aagaaatcaa acccagatgg     960

cccatgatta tccttcgtac ccctaagggt aaaggatgtc ccaagtattt gaatggcaaa    1020

tttttagaag gtaccttccg tgctcaccaa gttcctttga aattggctcg caccgatacc    1080

aaccagcgca atcttctaaa ggattggctg aacagctaca actgccaaga cttcttagac    1140

gaacatggac ttcctactaa gggcatcacc gagcatcttc cgcctcgtga gaagcgcatg    1200

ggtcagcgtc atgagacata caattcttat ctacctttga aggtacctga ttggaaaaaa    1260

tacggtgtca agaagggaga aaccactagt gccacttcgg tcgttggtca atatcttgat    1320

gaactcctcg taaccaacga ttcaaccctt agaattttct cacccgatga gttggaaagt    1380

aataaattag atggcgcttt gaagcactca tatcgtacca tgcaaactga tccagagctc    1440

atggcaaagc gtggtcgcgt taccgaagtc ctttcagagc acctttgcca aggtttcatg    1500

cagggttata ctttaactgg acgtaccgcg attttcccct catatgaagc ctttatgact    1560

attgttgtta gtatgcttgt tcagtactcc aaatttttga agatgggctt ggagaccgga    1620

tggcatggaa aatttggtag cttgaactat gttacttcca gtacttgggc aagacaagag    1680

cataacggtt tctcccatca atcacccagg tttatcacca ctatgctctc tctgaaacct    1740

ggtgttagcc gcgtatactt cccaccggat gccaattgct tcttagcaac cgtcgcccga    1800
```

```
tgcatgaagt ctgagaatac tatcaacctt atggtttcta gtaaaaatcc acaaccagcc   1860

tacctatctg ttgaagaggc cgaacatcat tgcaaggccg gtgctagtgt ttggaagttt   1920

gctagtacag ataatggcga aaatcctgat gttgttattg ccggcgtcgg aaatgagatt   1980

atgtttgaag tagttaaagc cgcagagatg cttcaaaatg acattcctga gctccgagtg   2040

cgtgtcatta acgtcactga cttgatggta ctttcgagct tacatcccca tggtatgaat   2100

cctgcggaat ttgattcttt gtttaccaaa gatcgccatg ttcatttcaa ctatcacggt   2160

tatgtgatgg acttgaaggc tctcttgttt gatcgcatac aaggtacacg ggtcactatg   2220

gagggctatc gagaggaagg tactactacc actcctttta atatgatgat gtgtaacaat   2280

acctctcgtt atcatgttgc aagaatggct ttgcaacatg ctttacacaa tcctaccgtg   2340

gccgttaatt gtaacatgtt gtgtgccaaa tatgcttgga agctcgaaga gattgaaaat   2400

tatattatgg aaaacaagga tgatcctcct gaaatttatg ctgctcctgt ctttaaaaat   2460

aagacttcca cattatag                                                 2478
```

<210> SEQ ID NO 39
<211> LENGTH: 825
<212> TYPE: PRT
<213> ORGANISM: Schizosaccharomyces_pombe

<400> SEQUENCE: 39

```
Met Ala Thr Gln Asn Asp Ile Pro Asn Ser Thr Pro Glu Asp Leu Ala
1               5                   10                  15

Lys Gln Val Glu Ile Ala Glu Lys His Pro Asp Pro Pro Ala Met Pro
            20                  25                  30

Ser Arg Leu Pro Asp Ser Leu Lys Thr Leu Glu Ala Lys Ile Asp Thr
        35                  40                  45

Ser Lys Ile Thr Asp Glu Glu Val Ala Asn Val His Arg Phe Gln Arg
    50                  55                  60

Ala Cys Asp Tyr Leu Ala Ala Ser Leu Ile Phe Leu Ser Asn Gly Leu
65                  70                  75                  80

Tyr Thr Gly Gly Asp Leu Glu Glu Lys Asp Ile Lys Thr Arg Leu Leu
                85                  90                  95

Gly His Trp Gly Thr Cys Pro Gly Leu Ser Ile Val Tyr Ser His Cys
            100                 105                 110

Asn Arg Ile Ile Asn Lys Tyr Asp Leu Asn Met Leu Phe Val Val Gly
        115                 120                 125

Pro Gly His Gly Ala Pro Ala Ile Leu Ser Ala Leu Phe Leu Glu Asp
    130                 135                 140

Ser Leu Gly Pro Phe Tyr Pro Arg Tyr Gln Phe Thr Lys Glu Gly Leu
145                 150                 155                 160

Asn Asn Leu Ile Asn Thr Phe Ser Leu Pro Gly Gly Phe Pro Ser His
                165                 170                 175

Val Asn Ala Glu Val Pro Gly Ala Ile His Glu Gly Gly Glu Leu Gly
            180                 185                 190

Tyr Ala Leu Ser Val Ser Tyr Gly Ala Val Leu Asp Arg Pro Asp Leu
        195                 200                 205

Ile Val Thr Cys Val Val Gly Asp Gly Glu Ala Glu Thr Gly Pro Thr
    210                 215                 220

Ala Thr Ser Trp His Ala His Lys Phe Leu Asp Pro Ala Glu Ser Gly
225                 230                 235                 240

Ala Val Ile Pro Val Leu Glu Leu Asn Gly Tyr Lys Ile Ser Glu Arg
```

-continued

```
                245                 250                 255

Thr Ile Tyr Gly Cys Met Asp Asp Ser Glu Leu Leu Ser Leu Phe Ser
            260                 265                 270

Gly Phe Gly Tyr Glu Val Ala Ile Val Asn Asp Thr Pro Asp Gln Asn
        275                 280                 285

Arg Val Met Ala Ala Thr Met Asp Trp Ala Val Glu Arg Ile His Asp
    290                 295                 300

Ile Gln His Arg Ala Arg Val Asn Arg Glu Glu Ile Lys Pro Arg Trp
305                 310                 315                 320

Pro Met Ile Ile Leu Arg Thr Pro Lys Gly Lys Gly Cys Pro Lys Tyr
                325                 330                 335

Leu Asn Gly Lys Phe Leu Glu Gly Thr Phe Arg Ala His Gln Val Pro
            340                 345                 350

Leu Lys Leu Ala Arg Thr Asp Thr Asn Gln Arg Asn Leu Leu Lys Asp
        355                 360                 365

Trp Leu Asn Ser Tyr Asn Cys Gln Asp Phe Leu Asp Glu His Gly Leu
    370                 375                 380

Pro Thr Lys Gly Ile Thr Glu His Leu Pro Pro Arg Glu Lys Arg Met
385                 390                 395                 400

Gly Gln Arg His Glu Thr Tyr Asn Ser Tyr Leu Pro Leu Lys Val Pro
                405                 410                 415

Asp Trp Lys Lys Tyr Gly Val Lys Lys Gly Glu Thr Thr Ser Ala Thr
            420                 425                 430

Ser Val Val Gly Gln Tyr Leu Asp Glu Leu Leu Val Thr Asn Asp Ser
        435                 440                 445

Thr Leu Arg Ile Phe Ser Pro Asp Glu Leu Glu Ser Asn Lys Leu Asp
    450                 455                 460

Gly Ala Leu Lys His Ser Tyr Arg Thr Met Gln Thr Asp Pro Glu Leu
465                 470                 475                 480

Met Ala Lys Arg Gly Arg Val Thr Glu Val Leu Ser Glu His Leu Cys
                485                 490                 495

Gln Gly Phe Met Gln Gly Tyr Thr Leu Thr Gly Arg Thr Ala Ile Phe
            500                 505                 510

Pro Ser Tyr Glu Ala Phe Met Thr Ile Val Val Ser Met Leu Val Gln
        515                 520                 525

Tyr Ser Lys Phe Leu Lys Met Gly Leu Glu Thr Gly Trp His Gly Lys
    530                 535                 540

Phe Gly Ser Leu Asn Tyr Val Thr Ser Ser Thr Trp Ala Arg Gln Glu
545                 550                 555                 560

His Asn Gly Phe Ser His Gln Ser Pro Arg Phe Ile Thr Thr Met Leu
                565                 570                 575

Ser Leu Lys Pro Gly Val Ser Arg Val Tyr Phe Pro Pro Asp Ala Asn
            580                 585                 590

Cys Phe Leu Ala Thr Val Ala Arg Cys Met Lys Ser Glu Asn Thr Ile
        595                 600                 605

Asn Leu Met Val Ser Ser Lys Asn Pro Gln Pro Ala Tyr Leu Ser Val
    610                 615                 620

Glu Glu Ala Glu His His Cys Lys Ala Gly Ala Ser Val Trp Lys Phe
625                 630                 635                 640

Ala Ser Thr Asp Asn Gly Glu Asn Pro Asp Val Val Ile Ala Gly Val
                645                 650                 655

Gly Asn Glu Ile Met Phe Glu Val Val Lys Ala Ala Glu Met Leu Gln
            660                 665                 670
```

```
Asn Asp Ile Pro Glu Leu Arg Val Arg Val Ile Asn Val Thr Asp Leu
        675                 680                 685

Met Val Leu Ser Ser Leu His Pro His Gly Met Asn Pro Ala Glu Phe
    690                 695                 700

Asp Ser Leu Phe Thr Lys Asp Arg His Val His Phe Asn Tyr His Gly
705                 710                 715                 720

Tyr Val Met Asp Leu Lys Ala Leu Leu Phe Asp Arg Ile Gln Gly Thr
                725                 730                 735

Arg Val Thr Met Glu Gly Tyr Arg Glu Glu Gly Thr Thr Thr Thr Pro
            740                 745                 750

Phe Asn Met Met Met Cys Asn Asn Thr Ser Arg Tyr His Val Ala Arg
        755                 760                 765

Met Ala Leu Gln His Ala Leu His Asn Pro Thr Val Ala Val Asn Cys
    770                 775                 780

Asn Met Leu Cys Ala Lys Tyr Ala Trp Lys Leu Glu Glu Ile Glu Asn
785                 790                 795                 800

Tyr Ile Met Glu Asn Lys Asp Asp Pro Pro Glu Ile Tyr Ala Ala Pro
                805                 810                 815

Val Phe Lys Asn Lys Thr Ser Thr Leu
            820                 825


<210> SEQ ID NO 40
<211> LENGTH: 2343
<212> TYPE: DNA
<213> ORGANISM: Aspergillus_niger

<400> SEQUENCE: 40

atgcctggtg aagtcataga aagacctaac cctgctccta agccatccca cgttcctgat     60

ttggtagaaa agttgattat ccctgcccaa aagactaagt tggaaaagtc agattgtgac    120

gctttacata aatatagaag agctgcagcc tacattgctg caggtcactg gggtacttgc    180

ccaggtttga tcttagttta ctctcatttg aactacttaa ttaaaaagca aaacttggat    240

atgttatatg ttgtcggtcc aggtcacggt gcccctggtt tgttagcttc attgtggtta    300

gaaggttcct tgggtaaatt ctacccacaa tacacaaagg ataaggaagg tttgcataat    360

ttgatatcaa ccttctctac ttcagcaggt ttaccatccc atataaacgc agaaactcct    420

ggtgccatcc acgaaggtgg tgaattgggt tatgccttat ccgttagttt tggtgctgtc    480

atggacaatc cagatttgat tgttacatgt gtagttggtg acggtgaagc tgaaaccggt    540

cctaccgcta cttcatggca cgctattaaa tatatcgatc cagccgaatc cggtgctgtt    600

ttgcctatat tgcatgtcaa cggttttaaa atctcagaaa gaaccatatt cggttgtatg    660

gacaacagag aaatagtttg cttgtttact ggttatggtt accaagttag aattgtcgaa    720

gatttggaag atatcgacaa cgatttgcat tctgcaatgt catgggccgt cgaagaaatt    780

agaaacatac aaaaagccgc tagaagtggt aaaccaatta tgaaaccaca atggcctatg    840

atagttttga gaacaccaaa gggttggtct ggtcctaaag aattacatgg tcaattcatt    900

gaaggttcct tccatagtca ccaagttcca ttgcctaatg ctaaaaagga tgacgaagaa    960

ttgcaagcat tacaaaagtg gttgtcttca tacaagccag atgaattgtt tactgaatct   1020

ggtgacgtta tcgatgaaat attgtccata atcccaagtg atgacaaaaa gttgggtatg   1080

agacctgaag catacaaaac tcatttgcca cctgacttac cagattggag acaattttgt   1140

gttaaaaagg gtgaccaatt cagtgctatg aaggcaattg gttcttttat agatcaagta   1200
```

-continued ttcgttaaaa atccacacac agttagattg ttttcacctg atgaattaga atctaacaag 1260
ttgtcagcag ccttatccca taccggtaga aacttccaat gggatgaatt ttctaacgct 1320
aaaggtggta gagtaatcga agttttgtct gaacacttat gccaaggttt tatgcaaggt 1380
tatacattga ccggtagaac aggtattttt ccatcttacg aatcattctt aggtatcatt 1440
cataccatga tggtacaata tgccaaattc gctaagatgg caaaagaaac tgcctggcat 1500
cacgatgttt ccagtataaa ttacatcgaa acttctacat gggctagaca agaacataat 1560
ggttttagtc accaaaaccc atctttcatt ggtgcagtct tgaaattaaa gccttatgct 1620
gcaagagtat acttgccacc tgatgctaac acatttttga ctacattgca tcactgtttg 1680
aagagtaaga attacataaa cttaatggtt ggttctaagc aaccaacacc tgtttactta 1740
agtccagaag aagctgaatc tcattgtaga gcaggtgcct caatttttaa gttctgctcc 1800
accgacggtg gtttgagacc tgatgtcgta ttagttggta tcggtgtcga agtaatgttt 1860
gaagtcataa aagccgctgc aatcttgaga gaaagatgcc cagaattaag agtaagagtt 1920
gtcaacgtta ctgatttgtt catattagaa aacgaaggtg ctcatcctca cgcattgaag 1980
catgaagcat tcgacaattt gtttactgaa gatagatcta tccatttcaa ctaccacggt 2040
tacgttaacg aattgcaagg tttgttattc ggtagaccaa gattagacag agctacaatt 2100
aagggttata aagaagaagg ttcaaccact acacctttcg atatgatgtt ggtcaacgaa 2160
gtatccagat accatgtcgc aaaggccgct gtaactggtg gtgccagatt caatgaaaag 2220
gttaagttga gacatcaaga attgtgttca gaatttgatc acaacatcgc tgaaactaga 2280
aagtacataa tgaacaacca tcaagaccca gaagatacat acaatatgcc ttccttcaac 2340
tag 2343

<210> SEQ ID NO 41
<211> LENGTH: 815
<212> TYPE: PRT
<213> ORGANISM: Aspergillus_niger

<400> SEQUENCE: 41

Met Pro Ser Asp Ser Asn Asp Gln Ser Ile Ser Ala Tyr Gly Ala Ala
1 5 10 15

Arg Ser Thr Val Lys Gly Gln Asn Leu Asp Pro Glu Glu Val Arg Lys
20 25 30

Met Asp Ala Tyr Phe Arg Ala Ser Met Tyr Leu Cys Leu Gly Met Leu
35 40 45

Tyr Leu Arg Glu Asn Val Leu Leu Lys Gln Pro Leu Lys Val Glu His
50 55 60

Leu Lys Ala Arg Leu Leu Gly His Trp Gly Ser Asp Ala Gly Gln Ser
65 70 75 80

Phe Thr Trp Ile His Met Asn Arg Leu Ile Lys Lys Tyr Asp Leu Asp
85 90 95

Val Leu Phe Ile Ser Gly Pro Gly His Gly Ala Pro Gly Ile Leu Ser
100 105 110

Gln Ser Tyr Leu Glu Gly Val Tyr Ser Glu Val Tyr Pro Asp Lys Ser
115 120 125

Glu Asp Glu Arg Gly Met Gln Arg Phe Phe Lys Gln Phe Ser Phe Pro
130 135 140

Gly Gly Ile Gly Ser His Ala Thr Pro Glu Thr Pro Gly Ser Leu His
145 150 155 160

Glu Gly Gly Glu Leu Gly Tyr Ser Ile Ser His Ala Phe Gly Thr Val

-continued

```
                165                 170                 175

Phe Asp His Pro Asn Leu Ile Thr Leu Thr Met Val Gly Asp Gly Glu
            180                 185                 190

Ala Glu Thr Gly Pro Leu Ala Thr Ser Trp His Ser Thr Lys Tyr Leu
        195                 200                 205

Asn Pro Cys Thr Asp Gly Ala Val Leu Pro Val Leu His Leu Asn Gly
    210                 215                 220

Tyr Lys Ile Asn Asn Pro Thr Leu Leu Ala Arg Ile Ser His Asp Glu
225                 230                 235                 240

Leu Ser Ala Leu Met Lys Gly Tyr Gly Trp Thr Pro Tyr Phe Val Glu
                245                 250                 255

Gly Ser Asp Arg Glu Thr Met His Gln Ala Met Ala Ala Thr Leu Glu
            260                 265                 270

His Cys Val Leu Glu Ile Arg Lys Phe Gln Lys Lys Ala Arg Glu Ser
        275                 280                 285

Lys Glu Pro Phe Arg Pro His Trp Pro Met Ile Ile Leu Arg Ser Pro
    290                 295                 300

Lys Gly Trp Ser Ala Pro Arg Glu Val Asp Gly Lys Leu Leu Glu Gly
305                 310                 315                 320

Phe Trp Arg Ala His Gln Ile Pro Ile Thr Asp Val Leu Thr Asn Pro
                325                 330                 335

Ser His Leu Gln Leu Leu Glu Ser Trp Met Lys Ser Tyr Lys Pro Glu
            340                 345                 350

Glu Leu Phe Thr His Asp Gly Arg Leu Ile Ser Glu Leu Lys Ala Leu
        355                 360                 365

Ala Pro Thr Gly Asn Ser Arg Met Ser Ala Asn Pro Val Gly Asn Gly
    370                 375                 380

Gly Leu Leu Arg Arg Pro Leu Asp Leu Pro Asp Phe Arg Lys Tyr Ala
385                 390                 395                 400

Leu Thr Ser Ile Asp Pro Gly Ala Thr Ile Arg Gly Ser Met Val Asn
                405                 410                 415

Met Ser His Tyr Leu Arg Asp Val Val Ala Phe Asn Gln Thr Asn Phe
            420                 425                 430

Arg Val Phe Gly Pro Asp Glu Thr Glu Ser Asn Lys Leu Ser Glu Ile
        435                 440                 445

Tyr Lys Ala Gly Lys Lys Val Trp Leu Ala Glu Tyr Phe Pro Glu Asp
    450                 455                 460

Asn Asn Gly Gly Asn Leu Ser Met Ala Gly Arg Val Met Glu Met Leu
465                 470                 475                 480

Ser Glu His Thr Cys Glu Gly Trp Leu Glu Gly Tyr Val Leu Ser Gly
                485                 490                 495

Arg His Gly Leu Leu Asn Ser Tyr Glu Pro Phe Ile His Ile Ile Asp
            500                 505                 510

Ser Met Val Asn Gln His Cys Lys Trp Ile Glu Lys Cys Leu Glu Val
        515                 520                 525

Glu Trp Arg Ala Lys Val Ala Ser Leu Asn Ile Leu Leu Thr Ala Thr
    530                 535                 540

Val Trp Arg Gln Asp His Asn Gly Phe Thr His Gln Asp Pro Gly Phe
545                 550                 555                 560

Leu Asp Val Val Ala Asn Lys Ser Pro Glu Val Val Arg Ile Tyr Leu
                565                 570                 575

Pro Pro Asp Gly Asn Ser Leu Leu Ser Val Met Asp His Cys Phe Arg
            580                 585                 590
```

```
Ser Ala Asn Tyr Val Asn Val Ile Val Ala Asp Lys Gln Asp His Ile
        595                 600                 605

Gln Phe Met Asp Met Asp Ala Ala Ile Ala His Cys Thr Lys Gly Val
    610                 615                 620

Gly Ile Trp Asp Trp Ala Ser Asn Asp Gln Gly Ala Glu Pro Asp Val
625                 630                 635                 640

Val Met Ala Ala Cys Gly Asp Val Pro Thr His Glu Ala Leu Ala Ala
                645                 650                 655

Thr Ala Leu Leu Arg Glu His Leu Pro Gln Leu Lys Val Arg Phe Val
            660                 665                 670

Asn Val Val Asp Leu Phe Lys Leu Met Ser Lys Ile His His Pro His
        675                 680                 685

Gly Met Ser Asp Arg Glu Trp Lys Ala Ile Phe Thr Ala Asp Arg Pro
    690                 695                 700

Ile Val Phe Asn Phe His Ser Tyr Pro Trp Leu Ile His Arg Leu Thr
705                 710                 715                 720

Tyr Lys Arg Pro Gly Gln Glu Asn Ile His Val Arg Gly Tyr Lys Glu
                725                 730                 735

Lys Gly Asn Ile Asp Thr Pro Phe Glu Leu Ala Val Arg Asn Gln Thr
            740                 745                 750

Asp Arg Tyr Ser Leu Ala Val Asp Ala Ile Asp His Ala Arg Gly Leu
        755                 760                 765

Gly Asn Thr Ala Ser Gly Val Arg Glu Lys Phe Leu Asn Met Gln Leu
    770                 775                 780

Leu Ala Lys Gln Lys Ala Tyr Asp Asp Gly Ile Asp Pro Asp Tyr Ile
785                 790                 795                 800

Arg Asn Trp Thr Trp Gln Tyr Pro Arg Lys Lys Gly Glu Gly Val
                805                 810                 815


<210> SEQ ID NO 42
<211> LENGTH: 2448
<212> TYPE: DNA
<213> ORGANISM: Acidithiobacillus_ferrooxidans

<400> SEQUENCE: 42

atgaccacag aacacgatgc tgcctgcgaa ggtgaaagta tatccgctta cggtacagcc      60

agagccacag tcgaagatca accattaaat actgatgact tgagaaaaat cgatgcctat     120

tggagagctt ctttgtactt atgtttgggc atgttgtatt tgagagataa cccattgtta     180

agagacccat taaagcctga acatataaag cctagattgt taggtcactg ggggttctgat     240

gctggtcaat gcttcacata catccatttc aacagattaa ttaacaaata tgacttgaat     300

gccatataca tctccggtcc aggtcacggt gctcctgcaa tattatctca agcatatttg     360

gaaggtacat attccgaaac ctacccagat aaaagtcaag acatcgctgg tatgagaaga     420

tttttcaagc aattttcttt ccctggtggt attggttcac atgctacccc agaaactcct     480

ggttctatac acgaaggtgg tgaattgggt tattccgtaa gtcatgcctt tggtactgtt     540

tacgataatc cagacttaat tgctttggtc atggttggtg acggtgaagc tgaaactggt     600

cctttagcaa catcttggca ttcaaataag ttcttgaacc caatcacaga tggtgctgta     660

ttgcctgttt tgcatttgaa cggttacaag attaataacc caaccatttt ggctagaata     720

actcacgaag aattagaagc attgtttata ggttacggtt acactccata cttcgtcgaa     780

ggttccgatc ctgccagtat gcatcaagct atggctgcaa caatggaaag atgtgtattg     840
```

-continued

```
aaaattagag aatttcaaga taaggccaga cacactggta cagctttcag accaagatgg    900
cctatgatta tattgagatc cccaaaaggt tggactgctc ctagaaaggt tgatggtcat    960
tatttggaag gtttttggag agcacatcaa attccaatac ctgacgttgt ctcaaatcca   1020
gcacatttgc aattgttaga atcttggatg agatcataca gacctgaaga attatttgat   1080
gcacaaggta gattgattcc agaattacat gaattggccc ctaaaggtaa aagaagaatg   1140
tccgcaaatc cagttgccaa cggtggtttg ttaagaagac cattagatat gcctgacttt   1200
agagttttca gtattgctgt ccaagatgca ggtggtacaa gagcagacaa tgttccaacc   1260
ttaggtcatt tcttgagaga aatcactaga agaaacatgc aaaactttag aattttcggt   1320
cctgatgaaa cccaatctaa caaattagat gctatctatg acgtcactca aaaagtatgg   1380
ttgggtgcat actttccaga agatgccgac ggtggtgcct tagctttgtc cggtagagtt   1440
atggaaatgt tgagtgaaca tacattagaa ggttggttgg aaggttattt gttatctggt   1500
agacatggtt tgattaattc atacgaagcc tttatccata tcatagattc tatgttcaac   1560
caacacgcta aatggttaga aaagtgtaac gaattgccat ggagagcaaa agtagcctca   1620
ttaaatttgt tgatcacagg tttggtttgg agacaagatc ataacggttt tacccaccaa   1680
gatccaggtt tcttagacgt agttgctaat aagtcaccta acgtcgtaag aatatatttg   1740
ccacctgatg caaattgttt gttatccgtc accgaccatt gcttgagaag tgtaaactac   1800
atcaacgtta tcgtcgctga taagcaaact catttgcaat acttggatat ggacgccgct   1860
atggctcact gtgcaaaggg tgccggtatt tgggaatggg catctaatga tatgggtgaa   1920
gaaccagacg ttgtcatggc ctcttgcggt gacgttccta ctatggaatc attagcagcc   1980
acagcattgt tgagacaaca tttgccagat atcaagatca gattcgttaa cgtagttgac   2040
ttattcaagt tggtcccaca caccgaacat cctcacggta tgactgatag agaatttgaa   2100
gcattgttta cttcttctaa gccagttatt tttaatttcc attcatatcc ttggttaatc   2160
cacagattga cctacagaag accagcacaa catcacatac atgttagagg ttacaaggaa   2220
aagggtaaca tcgatactcc tttagaattg gctataagaa accaaacaga cagattttct   2280
ttggctattg atgcaataga cagaatccca agattctgtg atacaggttc aggtgttaga   2340
gaaattttgt tgaatttgca attcgcatgc aagaaccatg cctatgaata cggtgtcgat   2400
ccacaagaaa taacagactg gcaatggcca ttcagagata ccccttaa                2448
```

<210> SEQ ID NO 43
<211> LENGTH: 815
<212> TYPE: PRT
<213> ORGANISM: Acidithiobacillus_ferrooxidans

<400> SEQUENCE: 43

```
Met Thr Thr Glu His Asp Ala Ala Cys Glu Gly Glu Ser Ile Ser Ala
1               5                   10                  15

Tyr Gly Thr Ala Arg Ala Thr Val Glu Asp Gln Pro Leu Asn Thr Asp
            20                  25                  30

Asp Leu Arg Lys Ile Asp Ala Tyr Trp Arg Ala Ser Leu Tyr Leu Cys
        35                  40                  45

Leu Gly Met Leu Tyr Leu Arg Asp Asn Pro Leu Leu Arg Asp Pro Leu
    50                  55                  60

Lys Pro Glu His Ile Lys Pro Arg Leu Leu Gly His Trp Gly Ser Asp
65                  70                  75                  80

Ala Gly Gln Cys Phe Thr Tyr Ile His Phe Asn Arg Leu Ile Asn Lys
                85                  90                  95
```

-continued

```
Tyr Asp Leu Asn Ala Ile Tyr Ile Ser Gly Pro Gly His Gly Ala Pro
            100                 105                 110

Ala Ile Leu Ser Gln Ala Tyr Leu Glu Gly Thr Tyr Ser Glu Thr Tyr
        115                 120                 125

Pro Asp Lys Ser Gln Asp Ile Ala Gly Met Arg Arg Phe Phe Lys Gln
    130                 135                 140

Phe Ser Phe Pro Gly Gly Ile Gly Ser His Ala Thr Pro Glu Thr Pro
145                 150                 155                 160

Gly Ser Ile His Glu Gly Gly Glu Leu Gly Tyr Ser Val Ser His Ala
                165                 170                 175

Phe Gly Thr Val Tyr Asp Asn Pro Asp Leu Ile Ala Leu Val Met Val
            180                 185                 190

Gly Asp Gly Glu Ala Glu Thr Gly Pro Leu Ala Thr Ser Trp His Ser
        195                 200                 205

Asn Lys Phe Leu Asn Pro Ile Thr Asp Gly Ala Val Leu Pro Val Leu
    210                 215                 220

His Leu Asn Gly Tyr Lys Ile Asn Asn Pro Thr Ile Leu Ala Arg Ile
225                 230                 235                 240

Thr His Glu Glu Leu Glu Ala Leu Phe Ile Gly Tyr Gly Tyr Thr Pro
                245                 250                 255

Tyr Phe Val Glu Gly Ser Asp Pro Ala Ser Met His Gln Ala Met Ala
            260                 265                 270

Ala Thr Met Glu Arg Cys Val Leu Lys Ile Arg Glu Phe Gln Asp Lys
        275                 280                 285

Ala Arg His Thr Gly Thr Ala Phe Arg Pro Arg Trp Pro Met Ile Ile
    290                 295                 300

Leu Arg Ser Pro Lys Gly Trp Thr Ala Pro Arg Lys Val Asp Gly His
305                 310                 315                 320

Tyr Leu Glu Gly Phe Trp Arg Ala His Gln Ile Pro Ile Pro Asp Val
                325                 330                 335

Val Ser Asn Pro Ala His Leu Gln Leu Leu Glu Ser Trp Met Arg Ser
            340                 345                 350

Tyr Arg Pro Glu Glu Leu Phe Asp Ala Gln Gly Arg Leu Ile Pro Glu
        355                 360                 365

Leu His Glu Leu Ala Pro Lys Gly Lys Arg Arg Met Ser Ala Asn Pro
    370                 375                 380

Val Ala Asn Gly Gly Leu Leu Arg Arg Pro Leu Asp Met Pro Asp Phe
385                 390                 395                 400

Arg Val Phe Ser Ile Ala Val Gln Asp Ala Gly Gly Thr Arg Ala Asp
                405                 410                 415

Asn Val Pro Thr Leu Gly His Phe Leu Arg Glu Ile Thr Arg Arg Asn
            420                 425                 430

Met Gln Asn Phe Arg Ile Phe Gly Pro Asp Glu Thr Gln Ser Asn Lys
        435                 440                 445

Leu Asp Ala Ile Tyr Asp Val Thr Gln Lys Val Trp Leu Gly Ala Tyr
    450                 455                 460

Phe Pro Glu Asp Ala Asp Gly Gly Ala Leu Ala Leu Ser Gly Arg Val
465                 470                 475                 480

Met Glu Met Leu Ser Glu His Thr Leu Glu Gly Trp Leu Glu Gly Tyr
                485                 490                 495

Leu Leu Ser Gly Arg His Gly Leu Ile Asn Ser Tyr Glu Ala Phe Ile
            500                 505                 510
```

```
His Ile Ile Asp Ser Met Phe Asn Gln His Ala Lys Trp Leu Glu Lys
        515                 520                 525

Cys Asn Glu Leu Pro Trp Arg Ala Lys Val Ala Ser Leu Asn Leu Leu
    530                 535                 540

Ile Thr Gly Leu Val Trp Arg Gln Asp His Asn Gly Phe Thr His Gln
545                 550                 555                 560

Asp Pro Gly Phe Leu Asp Val Val Ala Asn Lys Ser Pro Asn Val Val
                565                 570                 575

Arg Ile Tyr Leu Pro Pro Asp Ala Asn Cys Leu Leu Ser Val Thr Asp
            580                 585                 590

His Cys Leu Arg Ser Val Asn Tyr Ile Asn Val Ile Val Ala Asp Lys
        595                 600                 605

Gln Thr His Leu Gln Tyr Leu Asp Met Asp Ala Ala Met Ala His Cys
    610                 615                 620

Ala Lys Gly Ala Gly Ile Trp Glu Trp Ala Ser Asn Asp Met Gly Glu
625                 630                 635                 640

Glu Pro Asp Val Val Met Ala Ser Cys Gly Asp Val Pro Thr Met Glu
                645                 650                 655

Ser Leu Ala Ala Thr Ala Leu Leu Arg Gln His Leu Pro Asp Ile Lys
            660                 665                 670

Ile Arg Phe Val Asn Val Val Asp Leu Phe Lys Leu Val Pro His Thr
        675                 680                 685

Glu His Pro His Gly Met Thr Asp Arg Glu Phe Glu Ala Leu Phe Thr
    690                 695                 700

Ser Ser Lys Pro Val Ile Phe Asn Phe His Ser Tyr Pro Trp Leu Ile
705                 710                 715                 720

His Arg Leu Thr Tyr Arg Arg Pro Ala Gln His His Ile His Val Arg
                725                 730                 735

Gly Tyr Lys Glu Lys Gly Asn Ile Asp Thr Pro Leu Glu Leu Ala Ile
            740                 745                 750

Arg Asn Gln Thr Asp Arg Phe Ser Leu Ala Ile Asp Ala Ile Asp Arg
        755                 760                 765

Ile Pro Arg Phe Cys Asp Thr Gly Ser Gly Val Arg Glu Ile Leu Leu
    770                 775                 780

Asn Leu Gln Phe Ala Cys Lys Asn His Ala Tyr Glu Tyr Gly Val Asp
785                 790                 795                 800

Pro Gln Glu Ile Thr Asp Trp Gln Trp Pro Phe Arg Asp Thr Pro
                805                 810                 815
```

<210> SEQ ID NO 44
<211> LENGTH: 2475
<212> TYPE: DNA
<213> ORGANISM: Bifidobacterium_asteroids

<400> SEQUENCE: 44

```
atgacaaatc ctgtaatagg tactccttgg gcaaagttag aaacaccaat agccgaagaa      60

accatagaag ccgtagataa atactggaga gctgcaaact atttgtccat aggtcaaatc     120

tacttgagaa gtaatccatt aatgaaggaa ccttttacaa gagaagatgt caagcataga     180

ttagtaggtc actggggtac tacaccaggt ttgaacttct tgttgggtca tatcaacaga     240

ttgatcgctg atcaccaaca aaacactgtt attatcatgg gtccaggtca tggtggtcct     300

gcaggtacct cccaaagtta tttggatggt acttactcag aatactaccc aaagatcaca     360

aacgacgaag ctggtttgca aaagtttttc agacaatttt cctatccagg tggtatacct     420
```

-continued

```
agtcatttcg ctccagaaac tcctggttcc atccacgaag gtggtgaatt gggttatgca    480

ttatcccatg cttacggtgc aatcatgaat aacccaagtt tgtttgttcc ttgtattgtc    540

ggtgacggtg aagcagaaac cggtccatta gccactggtt ggcaatctaa caaattggtt    600

aatccaagaa ccgatggtat tgtcttgcct atcttgcatt tgaatggtta caagattgct    660

aatccaacta tcttgtctag aatctcagat gaagaattac acgaatactt caagggtatg    720

ggttacgaac cttttgaatt tgttgctggt ttcgatgacg aagatcattt gtcaatacac    780

agaagatttg cagatttgtt agaaacagtc ttcgacaaga tctgcaacat caaggctaga    840

gcagaaactg atgacatgac aagaccatgt taccctatga tcatttttag aacaccaaaa    900

ggttggacct gccctaagtt catagatggt aaaaagactg aaggttcttg gagagcacat    960

caagttccat tgacttcagc aagagacaca gaagcccact tccaaatctt gaaaaattgg   1020

ttagcttctt acaagcctga agaattgttc gatgaaaagg gtgcattaag accagaagtt   1080

acatcattca tgcctaaggg tgacttaaga attggtgaaa atccaaacgc taatggtggt   1140

agattgttga agccattgga attacctgat atccatgact acgaaataga tgttaaaaag   1200

catggtcacg gttggggtgc caccgaagct actagagtat tgggttatta cacaagagat   1260

gttttagcta agaatccaac cgattttaga attttcggtc ctgacgaaac tgcatctaac   1320

agattagccg ctgcatatga agtaacaaat aagcaatggg atgcagacta cttgtccgaa   1380

ttaacagatg aacatatggc ccacaccggt caagttatcg aacaattaag tgaacatcaa   1440

atggaaggtt tcttggaagg ttatttgtta actggtagac acggtatttg gtcttcatac   1500

gaatctttcg ttcatgtcat agattcaatg atcaatcaac acgctaaatg gttggaagca   1560

actgttagag aaataccatg gagaaagcct atcgctggtt tgaacttgtt agtaacatct   1620

catgtttgga gacaagatca taatggtttt tcacaccaag acccaggttt cgttgatata   1680

ttgttgaaca aaaacttcaa caacgatcat gttgtcaaca tctatttccc tgccgacgct   1740

aacatgttgt tgaacgttgg tgaaagatgt tacaaatcca caaactgcat caatgcaatt   1800

tttgccggta aacaaccagc cgctacctat caaagtgtcg atgaagcagc cgctgaattg   1860

gaaaaaggtg cagccagatg ggattgggct tctaatgcaa aggacgccga agatgctgac   1920

gttgttattg ctactgctgg tgacatacca actcaagaag cattggctgc tgatgacatg   1980

ttgcaaaaat tgggtgtaaa ggttcaattc gttaacgtcg tagatttgtt gaagatccaa   2040

gacgctgaag aaaacgatca agcattgtct gacgaagagt ttactgaatt attctcaaag   2100

gataagccag tcttgtttgc attccatgcc tatcctggtt caatctatag attgatacat   2160

ggtagaccaa accacgataa tttttccgta catggttatg aagaacaagg tagtaccact   2220

acacctttcg atatggtcag agtaaataac atggacagat ggtgtttagc cgcttctgcc   2280

ttgcaattag ttgatgctaa taagtacact gatcaaatag acaagtggac aaagtttaga   2340

gatgaagcct ttcaattcgc tgttgataaa ggttatgatc atccagacta caccgattgg   2400

gtatggcctg atgctaacag agcaggtcaa gaaactattt ctgccacagc agccaccgct   2460

ggtgacaatg aataa                                                    2475
```

<210> SEQ ID NO 45
<211> LENGTH: 824
<212> TYPE: PRT
<213> ORGANISM: Bifidobacterium_asteroids

<400> SEQUENCE: 45

Met Thr Asn Pro Val Ile Gly Thr Pro Trp Ala Lys Leu Glu Thr Pro

-continued

```
1               5                   10                  15

Ile Ala Glu Glu Thr Ile Glu Ala Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Leu Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ser Gln Ser Tyr Leu Asp Gly Thr Tyr
            100                 105                 110

Ser Glu Tyr Tyr Pro Lys Ile Thr Asn Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Pro Cys Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Tyr Phe Lys Gly Met
225                 230                 235                 240

Gly Tyr Glu Pro Phe Glu Phe Val Ala Gly Phe Asp Asp Glu Asp His
                245                 250                 255

Leu Ser Ile His Arg Arg Phe Ala Asp Leu Leu Glu Thr Val Phe Asp
            260                 265                 270

Lys Ile Cys Asn Ile Lys Ala Arg Ala Glu Thr Asp Asp Met Thr Arg
        275                 280                 285

Pro Cys Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Thr Ser Ala Arg Asp Thr Glu Ala His Phe Gln Ile
                325                 330                 335

Leu Lys Asn Trp Leu Ala Ser Tyr Lys Pro Glu Glu Leu Phe Asp Glu
            340                 345                 350

Lys Gly Ala Leu Arg Pro Glu Val Thr Ser Phe Met Pro Lys Gly Asp
        355                 360                 365

Leu Arg Ile Gly Glu Asn Pro Asn Ala Asn Gly Gly Arg Leu Leu Lys
    370                 375                 380

Pro Leu Glu Leu Pro Asp Ile His Asp Tyr Glu Ile Asp Val Lys Lys
385                 390                 395                 400

His Gly His Gly Trp Gly Ala Thr Glu Ala Thr Arg Val Leu Gly Tyr
                405                 410                 415

Tyr Thr Arg Asp Val Leu Ala Lys Asn Pro Thr Asp Phe Arg Ile Phe
            420                 425                 430
```

```
Gly Pro Asp Glu Thr Ala Ser Asn Arg Leu Ala Ala Ala Tyr Glu Val
        435                 440                 445

Thr Asn Lys Gln Trp Asp Ala Asp Tyr Leu Ser Glu Leu Thr Asp Glu
    450                 455                 460

His Met Ala His Thr Gly Gln Val Ile Glu Gln Leu Ser Glu His Gln
465                 470                 475                 480

Met Glu Gly Phe Leu Glu Gly Tyr Leu Leu Thr Gly Arg His Gly Ile
                485                 490                 495

Trp Ser Ser Tyr Glu Ser Phe Val His Val Ile Asp Ser Met Ile Asn
            500                 505                 510

Gln His Ala Lys Trp Leu Glu Ala Thr Val Arg Glu Ile Pro Trp Arg
        515                 520                 525

Lys Pro Ile Ala Gly Leu Asn Leu Leu Val Thr Ser His Val Trp Arg
    530                 535                 540

Gln Asp His Asn Gly Phe Ser His Gln Asp Pro Gly Phe Val Asp Ile
545                 550                 555                 560

Leu Leu Asn Lys Asn Phe Asn Asn Asp His Val Val Asn Ile Tyr Phe
                565                 570                 575

Pro Ala Asp Ala Asn Met Leu Leu Asn Val Gly Glu Arg Cys Tyr Lys
            580                 585                 590

Ser Thr Asn Cys Ile Asn Ala Ile Phe Ala Gly Lys Gln Pro Ala Ala
        595                 600                 605

Thr Tyr Gln Ser Val Asp Glu Ala Ala Ala Glu Leu Glu Lys Gly Ala
    610                 615                 620

Ala Arg Trp Asp Trp Ala Ser Asn Ala Lys Asp Ala Glu Asp Ala Asp
625                 630                 635                 640

Val Val Ile Ala Thr Ala Gly Asp Ile Pro Thr Gln Glu Ala Leu Ala
                645                 650                 655

Ala Asp Asp Met Leu Gln Lys Leu Gly Val Lys Val Gln Phe Val Asn
            660                 665                 670

Val Val Asp Leu Leu Lys Ile Gln Asp Ala Glu Glu Asn Asp Gln Ala
        675                 680                 685

Leu Ser Asp Glu Glu Phe Thr Glu Leu Phe Ser Lys Asp Lys Pro Val
    690                 695                 700

Leu Phe Ala Phe His Ala Tyr Pro Gly Ser Ile Tyr Arg Leu Ile His
705                 710                 715                 720

Gly Arg Pro Asn His Asp Asn Phe Ser Val His Gly Tyr Glu Glu Gln
                725                 730                 735

Gly Ser Thr Thr Thr Pro Phe Asp Met Val Arg Val Asn Asn Met Asp
            740                 745                 750

Arg Trp Cys Leu Ala Ala Ser Ala Leu Gln Leu Val Asp Ala Asn Lys
        755                 760                 765

Tyr Thr Asp Gln Ile Asp Lys Trp Thr Lys Phe Arg Asp Glu Ala Phe
    770                 775                 780

Gln Phe Ala Val Asp Lys Gly Tyr Asp His Pro Asp Tyr Thr Asp Trp
785                 790                 795                 800

Val Trp Pro Asp Ala Asn Arg Ala Gly Gln Glu Thr Ile Ser Ala Thr
                805                 810                 815

Ala Ala Thr Ala Gly Asp Asn Glu
            820
```

<210> SEQ ID NO 46
<211> LENGTH: 2478

-continued

<212> TYPE: DNA
<213> ORGANISM: Bifidobacterium_catenulatum

<400> SEQUENCE: 46
atgacctccc ctgtaattgg taccccatgg aagaagttaa acgctcctgt aagtgaagaa 60
gctattgaag gtgtcgataa gtattggggt gctgcaaact acttgtccat cggtcaaata 120
tatttgagaa gtaacccatt gatgaaagaa cctttcacta gagaagatgt aaagcataga 180
ttggttggtc actggggtac tacaccaggt ttgaactttt taatcggtca tatcaacaga 240
ttgatcgctg atcacaagca aaacaccgtt attatcatgg gtccaggtca tggtggtcct 300
gcaggtactg cccaatctta tttggatggt acctacactg aaacattccc taaaataact 360
aaggacgaag caggtttgca aaagtttttc agacaatttt cctacccagg tggtattcct 420
agtcattatg ctccagaaac acctggttca atacacgaag gtggtgaatt gggttacgca 480
ttatcccatg cttatggtgc agttatgaat aacccaagtt tgtttgttcc tgcaattgtc 540
ggtgacggtg aagccgaaac tggtccatta gcaacagcct gggattacga caacatcatt 600
aatccaagaa ctgatggtat cgttttgcct atattgcact taaacggtta caagatcgct 660
aacccaacaa tcttgtctag aatctcagat gaagaattgc atgaattttt ccacggtatg 720
ggttatgaac cttacgaatt tgttgctaga ttcgataatg aagaccattt gtctattcac 780
agaagatttg cagaattgtt cgaaactgtc ttcgacgaaa tctgtgatat caaagccgct 840
gcacataccg atgacatgac tagaccattc taccctatga taatctttag aaccccaaaa 900
ggttggactt gccctaagtt cattgatggt aaaaagacag aaggttcctg gagaagtcat 960
caagtaccat tggcttccgc aagagatacc gaagctcact ttgaagtttt gactaactgg 1020
ttggaatctt acaaccctga agaattgttc gatgaaaacg gtgctgtaaa accagaagtt 1080
acagctttta tgcctaccgg tgaattaaga atcggtgcta atccaaacgc aaatggtggt 1140
gttattagag aagaattgaa tttgcctgcc ttagaagatt acgaagtaaa agaagttgct 1200
gaatatggtc atggttgggg tcaattggaa gctactagaa gattaggtgt ttacacaaga 1260
gacattttta agaacaaccc agattctttt agaatattcg gtcctgatga aactgcatca 1320
aacagattgc aagccgctta cgacgtcaca aataagaaat gggatgcagg ttatttgtct 1380
tcacaagtag atgaccatat ggccgtcaca ggtcaagtaa ccgaacaatt gtctgaacac 1440
caaatggaag gtttcttgga agcttacttg ttaactggta gacatggtat ctggtccagt 1500
tatgaatcta ttgtccatgt aaacgattca atgttgaatc aacacgcaaa atggttcgca 1560
gccacagtta gagaaattcc atggagaaag cctatctctt caatgaattt gttagtttcc 1620
agtcatgtct ggagacaaga ccaaacaggt tttctcacc aagatccagg tgtcacctcc 1680
gtattgttga gtagatgttt caacaacgat aacgttatag gtatatactt tgctgtcgat 1740
tccgacatgt tgttagccgg tgctgataaa tgctatcaaa gtagaaaggt catgaatgcc 1800
ggtatagtag gtagagctcc agctgcaacc tggttgatct taggtgaagc aagagccgaa 1860
ttggaaaaag gtgccgctga atgggaatgg gcctctactg ctaagtcaaa tgacgaagct 1920
caaattgtat tagcttcagc aggtgacgtt cctgcacaag aaatcatggc agccgctgac 1980
aagttgaacg aattgggtat taagtttaaa gttgtcaacg tagttgattt ggttaagttg 2040
caatctacaa aggaaaatga ccaagctata tcagatgcag acttcgccga cttgtttacc 2100
gaagataagc cagtcttatt cgcttatcat tcttacgcat cagacgttag aggtttgatc 2160
tacgatagac caaatcatga tgactttaac gttcacggta atcaagaaca aggttctacc 2220
actacacctt acgacatggt tagagtcaac aacatcgatt catacgaatt ggttgccgaa 2280
gctttaagaa tgatagatgc cgacaagtac gctgatgaaa tcaacgaatt ggaagctttt 2340
agacaagaag catttcaatt cgccgttgat aatggttatg atcatccaga ctacactgat 2400
tgggtctatt ctggtgtcaa cacaaccaag caaggtgcag tctcagccac agcagcaacc 2460
gcaggtgaca acgaataa 2478

<210> SEQ ID NO 47
<211> LENGTH: 825
<212> TYPE: PRT
<213> ORGANISM: Bifidobacterium_catenulatum

<400> SEQUENCE: 47

Met Thr Ser Pro Val Ile Gly Thr Pro Trp Lys Lys Leu Asn Ala Pro
1 5 10 15

Val Ser Glu Glu Ala Ile Glu Gly Val Asp Lys Tyr Trp Gly Ala Ala
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Leu Ile Ala Asp His Lys Gln Asn Thr Val Ile Ile Met Gly Pro Gly
85 90 95

His Gly Gly Pro Ala Gly Thr Ala Gln Ser Tyr Leu Asp Gly Thr Tyr
100 105 110

Thr Glu Thr Phe Pro Lys Ile Thr Lys Asp Glu Ala Gly Leu Gln Lys
115 120 125

Phe Phe Arg Gln Phe Ser Tyr Pro Gly Gly Ile Pro Ser His Tyr Ala
130 135 140

Pro Glu Thr Pro Gly Ser Ile His Glu Gly Gly Glu Leu Gly Tyr Ala
145 150 155 160

Leu Ser His Ala Tyr Gly Ala Val Met Asn Asn Pro Ser Leu Phe Val
165 170 175

Pro Ala Ile Val Gly Asp Gly Glu Ala Glu Thr Gly Pro Leu Ala Thr
180 185 190

Ala Trp Asp Tyr Asp Asn Ile Ile Asn Pro Arg Thr Asp Gly Ile Val
195 200 205

Leu Pro Ile Leu His Leu Asn Gly Tyr Lys Ile Ala Asn Pro Thr Ile
210 215 220

Leu Ser Arg Ile Ser Asp Glu Glu Leu His Glu Phe Phe His Gly Met
225 230 235 240

Gly Tyr Glu Pro Tyr Glu Phe Val Ala Arg Phe Asp Asn Glu Asp His
245 250 255

Leu Ser Ile His Arg Arg Phe Ala Glu Leu Phe Glu Thr Val Phe Asp
260 265 270

Glu Ile Cys Asp Ile Lys Ala Ala Ala His Thr Asp Asp Met Thr Arg
275 280 285

Pro Phe Tyr Pro Met Ile Ile Phe Arg Thr Pro Lys Gly Trp Thr Cys
290 295 300

Pro Lys Phe Ile Asp Gly Lys Lys Thr Glu Gly Ser Trp Arg Ser His
305 310 315 320

Gln Val Pro Leu Ala Ser Ala Arg Asp Thr Glu Ala His Phe Glu Val

-continued

```
                325                 330                 335

Leu Thr Asn Trp Leu Glu Ser Tyr Asn Pro Glu Glu Leu Phe Asp Glu
            340                 345                 350

Asn Gly Ala Val Lys Pro Glu Val Thr Ala Phe Met Pro Thr Gly Glu
        355                 360                 365

Leu Arg Ile Gly Ala Asn Pro Asn Ala Asn Gly Gly Val Ile Arg Glu
    370                 375                 380

Glu Leu Asn Leu Pro Ala Leu Glu Asp Tyr Glu Val Lys Glu Val Ala
385                 390                 395                 400

Glu Tyr Gly His Gly Trp Gly Gln Leu Glu Ala Thr Arg Arg Leu Gly
                405                 410                 415

Val Tyr Thr Arg Asp Ile Phe Lys Asn Asn Pro Asp Ser Phe Arg Ile
            420                 425                 430

Phe Gly Pro Asp Glu Thr Ala Ser Asn Arg Leu Gln Ala Ala Tyr Asp
        435                 440                 445

Val Thr Asn Lys Lys Trp Asp Ala Gly Tyr Leu Ser Ser Gln Val Asp
    450                 455                 460

Asp His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Ile Val His Val Asn Asp Ser Met Leu
            500                 505                 510

Asn Gln His Ala Lys Trp Phe Ala Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp Gln Thr Gly Phe Ser His Gln Asp Pro Gly Val Thr Ser
545                 550                 555                 560

Val Leu Leu Ser Arg Cys Phe Asn Asn Asp Asn Val Ile Gly Ile Tyr
                565                 570                 575

Phe Ala Val Asp Ser Asp Met Leu Leu Ala Gly Ala Asp Lys Cys Tyr
            580                 585                 590

Gln Ser Arg Lys Val Met Asn Ala Gly Ile Val Gly Arg Ala Pro Ala
        595                 600                 605

Ala Thr Trp Leu Ile Leu Gly Glu Ala Arg Ala Glu Leu Glu Lys Gly
    610                 615                 620

Ala Ala Glu Trp Glu Trp Ala Ser Thr Ala Lys Ser Asn Asp Glu Ala
625                 630                 635                 640

Gln Ile Val Leu Ala Ser Ala Gly Asp Val Pro Ala Gln Glu Ile Met
                645                 650                 655

Ala Ala Ala Asp Lys Leu Asn Glu Leu Gly Ile Lys Phe Lys Val Val
            660                 665                 670

Asn Val Val Asp Leu Val Lys Leu Gln Ser Thr Lys Glu Asn Asp Gln
        675                 680                 685

Ala Ile Ser Asp Ala Asp Phe Ala Asp Leu Phe Thr Glu Asp Lys Pro
    690                 695                 700

Val Leu Phe Ala Tyr His Ser Tyr Ala Ser Asp Val Arg Gly Leu Ile
705                 710                 715                 720

Tyr Asp Arg Pro Asn His Asp Asp Phe Asn Val His Gly Asn Gln Glu
                725                 730                 735

Gln Gly Ser Thr Thr Thr Pro Tyr Asp Met Val Arg Val Asn Asn Ile
            740                 745                 750
```

Asp Ser Tyr Glu Leu Val Ala Glu Ala Leu Arg Met Ile Asp Ala Asp
755 760 765

Lys Tyr Ala Asp Glu Ile Asn Glu Leu Glu Ala Phe Arg Gln Glu Ala
770 775 780

Phe Gln Phe Ala Val Asp Asn Gly Tyr Asp His Pro Asp Tyr Thr Asp
785 790 795 800

Trp Val Tyr Ser Gly Val Asn Thr Thr Lys Gln Gly Ala Val Ser Ala
805 810 815

Thr Ala Ala Thr Ala Gly Asp Asn Glu
820 825

<210> SEQ ID NO 48
<211> LENGTH: 2376
<212> TYPE: DNA
<213> ORGANISM: Clostridium_butyricum

<400> SEQUENCE: 48
atgacaaaca tcaactattc ctcagaatca tacttaaaga aggtagacgc ttattggaga 60
gccacaaact acatttcagt cggtcaattg tatttgaagg gtaacccatt gttaagagaa 120
ccattaaagc ctgaacatgt taaaaatgct gtttttggtc actggggtac tatagctggt 180
caaaacttca tctacgcaca tttgaataga gttatcaaca aatacgattt gtccatgttg 240
tacattagtg gtccaggtca cggtggtcaa gtcatggtat ctaactcata tttggatggt 300
tcctatagtg aagtttaccc tgaaattact caagacttgg aaggtttatc caagttgtac 360
aagcaatttt ctttctcagg tggtatcggt tctcatgcta caccacaagc acctggttca 420
attcacgaag gtggtgaatt aggttattct ttggttcatg gttttggtgc catcttagat 480
aatccagact tgattgctac cgttgtcgta ggtgacggtg aagccgaaac tggtccttta 540
gctacatctt ggcaattgaa taagtttata aacccagtta cagatggtgt tgtcttacct 600
atcttgtatt tgaatggttt caaaatctca aacccaacaa ttatggctaa gatgaccgat 660
gaagaattac aaaagtactt cgaaggtttg ggttgggacc caattttcgt cgagggtaat 720
gaacctgaag taatgcatca attgatggca gaaaagatgg atgaagccat agaaaagatt 780
ttgacaatca aaaagcacgc attggaagaa aatgatatgt ctagaccaaa gtggcctgtt 840
attttaaaca gaaccccaaa aggttggact ggtcctaagg aattggatgg taaaccaatt 900
gaaggttcct ttagagccca tcaagttcca atacctttcg atagtaagca catggaatgt 960
gctgatgact ttgtcaaatg gatgaatacc tatggtcctg aagaattatt cactgaagat 1020
ggtaaattgg ttgaagaaat cgcagaaatc atcccaaagg gtgacagaag aatgtcatgc 1080
aatcctgcca ctaacggtgg taaaaataatg aagggtttga gattgccaga ttatagagaa 1140
tacgcaatcg acaataagga aaagggtaaa aacgttgccc aagatatgtt gatattgggt 1200
aaatacgtca gagatgtaat gaagttaaac gacaaggaaa gaaactttag agtcttctct 1260
ccagatgaag ctgcatcaaa cagattgtac gctatgttcg aagaaacaaa gagacaatgg 1320
gttggtgaaa ttgatgaacc atacgacgaa tttttagcac ctgatggtag aattttagac 1380
tccatgttga gtgaacatat agctgaaggt gcattggaag cctatttgtt aacaggtaga 1440
catggtttta tccactctta cgaatcattc ttaagagtag ttgattcaat gatcacccaa 1500
catttcaagt ggttgaacca atgtgaagat attccatgga gagctgacat cccttccttg 1560
aatttgatta atacttctca tatctggcaa caagatcata acggttatac acaccaagac 1620
ccaggcatgt taggtcattt ggctgataaa aattctggtt taattcacga atacttgcct 1680

-continued

```
gttgatgcaa acacattgtt agtcaccttc gacaagtgca ttagatctat aaatcaagtt   1740

aacgtcatga cagcctcaaa acatccaaga caacaatggt tcaccatcga agaagctgaa   1800

tatttggtaa ataagggttt gggtatcgtt gattgggcat ctactgacaa aaacggtgaa   1860

acagatattg tatttgcaat ggccggtgac accccaactt tagaaggttt ggccgctgtt   1920

caattgttac atgattattt gcctgacttg aagattagat tcgttaacat cgtcgatttg   1980

ttgaaattgc aatccccaga agtttacgaa catggtatca gtgatgaaga gtttaatatg   2040

atcttcacca aggacaaacc tatcattttt ggtttccacg gttacgaaaa cttagtcgat   2100

actttgtttt tcaagagaga caaccataac gtatctgttc acggttacag agataaaggt   2160

gaaataacta caggttttga catgagagtc atgaacgaat tagatagatt caacttggta   2220

aaggacgcta tctataattt gccacaattg ggtaacaaag gtgcacatat catccaagaa   2280

atgaacgaaa agttggaaat ccatactaag ttcgttcacg aaaacggtat cgatttgcct   2340

gaaattgcta actggcaatg gaagggtttg aaataa                             2376
```

<210> SEQ ID NO 49
<211> LENGTH: 791
<212> TYPE: PRT
<213> ORGANISM: Clostridium_butyricum

<400> SEQUENCE: 49

```
Met Thr Asn Ile Asn Tyr Ser Ser Glu Ser Tyr Leu Lys Lys Val Asp
1               5                   10                  15

Ala Tyr Trp Arg Ala Thr Asn Tyr Ile Ser Val Gly Gln Leu Tyr Leu
            20                  25                  30

Lys Gly Asn Pro Leu Leu Arg Glu Pro Leu Lys Pro Glu His Val Lys
        35                  40                  45

Asn Ala Val Phe Gly His Trp Gly Thr Ile Ala Gly Gln Asn Phe Ile
    50                  55                  60

Tyr Ala His Leu Asn Arg Val Ile Asn Lys Tyr Asp Leu Ser Met Leu
65                  70                  75                  80

Tyr Ile Ser Gly Pro Gly His Gly Gly Gln Val Met Val Ser Asn Ser
                85                  90                  95

Tyr Leu Asp Gly Ser Tyr Ser Glu Val Tyr Pro Glu Ile Thr Gln Asp
            100                 105                 110

Leu Glu Gly Leu Ser Lys Leu Tyr Lys Gln Phe Ser Phe Ser Gly Gly
        115                 120                 125

Ile Gly Ser His Ala Thr Pro Gln Ala Pro Gly Ser Ile His Glu Gly
    130                 135                 140

Gly Glu Leu Gly Tyr Ser Leu Val His Gly Phe Gly Ala Ile Leu Asp
145                 150                 155                 160

Asn Pro Asp Leu Ile Ala Thr Val Val Val Gly Asp Gly Glu Ala Glu
                165                 170                 175

Thr Gly Pro Leu Ala Thr Ser Trp Gln Leu Asn Lys Phe Ile Asn Pro
            180                 185                 190

Val Thr Asp Gly Val Val Leu Pro Ile Leu Tyr Leu Asn Gly Phe Lys
        195                 200                 205

Ile Ser Asn Pro Thr Ile Met Ala Lys Met Thr Asp Glu Glu Leu Gln
    210                 215                 220

Lys Tyr Phe Glu Gly Leu Gly Trp Asp Pro Ile Phe Val Glu Gly Asn
225                 230                 235                 240

Glu Pro Glu Val Met His Gln Leu Met Ala Glu Lys Met Asp Glu Ala
```

-continued

```
                245                 250                 255

Ile Glu Lys Ile Leu Thr Ile Lys Lys His Ala Leu Glu Glu Asn Asp
            260                 265                 270

Met Ser Arg Pro Lys Trp Pro Val Ile Leu Asn Arg Thr Pro Lys Gly
        275                 280                 285

Trp Thr Gly Pro Lys Glu Leu Asp Gly Lys Pro Ile Glu Gly Ser Phe
    290                 295                 300

Arg Ala His Gln Val Pro Ile Pro Phe Asp Ser Lys His Met Glu Cys
305                 310                 315                 320

Ala Asp Asp Phe Val Lys Trp Met Asn Thr Tyr Gly Pro Glu Glu Leu
                325                 330                 335

Phe Thr Glu Asp Gly Lys Leu Val Glu Glu Ile Ala Glu Ile Ile Pro
            340                 345                 350

Lys Gly Asp Arg Arg Met Ser Cys Asn Pro Ala Thr Asn Gly Gly Lys
        355                 360                 365

Ile Met Lys Gly Leu Arg Leu Pro Asp Tyr Arg Glu Tyr Ala Ile Asp
    370                 375                 380

Asn Lys Glu Lys Gly Lys Asn Val Ala Gln Asp Met Leu Ile Leu Gly
385                 390                 395                 400

Lys Tyr Val Arg Asp Val Met Lys Leu Asn Asp Lys Glu Arg Asn Phe
                405                 410                 415

Arg Val Phe Ser Pro Asp Glu Ala Ala Ser Asn Arg Leu Tyr Ala Met
            420                 425                 430

Phe Glu Glu Thr Lys Arg Gln Trp Val Gly Glu Ile Asp Glu Pro Tyr
        435                 440                 445

Asp Glu Phe Leu Ala Pro Asp Gly Arg Ile Leu Asp Ser Met Leu Ser
    450                 455                 460

Glu His Ile Ala Glu Gly Ala Leu Glu Ala Tyr Leu Leu Thr Gly Arg
465                 470                 475                 480

His Gly Phe Ile His Ser Tyr Glu Ser Phe Leu Arg Val Val Asp Ser
                485                 490                 495

Met Ile Thr Gln His Phe Lys Trp Leu Asn Gln Cys Glu Asp Ile Pro
            500                 505                 510

Trp Arg Ala Asp Ile Pro Ser Leu Asn Leu Ile Asn Thr Ser His Ile
        515                 520                 525

Trp Gln Gln Asp His Asn Gly Tyr Thr His Gln Asp Pro Gly Met Leu
    530                 535                 540

Gly His Leu Ala Asp Lys Asn Ser Gly Leu Ile His Glu Tyr Leu Pro
545                 550                 555                 560

Val Asp Ala Asn Thr Leu Leu Val Thr Phe Asp Lys Cys Ile Arg Ser
                565                 570                 575

Ile Asn Gln Val Asn Val Met Thr Ala Ser Lys His Pro Arg Gln Gln
            580                 585                 590

Trp Phe Thr Ile Glu Glu Ala Glu Tyr Leu Val Asn Lys Gly Leu Gly
        595                 600                 605

Ile Val Asp Trp Ala Ser Thr Asp Lys Asn Gly Glu Thr Asp Ile Val
    610                 615                 620

Phe Ala Met Ala Gly Asp Thr Pro Thr Leu Glu Gly Leu Ala Ala Val
625                 630                 635                 640

Gln Leu Leu His Asp Tyr Leu Pro Asp Leu Lys Ile Arg Phe Val Asn
                645                 650                 655

Ile Val Asp Leu Leu Lys Leu Gln Ser Pro Glu Val Tyr Glu His Gly
            660                 665                 670
```

```
Ile Ser Asp Glu Glu Phe Asn Met Ile Phe Thr Lys Asp Lys Pro Ile
        675                 680                 685

Ile Phe Gly Phe His Gly Tyr Glu Asn Leu Val Asp Thr Leu Phe Phe
    690                 695                 700

Lys Arg Asp Asn His Asn Val Ser Val His Gly Tyr Arg Asp Lys Gly
705                 710                 715                 720

Glu Ile Thr Thr Gly Phe Asp Met Arg Val Met Asn Glu Leu Asp Arg
                725                 730                 735

Phe Asn Leu Val Lys Asp Ala Ile Tyr Asn Leu Pro Gln Leu Gly Asn
            740                 745                 750

Lys Gly Ala His Ile Ile Gln Glu Met Asn Glu Lys Leu Glu Ile His
        755                 760                 765

Thr Lys Phe Val His Glu Asn Gly Ile Asp Leu Pro Glu Ile Ala Asn
    770                 775                 780

Trp Gln Trp Lys Gly Leu Lys
785                 790


<210> SEQ ID NO 50
<211> LENGTH: 2505
<212> TYPE: DNA
<213> ORGANISM: Cryptococcus_neoformans

<400> SEQUENCE: 50

atggcagaag aaacctcatc attaacatca ttcggtcaag caagatccac tgtcaaagac      60

caaccattaa ctgtagaaga attaaaaaaa attgatgcct atatgagagc ttctttgtac     120

ttatgtttgg gcatgttgta tttgagacaa aacccattgt tgaaggaacc tttgaagaaa     180

gaacatttga aggccagatt gttaggtcac tggggttccg atgctggtca aatctttact     240

tacatccata tgaacagatt gattaagaaa tacgatttgg acgctttgtt cgttagtggt     300

ccaggtcacg gtgcacctgc cgtcttatcc caaagttatt tggaaggtgt atataccgaa     360

gtttacccaa atattactga agatgtcgag ggtatgagaa gatttttcaa gcaattttcc     420

ttccctggtg gtgttggtag tcatgcaaca ccagaaaccc ctggttcttt acacgaaggt     480

ggtgaattgg gttactctat ttcacatgct tttggtacag tcttcgataa cccaaactta     540

atcactttga caatggttgg tgacggtgaa tcagaaaccg gtcctttagc tgcatcctgg     600

catagtacaa agttcttgaa cccaatcacc gatggtgctg tattgcctgt tttgcatttg     660

aatggttaca agatcaataa cccaacagtt ttagctagaa tatcccacga agaaatcgaa     720

gcattgttta ttggttatgg ttggaaacct tacttcgttg aaggttctga tttgacctca     780

atgcatcaag caatggccgc tactttagaa aaggccgttt tggaaattaa agcataccaa     840

aagcaagcca gagattctgg taaagccttt agaccaagat ggcctatgat tatattaaga     900

tctccaaagg gttggactgc acctagaaac gtttcaggtc atcacttgga aggttattgg     960

agagcccatc aaattccatt agccgatgtt gcttccaata gtgaacactt gaaattgtta    1020

gaagactgga tgagatctta caagccagaa gaattattca cagaagatgg taaattgata    1080

cctgaattaa aggcattgcc acctgcaggt caagccagaa tgtctgccaa tccagtctca    1140

aacggtggtt tagtaagaaa agcattaaac ttgcctgatt tcaaggacta cgctattaag    1200

gatatagcac caggtgttac tttagcccct tctatgtcaa atatggcttt gttcgtcaga    1260

gatgtaatta aaaagaatca aacaaacttc agattattcg gtccagacga aaccgaatca    1320

aacaaattgg cagccgttta tgaagctggt aaaaaggtct ggatgggtga atacttacca    1380
```

-continued

```
gaagataccg acggtggtaa tttggctcat gcaggtagag ttatggaaat tttgtccgaa   1440

cacactgtcg aaggttggtt agaaggttat gtattgtctg gtagacatgg tttgttaaac   1500

tcatacgaac cttttattca tatcatcgat agtatggtta accaacactg taagtggata   1560

gaaaagtgct tagaagtcga atggagagtt aaagtctctt cattgaacat cttgttgacc   1620

gcaactgttt ggagacaaga tcataatggt tttactcacc aagatccagg tttcttagac   1680

gttgtcgcta ataagtctcc tgaagtagtt agaatatatt tgccacctga tggtaattgt   1740

ttgttatccg taatgaacca ttgcttcgac agtaaaaatt acgttaacgt cgtagttgct   1800

gataagcaag accatttgca atacttggat atggaagctg cagtagctca ctgtacaaaa   1860

ggtttaggta tttgggaatg ggcatgcgtt ggtgacccaa atgaaaaccc tgacttagta   1920

atggcatgtt gcggtgacgt tccaactatg gaatctttgg ccgctacagc tttgttgaag   1980

gaatatttgc ctgaattgaa gatcagattc gttaacgtcg ttgatttgtt taaattgata   2040

tcacatgtcg atcatccaca cggtttgacc gacagacaat gggtatccta cttcactgaa   2100

gacacaccaa tcatctttaa tttccatagt tacccttggt taatacacag attgacatac   2160

aagagaccag gttcacaaaa catccatgtt agaggttaca aggaaaaggg taacatagat   2220

actcctttag aattggcaat cagaaatgaa acagacagat actctttagc tatggatgca   2280

atagacagat tgccacattt gaaaaataag ggttcaatgg ctagagaaaa attgtacgat   2340

gcacaaatta aggccagaga ctgggctttt gaacacggta tagatccaga agacgttaga   2400

aaatggaagt ggccatacgg tcctaaaact gaaggtattg cctctaagtt gggtttcggt   2460

ggtgaaaata agcaacaagt tgcttccgtc ggtacaagtg aataa                   2505
```

<210> SEQ ID NO 51
<211> LENGTH: 834
<212> TYPE: PRT
<213> ORGANISM: Cryptococcus_neoformans

<400> SEQUENCE: 51

```
Met Ala Glu Glu Thr Ser Ser Leu Thr Ser Phe Gly Gln Ala Arg Ser
1               5                   10                  15

Thr Val Lys Asp Gln Pro Leu Thr Val Glu Glu Leu Lys Lys Ile Asp
            20                  25                  30

Ala Tyr Met Arg Ala Ser Leu Tyr Leu Cys Leu Gly Met Leu Tyr Leu
        35                  40                  45

Arg Gln Asn Pro Leu Leu Lys Glu Pro Leu Lys Lys Glu His Leu Lys
    50                  55                  60

Ala Arg Leu Leu Gly His Trp Gly Ser Asp Ala Gly Gln Ile Phe Thr
65                  70                  75                  80

Tyr Ile His Met Asn Arg Leu Ile Lys Lys Tyr Asp Leu Asp Ala Leu
                85                  90                  95

Phe Val Ser Gly Pro Gly His Gly Ala Pro Ala Val Leu Ser Gln Ser
            100                 105                 110

Tyr Leu Glu Gly Val Tyr Thr Glu Val Tyr Pro Asn Ile Thr Glu Asp
        115                 120                 125

Val Glu Gly Met Arg Arg Phe Phe Lys Gln Phe Ser Phe Pro Gly Gly
    130                 135                 140

Val Gly Ser His Ala Thr Pro Glu Thr Pro Gly Ser Leu His Glu Gly
145                 150                 155                 160

Gly Glu Leu Gly Tyr Ser Ile Ser His Ala Phe Gly Thr Val Phe Asp
                165                 170                 175
```

-continued

```
Asn Pro Asn Leu Ile Thr Leu Thr Met Val Gly Asp Gly Glu Ser Glu
            180                 185                 190

Thr Gly Pro Leu Ala Ala Ser Trp His Ser Thr Lys Phe Leu Asn Pro
        195                 200                 205

Ile Thr Asp Gly Ala Val Leu Pro Val Leu His Leu Asn Gly Tyr Lys
    210                 215                 220

Ile Asn Asn Pro Thr Val Leu Ala Arg Ile Ser His Glu Glu Ile Glu
225                 230                 235                 240

Ala Leu Phe Ile Gly Tyr Gly Trp Lys Pro Tyr Phe Val Glu Gly Ser
                245                 250                 255

Asp Leu Thr Ser Met His Gln Ala Met Ala Ala Thr Leu Glu Lys Ala
            260                 265                 270

Val Leu Glu Ile Lys Ala Tyr Gln Lys Gln Ala Arg Asp Ser Gly Lys
        275                 280                 285

Ala Phe Arg Pro Arg Trp Pro Met Ile Ile Leu Arg Ser Pro Lys Gly
    290                 295                 300

Trp Thr Ala Pro Arg Asn Val Ser Gly His His Leu Glu Gly Tyr Trp
305                 310                 315                 320

Arg Ala His Gln Ile Pro Leu Ala Asp Val Ala Ser Asn Ser Glu His
                325                 330                 335

Leu Lys Leu Leu Glu Asp Trp Met Arg Ser Tyr Lys Pro Glu Glu Leu
            340                 345                 350

Phe Thr Glu Asp Gly Lys Leu Ile Pro Glu Leu Lys Ala Leu Pro Pro
        355                 360                 365

Ala Gly Gln Ala Arg Met Ser Ala Asn Pro Val Ser Asn Gly Gly Leu
    370                 375                 380

Val Arg Lys Ala Leu Asn Leu Pro Asp Phe Lys Asp Tyr Ala Ile Lys
385                 390                 395                 400

Asp Ile Ala Pro Gly Val Thr Leu Ala Pro Ser Met Ser Asn Met Ala
                405                 410                 415

Leu Phe Val Arg Asp Val Ile Lys Lys Asn Gln Thr Asn Phe Arg Leu
            420                 425                 430

Phe Gly Pro Asp Glu Thr Glu Ser Asn Lys Leu Ala Ala Val Tyr Glu
        435                 440                 445

Ala Gly Lys Lys Val Trp Met Gly Glu Tyr Leu Pro Glu Asp Thr Asp
    450                 455                 460

Gly Gly Asn Leu Ala His Ala Gly Arg Val Met Glu Ile Leu Ser Glu
465                 470                 475                 480

His Thr Val Glu Gly Trp Leu Glu Gly Tyr Val Leu Ser Gly Arg His
                485                 490                 495

Gly Leu Leu Asn Ser Tyr Glu Pro Phe Ile His Ile Ile Asp Ser Met
            500                 505                 510

Val Asn Gln His Cys Lys Trp Ile Glu Lys Cys Leu Glu Val Glu Trp
        515                 520                 525

Arg Val Lys Val Ser Ser Leu Asn Ile Leu Leu Thr Ala Thr Val Trp
    530                 535                 540

Arg Gln Asp His Asn Gly Phe Thr His Gln Asp Pro Gly Phe Leu Asp
545                 550                 555                 560

Val Val Ala Asn Lys Ser Pro Glu Val Val Arg Ile Tyr Leu Pro Pro
                565                 570                 575

Asp Gly Asn Cys Leu Leu Ser Val Met Asn His Cys Phe Asp Ser Lys
            580                 585                 590

Asn Tyr Val Asn Val Val Val Ala Asp Lys Gln Asp His Leu Gln Tyr
```

595 600 605

Leu Asp Met Glu Ala Ala Val Ala His Cys Thr Lys Gly Leu Gly Ile
610 615 620

Trp Glu Trp Ala Cys Val Gly Asp Pro Asn Glu Asn Pro Asp Leu Val
625 630 635 640

Met Ala Cys Cys Gly Asp Val Pro Thr Met Glu Ser Leu Ala Ala Thr
645 650 655

Ala Leu Leu Lys Glu Tyr Leu Pro Glu Leu Lys Ile Arg Phe Val Asn
660 665 670

Val Val Asp Leu Phe Lys Leu Ile Ser His Val Asp His Pro His Gly
675 680 685

Leu Thr Asp Arg Gln Trp Val Ser Tyr Phe Thr Glu Asp Thr Pro Ile
690 695 700

Ile Phe Asn Phe His Ser Tyr Pro Trp Leu Ile His Arg Leu Thr Tyr
705 710 715 720

Lys Arg Pro Gly Ser Gln Asn Ile His Val Arg Gly Tyr Lys Glu Lys
725 730 735

Gly Asn Ile Asp Thr Pro Leu Glu Leu Ala Ile Arg Asn Glu Thr Asp
740 745 750

Arg Tyr Ser Leu Ala Met Asp Ala Ile Asp Arg Leu Pro His Leu Lys
755 760 765

Asn Lys Gly Ser Met Ala Arg Glu Lys Leu Tyr Asp Ala Gln Ile Lys
770 775 780

Ala Arg Asp Trp Ala Phe Glu His Gly Ile Asp Pro Glu Asp Val Arg
785 790 795 800

Lys Trp Lys Trp Pro Tyr Gly Pro Lys Thr Glu Gly Ile Ala Ser Lys
805 810 815

Leu Gly Phe Gly Gly Glu Asn Lys Gln Gln Val Ala Ser Val Gly Thr
820 825 830

Ser Glu

<210> SEQ ID NO 52
<211> LENGTH: 2409
<212> TYPE: DNA
<213> ORGANISM: Cyanothece

<400> SEQUENCE: 52
atggttgcca cacctgaaag acctacatta gaacaaaccc cattatccgc agaagaatta 60
agacaaatac aagcatactg gagagcatgt aactatttgg ctgttggtat gatatatttg 120
agagataacc cattgttgaa agaccctttg actgaagatc atgttaagaa tagattgttg 180
ggtcactggg gttcttcacc aggtttgtct tttatatata tccatttgaa cagattaatt 240
aaaaagtatg gtttagatgt tatatacatg gccggtccag gtcacggtgc tcctggtatt 300
ttgggtccag tctacttaga aggtacttat tccgaaacat accctgacaa aagtgaagat 360
gaagagggta tgaaaaagtt tttcaagcaa ttttctttcc caggtggtat tggttcacat 420
tgtaccccag aaactcctgg ttctatacac gaaggtggtg aattgggtta ttccttaagt 480
catgcttacg gtgctgcatt ggacaatcct gatttgattg ttgccgctgt tgtcggtgac 540
ggtgaagcag aaacaggtcc attggccacc gcttggcatt ctaataagtt tattaaccct 600
attagagatg gtgctgtttt gccaatcttg catttgaatg gttataagat tgcaaaccca 660
actatcttag ccagaatttc ccacgaagaa ttggaatatt tgtttaaagg ttacggttac 720
aagccttact ttgttgaagg tagtgatcca gaagtcatgc atcaaaagat ggcagccaca 780

```
ttagaaaccg caatagccga aatcaagcac attcaacaag aagctagaac atcaggtgtc    840
gcaaaaagac caatatggcc tatgatcgta ttgagatctc ctaagggttg gactggtcca    900
gcttcagttg acggtaaaaa gacagaagat ttctggagat ctcatcaagt ccctttatca    960
ggcatgcatg gtaatccagc acacattaaa gtattggaag actggttaaa gtcctatacc   1020
cctgaagaat tgttcgatga aaacggtact ttaattcctg aattgaagga attagctcca   1080
actggtcatc acagaatgtc agcaaatcca catgccaacg gtggtttgtt aagaaaagac   1140
ttgaagatgc ctgatttcag aaattacggt gtagaagttg ctaaaccagg tactgtcgaa   1200
gttggtaaca cagcattgtt gggtaacttt ttaagagatg ttatggccaa caacatgaca   1260
aacttcagag tcttcggtcc tgatgaaacc gcctctaata gattgaacgc tatctatgaa   1320
atctctaaga aagtttggat gggtgaaata ttaccagaag atgcagacgg tactgaaatc   1380
actacagatg gtagagttat ggaaatgtta tcagaacata cattgcaagg ttggttagaa   1440
ggttatttgt taacaggtag acatggtttc tttcacacct acgaagcatt tgcacatgta   1500
gttgactcta tgtttaatca acacgctaaa tggttggata tttgtaagaa cgaagtccca   1560
tggagagcat cagtatccag tttaaacatc ttgttatctt caacagtttg gagacaagat   1620
cataacggtt tctcccacca agacccaggt tatgttgatt tggtcaccaa taagagtgct   1680
gacgtcgtaa gagtctactt tccacctgat gcaaattgtt tgttatccgt agccaaccat   1740
tgcttgaaaa gtacagacta cgttaacgtc atcgtatctg ataagcaaat ccatttgcaa   1800
tacttaaaca tggaccaagc cattaaacac tgcaccaagg gtattggtat atgggattgg   1860
gcttctaatg atgactgtgg tactgaacca gaccatcctg atgtaataat ggcatcatgc   1920
ggtgacgttg ctaccaaaga agcattggct gcaactgcca tattaagaga agaatttcct   1980
gacttgaaag ttagattcat caacgttgtc gatttgttta agttacaatc cgaaatagaa   2040
catccacacg gtttgagtga tagagacttc gataatttgt ttactaagga taagcctatc   2100
attttcaatt tccatggtta cccatggttg attcacaaat taacctacag aagaactaac   2160
catcacaact tacatgttag aggttacaag gaaaagggta acatcaacac acctttggaa   2220
ttagctatta ataaccaaat cgacagattc aatttggtta ttgatgttat aaacagagta   2280
ccaaaattag gttctgccgc tgcatacgtt tacgaaagaa tgaagaacgc aatcatagaa   2340
catagagcct atgcttacga acacggtatc gataagcctg aaattaataa ctggaagtgg   2400
ccacattaa                                                           2409
```

<210> SEQ ID NO 53
<211> LENGTH: 802
<212> TYPE: PRT
<213> ORGANISM: Cyanothece

<400> SEQUENCE: 53

```
Met Val Ala Thr Pro Glu Arg Pro Thr Leu Glu Gln Thr Pro Leu Ser
1               5                   10                  15

Ala Glu Glu Leu Arg Gln Ile Gln Ala Tyr Trp Arg Ala Cys Asn Tyr
            20                  25                  30

Leu Ala Val Gly Met Ile Tyr Leu Arg Asp Asn Pro Leu Leu Lys Asp
        35                  40                  45

Pro Leu Thr Glu Asp His Val Lys Asn Arg Leu Leu Gly His Trp Gly
    50                  55                  60

Ser Ser Pro Gly Leu Ser Phe Ile Tyr Ile His Leu Asn Arg Leu Ile
65                  70                  75                  80
```

```
Lys Lys Tyr Gly Leu Asp Val Ile Tyr Met Ala Gly Pro Gly His Gly
                85                  90                  95

Ala Pro Gly Ile Leu Gly Pro Val Tyr Leu Glu Gly Thr Tyr Ser Glu
            100                 105                 110

Thr Tyr Pro Asp Lys Ser Glu Asp Glu Glu Gly Met Lys Lys Phe Phe
        115                 120                 125

Lys Gln Phe Ser Phe Pro Gly Gly Ile Gly Ser His Cys Thr Pro Glu
    130                 135                 140

Thr Pro Gly Ser Ile His Glu Gly Gly Glu Leu Gly Tyr Ser Leu Ser
145                 150                 155                 160

His Ala Tyr Gly Ala Ala Leu Asp Asn Pro Asp Leu Ile Val Ala Ala
                165                 170                 175

Val Val Gly Asp Gly Glu Ala Glu Thr Gly Pro Leu Ala Thr Ala Trp
            180                 185                 190

His Ser Asn Lys Phe Ile Asn Pro Ile Arg Asp Gly Ala Val Leu Pro
        195                 200                 205

Ile Leu His Leu Asn Gly Tyr Lys Ile Ala Asn Pro Thr Ile Leu Ala
    210                 215                 220

Arg Ile Ser His Glu Glu Leu Glu Tyr Leu Phe Lys Gly Tyr Gly Tyr
225                 230                 235                 240

Lys Pro Tyr Phe Val Glu Gly Ser Asp Pro Glu Val Met His Gln Lys
                245                 250                 255

Met Ala Ala Thr Leu Glu Thr Ala Ile Ala Glu Ile Lys His Ile Gln
            260                 265                 270

Gln Glu Ala Arg Thr Ser Gly Val Ala Lys Arg Pro Ile Trp Pro Met
        275                 280                 285

Ile Val Leu Arg Ser Pro Lys Gly Trp Thr Gly Pro Ala Ser Val Asp
    290                 295                 300

Gly Lys Lys Thr Glu Asp Phe Trp Arg Ser His Gln Val Pro Leu Ser
305                 310                 315                 320

Gly Met His Gly Asn Pro Ala His Ile Lys Val Leu Glu Asp Trp Leu
                325                 330                 335

Lys Ser Tyr Thr Pro Glu Glu Leu Phe Asp Glu Asn Gly Thr Leu Ile
            340                 345                 350

Pro Glu Leu Lys Glu Leu Ala Pro Thr Gly His His Arg Met Ser Ala
        355                 360                 365

Asn Pro His Ala Asn Gly Gly Leu Leu Arg Lys Asp Leu Lys Met Pro
    370                 375                 380

Asp Phe Arg Asn Tyr Gly Val Glu Val Ala Lys Pro Gly Thr Val Glu
385                 390                 395                 400

Val Gly Asn Thr Ala Leu Leu Gly Asn Phe Leu Arg Asp Val Met Ala
                405                 410                 415

Asn Asn Met Thr Asn Phe Arg Val Phe Gly Pro Asp Glu Thr Ala Ser
            420                 425                 430

Asn Arg Leu Asn Ala Ile Tyr Glu Ile Ser Lys Lys Val Trp Met Gly
        435                 440                 445

Glu Ile Leu Pro Glu Asp Ala Asp Gly Thr Glu Ile Thr Thr Asp Gly
    450                 455                 460

Arg Val Met Glu Met Leu Ser Glu His Thr Leu Gln Gly Trp Leu Glu
465                 470                 475                 480

Gly Tyr Leu Leu Thr Gly Arg His Gly Phe Phe His Thr Tyr Glu Ala
                485                 490                 495
```

-continued

```
Phe Ala His Val Val Asp Ser Met Phe Asn Gln His Ala Lys Trp Leu
            500                 505                 510

Asp Ile Cys Lys Asn Glu Val Pro Trp Arg Ala Ser Val Ser Ser Leu
        515                 520                 525

Asn Ile Leu Leu Ser Ser Thr Val Trp Arg Gln Asp His Asn Gly Phe
    530                 535                 540

Ser His Gln Asp Pro Gly Tyr Val Asp Leu Val Thr Asn Lys Ser Ala
545                 550                 555                 560

Asp Val Val Arg Val Tyr Phe Pro Pro Asp Ala Asn Cys Leu Leu Ser
                565                 570                 575

Val Ala Asn His Cys Leu Lys Ser Thr Asp Tyr Val Asn Val Ile Val
            580                 585                 590

Ser Asp Lys Gln Ile His Leu Gln Tyr Leu Asn Met Asp Gln Ala Ile
        595                 600                 605

Lys His Cys Thr Lys Gly Ile Gly Ile Trp Asp Trp Ala Ser Asn Asp
    610                 615                 620

Asp Cys Gly Thr Glu Pro Asp His Pro Asp Val Ile Met Ala Ser Cys
625                 630                 635                 640

Gly Asp Val Ala Thr Lys Glu Ala Leu Ala Ala Thr Ala Ile Leu Arg
                645                 650                 655

Glu Glu Phe Pro Asp Leu Lys Val Arg Phe Ile Asn Val Val Asp Leu
            660                 665                 670

Phe Lys Leu Gln Ser Glu Ile Glu His Pro His Gly Leu Ser Asp Arg
        675                 680                 685

Asp Phe Asp Asn Leu Phe Thr Lys Asp Lys Pro Ile Ile Phe Asn Phe
    690                 695                 700

His Gly Tyr Pro Trp Leu Ile His Lys Leu Thr Tyr Arg Arg Thr Asn
705                 710                 715                 720

His His Asn Leu His Val Arg Gly Tyr Lys Glu Lys Gly Asn Ile Asn
                725                 730                 735

Thr Pro Leu Glu Leu Ala Ile Asn Asn Gln Ile Asp Arg Phe Asn Leu
            740                 745                 750

Val Ile Asp Val Ile Asn Arg Val Pro Lys Leu Gly Ser Ala Ala Ala
        755                 760                 765

Tyr Val Tyr Glu Arg Met Lys Asn Ala Ile Ile Glu His Arg Ala Tyr
    770                 775                 780

Ala Tyr Glu His Gly Ile Asp Lys Pro Glu Ile Asn Asn Trp Lys Trp
785                 790                 795                 800

Pro His
```

<210> SEQ ID NO 54
<211> LENGTH: 2367
<212> TYPE: DNA
<213> ORGANISM: Eremococcus_coleocola

<400> SEQUENCE: 54

```
atgactgtag actataactc aaaagaatac ttaacattgg tcgataaatg gtggagagca      60

gcaaactact tgtccgttgg tcaaatgttc ttgagagata acccattgtt gcaagaagaa     120

gttactgcag accatgtcaa attgaatcct atcggtcact ggggtacaat tggtggtcaa     180

aacttcttgt atgctcattt gaatagaatt ataaacaagt acaatgttaa catgttttac     240

attgaaggtc caggtcacgg tggtcaagtc atggtaacta attcctactt ggatggtagt     300

tatactgaaa gatacccaga gtttactcaa gacatcgctg gtatgaagaa attgtttaaa     360
```

-continued

```
accttttctt tccctggtgg tattggttca catgctgcac cagaaactcc tggttccatg    420
cacgaaggtg gtgaattggg ttatgcttta agtcatgcaa caggtgccat attggataac    480
ccagacgtta tcgccgctac agttgtcggt gacggtgaag cagaaaccgg tcctttggca    540
gccggttggt tttccaatgt attcataaac ccagttagtg atggtgctgt cttacctatc    600
ttgtacttaa atggtggtaa aattgctaac ccaaccatct tggcaagaaa gtcaaacgaa    660
gatttgacta agtactttga gggtatgggt tggaaacctt acatcgtcga aggtactgat    720
ccagaacaag tacatcctat tatggctaag gtattggatg aagttatcga agaaattcaa    780
gcaatacaag ccgaagctag aaagggtaaa gctgaagatg caaaaatgcc acattggcct    840
atgattttat atagaacccc aaaaggttgg actggtcctg aagaagttga aggtaaaact    900
attcaaggtt cttttagagc acatcaagtc ccaatacctg tatcaggtag aaacatggaa    960
gatatcgact tgttaatcaa ctggttgaag tcttacggtc cagaagaatt attcacagaa   1020
aacggtgaat tggttgatga attaaaggaa tttgccccaa agggtgacca tagaatggct   1080
atgaatcctt tgactaatgg tggtaaccca aaacctttaa atatgccaaa ctggaaggat   1140
tatgctttgg aaataggtac acctggttct aaagatgcac aagacatgat cgaatttggt   1200
ggtttcgcca gagatatagt taaggaaaac ccagaaaact ttagaatttt cggtcctgat   1260
gaaacaaagt ctaacagatt gaacaaggtt ttcgaagtca ccaatagaca atggttagaa   1320
ccaatttcag aaaagttcga tgaaaacatg tctgcttcag gtagagttat agactctcaa   1380
ttgtcagaac atcaaaacca aggtttcttg gaagcatatg tcttaacagg tagacacggt   1440
ttctttgctt cttacgaatc tttctttaga acagttgatt ccatgataac ccaacatttc   1500
aagtggataa gaaaatctgc caagcactca tggagaaagc catatcaaag tttgaatttg   1560
atctccgcta gtacagtttt tcaacaagat cataacggtt acacccacca agacccaggt   1620
ttgttaactc atattggtga aaaacacggt gaatatatga gagcttactt acctgcagat   1680
accaattctt tgttagccgt tatggacaag gcttttagat ccgaaaacgt cattaactac   1740
gtagttactt ctaagcatcc aagacctcaa tttttcacag ccgatgaagc tgaagaattg   1800
gtaaacgaag gtttgaaagt tatagattgg gcttctacag ttaaggataa cgaagaacca   1860
gacgtcgtaa tcgctgcagc cggtaccgaa cctaatttcg aagctatcgc tgcaatttca   1920
tatttggtaa aagcatttcc agaattaaag atcagattcg ttaacgttgt cgatttgttt   1980
agattgagat ctccagaaat cgaccctaga ggtttgtcag atgacgaatt tgatgcaatc   2040
ttcaccaaag acaagccagt tttctttgcc tttcattcct acgaaggcat gttgaaggat   2100
attttcttta ctagacataa ccacaactta tacgcacacg gttacagaga aaatggtgaa   2160
ataactacac ctttcgatat gagagtcttg aacgaattag acagatttca tttgtcagca   2220
cacgtagccg atgtagttta tggtgacaag gcaagagact acgtcgccga aatgaagggt   2280
aaagtacaag aacatagaga ttacgttgaa gaatacggtg ctgacatgcc agaagttgaa   2340
gattggaaat gggaagacat taagtaa                                       2367
```

<210> SEQ ID NO 55
<211> LENGTH: 788
<212> TYPE: PRT
<213> ORGANISM: Eremococcus_coleocola

<400> SEQUENCE: 55

```
Met Thr Val Asp Tyr Asn Ser Lys Glu Tyr Leu Thr Leu Val Asp Lys
1               5                   10                  15
```

-continued

```
Trp Trp Arg Ala Ala Asn Tyr Leu Ser Val Gly Gln Met Phe Leu Arg
            20                  25                  30

Asp Asn Pro Leu Leu Gln Glu Glu Val Thr Ala Asp His Val Lys Leu
        35                  40                  45

Asn Pro Ile Gly His Trp Gly Thr Ile Gly Gly Gln Asn Phe Leu Tyr
    50                  55                  60

Ala His Leu Asn Arg Ile Ile Asn Lys Tyr Asn Val Asn Met Phe Tyr
65                  70                  75                  80

Ile Glu Gly Pro Gly His Gly Gly Gln Val Met Val Thr Asn Ser Tyr
                85                  90                  95

Leu Asp Gly Ser Tyr Thr Glu Arg Tyr Pro Glu Phe Thr Gln Asp Ile
            100                 105                 110

Ala Gly Met Lys Lys Leu Phe Lys Thr Phe Ser Phe Pro Gly Gly Ile
        115                 120                 125

Gly Ser His Ala Ala Pro Glu Thr Pro Gly Ser Met His Glu Gly Gly
    130                 135                 140

Glu Leu Gly Tyr Ala Leu Ser His Ala Thr Gly Ala Ile Leu Asp Asn
145                 150                 155                 160

Pro Asp Val Ile Ala Ala Thr Val Val Gly Asp Gly Glu Ala Glu Thr
                165                 170                 175

Gly Pro Leu Ala Ala Gly Trp Phe Ser Asn Val Phe Ile Asn Pro Val
            180                 185                 190

Ser Asp Gly Ala Val Leu Pro Ile Leu Tyr Leu Asn Gly Gly Lys Ile
        195                 200                 205

Ala Asn Pro Thr Ile Leu Ala Arg Lys Ser Asn Glu Asp Leu Thr Lys
    210                 215                 220

Tyr Phe Glu Gly Met Gly Trp Lys Pro Tyr Ile Val Glu Gly Thr Asp
225                 230                 235                 240

Pro Glu Gln Val His Pro Ile Met Ala Lys Val Leu Asp Glu Val Ile
                245                 250                 255

Glu Glu Ile Gln Ala Ile Gln Ala Glu Ala Arg Lys Gly Lys Ala Glu
            260                 265                 270

Asp Ala Lys Met Pro His Trp Pro Met Ile Leu Tyr Arg Thr Pro Lys
        275                 280                 285

Gly Trp Thr Gly Pro Glu Glu Val Glu Gly Lys Thr Ile Gln Gly Ser
    290                 295                 300

Phe Arg Ala His Gln Val Pro Ile Pro Val Ser Gly Arg Asn Met Glu
305                 310                 315                 320

Asp Ile Asp Leu Leu Ile Asn Trp Leu Lys Ser Tyr Gly Pro Glu Glu
                325                 330                 335

Leu Phe Thr Glu Asn Gly Glu Leu Val Asp Glu Leu Lys Glu Phe Ala
            340                 345                 350

Pro Lys Gly Asp His Arg Met Ala Met Asn Pro Leu Thr Asn Gly Gly
        355                 360                 365

Asn Pro Lys Pro Leu Asn Met Pro Asn Trp Lys Asp Tyr Ala Leu Glu
    370                 375                 380

Ile Gly Thr Pro Gly Ser Lys Asp Ala Gln Asp Met Ile Glu Phe Gly
385                 390                 395                 400

Gly Phe Ala Arg Asp Ile Val Lys Glu Asn Pro Glu Asn Phe Arg Ile
                405                 410                 415

Phe Gly Pro Asp Glu Thr Lys Ser Asn Arg Leu Asn Lys Val Phe Glu
            420                 425                 430

Val Thr Asn Arg Gln Trp Leu Glu Pro Ile Ser Glu Lys Phe Asp Glu
```

```
        435                 440                 445

Asn Met Ser Ala Ser Gly Arg Val Ile Asp Ser Gln Leu Ser Glu His
    450                 455                 460

Gln Asn Gln Gly Phe Leu Glu Ala Tyr Val Leu Thr Gly Arg His Gly
465                 470                 475                 480

Phe Phe Ala Ser Tyr Glu Ser Phe Phe Arg Thr Val Asp Ser Met Ile
                485                 490                 495

Thr Gln His Phe Lys Trp Ile Arg Lys Ser Ala Lys His Ser Trp Arg
            500                 505                 510

Lys Pro Tyr Gln Ser Leu Asn Leu Ile Ser Ala Ser Thr Val Phe Gln
        515                 520                 525

Gln Asp His Asn Gly Tyr Thr His Gln Asp Pro Gly Leu Leu Thr His
    530                 535                 540

Ile Gly Glu Lys His Gly Glu Tyr Met Arg Ala Tyr Leu Pro Ala Asp
545                 550                 555                 560

Thr Asn Ser Leu Leu Ala Val Met Asp Lys Ala Phe Arg Ser Glu Asn
                565                 570                 575

Val Ile Asn Tyr Val Val Thr Ser Lys His Pro Arg Pro Gln Phe Phe
            580                 585                 590

Thr Ala Asp Glu Ala Glu Glu Leu Val Asn Glu Gly Leu Lys Val Ile
        595                 600                 605

Asp Trp Ala Ser Thr Val Lys Asp Asn Glu Glu Pro Asp Val Val Ile
    610                 615                 620

Ala Ala Ala Gly Thr Glu Pro Asn Phe Glu Ala Ile Ala Ala Ile Ser
625                 630                 635                 640

Tyr Leu Val Lys Ala Phe Pro Glu Leu Lys Ile Arg Phe Val Asn Val
                645                 650                 655

Val Asp Leu Phe Arg Leu Arg Ser Pro Glu Ile Asp Pro Arg Gly Leu
            660                 665                 670

Ser Asp Asp Glu Phe Asp Ala Ile Phe Thr Lys Asp Lys Pro Val Phe
        675                 680                 685

Phe Ala Phe His Ser Tyr Glu Gly Met Leu Lys Asp Ile Phe Phe Thr
    690                 695                 700

Arg His Asn His Asn Leu Tyr Ala His Gly Tyr Arg Glu Asn Gly Glu
705                 710                 715                 720

Ile Thr Thr Pro Phe Asp Met Arg Val Leu Asn Glu Leu Asp Arg Phe
                725                 730                 735

His Leu Ser Ala His Val Ala Asp Val Val Tyr Gly Asp Lys Ala Arg
            740                 745                 750

Asp Tyr Val Ala Glu Met Lys Gly Lys Val Gln Glu His Arg Asp Tyr
        755                 760                 765

Val Glu Glu Tyr Gly Ala Asp Met Pro Glu Val Glu Asp Trp Lys Trp
    770                 775                 780

Glu Asp Ile Lys
785
```

<210> SEQ ID NO 56
<211> LENGTH: 2479
<212> TYPE: DNA
<213> ORGANISM: Gardnerella_vaginalis

<400> SEQUENCE: 56

```
atgacctccc ctgtaatcgg taccccatgg aaaaagttaa atgccccagt atcagaagca      60

gccatagaag gtgtagacaa gtattggaga gttgctaact atttgtccat tggtcaaata     120
```

-continued

```
tacttgagaa gtaatccatt aatgaaggaa ccttttacaa gagaagatgt caagcataga    180

ttagtaggtc actggggtac tacaccaggt ttgaacttct taatcggtca tatcaacaga    240

ttcattgcag aacaccaaca aaacaccgtt attatcatgg gtccaggtca tggtggtcct    300

gccggtactg ctcaatccta tttggatggt acctacactg aatattaccc aaaaattacc    360

aaggacgaag ctggtttgca aaagtttttc agacaattct cttatccagg tggtatacct    420

tcacattttg ctccagaaac tcctggttca atccacgaag gtggtgaatt gggttatgca    480

ttatctcatg catacggtgc cgttatgaat aacccatcat tgtttgttcc tgcaattgtc    540

ggtgacggtg aagccgaaac cggtccattg gctactggtt ggcaatcaaa caagttagtc    600

aatccaagaa ctgatggtat cgtattgcct atattgcatt tgaatggtta caagattgct    660

aatccaacaa tattgtccag aatcagtgat gaagaattac atgaattttt ccacggtatg    720

ggttatgaac cttacgaatt tgttgcaggt ttcgatgacg aagaccatat gtctatacac    780

agaagatttg ccgatatgtt cgaaactatc ttcgacgaaa tctgtgatat caaagccgaa    840

gctcaaacca atgatgttac tagaccattc taccctatga tcatttttag aacaccaaag    900

ggttggacct gccctaagtt cattgatggt aaaaagacag aaggttcctg gagagcccat    960

caagttccat tggcaagtgc cagagatacc gaagctcact ttgaagtctt gaagaactgg   1020

ttgaagtctt acaagcctga agaattattc aatgaagacg gttccattaa agaagatgtt   1080

ttgagtttta tgccacaggg tgaattaaga attggtcaaa atcctaacgc taatggtggt   1140

agaataagag aagatttgaa attgccaaat ttggatgact acgaagtaaa ggaagttaag   1200

gaatttggtc atggttgggg tcaattggaa gccactagaa gattaggtgt ttacacaaga   1260

gacgtcatca agaataaccc agattccttt agaattttcg gtcctgatga aactgctagt   1320

aacagattgc aagctgcata cgaagtaaca aataagcaat gggacgctgg ttacttgtcc   1380

gaattagttg atgaacatat ggcagtaaca ggtcaagtta ccgaacaatt gagtgaacac   1440

caaatggaag gtttcttaga agcatatttg ttaacaggta gacatggtat ctggtcttca   1500

tacgaatctt ttgtccatgt aatcgattca atgttgaatc aacacgcaaa gtggttagaa   1560

gccactgtta gagaaattcc atggagaaaa cctatatcca gtatgaactt gttagtctct   1620

tcacatgtat ggagacaaga ccataatggt ttctctcacc aagatccagg tgtcacctca   1680

gtattgttga acaaaacttt caataacgac catgtaatcg gtatctattt ccctgttgat   1740

tctaacatgt tgttagctgt tggtgaaaag gtctacaagt caacaaacat gatcaacgct   1800

atcttcgcag gtaaacaacc agccgctact tggttgacat tagatgaagc aagagaagaa   1860

ttggaaaaag gtgcagccga atggaagtgg gcctctaatg ctaaaaataa cgacgaagta   1920

caagttgtct tggctggtat tggtgacgtt cctcaacaag aattaatggc tgcagccgac   1980

aaattgaaca agttaggtgt taagtttaaa gtagttaaca tcgtcgattt gttgaaattg   2040

caatctgcaa aggaaaataa cgaagccttg actgacgaag agtttactga attgtttact   2100

gctgataagc cagtcttgtt agcttatcat tcttacgcac acgatgtaag aggtttaatt   2160

ttcgacagac caaaccatga taacttcaac gttcacggtt acaaggaaca aggttcaacc   2220

actacacctt acgatatggt tagagtcaat gatatggaca gatatgaatt gacagctgaa   2280

gcattaagaa tggtcgatgc tgacaagtac gcagacgaaa ttaaaaagtt ggaagatttc   2340

agattagaag cctttcaatt cgctgttgat aaaggttatg atcatccaga ctacacagac   2400

tgggtatggc caggtgttaa aaccgataag cctggtgcag ttacagccac cgctgcaact   2460
```

gctggtgaca atgaataat 2479

<210> SEQ ID NO 57
<211> LENGTH: 825
<212> TYPE: PRT
<213> ORGANISM: Gardnerella_vaginalis

<400> SEQUENCE: 57

Met Thr Ser Pro Val Ile Gly Thr Pro Trp Lys Lys Leu Asn Ala Pro
1 5 10 15

Val Ser Glu Ala Ala Ile Glu Gly Val Asp Lys Tyr Trp Arg Val Ala
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Phe Ile Ala Glu His Gln Gln Asn Thr Val Ile Ile Met Gly Pro Gly
85 90 95

His Gly Gly Pro Ala Gly Thr Ala Gln Ser Tyr Leu Asp Gly Thr Tyr
100 105 110

Thr Glu Tyr Tyr Pro Lys Ile Thr Lys Asp Glu Ala Gly Leu Gln Lys
115 120 125

Phe Phe Arg Gln Phe Ser Tyr Pro Gly Gly Ile Pro Ser His Phe Ala
130 135 140

Pro Glu Thr Pro Gly Ser Ile His Glu Gly Gly Glu Leu Gly Tyr Ala
145 150 155 160

Leu Ser His Ala Tyr Gly Ala Val Met Asn Asn Pro Ser Leu Phe Val
165 170 175

Pro Ala Ile Val Gly Asp Gly Glu Ala Glu Thr Gly Pro Leu Ala Thr
180 185 190

Gly Trp Gln Ser Asn Lys Leu Val Asn Pro Arg Thr Asp Gly Ile Val
195 200 205

Leu Pro Ile Leu His Leu Asn Gly Tyr Lys Ile Ala Asn Pro Thr Ile
210 215 220

Leu Ser Arg Ile Ser Asp Glu Glu Leu His Glu Phe Phe His Gly Met
225 230 235 240

Gly Tyr Glu Pro Tyr Glu Phe Val Ala Gly Phe Asp Asp Glu Asp His
245 250 255

Met Ser Ile His Arg Arg Phe Ala Asp Met Phe Glu Thr Ile Phe Asp
260 265 270

Glu Ile Cys Asp Ile Lys Ala Glu Ala Gln Thr Asn Asp Val Thr Arg
275 280 285

Pro Phe Tyr Pro Met Ile Ile Phe Arg Thr Pro Lys Gly Trp Thr Cys
290 295 300

Pro Lys Phe Ile Asp Gly Lys Lys Thr Glu Gly Ser Trp Arg Ala His
305 310 315 320

Gln Val Pro Leu Ala Ser Ala Arg Asp Thr Glu Ala His Phe Glu Val
325 330 335

Leu Lys Asn Trp Leu Lys Ser Tyr Lys Pro Glu Glu Leu Phe Asn Glu
340 345 350

Asp Gly Ser Ile Lys Glu Asp Val Leu Ser Phe Met Pro Gln Gly Glu
355 360 365

-continued

```
Leu Arg Ile Gly Gln Asn Pro Asn Ala Asn Gly Gly Arg Ile Arg Glu
    370                 375                 380

Asp Leu Lys Leu Pro Asn Leu Asp Asp Tyr Glu Val Lys Glu Val Lys
385                 390                 395                 400

Glu Phe Gly His Gly Trp Gly Gln Leu Glu Ala Thr Arg Arg Leu Gly
                405                 410                 415

Val Tyr Thr Arg Asp Val Ile Lys Asn Asn Pro Asp Ser Phe Arg Ile
            420                 425                 430

Phe Gly Pro Asp Glu Thr Ala Ser Asn Arg Leu Gln Ala Ala Tyr Glu
        435                 440                 445

Val Thr Asn Lys Gln Trp Asp Ala Gly Tyr Leu Ser Glu Leu Val Asp
    450                 455                 460

Glu His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Thr Ser
545                 550                 555                 560

Val Leu Leu Asn Lys Thr Phe Asn Asn Asp His Val Ile Gly Ile Tyr
                565                 570                 575

Phe Pro Val Asp Ser Asn Met Leu Leu Ala Val Gly Glu Lys Val Tyr
            580                 585                 590

Lys Ser Thr Asn Met Ile Asn Ala Ile Phe Ala Gly Lys Gln Pro Ala
        595                 600                 605

Ala Thr Trp Leu Thr Leu Asp Glu Ala Arg Glu Glu Leu Glu Lys Gly
    610                 615                 620

Ala Ala Glu Trp Lys Trp Ala Ser Asn Ala Lys Asn Asn Asp Glu Val
625                 630                 635                 640

Gln Val Val Leu Ala Gly Ile Gly Asp Val Pro Gln Gln Glu Leu Met
                645                 650                 655

Ala Ala Ala Asp Lys Leu Asn Lys Leu Gly Val Lys Phe Lys Val Val
            660                 665                 670

Asn Ile Val Asp Leu Leu Lys Leu Gln Ser Ala Lys Glu Asn Asn Glu
        675                 680                 685

Ala Leu Thr Asp Glu Glu Phe Thr Glu Leu Phe Thr Ala Asp Lys Pro
    690                 695                 700

Val Leu Leu Ala Tyr His Ser Tyr Ala His Asp Val Arg Gly Leu Ile
705                 710                 715                 720

Phe Asp Arg Pro Asn His Asp Asn Phe Asn Val His Gly Tyr Lys Glu
                725                 730                 735

Gln Gly Ser Thr Thr Thr Pro Tyr Asp Met Val Arg Val Asn Asp Met
            740                 745                 750

Asp Arg Tyr Glu Leu Thr Ala Glu Ala Leu Arg Met Val Asp Ala Asp
        755                 760                 765

Lys Tyr Ala Asp Glu Ile Lys Lys Leu Glu Asp Phe Arg Leu Glu Ala
    770                 775                 780

Phe Gln Phe Ala Val Asp Lys Gly Tyr Asp His Pro Asp Tyr Thr Asp
```

-continued

```
785                 790                 795                 800

Trp Val Trp Pro Gly Val Lys Thr Asp Lys Pro Gly Ala Val Thr Ala
                805                 810                 815

Thr Ala Ala Thr Ala Gly Asp Asn Glu
            820                 825


<210> SEQ ID NO 58
<211> LENGTH: 2517
<212> TYPE: DNA
<213> ORGANISM: Glaciibacter_superstes

<400> SEQUENCE: 58

atgacagact ccgctacagc cccagttcct gacagaagag ccaccgcttt cgcacataga     60

gacccagcag aattagacga tggtacattg gctgcattag atgcctggtg gagaactgct    120

aactatttgt ctgttggtca aatatacttg ttggataacc cattgttaag acaacctttg    180

gaaagagaac aattaaagcc aagattgtta ggtcattggg gtactacacc tggtttgaat    240

ttcttgtacg ctcacttgaa cagagttatc agagaaagag atttgtctac tatcttcatt    300

accggtccag gtcatggtgg tcctggtatg gtcgcaaatg cctatttgga tggtacttat    360

tccgaattat acccacacgt agcaagaagt gaagacggta ttagagaatt gtttagacaa    420

ttttcattcc caggtggtat tccttctcat gcttcaccag aaacacctgg ttccatacac    480

gaaggtggtg aattgggtta tgccttaagt catgcttacg gtgccgcttt tgataatcca    540

ggtttgttag ttgcagccgt tgtcggtgac ggtgaagccg aaactggtcc tttagctaca    600

tcctggcata gtaacaagtt cttagatcca ttagctgacg gtgtagtttt gcctatcttg    660

cacttaaatg gttacaaaat cgcaaaccca acagttttgg ctagaatacc agaacatgaa    720

ttgttatcct tgatgagagg ttatggtcac accccatact tagttagtgg tggttttgat    780

ggtgaagacc ctgctgcagt acatagaaga ttcgctaaga ccttggatac tgttttgaac    840

caaatcgcag aaatcaaagc ctcagccgct gcaggtacat tggaaggtag accagcatgg    900

cctatgatta tattaagaac cccaaaaggt tggacttgtc ctgaagaaat tgatggtttg    960

ccagctgaaa actcttggag atcacatcaa gtaccattag cttctgcaag agatactcct   1020

gaacacttgg gtgttttaga cggttggttg agatcataca gaccagaaga attatttgat   1080

gccgctggtg caccaatgcc tgttgccaca gctttggcac cagatggtga attaagaatg   1140

tctgctaatc ctgtcgcaaa cggtggtatt ttgaagagag atttggtatt accagatttc   1200

agagactatg ctgttgacgt cccagtacct ggtgcaacag tcaatgaagc caccagagta   1260

ttgggtcaat ggttagctga tgttattaga gcaaacccag acacttttag aatattcggt   1320

cctgatgaaa ccgcttccaa tagattgggt gcagttttag aagtcactga taaacaatgg   1380

aacgctgaat acttgccaac agacgaacat ttggctagaa gaggtagagt tattgaaatg   1440

ttgagtgaac accaatgcca aggttggtta gaaggttatt tgttaaccgg tagacatggt   1500

ttgtttaata cttacgaagc attcgtacat atcgttggtt ctatgttcaa ccaacacgct   1560

aaatggttga aggtttcaaa agaaatccca tggagaagac ctattgcatc cttaaactac   1620

ttgttgactt ctcatgtttg gagacaagat cataacggtt tatctcacca agatccaggt   1680

tttattgacc acgtcgtaaa taagaaagct gatgttgtca gagtttattt gcctttcgac   1740

gccaacacct tgttgtctgc ttacgatcat tgtttgagat cagttgatta cgtaaacgta   1800

gttgtcgcag gtaaacaacc aacttttaac tggttgtcca tggatagagc catcgctcat   1860

atgaccagag gtttaggtat tttcgaatgg gctggaactg aagttgaagg tgaagaacca   1920
```

```
gatgttgttt tggcttgtgc tggtgacgta cctacattgg aagttttagc agccgcttct   1980

attttgagac aagctatacc agatttgaag gttagagtcg taaacgttgt tgatttgatg   2040

agattagtct ctgaaggtga acatcctcac ggcatgtcag atagagaata tgacgccgtt   2100

tttactaaag atagaccagt catattcgct tatcatggtt acccttggtt gatccacaga   2160

ttaacatata gaagaaacgg tcatgctaac ttgcacgtta gaggttacaa agaagaaggt   2220

accactacaa ccccattcga tatggtcatg ttgaacgata tcgacagata ccatttggta   2280

gttgatgtcg tagacagagt tcctggttta ggtgaaagat atgctggttt gagacaaaga   2340

atgttagatg ccagagtaag agctagagca tatacaagag aacatggtga agatatacca   2400

gaagttgcag actggacttg gacagccggt cctgaaagac aagctagaga agtcaatacc   2460

ggtgttggtc aagtcaatac tggtgctgct gctactggtg gtgacaatga atcataa      2517
```

<210> SEQ ID NO 59
<211> LENGTH: 838
<212> TYPE: PRT
<213> ORGANISM: Glaciibacter_superstes

<400> SEQUENCE: 59

```
Met Thr Asp Ser Ala Thr Ala Pro Val Pro Asp Arg Arg Ala Thr Ala
1               5                   10                  15

Phe Ala His Arg Asp Pro Ala Glu Leu Asp Asp Gly Thr Leu Ala Ala
            20                  25                  30

Leu Asp Ala Trp Trp Arg Thr Ala Asn Tyr Leu Ser Val Gly Gln Ile
        35                  40                  45

Tyr Leu Leu Asp Asn Pro Leu Leu Arg Gln Pro Leu Glu Arg Glu Gln
    50                  55                  60

Leu Lys Pro Arg Leu Leu Gly His Trp Gly Thr Thr Pro Gly Leu Asn
65                  70                  75                  80

Phe Leu Tyr Ala His Leu Asn Arg Val Ile Arg Glu Arg Asp Leu Ser
                85                  90                  95

Thr Ile Phe Ile Thr Gly Pro Gly His Gly Gly Pro Gly Met Val Ala
            100                 105                 110

Asn Ala Tyr Leu Asp Gly Thr Tyr Ser Glu Leu Tyr Pro His Val Ala
        115                 120                 125

Arg Ser Glu Asp Gly Ile Arg Glu Leu Phe Arg Gln Phe Ser Phe Pro
    130                 135                 140

Gly Gly Ile Pro Ser His Ala Ser Pro Glu Thr Pro Gly Ser Ile His
145                 150                 155                 160

Glu Gly Gly Glu Leu Gly Tyr Ala Leu Ser His Ala Tyr Gly Ala Ala
                165                 170                 175

Phe Asp Asn Pro Gly Leu Leu Val Ala Ala Val Val Gly Asp Gly Glu
            180                 185                 190

Ala Glu Thr Gly Pro Leu Ala Thr Ser Trp His Ser Asn Lys Phe Leu
        195                 200                 205

Asp Pro Leu Ala Asp Gly Val Val Leu Pro Ile Leu His Leu Asn Gly
    210                 215                 220

Tyr Lys Ile Ala Asn Pro Thr Val Leu Ala Arg Ile Pro Glu His Glu
225                 230                 235                 240

Leu Leu Ser Leu Met Arg Gly Tyr Gly His Thr Pro Tyr Leu Val Ser
                245                 250                 255

Gly Gly Phe Asp Gly Glu Asp Pro Ala Ala Val His Arg Arg Phe Ala
            260                 265                 270
```

-continued

```
Lys Thr Leu Asp Thr Val Leu Asn Gln Ile Ala Glu Ile Lys Ala Ser
        275                 280                 285

Ala Ala Ala Gly Thr Leu Glu Gly Arg Pro Ala Trp Pro Met Ile Ile
    290                 295                 300

Leu Arg Thr Pro Lys Gly Trp Thr Cys Pro Glu Glu Ile Asp Gly Leu
305                 310                 315                 320

Pro Ala Glu Asn Ser Trp Arg Ser His Gln Val Pro Leu Ala Ser Ala
                325                 330                 335

Arg Asp Thr Pro Glu His Leu Gly Val Leu Asp Gly Trp Leu Arg Ser
            340                 345                 350

Tyr Arg Pro Glu Glu Leu Phe Asp Ala Ala Gly Ala Pro Met Pro Val
        355                 360                 365

Ala Thr Ala Leu Ala Pro Asp Gly Glu Leu Arg Met Ser Ala Asn Pro
    370                 375                 380

Val Ala Asn Gly Gly Ile Leu Lys Arg Asp Leu Val Leu Pro Asp Phe
385                 390                 395                 400

Arg Asp Tyr Ala Val Asp Val Pro Val Pro Gly Ala Thr Val Asn Glu
                405                 410                 415

Ala Thr Arg Val Leu Gly Gln Trp Leu Ala Asp Val Ile Arg Ala Asn
            420                 425                 430

Pro Asp Thr Phe Arg Ile Phe Gly Pro Asp Glu Thr Ala Ser Asn Arg
        435                 440                 445

Leu Gly Ala Val Leu Glu Val Thr Asp Lys Gln Trp Asn Ala Glu Tyr
    450                 455                 460

Leu Pro Thr Asp Glu His Leu Ala Arg Arg Gly Arg Val Ile Glu Met
465                 470                 475                 480

Leu Ser Glu His Gln Cys Gln Gly Trp Leu Glu Gly Tyr Leu Leu Thr
                485                 490                 495

Gly Arg His Gly Leu Phe Asn Thr Tyr Glu Ala Phe Val His Ile Val
            500                 505                 510

Gly Ser Met Phe Asn Gln His Ala Lys Trp Leu Lys Val Ser Lys Glu
        515                 520                 525

Ile Pro Trp Arg Arg Pro Ile Ala Ser Leu Asn Tyr Leu Leu Thr Ser
    530                 535                 540

His Val Trp Arg Gln Asp His Asn Gly Leu Ser His Gln Asp Pro Gly
545                 550                 555                 560

Phe Ile Asp His Val Val Asn Lys Lys Ala Asp Val Val Arg Val Tyr
                565                 570                 575

Leu Pro Phe Asp Ala Asn Thr Leu Leu Ser Ala Tyr Asp His Cys Leu
            580                 585                 590

Arg Ser Val Asp Tyr Val Asn Val Val Val Ala Gly Lys Gln Pro Thr
        595                 600                 605

Phe Asn Trp Leu Ser Met Asp Arg Ala Ile Ala His Met Thr Arg Gly
    610                 615                 620

Leu Gly Ile Phe Glu Trp Ala Gly Thr Glu Val Glu Gly Glu Glu Pro
625                 630                 635                 640

Asp Val Val Leu Ala Cys Ala Gly Asp Val Pro Thr Leu Glu Val Leu
                645                 650                 655

Ala Ala Ala Ser Ile Leu Arg Gln Ala Ile Pro Asp Leu Lys Val Arg
            660                 665                 670

Val Val Asn Val Val Asp Leu Met Arg Leu Val Ser Glu Gly Glu His
        675                 680                 685
```

-continued

```
Pro His Gly Met Ser Asp Arg Glu Tyr Asp Ala Val Phe Thr Lys Asp
    690                 695                 700

Arg Pro Val Ile Phe Ala Tyr His Gly Tyr Pro Trp Leu Ile His Arg
705                 710                 715                 720

Leu Thr Tyr Arg Arg Asn Gly His Ala Asn Leu His Val Arg Gly Tyr
                725                 730                 735

Lys Glu Glu Gly Thr Thr Thr Thr Pro Phe Asp Met Val Met Leu Asn
            740                 745                 750

Asp Ile Asp Arg Tyr His Leu Val Val Asp Val Val Asp Arg Val Pro
        755                 760                 765

Gly Leu Gly Glu Arg Tyr Ala Gly Leu Arg Gln Arg Met Leu Asp Ala
    770                 775                 780

Arg Val Arg Ala Arg Ala Tyr Thr Arg Glu His Gly Glu Asp Ile Pro
785                 790                 795                 800

Glu Val Ala Asp Trp Thr Trp Thr Ala Gly Pro Glu Arg Gln Ala Arg
                805                 810                 815

Glu Val Asn Thr Gly Val Gly Gln Val Asn Thr Gly Ala Ala Ala Thr
            820                 825                 830

Gly Gly Asp Asn Glu Ser
        835


<210> SEQ ID NO 60
<211> LENGTH: 2379
<212> TYPE: DNA
<213> ORGANISM: Kingella_kingae

<400> SEQUENCE: 60

atgactaata agacacaatt tgacacccct gaatacttgg gtaaagtcga tgcttggtgg      60

agagccgcta actacatttc cgtcgctcaa atgtatttga aggataaccc attgttgaag     120

acacctttag tagcaaacga cgttaaagcc catccaattg gtcattgggg tactgttcct     180

ggtcaaaact tcatctatgc tcatttgaat agagcaatca acaagtatga tgttgacatg     240

ttctacatag aaggtccagg tcacggtggt caagtcatgg tatctaattc atacttagat     300

ggttcttaca ctgaaatcta cccagatatt acacaagaca ccgcaggttt gaaaaagtta     360

tgcaagatat tttctttccc tggtggtatc gcctcacatg ctgcaccaga aacacctggt     420

tctattcacg aaggtggtga attgggttat gctttatcac atgcctttgg tgctgttttg     480

gataatccaa acgttatagc cgctgcagtc atcggtgacg gtgaagcaga aacaggtcct     540

ttgtgcgccg gttggtttgg taatacttc ataaatccag taaacgatgg tgctgtttta     600

cctatcttgt acttaaatgg tggtaaaata cataacccaa caatattggc aagaaaaacc     660

gatgaagaat taaagcaata cttcaacggt atgggttggg aacctatctt cgttgatgtc     720

aataacgttg acaactacca tgaaattatg tcccaaaaag tcgatgaagc tgtagaacac     780

atcttgagta tttggcaaac tgcaagaaca caaaaggcag aagatgccac tatgccacat     840

tggcctgttt tggttgctag aataccaaaa ggttggaccg gtcctaagac ttggcacggt     900

gaaccaattg aaggtggttt tagagcacat caagttccaa tacctgcatc ttcacacgat     960

atggaaacag ctggtgaatt ggaaaagtgg ttaagatctt atagacctga agaattgttc    1020

gatgacaatg gttgtttctt agacaagtgg agagacattt ccccaaaagg tgcaaagaga    1080

atgagtgttc atcctatcac taatggtggt attaacccaa aagcattggt catgcctgat    1140

tggacacaac acgccttaga aattggtgtc ccaggttctc aagatgctca agacatggta    1200

gaatgcggta gattaatggc cgatgttgtc actgctaacc caaacaactt tagaattttc    1260
```

```
ggtcctgacg aaaccaagtc aaacagattg aaccaagtct tccaagtaac taagagacaa   1320
tggttaggta gaagagatga agcatatgac gaatggattg caccagttgg tagagtcata   1380
gattcccaat tgagtgaaca tcaagctgaa ggtttcttgg aaggttatgt tttaacaggt   1440
agacacggtt tctttgcttc ttacgaatca tttttcagag tagttgattc catgatcact   1500
caacatttca agtggttgag aaagtgtaag acacacgccg cttggagaaa tgattatcca   1560
tccttgaact tagtcgctac cagtactgta ttccaacaag atcataacgg ttacactcac   1620
caagaccctg gtttgttaac acatttggcc gaaaagaaac cagaatttgt aagagaatat   1680
ttgcctgctg attcaaacac cttaatggca gttatgtccg aagccttaac ttctagagat   1740
agaattaatt tgatcgtttc cagtaagcat ttgagaccac aatttttcaa cgctgaagaa   1800
gcaaaagaat tggttagaga aggttacaag gtcatagatt gggcttccac ctgtcatgat   1860
ggtgaaccag acgtcgtaat cgcagccgct ggtactgaac ctaatatgga agcattggca   1920
gccattagta tcttgcataa gcaattccca gaattaaaga ttagattcat aaacgttgtc   1980
gatatattga aattgagaca cccatctata gaccctagag gtttgtcaga tgaacaattt   2040
gacgctttat tcactcaaga aaagccagta gttttctgtt tccatggtta tgaaggtatg   2100
attagagatt tgtttttccc tagagcaaat cataacgtta gaatccacgg ttacagagaa   2160
aatggtgaca ttactacacc atttgacatg agagttttat cagaaatgga tagattccat   2220
gtagccaaag acgctgcaca agctgtttat ggtgacaagg cctctgaatt tgctaaaaag   2280
atgggtgaaa cagtcgcttt ccatagatca tacatcagag aacacggtac cgatattcca   2340
gaagttgccg aatggaaatg gcaacctttg gctaagtaa                          2379
```

<210> SEQ ID NO 61
<211> LENGTH: 792
<212> TYPE: PRT
<213> ORGANISM: Kingella_kingae

<400> SEQUENCE: 61

```
Met Thr Asn Lys Thr Gln Phe Asp Thr Pro Glu Tyr Leu Gly Lys Val
1               5                   10                  15

Asp Ala Trp Trp Arg Ala Ala Asn Tyr Ile Ser Val Ala Gln Met Tyr
            20                  25                  30

Leu Lys Asp Asn Pro Leu Leu Lys Thr Pro Leu Val Ala Asn Asp Val
        35                  40                  45

Lys Ala His Pro Ile Gly His Trp Gly Thr Val Pro Gly Gln Asn Phe
    50                  55                  60

Ile Tyr Ala His Leu Asn Arg Ala Ile Asn Lys Tyr Asp Val Asp Met
65                  70                  75                  80

Phe Tyr Ile Glu Gly Pro Gly His Gly Gly Gln Val Met Val Ser Asn
                85                  90                  95

Ser Tyr Leu Asp Gly Ser Tyr Thr Glu Ile Tyr Pro Asp Ile Thr Gln
            100                 105                 110

Asp Thr Ala Gly Leu Lys Lys Leu Cys Lys Ile Phe Ser Phe Pro Gly
        115                 120                 125

Gly Ile Ala Ser His Ala Ala Pro Glu Thr Pro Gly Ser Ile His Glu
    130                 135                 140

Gly Gly Glu Leu Gly Tyr Ala Leu Ser His Ala Phe Gly Ala Val Leu
145                 150                 155                 160

Asp Asn Pro Asn Val Ile Ala Ala Ala Val Ile Gly Asp Gly Glu Ala
                165                 170                 175
```

-continued

```
Glu Thr Gly Pro Leu Cys Ala Gly Trp Phe Gly Asn Thr Phe Ile Asn
            180                 185                 190

Pro Val Asn Asp Gly Ala Val Leu Pro Ile Leu Tyr Leu Asn Gly Gly
        195                 200                 205

Lys Ile His Asn Pro Thr Ile Leu Ala Arg Lys Thr Asp Glu Glu Leu
    210                 215                 220

Lys Gln Tyr Phe Asn Gly Met Gly Trp Glu Pro Ile Phe Val Asp Val
225                 230                 235                 240

Asn Asn Val Asp Asn Tyr His Glu Ile Met Ser Gln Lys Val Asp Glu
                245                 250                 255

Ala Val Glu His Ile Leu Ser Ile Trp Gln Thr Ala Arg Thr Gln Lys
            260                 265                 270

Ala Glu Asp Ala Thr Met Pro His Trp Pro Val Leu Val Ala Arg Ile
        275                 280                 285

Pro Lys Gly Trp Thr Gly Pro Lys Thr Trp His Gly Glu Pro Ile Glu
    290                 295                 300

Gly Gly Phe Arg Ala His Gln Val Pro Ile Pro Ala Ser Ser His Asp
305                 310                 315                 320

Met Glu Thr Ala Gly Glu Leu Glu Lys Trp Leu Arg Ser Tyr Arg Pro
                325                 330                 335

Glu Glu Leu Phe Asp Asp Asn Gly Cys Phe Leu Asp Lys Trp Arg Asp
            340                 345                 350

Ile Ser Pro Lys Gly Ala Lys Arg Met Ser Val His Pro Ile Thr Asn
        355                 360                 365

Gly Gly Ile Asn Pro Lys Ala Leu Val Met Pro Asp Trp Thr Gln His
    370                 375                 380

Ala Leu Glu Ile Gly Val Pro Gly Ser Gln Asp Ala Gln Asp Met Val
385                 390                 395                 400

Glu Cys Gly Arg Leu Met Ala Asp Val Val Thr Ala Asn Pro Asn Asn
                405                 410                 415

Phe Arg Ile Phe Gly Pro Asp Glu Thr Lys Ser Asn Arg Leu Asn Gln
            420                 425                 430

Val Phe Gln Val Thr Lys Arg Gln Trp Leu Gly Arg Arg Asp Glu Ala
        435                 440                 445

Tyr Asp Glu Trp Ile Ala Pro Val Gly Arg Val Ile Asp Ser Gln Leu
    450                 455                 460

Ser Glu His Gln Ala Glu Gly Phe Leu Glu Gly Tyr Val Leu Thr Gly
465                 470                 475                 480

Arg His Gly Phe Phe Ala Ser Tyr Glu Ser Phe Phe Arg Val Val Asp
                485                 490                 495

Ser Met Ile Thr Gln His Phe Lys Trp Leu Arg Lys Cys Lys Thr His
            500                 505                 510

Ala Ala Trp Arg Asn Asp Tyr Pro Ser Leu Asn Leu Val Ala Thr Ser
        515                 520                 525

Thr Val Phe Gln Gln Asp His Asn Gly Tyr Thr His Gln Asp Pro Gly
    530                 535                 540

Leu Leu Thr His Leu Ala Glu Lys Lys Pro Glu Phe Val Arg Glu Tyr
545                 550                 555                 560

Leu Pro Ala Asp Ser Asn Thr Leu Met Ala Val Met Ser Glu Ala Leu
                565                 570                 575

Thr Ser Arg Asp Arg Ile Asn Leu Ile Val Ser Ser Lys His Leu Arg
            580                 585                 590
```

```
Pro Gln Phe Phe Asn Ala Glu Glu Ala Lys Glu Leu Val Arg Glu Gly
        595                 600                 605

Tyr Lys Val Ile Asp Trp Ala Ser Thr Cys His Asp Gly Glu Pro Asp
    610                 615                 620

Val Val Ile Ala Ala Ala Gly Thr Glu Pro Asn Met Glu Ala Leu Ala
625                 630                 635                 640

Ala Ile Ser Ile Leu His Lys Gln Phe Pro Glu Leu Lys Ile Arg Phe
                645                 650                 655

Ile Asn Val Val Asp Ile Leu Lys Leu Arg His Pro Ser Ile Asp Pro
            660                 665                 670

Arg Gly Leu Ser Asp Glu Gln Phe Asp Ala Leu Phe Thr Gln Glu Lys
        675                 680                 685

Pro Val Val Phe Cys Phe His Gly Tyr Glu Gly Met Ile Arg Asp Leu
    690                 695                 700

Phe Phe Pro Arg Ala Asn His Asn Val Arg Ile His Gly Tyr Arg Glu
705                 710                 715                 720

Asn Gly Asp Ile Thr Thr Pro Phe Asp Met Arg Val Leu Ser Glu Met
                725                 730                 735

Asp Arg Phe His Val Ala Lys Asp Ala Ala Gln Ala Val Tyr Gly Asp
            740                 745                 750

Lys Ala Ser Glu Phe Ala Lys Lys Met Gly Glu Thr Val Ala Phe His
        755                 760                 765

Arg Ser Tyr Ile Arg Glu His Gly Thr Asp Ile Pro Glu Val Ala Glu
    770                 775                 780

Trp Lys Trp Gln Pro Leu Ala Lys
785                 790
```

<210> SEQ ID NO 62
<211> LENGTH: 2367
<212> TYPE: DNA
<213> ORGANISM: Lactobacillus plantarum

<400> SEQUENCE: 62

```
atgacaacag attactcatc ccctgcatac ttacaaaagg tagacaaata ctggagagcc      60

gctaactact tatccgtcgg tcaattatat ttgaaggaca acccattgtt gcaaagacct     120

ttaaaagcat ctgatgtaaa ggttcatcca ataggtcact ggggtactat cgctggtcaa     180

aacttcatct atgcacattt gaatagagtc attaacaaat acggtttgaa gatgttctac     240

gtagaaggtc ctggtcacgg tggtcaagtc atggtatcta attcatactt ggacggtaca     300

tataccgata tctatccaga aataacccaa gatgttgagg gtatgcaaaa attgtttaaa     360

caattttctt tccctggtgg tgtcgcttca catgctgcac cagaaacacc tggttccatt     420

cacgaaggtg gtgaattggg ttattccata agtcatggtg ttggtgcaat cttagataat     480

ccagacgaaa ttgccgctgt tgtcgtaggt gacggtgaat cagaaactgg tcctttggct     540

acatcttggc aatcaaccaa gtttatcaat ccaattaacg atggtgcagt tttacctata     600

ttgaatttga atggttttaa aatctctaat ccaactattt tcggtagaac atcagatgct     660

aagattaaag aatacttcga atcaatgaac tgggaaccta tcttcgtaga aggtgacgac     720

ccagaaaagg ttcatcctgc cttggctaaa gcaatggatg aagcagttga aaagattaaa     780

gccatccaaa aacacgctag agaaaataac gatgctactt taccagtctg gcctatgata     840

gtttttagag caccaaaagg ttggacaggt cctaagtcct gggatggtga caaaatcgaa     900

ggttctttta gagcacatca aattccaata cctgttgatc aaaatgacat ggaacacgcc     960
```

```
gatgctttgg ttgattggtt agaatcctat caaccaaagg aattgtttaa cgaagatggt   1020
agtttaaagg atgacataaa ggaaataata ccaacaggtg actctagaat ggcagccaat   1080
cctataacca acggtggtgt cgatccaaaa gcattgaatt tgcctaactt cagagattat   1140
gcagtagaca cttctaagga aggtgccaat gttaaacaag atatgatcgt ctggtcagat   1200
tacttgagag acgttattaa aaagaatcca gacaacttca gattgttcgg tcctgatgaa   1260
acaatgtcta acagattgta cggtgttttt gaaactacaa acagacaatg gatggaagac   1320
attcatccag attccgacca atacgaagca cctgccggta gagtattgga tgcccaatta   1380
agtgaacatc aagctgaagg ttggttggaa ggttatgttt taacaggtag acacggtttg   1440
tttgcatctt acgaagcctt cttgagagtt gtcgattcaa tgttgaccca acatttcaag   1500
tggttgagaa aggctaacga attagattgg agaaagaaat acccatcctt aaacatcata   1560
gctgcaagta ctgttttcca acaagaccat aatggttaca cccaccaaga tcctggtgca   1620
ttgactcatt tggccgaaaa gaaaccagaa tacattagag aatacttgcc tgctgacgca   1680
aataccttgt tagctgtagg tgacgttatt tttagatcac aagaaaagat caactacgta   1740
gttacttcta aacacccaag acaacaatgg ttctcaattg aagaagccaa acaattggtc   1800
gataatggtt taggtataat cgactgggct tccactgatc aaggtagtga accagatatc   1860
gtttttgccg ctgcaggtac tgaacctaca ttggaaacct tagccgctat tcaattgtta   1920
catgattctt tcccagaaat gaagatcaga ttcgttaacg tcgtagacat cttgaagtta   1980
agatccccag aaaaagatcc tagaggtttg agtgatgcag aatttgacca ttacttcaca   2040
aaggataagc cagttgtctt tgccttccac ggttacgaag atttggttag agatattttc   2100
tttgatagac ataaccacaa cttatacgtt catggttaca gagaaaacgg tgacataacc   2160
actccatttg atgttagagt catgaaccaa atggatagat tcgacttggc caagtctgct   2220
attgcagccc aacctgctat ggaaaatact ggtgctgcat ttgttcaatc aatggataac   2280
atgttagcta aacataacgc atacattaga gacgcaggta cagatttgcc agaagttaac   2340
gattggcaat ggaaaggttt aaagtaa                                        2367
```

```
<210> SEQ ID NO 63
<211> LENGTH: 788
<212> TYPE: PRT
<213> ORGANISM: Lactobacillus plantarum

<400> SEQUENCE: 63

Met Thr Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val
            100                 105                 110

Glu Gly Met Gln Lys Leu Phe Lys Gln Phe Ser Phe Pro Gly Gly Val
        115                 120                 125
```

```
Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Glu Ile Ala Ala Val Val Val Gly Asp Gly Glu Ser Glu Thr
                165                 170                 175

Gly Pro Leu Ala Thr Ser Trp Gln Ser Thr Lys Phe Ile Asn Pro Ile
            180                 185                 190

Asn Asp Gly Ala Val Leu Pro Ile Leu Asn Leu Asn Gly Phe Lys Ile
        195                 200                 205

Ser Asn Pro Thr Ile Phe Gly Arg Thr Ser Asp Ala Lys Ile Lys Glu
    210                 215                 220

Tyr Phe Glu Ser Met Asn Trp Glu Pro Ile Phe Val Glu Gly Asp Asp
225                 230                 235                 240

Pro Glu Lys Val His Pro Ala Leu Ala Lys Ala Met Asp Glu Ala Val
                245                 250                 255

Glu Lys Ile Lys Ala Ile Gln Lys His Ala Arg Glu Asn Asn Asp Ala
            260                 265                 270

Thr Leu Pro Val Trp Pro Met Ile Val Phe Arg Ala Pro Lys Gly Trp
        275                 280                 285

Thr Gly Pro Lys Ser Trp Asp Gly Asp Lys Ile Glu Gly Ser Phe Arg
    290                 295                 300

Ala His Gln Ile Pro Ile Pro Val Asp Gln Asn Asp Met Glu His Ala
305                 310                 315                 320

Asp Ala Leu Val Asp Trp Leu Glu Ser Tyr Gln Pro Lys Glu Leu Phe
                325                 330                 335

Asn Glu Asp Gly Ser Leu Lys Asp Asp Ile Lys Glu Ile Ile Pro Thr
            340                 345                 350

Gly Asp Ser Arg Met Ala Ala Asn Pro Ile Thr Asn Gly Gly Val Asp
        355                 360                 365

Pro Lys Ala Leu Asn Leu Pro Asn Phe Arg Asp Tyr Ala Val Asp Thr
    370                 375                 380

Ser Lys Glu Gly Ala Asn Val Lys Gln Asp Met Ile Val Trp Ser Asp
385                 390                 395                 400

Tyr Leu Arg Asp Val Ile Lys Lys Asn Pro Asp Asn Phe Arg Leu Phe
                405                 410                 415

Gly Pro Asp Glu Thr Met Ser Asn Arg Leu Tyr Gly Val Phe Glu Thr
            420                 425                 430

Thr Asn Arg Gln Trp Met Glu Asp Ile His Pro Asp Ser Asp Gln Tyr
        435                 440                 445

Glu Ala Pro Ala Gly Arg Val Leu Asp Ala Gln Leu Ser Glu His Gln
    450                 455                 460

Ala Glu Gly Trp Leu Glu Gly Tyr Val Leu Thr Gly Arg His Gly Leu
465                 470                 475                 480

Phe Ala Ser Tyr Glu Ala Phe Leu Arg Val Val Asp Ser Met Leu Thr
                485                 490                 495

Gln His Phe Lys Trp Leu Arg Lys Ala Asn Glu Leu Asp Trp Arg Lys
            500                 505                 510

Lys Tyr Pro Ser Leu Asn Ile Ile Ala Ala Ser Thr Val Phe Gln Gln
        515                 520                 525

Asp His Asn Gly Tyr Thr His Gln Asp Pro Gly Ala Leu Thr His Leu
    530                 535                 540
```

```
Ala Glu Lys Lys Pro Glu Tyr Ile Arg Glu Tyr Leu Pro Ala Asp Ala
545                 550                 555                 560

Asn Thr Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
            580                 585                 590

Ile Glu Glu Ala Lys Gln Leu Val Asp Asn Gly Leu Gly Ile Ile Asp
        595                 600                 605

Trp Ala Ser Thr Asp Gln Gly Ser Glu Pro Asp Ile Val Phe Ala Ala
    610                 615                 620

Ala Gly Thr Glu Pro Thr Leu Glu Thr Leu Ala Ala Ile Gln Leu Leu
625                 630                 635                 640

His Asp Ser Phe Pro Glu Met Lys Ile Arg Phe Val Asn Val Val Asp
                645                 650                 655

Ile Leu Lys Leu Arg Ser Pro Glu Lys Asp Pro Arg Gly Leu Ser Asp
            660                 665                 670

Ala Glu Phe Asp His Tyr Phe Thr Lys Asp Lys Pro Val Val Phe Ala
        675                 680                 685

Phe His Gly Tyr Glu Asp Leu Val Arg Asp Ile Phe Phe Asp Arg His
    690                 695                 700

Asn His Asn Leu Tyr Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
            740                 745                 750

Ala Phe Val Gln Ser Met Asp Asn Met Leu Ala Lys His Asn Ala Tyr
        755                 760                 765

Ile Arg Asp Ala Gly Thr Asp Leu Pro Glu Val Asn Asp Trp Gln Trp
    770                 775                 780

Lys Gly Leu Lys
785
```

<210> SEQ ID NO 64
<211> LENGTH: 2454
<212> TYPE: DNA
<213> ORGANISM: Leuconostoc_citreum

<400> SEQUENCE: 64

```
atggcagact tcgactcaaa ggaatactta gaattggtag acaaatggtg gagagcaaca      60

aactacttat ccgctggtat gattttcttg aaaagtaatc cattattttc tgttacaaac     120

acccctattc aagctgaaga tgttaaagtc aagccaattg gtcattgggg tactatatct     180

ggtcaaacat tcttgtatgc ccacgctaac agattgatta acaaatacga tttgaatatg     240

ttttacatag gtggtccagg tcatggtggt caagtaatgg ttactaacgc atacttagat     300

ggtgaatata ccgaagacta ccctgaaatt actcaagatt tggaaggcat gtctagattg     360

tttaaaagat tttctttccc aggtggtatc ggttcacata tgacagctca aacccctggt     420

tctttgcacg aaggtggtga attgggttat tccttaagtc atgccttcgg tgctgtttta     480

gataatccag accaaattgc atttgccgtt gtcggtgacg gtgaagcaga aaccggtcct     540

tccatgactt cttggcactc tacaaaattc ttgaatgcaa agaacgatgg tgccgtctta     600

ccaatcttgg acttaaatgg tttcaaaatc tctaacccta caattttctc tagaatgtcc     660

gatgaagaaa tcactaagtt tttcgaaggt ttgggttact caccaagatt cattgaaaac     720
```

```
gatgacatcc atgattatgc tgcataccac gaattggccg ctaaagtttt agatcaagct    780
atcgaagaca ttcaagctat acaaaaagat gcaagagaaa acggtaaata cgaagacggt    840
acaattccag catggcctgt cattatagcc agattgccaa agggttgggg tggtcctact    900
catgatgaag acggtaaccc aatcgaaaat tcttttagag cacatcaagt accattgcct    960
ttagcacaaa ataagttgga aactttgtct caattcgaag attggatgaa ctcttacaag   1020
cctgaagaat tgtttaatgc agatggttcc ttgaaagacg aattaaaggc tatagcacca   1080
aaaggtgaca agagaatgag tgcaaatcct atcgccaacg gtggtagaag aagaggtgaa   1140
gaagctactg atttgacatt accagactgg agacaattca caaacgatat aaccaacgaa   1200
aacagaggtc atgaattgcc taaggttact caaaacatgg atatgactac attgtctaac   1260
tatttggaag aagtcgctaa gttaaaccca acatcattca gagtatttgg tcctgatgaa   1320
actatgtcaa acagattgtg gtccttgttt aataccacta acagacaatg gatggaagaa   1380
gtaaaagaac caaatgatca atacgttggt cctgaaggta gaatcattga cagtcaatta   1440
tctgaacatc aagccgaagg ttggttggaa ggttacactt tgacaggtag agtaggtata   1500
ttcgcttcat acgaatcctt tttgagagta gttgacacta tggttactca acatttcaag   1560
tggttgagac acgcttctga acaagcatgg agaaacgatt acccatcctt gaacttaatt   1620
gccaccagta ctgctttcca acaagatcat aatggttaca cacaccaaga cccaggcatg   1680
ttgacccatt tggctgaaaa gaaatctaac ttcattagag aatatttgcc tgcagatggt   1740
aactccttgt tagccgttca agacagagct tttagtgaaa gacacaaggt caatttgata   1800
atcgcatcta agcaaccaag acaacaatgg ttcacagcag atgaagccga cgaattggct   1860
aacgaaggtt tgaagatcat cgattgggct tcaacagcac catccggtga cgttgacatt   1920
acctttgcat cttcaggtac agaacctacc atagaaactt tggcagcctt gtggttaatc   1980
aatcaagcat ttccagaggt taagtttaga tacgtcaacg tcgtagaatt gttgagattg   2040
caaaagaaat ctgaatctca tatgaacgat gaaagagaat tatccgacgc cgagtttaat   2100
aagtttttcc aagctgataa gcctgttatc ttcggttttc atgcttacga agacttaatc   2160
gaatcatttt tctttgaaag aaaattcaag ggtgacgtct atgtacacgg ttacagagaa   2220
gatggtgaca ttacaaccac ttacgatatg agagtttact ctaaattgga cagatttcat   2280
caagcaaagg aagctgcaga aatcttaagt gccaattcta ctattgatca agccgctgca   2340
gacacattca tcgaaaagat ggatgccacc ttggctaagc attttgaagt tactagaaat   2400
gaaggtagag atattgaaga gtttactgac tggaactggt cagctttaaa ataa         2454
```

<210> SEQ ID NO 65
<211> LENGTH: 817
<212> TYPE: PRT
<213> ORGANISM: Leuconostoc_citreum

<400> SEQUENCE: 65

```
Met Ala Asp Phe Asp Ser Lys Glu Tyr Leu Glu Leu Val Asp Lys Trp
1               5                   10                  15

Trp Arg Ala Thr Asn Tyr Leu Ser Ala Gly Met Ile Phe Leu Lys Ser
            20                  25                  30

Asn Pro Leu Phe Ser Val Thr Asn Thr Pro Ile Gln Ala Glu Asp Val
        35                  40                  45

Lys Val Lys Pro Ile Gly His Trp Gly Thr Ile Ser Gly Gln Thr Phe
    50                  55                  60
```

```
Leu Tyr Ala His Ala Asn Arg Leu Ile Asn Lys Tyr Asp Leu Asn Met
65                  70                  75                  80

Phe Tyr Ile Gly Gly Pro Gly His Gly Gly Gln Val Met Val Thr Asn
                85                  90                  95

Ala Tyr Leu Asp Gly Glu Tyr Thr Glu Asp Tyr Pro Glu Ile Thr Gln
            100                 105                 110

Asp Leu Glu Gly Met Ser Arg Leu Phe Lys Arg Phe Ser Phe Pro Gly
        115                 120                 125

Gly Ile Gly Ser His Met Thr Ala Gln Thr Pro Gly Ser Leu His Glu
    130                 135                 140

Gly Gly Glu Leu Gly Tyr Ser Leu Ser His Ala Phe Gly Ala Val Leu
145                 150                 155                 160

Asp Asn Pro Asp Gln Ile Ala Phe Ala Val Val Gly Asp Gly Glu Ala
                165                 170                 175

Glu Thr Gly Pro Ser Met Thr Ser Trp His Ser Thr Lys Phe Leu Asn
            180                 185                 190

Ala Lys Asn Asp Gly Ala Val Leu Pro Ile Leu Asp Leu Asn Gly Phe
        195                 200                 205

Lys Ile Ser Asn Pro Thr Ile Phe Ser Arg Met Ser Asp Glu Glu Ile
    210                 215                 220

Thr Lys Phe Phe Glu Gly Leu Gly Tyr Ser Pro Arg Phe Ile Glu Asn
225                 230                 235                 240

Asp Asp Ile His Asp Tyr Ala Ala Tyr His Glu Leu Ala Ala Lys Val
                245                 250                 255

Leu Asp Gln Ala Ile Glu Asp Ile Gln Ala Ile Gln Lys Asp Ala Arg
            260                 265                 270

Glu Asn Gly Lys Tyr Glu Asp Gly Thr Ile Pro Ala Trp Pro Val Ile
        275                 280                 285

Ile Ala Arg Leu Pro Lys Gly Trp Gly Gly Pro Thr His Asp Glu Asp
    290                 295                 300

Gly Asn Pro Ile Glu Asn Ser Phe Arg Ala His Gln Val Pro Leu Pro
305                 310                 315                 320

Leu Ala Gln Asn Lys Leu Glu Thr Leu Ser Gln Phe Glu Asp Trp Met
                325                 330                 335

Asn Ser Tyr Lys Pro Glu Glu Leu Phe Asn Ala Asp Gly Ser Leu Lys
            340                 345                 350

Asp Glu Leu Lys Ala Ile Ala Pro Lys Gly Asp Lys Arg Met Ser Ala
        355                 360                 365

Asn Pro Ile Ala Asn Gly Gly Arg Arg Arg Gly Glu Glu Ala Thr Asp
    370                 375                 380

Leu Thr Leu Pro Asp Trp Arg Gln Phe Thr Asn Asp Ile Thr Asn Glu
385                 390                 395                 400

Asn Arg Gly His Glu Leu Pro Lys Val Thr Gln Asn Met Asp Met Thr
                405                 410                 415

Thr Leu Ser Asn Tyr Leu Glu Glu Val Ala Lys Leu Asn Pro Thr Ser
            420                 425                 430

Phe Arg Val Phe Gly Pro Asp Glu Thr Met Ser Asn Arg Leu Trp Ser
        435                 440                 445

Leu Phe Asn Thr Thr Asn Arg Gln Trp Met Glu Glu Val Lys Glu Pro
    450                 455                 460

Asn Asp Gln Tyr Val Gly Pro Glu Gly Arg Ile Ile Asp Ser Gln Leu
465                 470                 475                 480

Ser Glu His Gln Ala Glu Gly Trp Leu Glu Gly Tyr Thr Leu Thr Gly
```

```
                485                 490                 495

Arg Val Gly Ile Phe Ala Ser Tyr Glu Ser Phe Leu Arg Val Val Asp
            500                 505                 510

Thr Met Val Thr Gln His Phe Lys Trp Leu Arg His Ala Ser Glu Gln
        515                 520                 525

Ala Trp Arg Asn Asp Tyr Pro Ser Leu Asn Leu Ile Ala Thr Ser Thr
    530                 535                 540

Ala Phe Gln Gln Asp His Asn Gly Tyr Thr His Gln Asp Pro Gly Met
545                 550                 555                 560

Leu Thr His Leu Ala Glu Lys Lys Ser Asn Phe Ile Arg Glu Tyr Leu
                565                 570                 575

Pro Ala Asp Gly Asn Ser Leu Leu Ala Val Gln Asp Arg Ala Phe Ser
            580                 585                 590

Glu Arg His Lys Val Asn Leu Ile Ile Ala Ser Lys Gln Pro Arg Gln
        595                 600                 605

Gln Trp Phe Thr Ala Asp Glu Ala Asp Glu Leu Ala Asn Glu Gly Leu
    610                 615                 620

Lys Ile Ile Asp Trp Ala Ser Thr Ala Pro Ser Gly Asp Val Asp Ile
625                 630                 635                 640

Thr Phe Ala Ser Ser Gly Thr Glu Pro Thr Ile Glu Thr Leu Ala Ala
                645                 650                 655

Leu Trp Leu Ile Asn Gln Ala Phe Pro Glu Val Lys Phe Arg Tyr Val
            660                 665                 670

Asn Val Val Glu Leu Leu Arg Leu Gln Lys Lys Ser Glu Ser His Met
        675                 680                 685

Asn Asp Glu Arg Glu Leu Ser Asp Ala Glu Phe Asn Lys Phe Phe Gln
    690                 695                 700

Ala Asp Lys Pro Val Ile Phe Gly Phe His Ala Tyr Glu Asp Leu Ile
705                 710                 715                 720

Glu Ser Phe Phe Phe Glu Arg Lys Phe Lys Gly Asp Val Tyr Val His
                725                 730                 735

Gly Tyr Arg Glu Asp Gly Asp Ile Thr Thr Thr Tyr Asp Met Arg Val
            740                 745                 750

Tyr Ser Lys Leu Asp Arg Phe His Gln Ala Lys Glu Ala Ala Glu Ile
        755                 760                 765

Leu Ser Ala Asn Ser Thr Ile Asp Gln Ala Ala Ala Asp Thr Phe Ile
    770                 775                 780

Glu Lys Met Asp Ala Thr Leu Ala Lys His Phe Glu Val Thr Arg Asn
785                 790                 795                 800

Glu Gly Arg Asp Ile Glu Glu Phe Thr Asp Trp Asn Trp Ser Ala Leu
                805                 810                 815

Lys
```

<210> SEQ ID NO 66
<211> LENGTH: 2475
<212> TYPE: DNA
<213> ORGANISM: Metascardovia_criceti

<400> SEQUENCE: 66

```
atgacatccc cagttattgg taccccatgg agaaagttgg acgcccctgt atccgaagaa     60

gcattagaag gtgtagacaa gtattggaga gcttccaact atttgagtat aggtcaaatc    120

tacttgagat caaacccatt gatgaaggaa cctttcacaa gagaagatgt caagcataga    180

ttagtaggtc actggggtac tacaccaggt ttgaactttt taataggtca tatcaacaga    240
```

ttgatcgcag atcacggtca aaacactgtt attatcatgg gtccaggtca tggtggtcct 300
gctggtacat cccaaagtta tttggacggt acctactctg aatacttccc agaaatcaca 360
aaggatgaag caggtttgca aaagtttttc agacaattct cttacccagg tggtatccct 420
tcacattttg caccagaaac ccctggttca attcacgaag gtggtgaatt gggttatgct 480
ttatctcatg cctacggtgc tgttatgaat aacccatcat tatttgtacc tgctattgtt 540
ggtgacggtg aagctgaaac aggtccatta gcaaccggtt ggcaatctaa caaattggtt 600
aatccaagaa ccgatggtat agtcttgcct atcttgcatt tgaacggtta taagattgcc 660
aatccaacta tattggctag aatctctgat gaagaattgc atgaattttt ccacggtatg 720
ggttatgaac cttacgaatt tgttgctggt ttcgatgacg aagacgcaat gtcaattcac 780
agaagatttg ctgatttgtt cgaaacagtt ttcgacgaaa tctgtgatat caaggctacc 840
gcacaaacta acgatgttga cagaccattc taccctatga tcatttttag aactccaaag 900
ggttggacat gccctaagtt cattgatggt aaaaagacag aaggttcttg gagatcacat 960
caagtaccat tggcctccgc tagagatacc gaagaacact ttgaagtttt gaaaaattgg 1020
ttggaaagtt acaagcctga agaattattc actgaagatg gtgccgtcag accagaagta 1080
acagctttta tgcctgaggg tgaattgaga ataggtgaaa atccaaacgc caatggtggt 1140
agaatcagag aagaattgga cttacctgct ttggaagatt acgaagtaac tgaagttaaa 1200
gaatttggtc atggttgggg tcaattggaa gcaaccagaa agttgggtga atacactaga 1260
gacataatca agagaaaccc agattccttt agaattttcg gtcctgatga aaccgctagt 1320
aatagattgc aagctgcata tgaagtcact aacaaacaat gggacaatgg ttacttgtct 1380
gaattagttg atgaacatat ggcagttact ggtcaagtca cagaacaatt atcagaacac 1440
caaatggaag gtttcttgga agcttatttg ttaacaggta gacatggtat ttggtcttca 1500
tacgaatcct tcgtccatgt aatcgatagt atgttgaacc aacacgctaa atggttagaa 1560
gcaactgtta gagaaatccc atggagaaag cctatttcca gtatgaactt gttagtatct 1620
tcacatgttt ggagacaaga tcataatggt tttcccacc aagacccagg tgttatcgat 1680
atattgttga acaaaaactt caacaacgac cacgttgtcg gtatctattt ccctgtagat 1740
tctaacatgt tgttagccgt ttccgaaaag gcttacaaga gtacaaacat gatcaacgca 1800
ataatcgccg gtaaacaacc agccgctaca tggttgacct tagatgaagc aagagaagaa 1860
ttagccaaag gtgcagccga atggaagtgg gcttctaacg cagaaggtga cgacgttgat 1920
attgtattgg cttcagttgg tgacgtccct actcaagaat tgatggctgc agccgacaaa 1980
ttaaagggtt acggtataaa atacaagttc gttaacgtag ttgatttgtt atctatccaa 2040
aacgcatcag aaaatgacca agccttgtct gatgaagagt ttactgaatt gtttactgca 2100
gataaaccag tcttgatggc ctatcatgca tacgccagag aagtaagatc cttaatttgg 2160
gacagaccaa atcatgataa cttcaatgtt cacggttatg aagaacaagg tagtaccact 2220
acaccttttg acatggttag agtcaacaac atagatagat acgaattgac tgctgaagca 2280
ttaagagccg ttgatgctga caaattcgct gacgaaatag aaaagttgga agcttttaga 2340
actgaagcat ttcaattcgc cgttgataat ggttatgatc atccagacta cacagattgg 2400
gtctggtctg gtgtccaaac tgaaaagcca ggtgctgtat ctgccactgc tgccactgcc 2460
ggtgacaacg aataa 2475

<210> SEQ ID NO 67

<211> LENGTH: 824
<212> TYPE: PRT
<213> ORGANISM: Metascardovia_criceti

<400> SEQUENCE: 67

Met Thr Ser Pro Val Ile Gly Thr Pro Trp Arg Lys Leu Asp Ala Pro
1 5 10 15

Val Ser Glu Glu Ala Leu Glu Gly Val Asp Lys Tyr Trp Arg Ala Ser
20 25 30

Asn Tyr Leu Ser Ile Gly Gln Ile Tyr Leu Arg Ser Asn Pro Leu Met
35 40 45

Lys Glu Pro Phe Thr Arg Glu Asp Val Lys His Arg Leu Val Gly His
50 55 60

Trp Gly Thr Thr Pro Gly Leu Asn Phe Leu Ile Gly His Ile Asn Arg
65 70 75 80

Leu Ile Ala Asp His Gly Gln Asn Thr Val Ile Ile Met Gly Pro Gly
85 90 95

His Gly Gly Pro Ala Gly Thr Ser Gln Ser Tyr Leu Asp Gly Thr Tyr
100 105 110

Ser Glu Tyr Phe Pro Glu Ile Thr Lys Asp Glu Ala Gly Leu Gln Lys
115 120 125

Phe Phe Arg Gln Phe Ser Tyr Pro Gly Gly Ile Pro Ser His Phe Ala
130 135 140

Pro Glu Thr Pro Gly Ser Ile His Glu Gly Gly Glu Leu Gly Tyr Ala
145 150 155 160

Leu Ser His Ala Tyr Gly Ala Val Met Asn Asn Pro Ser Leu Phe Val
165 170 175

Pro Ala Ile Val Gly Asp Gly Glu Ala Glu Thr Gly Pro Leu Ala Thr
180 185 190

Gly Trp Gln Ser Asn Lys Leu Val Asn Pro Arg Thr Asp Gly Ile Val
195 200 205

Leu Pro Ile Leu His Leu Asn Gly Tyr Lys Ile Ala Asn Pro Thr Ile
210 215 220

Leu Ala Arg Ile Ser Asp Glu Glu Leu His Glu Phe Phe His Gly Met
225 230 235 240

Gly Tyr Glu Pro Tyr Glu Phe Val Ala Gly Phe Asp Asp Glu Asp Ala
245 250 255

Met Ser Ile His Arg Arg Phe Ala Asp Leu Phe Glu Thr Val Phe Asp
260 265 270

Glu Ile Cys Asp Ile Lys Ala Thr Ala Gln Thr Asn Asp Val Asp Arg
275 280 285

Pro Phe Tyr Pro Met Ile Ile Phe Arg Thr Pro Lys Gly Trp Thr Cys
290 295 300

Pro Lys Phe Ile Asp Gly Lys Lys Thr Glu Gly Ser Trp Arg Ser His
305 310 315 320

Gln Val Pro Leu Ala Ser Ala Arg Asp Thr Glu Glu His Phe Glu Val
325 330 335

Leu Lys Asn Trp Leu Glu Ser Tyr Lys Pro Glu Glu Leu Phe Thr Glu
340 345 350

Asp Gly Ala Val Arg Pro Glu Val Thr Ala Phe Met Pro Glu Gly Glu
355 360 365

Leu Arg Ile Gly Glu Asn Pro Asn Ala Asn Gly Gly Arg Ile Arg Glu
370 375 380

Glu Leu Asp Leu Pro Ala Leu Glu Asp Tyr Glu Val Thr Glu Val Lys

-continued

```
385                 390                 395                 400

Glu Phe Gly His Gly Trp Gly Gln Leu Glu Ala Thr Arg Lys Leu Gly
                405                 410                 415

Glu Tyr Thr Arg Asp Ile Ile Lys Arg Asn Pro Asp Ser Phe Arg Ile
            420                 425                 430

Phe Gly Pro Asp Glu Thr Ala Ser Asn Arg Leu Gln Ala Ala Tyr Glu
        435                 440                 445

Val Thr Asn Lys Gln Trp Asp Asn Gly Tyr Leu Ser Glu Leu Val Asp
    450                 455                 460

Glu His Met Ala Val Thr Gly Gln Val Thr Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Met Asn Leu Leu Val Ser Ser His Val Trp
    530                 535                 540

Arg Gln Asp His Asn Gly Phe Ser His Gln Asp Pro Gly Val Ile Asp
545                 550                 555                 560

Ile Leu Leu Asn Lys Asn Phe Asn Asn Asp His Val Val Gly Ile Tyr
                565                 570                 575

Phe Pro Val Asp Ser Asn Met Leu Leu Ala Val Ser Glu Lys Ala Tyr
            580                 585                 590

Lys Ser Thr Asn Met Ile Asn Ala Ile Ile Ala Gly Lys Gln Pro Ala
        595                 600                 605

Ala Thr Trp Leu Thr Leu Asp Glu Ala Arg Glu Glu Leu Ala Lys Gly
    610                 615                 620

Ala Ala Glu Trp Lys Trp Ala Ser Asn Ala Glu Gly Asp Asp Val Asp
625                 630                 635                 640

Ile Val Leu Ala Ser Val Gly Asp Val Pro Thr Gln Glu Leu Met Ala
                645                 650                 655

Ala Ala Asp Lys Leu Lys Gly Tyr Gly Ile Lys Tyr Lys Phe Val Asn
            660                 665                 670

Val Val Asp Leu Leu Ser Ile Gln Asn Ala Ser Glu Asn Asp Gln Ala
        675                 680                 685

Leu Ser Asp Glu Glu Phe Thr Glu Leu Phe Thr Ala Asp Lys Pro Val
    690                 695                 700

Leu Met Ala Tyr His Ala Tyr Ala Arg Glu Val Arg Ser Leu Ile Trp
705                 710                 715                 720

Asp Arg Pro Asn His Asp Asn Phe Asn Val His Gly Tyr Glu Glu Gln
                725                 730                 735

Gly Ser Thr Thr Thr Pro Phe Asp Met Val Arg Val Asn Asn Ile Asp
            740                 745                 750

Arg Tyr Glu Leu Thr Ala Glu Ala Leu Arg Ala Val Asp Ala Asp Lys
        755                 760                 765

Phe Ala Asp Glu Ile Glu Lys Leu Glu Ala Phe Arg Thr Glu Ala Phe
    770                 775                 780

Gln Phe Ala Val Asp Asn Gly Tyr Asp His Pro Asp Tyr Thr Asp Trp
785                 790                 795                 800

Val Trp Ser Gly Val Gln Thr Glu Lys Pro Gly Ala Val Ser Ala Thr
                805                 810                 815
```

Ala Ala Thr Ala Gly Asp Asn Glu
820

<210> SEQ ID NO 68
<211> LENGTH: 2385
<212> TYPE: DNA
<213> ORGANISM: Oenococcus oeni

<400> SEQUENCE: 68
atgactatca actacgattc aaaagactac ttaaaatacg tcgatgctta ctggagagcc 60
gctaactact tatccgtcgg tcaattgttc ttgagaaaca acccattgtt gaaggatgaa 120
ttacaatcta aggacgtcaa aatcaagcca attggtcatt ggggtactgt agctcctcaa 180
aactttatct atgcacactt gaatagagcc attttgaaat atgatttgaa tatgttctac 240
attgaaggta gtggtcatgg tggtcaagtt atggtctcta actcatactt ggatggttct 300
tataccgaaa cttacccaaa agttacacaa gatattcagg gtatgcaaag attgtttaaa 360
caattttcat tccctggtgg tatagcttcc catgctgcac cagaaacccc tggttctatc 420
cacgaaggtg gtgaattggg ttattccatt agtcatggtg ttggtgcaat attagataat 480
ccagacgtca ttgccgctgt agaaataggt gacggtgaat ctgaaacagg tcctttggca 540
gcctcttggt tctcagataa attcataaac ccaatccatg acggtgctgt tttacctatc 600
gtccaaatta atggttttaa gatctcaaac ccaacaatat tgtccagaat gagtgataga 660
gacttaacca actactacca tggtatgggt tgggaacctt tgtttgttga aactgatggt 720
tccgacaact tcaaagttca cgcagaaatg gcagatgccg ttgataaagc catcgaaaag 780
attaaagcta tccaaaagaa tgcaagaaac aacaacgatg acagtttgcc aatatggcct 840
atgatcgttt taagagcacc aaaaggttgg acaggtccta aaaaggattt ggacggtaac 900
ccaatcgaaa attcttttag agcacatcaa gtaccaattc ctgttgatgc aaaccatttg 960
gaacacaagg atatgttgat cgactggatg aagagttaca agcctgaaga attgttcaac 1020
gaagatggtt ctttaaagga aatcgtaaag gttaaccaac caaaaggtca aagaagaatg 1080
gctatgaacc ctataacaaa tggtggtatc aagccaagaa ccttgaacat gcctgatatg 1140
gaaagatttg cattccctaa aaattctttg aagaacaata agaaacctgg tatggatttg 1200
caagttgtct ccacttttat agctgaaatt attaagaaaa atccaatcaa tttcagacaa 1260
ttcggtcctg atgaaactat gtcaaacaga ttgtgggatg agtttaaagt aacaaacaga 1320
caatggatgc aagccgttca tgaaccaaat gatcaataca tggctcacag tggtagaatt 1380
ttggatgccc aattatctga acatcaagct gaaggttgga tggaaggtta tgttttgaca 1440
ggtagacacg cctttttcgc ttcatacgaa gcctttacta gaatcatcga ttccatgttg 1500
acacaatact acaagtggtt gagaaaggcc gttgaacaag attggagaca tgactatcca 1560
agtttaaacg tcattaatgc atctcacgcc ttccaacaag atcataatgg ttacacccac 1620
caagacccag gcatgttaac tcatatggct gaaaagggtc acgaatttgt taacgaattt 1680
ttgcctgctg atgcaaactc attgttagca gtcatgaata agtctttgca agtaagaaac 1740
aagattaata tcatcgtcgc atcaaagcat ccaagaactc aatggtttac aatagatgaa 1800
gccaaggaat tggtagacaa cggtttaggt attataccat gggcttccaa tgatgacggt 1860
gttgaacctg atgtagtttt tgctgcaggt ggtacagaag ctaccatgga atctttggcc 1920
gctatttcat tgttacatga atccttccca gaattaaagt ttagattcat taacgttatt 1980
gatttgttaa agttgagaaa gaaaggtgac aatgatgact atagaggttt gtcagatttg 2040

```
gaatttgacc attacttcac tagagaaaaa ccagtcgttt tctctttcca cggtttcgaa   2100

tctttggcta gagatttgtt ttatgacaga cataaccaca atgtcatttt tcatggttac   2160

agagaaaacg gtgacataac tacacctttt gacatgagag tattgaatca tttggataga   2220

ttccacttag ctaaagacgc aattaacgcc accaagtatg ctgatgttgc aggtcaattt   2280

gaccaaagaa tggatgacat gttagccaaa catactgctt acatttgtga tcaaggtacc   2340

gacttgccag aagttacttc ttggcaatgg caagatatta agtaa                    2385


<210> SEQ ID NO 69
<211> LENGTH: 794
<212> TYPE: PRT
<213> ORGANISM: Oenococcus oeni

<400> SEQUENCE: 69

Met Thr Ile Asn Tyr Asp Ser Lys Asp Tyr Leu Lys Tyr Val Asp Ala
1               5                   10                  15

Tyr Trp Arg Ala Ala Asn Tyr Leu Ser Val Gly Gln Leu Phe Leu Arg
            20                  25                  30

Asn Asn Pro Leu Leu Lys Asp Glu Leu Gln Ser Lys Asp Val Lys Ile
        35                  40                  45

Lys Pro Ile Gly His Trp Gly Thr Val Ala Pro Gln Asn Phe Ile Tyr
    50                  55                  60

Ala His Leu Asn Arg Ala Ile Leu Lys Tyr Asp Leu Asn Met Phe Tyr
65                  70                  75                  80

Ile Glu Gly Ser Gly His Gly Gly Gln Val Met Val Ser Asn Ser Tyr
                85                  90                  95

Leu Asp Gly Ser Tyr Thr Glu Thr Tyr Pro Lys Val Thr Gln Asp Ile
            100                 105                 110

Gln Gly Met Gln Arg Leu Phe Lys Gln Phe Ser Phe Pro Gly Gly Ile
        115                 120                 125

Ala Ser His Ala Ala Pro Glu Thr Pro Gly Ser Ile His Glu Gly Gly
    130                 135                 140

Glu Leu Gly Tyr Ser Ile Ser His Gly Val Gly Ala Ile Leu Asp Asn
145                 150                 155                 160

Pro Asp Val Ile Ala Ala Val Glu Ile Gly Asp Gly Glu Ser Glu Thr
                165                 170                 175

Gly Pro Leu Ala Ala Ser Trp Phe Ser Asp Lys Phe Ile Asn Pro Ile
            180                 185                 190

His Asp Gly Ala Val Leu Pro Ile Val Gln Ile Asn Gly Phe Lys Ile
        195                 200                 205

Ser Asn Pro Thr Ile Leu Ser Arg Met Ser Asp Arg Asp Leu Thr Asn
    210                 215                 220

Tyr Tyr His Gly Met Gly Trp Glu Pro Leu Phe Val Glu Thr Asp Gly
225                 230                 235                 240

Ser Asp Asn Phe Lys Val His Ala Glu Met Ala Asp Ala Val Asp Lys
                245                 250                 255

Ala Ile Glu Lys Ile Lys Ala Ile Gln Lys Asn Ala Arg Asn Asn Asn
            260                 265                 270

Asp Asp Ser Leu Pro Ile Trp Pro Met Ile Val Leu Arg Ala Pro Lys
        275                 280                 285

Gly Trp Thr Gly Pro Lys Lys Asp Leu Asp Gly Asn Pro Ile Glu Asn
    290                 295                 300

Ser Phe Arg Ala His Gln Val Pro Ile Pro Val Asp Ala Asn His Leu
```

-continued

```
305                 310                 315                 320

Glu His Lys Asp Met Leu Ile Asp Trp Met Lys Ser Tyr Lys Pro Glu
                325                 330                 335

Glu Leu Phe Asn Glu Asp Gly Ser Leu Lys Glu Ile Val Lys Val Asn
            340                 345                 350

Gln Pro Lys Gly Gln Arg Arg Met Ala Met Asn Pro Ile Thr Asn Gly
        355                 360                 365

Gly Ile Lys Pro Arg Thr Leu Asn Met Pro Asp Met Glu Arg Phe Ala
    370                 375                 380

Phe Pro Lys Asn Ser Leu Lys Asn Asn Lys Lys Pro Gly Met Asp Leu
385                 390                 395                 400

Gln Val Val Ser Thr Phe Ile Ala Glu Ile Ile Lys Lys Asn Pro Ile
                405                 410                 415

Asn Phe Arg Gln Phe Gly Pro Asp Glu Thr Met Ser Asn Arg Leu Trp
            420                 425                 430

Asp Glu Phe Lys Val Thr Asn Arg Gln Trp Met Gln Ala Val His Glu
        435                 440                 445

Pro Asn Asp Gln Tyr Met Ala His Ser Gly Arg Ile Leu Asp Ala Gln
    450                 455                 460

Leu Ser Glu His Gln Ala Glu Gly Trp Met Glu Gly Tyr Val Leu Thr
465                 470                 475                 480

Gly Arg His Ala Phe Phe Ala Ser Tyr Glu Ala Phe Thr Arg Ile Ile
                485                 490                 495

Asp Ser Met Leu Thr Gln Tyr Tyr Lys Trp Leu Arg Lys Ala Val Glu
            500                 505                 510

Gln Asp Trp Arg His Asp Tyr Pro Ser Leu Asn Val Ile Asn Ala Ser
        515                 520                 525

His Ala Phe Gln Gln Asp His Asn Gly Tyr Thr His Gln Asp Pro Gly
    530                 535                 540

Met Leu Thr His Met Ala Glu Lys Gly His Glu Phe Val Asn Glu Phe
545                 550                 555                 560

Leu Pro Ala Asp Ala Asn Ser Leu Leu Ala Val Met Asn Lys Ser Leu
                565                 570                 575

Gln Val Arg Asn Lys Ile Asn Ile Ile Val Ala Ser Lys His Pro Arg
            580                 585                 590

Thr Gln Trp Phe Thr Ile Asp Glu Ala Lys Glu Leu Val Asp Asn Gly
        595                 600                 605

Leu Gly Ile Ile Pro Trp Ala Ser Asn Asp Asp Gly Val Glu Pro Asp
    610                 615                 620

Val Val Phe Ala Ala Gly Gly Thr Glu Ala Thr Met Glu Ser Leu Ala
625                 630                 635                 640

Ala Ile Ser Leu Leu His Glu Ser Phe Pro Glu Leu Lys Phe Arg Phe
                645                 650                 655

Ile Asn Val Ile Asp Leu Leu Lys Leu Arg Lys Lys Gly Asp Asn Asp
            660                 665                 670

Asp Tyr Arg Gly Leu Ser Asp Leu Glu Phe Asp His Tyr Phe Thr Arg
        675                 680                 685

Glu Lys Pro Val Val Phe Ser Phe His Gly Phe Glu Ser Leu Ala Arg
    690                 695                 700

Asp Leu Phe Tyr Asp Arg His Asn His Asn Val Ile Phe His Gly Tyr
705                 710                 715                 720

Arg Glu Asn Gly Asp Ile Thr Thr Pro Phe Asp Met Arg Val Leu Asn
                725                 730                 735
```

```
His Leu Asp Arg Phe His Leu Ala Lys Asp Ala Ile Asn Ala Thr Lys
            740                 745                 750

Tyr Ala Asp Val Ala Gly Gln Phe Asp Gln Arg Met Asp Asp Met Leu
        755                 760                 765

Ala Lys His Thr Ala Tyr Ile Cys Asp Gln Gly Thr Asp Leu Pro Glu
    770                 775                 780

Val Thr Ser Trp Gln Trp Gln Asp Ile Lys
785                 790


<210> SEQ ID NO 70
<211> LENGTH: 2598
<212> TYPE: DNA
<213> ORGANISM: Rhodosporidium toruloides

<400> SEQUENCE: 70

atggctgaca acgccgacgc tccaccacct ccaatagtcc cttcacaata cgctcaacat      60

ccagacgctc cattatcctc attaccagtt caattggacc cttctcaata tacagctaaa     120

tacccagcaa agcatttgga tgccattgtc gctaattgga gattgtcctg ttatttgggt     180

gctagtcaaa ttttcttgca atctaacgca atcttgtcaa gaaaattgac taaggatgac     240

gtaaaaccaa gaagagcaca tacaaatttg gctggtgaca tccaaggtgg tttgtcttta     300

gcctacgttc acacccaagc attgatcaga agaaaaggtg acgaagaagg tgctgaacca     360

aagatgattt tcgtcactgg tccaggtcat ggtgcccctg ctatattgtc tccattgtac     420

atcgaaggtg ctatctcaaa gttctaccca caatacccttt tgaacgaaca aggtttagaa     480

aagttcgtta agtacttctc ctggccaggt ggtttcccta gtcatgtcaa cgctgaaaca     540

ccaggttgca tacacgaagg tggtgaattg ggttatgcct taggtgtagc ttacggttcc     600

gttatggaca gacctgaaca aatcagtgtt gtcgtagttg gtgacggtga atctgaaact     660

ggtccaactg caacagcctg gcattcacac aaatggttag atcctgcaga atccggtgcc     720

gttttgccaa tcttgcatgt caacggtttt aagatctctg aaagaactat cccaggtaca     780

atggataacg ttgaattgtc tttgttgtac tcaggttacg gttaccaagt cagattcgta     840

gaatacaaag ctcaaggtga agcacatatg ggtggtaatg atcctgctga cagagttttg     900

cacgaagaca tggctgcaag tttagattgg gcatatggtg aaataagaaa aatccaaaag     960

gccgctagat ctggtggtaa accaattgat aagccaagat ggcctatgat aatcttgaga    1020

tcacctaagg gttggacagg tccatcttca gaacatggta aacaattgtt gaacaacttt    1080

gcctctcacc aagttccatt gcctgatgct aaaactgatg acgaagctaa cgcatatttg    1140

gaaagatggt tgaagagtta cgaagctgat aagttgttcg acttctctga agataactta    1200

aagagaggta caatcttcga ccaattgttg tacgaagcat tgcctaagga tatggaaaga    1260

agattaggtt tcgttaagga aacttacaac ggttacaagc cattggaatt agatgactgg    1320

aaaaagtacg gttttaaaaa gggtgaagac gtatcatgta tgaaagccat cgctggttac    1380

ttaacagatg ttattaaaag aaaccctaag gagtttagaa ttttcagtcc agacgaattg    1440

gctttaaata agttggatgg tgttttctct gtcactgaaa gaaacatgca atgggaccca    1500

gaaactgctc ataagggtgg tagagttaca gaaatgttgt ctgaacactc attgcaagca    1560

tggttacaag gttatacctt aactggtaga catggtgttt ttccatctta cgaagcattc    1620

ttgggtattg tcgccacaat gaccgtacaa tataccaagt ttatgaagat ggcattggaa    1680

actaattgga gaggtcctac cgcctcttta acttacatcg aaacttcaac atggaccaga    1740
```

-continued

```
caagaacata atggttactc ccaccaaaac ccaggtttcg taagtactgt tttgtcctta   1800

cctagtcaat tagctagagt ttactttcca tcagatgcaa atacatccgt aagtgttatc   1860

gcccattgtt tgagatccaa aaattacata aacttaatag ttggtacaaa ggctccaacc   1920

cctgtctact tgtctgtaga agaagcagaa agacattgca ttgcaggtgc ctctgtttgg   1980

gaaaattatt cagttgataa gggtgtcgat ccagacgtcg tattggtagg catcggttac   2040

gaattaacag aagaagttat ccatgcagcc gctttgttga gaaaggattt tggtactgaa   2100

ttgagagtca gagttgtcaa cgtagttgat ttgttagtat tagctcctaa gggtgaccat   2160

ccacacgcct tggatgaagc tggttttaat tcattattcc cacctggtgt tcctatcatt   2220

tttaactacc atggttacgc aggtcaatta gcctccttgt tattcgatag aaaacactcc   2280

gttggtagaa gtagaatgag aatcttcgct tactcagaac aaggtactac aaccactcca   2340

tttgcaatga tgtgttgcaa taacactgat agattcaatt tggctgctga agcattggaa   2400

atggtcacat tgaatttgac aacccaacat aacattaccg gtgaagaaaa gagacacaga   2460

gtaggttcag tcgtagctag agcacatgaa agaatgtcct tctacaagca caaaaaggtt   2520

gtcatgatga gatacgctgc agaaacccaa aaggatcatc cagaaattgg tgaagttgca   2580

actttggccg aacaataa                                                 2598
```

<210> SEQ ID NO 71
<211> LENGTH: 865
<212> TYPE: PRT
<213> ORGANISM: Rhodosporidium toruloides

<400> SEQUENCE: 71

```
Met Ala Asp Asn Ala Asp Ala Pro Pro Pro Pro Ile Val Pro Ser Gln
1               5                   10                  15

Tyr Ala Gln His Pro Asp Ala Pro Leu Ser Ser Leu Pro Val Gln Leu
            20                  25                  30

Asp Pro Ser Gln Tyr Thr Ala Lys Tyr Pro Ala Lys His Leu Asp Ala
        35                  40                  45

Ile Val Ala Asn Trp Arg Leu Ser Cys Tyr Leu Gly Ala Ser Gln Ile
    50                  55                  60

Phe Leu Gln Ser Asn Ala Ile Leu Ser Arg Lys Leu Thr Lys Asp Asp
65                  70                  75                  80

Val Lys Pro Arg Arg Ala His Thr Asn Leu Ala Gly Asp Ile Gln Gly
                85                  90                  95

Gly Leu Ser Leu Ala Tyr Val His Thr Gln Ala Leu Ile Arg Arg Lys
            100                 105                 110

Gly Asp Glu Glu Gly Ala Glu Pro Lys Met Ile Phe Val Thr Gly Pro
        115                 120                 125

Gly His Gly Ala Pro Ala Ile Leu Ser Pro Leu Tyr Ile Glu Gly Ala
    130                 135                 140

Ile Ser Lys Phe Tyr Pro Gln Tyr Pro Leu Asn Glu Gln Gly Leu Glu
145                 150                 155                 160

Lys Phe Val Lys Tyr Phe Ser Trp Pro Gly Gly Phe Pro Ser His Val
                165                 170                 175

Asn Ala Glu Thr Pro Gly Cys Ile His Glu Gly Gly Glu Leu Gly Tyr
            180                 185                 190

Ala Leu Gly Val Ala Tyr Gly Ser Val Met Asp Arg Pro Glu Gln Ile
        195                 200                 205

Ser Val Val Val Val Gly Asp Gly Glu Ser Glu Thr Gly Pro Thr Ala
    210                 215                 220
```

```
Thr Ala Trp His Ser His Lys Trp Leu Asp Pro Ala Glu Ser Gly Ala
225                 230                 235                 240

Val Leu Pro Ile Leu His Val Asn Gly Phe Lys Ile Ser Glu Arg Thr
                245                 250                 255

Ile Pro Gly Thr Met Asp Asn Val Glu Leu Ser Leu Leu Tyr Ser Gly
            260                 265                 270

Tyr Gly Tyr Gln Val Arg Phe Val Glu Tyr Lys Ala Gln Gly Glu Ala
        275                 280                 285

His Met Gly Gly Asn Asp Pro Ala Asp Arg Val Leu His Glu Asp Met
    290                 295                 300

Ala Ala Ser Leu Asp Trp Ala Tyr Gly Glu Ile Arg Lys Ile Gln Lys
305                 310                 315                 320

Ala Ala Arg Ser Gly Gly Lys Pro Ile Asp Lys Pro Arg Trp Pro Met
                325                 330                 335

Ile Ile Leu Arg Ser Pro Lys Gly Trp Thr Gly Pro Ser Ser Glu His
            340                 345                 350

Gly Lys Gln Leu Leu Asn Asn Phe Ala Ser His Gln Val Pro Leu Pro
        355                 360                 365

Asp Ala Lys Thr Asp Asp Glu Ala Asn Ala Tyr Leu Glu Arg Trp Leu
    370                 375                 380

Lys Ser Tyr Glu Ala Asp Lys Leu Phe Asp Phe Ser Glu Asp Asn Leu
385                 390                 395                 400

Lys Arg Gly Thr Ile Phe Asp Gln Leu Leu Tyr Glu Ala Leu Pro Lys
                405                 410                 415

Asp Met Glu Arg Arg Leu Gly Phe Val Lys Glu Thr Tyr Asn Gly Tyr
            420                 425                 430

Lys Pro Leu Glu Leu Asp Asp Trp Lys Lys Tyr Gly Phe Lys Lys Gly
        435                 440                 445

Glu Asp Val Ser Cys Met Lys Ala Ile Ala Gly Tyr Leu Thr Asp Val
    450                 455                 460

Ile Lys Arg Asn Pro Lys Glu Phe Arg Ile Phe Ser Pro Asp Glu Leu
465                 470                 475                 480

Ala Leu Asn Lys Leu Asp Gly Val Phe Ser Val Thr Glu Arg Asn Met
                485                 490                 495

Gln Trp Asp Pro Glu Thr Ala His Lys Gly Gly Arg Val Thr Glu Met
            500                 505                 510

Leu Ser Glu His Ser Leu Gln Ala Trp Leu Gln Gly Tyr Thr Leu Thr
        515                 520                 525

Gly Arg His Gly Val Phe Pro Ser Tyr Glu Ala Phe Leu Gly Ile Val
    530                 535                 540

Ala Thr Met Thr Val Gln Tyr Thr Lys Phe Met Lys Met Ala Leu Glu
545                 550                 555                 560

Thr Asn Trp Arg Gly Pro Thr Ala Ser Leu Thr Tyr Ile Glu Thr Ser
                565                 570                 575

Thr Trp Thr Arg Gln Glu His Asn Gly Tyr Ser His Gln Asn Pro Gly
            580                 585                 590

Phe Val Ser Thr Val Leu Ser Leu Pro Ser Gln Leu Ala Arg Val Tyr
        595                 600                 605

Phe Pro Ser Asp Ala Asn Thr Ser Val Ser Val Ile Ala His Cys Leu
    610                 615                 620

Arg Ser Lys Asn Tyr Ile Asn Leu Ile Val Gly Thr Lys Ala Pro Thr
625                 630                 635                 640
```

```
Pro Val Tyr Leu Ser Val Glu Glu Ala Glu Arg His Cys Ile Ala Gly
                645                 650                 655

Ala Ser Val Trp Glu Asn Tyr Ser Val Asp Lys Gly Val Asp Pro Asp
            660                 665                 670

Val Val Leu Val Gly Ile Gly Tyr Glu Leu Thr Glu Glu Val Ile His
        675                 680                 685

Ala Ala Ala Leu Leu Arg Lys Asp Phe Gly Thr Glu Leu Arg Val Arg
    690                 695                 700

Val Val Asn Val Val Asp Leu Leu Val Leu Ala Pro Lys Gly Asp His
705                 710                 715                 720

Pro His Ala Leu Asp Glu Ala Gly Phe Asn Ser Leu Phe Pro Pro Gly
                725                 730                 735

Val Pro Ile Ile Phe Asn Tyr His Gly Tyr Ala Gly Gln Leu Ala Ser
            740                 745                 750

Leu Leu Phe Asp Arg Lys His Ser Val Gly Arg Ser Arg Met Arg Ile
        755                 760                 765

Phe Ala Tyr Ser Glu Gln Gly Thr Thr Thr Thr Pro Phe Ala Met Met
    770                 775                 780

Cys Cys Asn Asn Thr Asp Arg Phe Asn Leu Ala Ala Glu Ala Leu Glu
785                 790                 795                 800

Met Val Thr Leu Asn Leu Thr Thr Gln His Asn Ile Thr Gly Glu Glu
                805                 810                 815

Lys Arg His Arg Val Gly Ser Val Val Ala Arg Ala His Glu Arg Met
            820                 825                 830

Ser Phe Tyr Lys His Lys Lys Val Val Met Met Arg Tyr Ala Ala Glu
        835                 840                 845

Thr Gln Lys Asp His Pro Glu Ile Gly Glu Val Ala Thr Leu Ala Glu
    850                 855                 860

Gln
865
```

<210> SEQ ID NO 72
<211> LENGTH: 2478
<212> TYPE: DNA
<213> ORGANISM: Scardovia inopinata

<400> SEQUENCE: 72

```
atgacatctc ctgtaattgg taccccatgg aagaagttgg atagacctgt aaccgacgaa     60

gcattggaag gtgttgataa gtattggaga gctgcaaact atatgtccat cggtcaaata    120

tatttgagaa gtaatccatt aatgaaggaa ccttttacaa gagaagatgt aaagcataga    180

ttggttggtc actggggtac tacaccaggt ttgaactttt tattcggtca tatcaacaga    240

ttgatcgcag atcaccaaca aaacactgtt ttcattatgg gtccaggtca tggtggtcct    300

gctggtactt ctcaatctta tttggatggt acctacactg aatactaccc aaagataaca    360

aacgacgaag ctggtttgca aaagtttttc agacaatttt cctacccagg tggtatccct    420

agtcattacg caccagaaac tcctggttca attcacgaag gtggtgaatt gggttatgct    480

ttatctcatg cctacggtgc tatcatgaat aacccatcat tgtttgtagc cgctattgtt    540

ggtgacggtg aagctgaaac tggtccttta gcaacaggtt ggcaatctaa caagttggtc    600

aatccaagaa cagatggtat cgtattgcct atattgcatt tgaatggtta caagattgcc    660

aatccaacca tattggctag aatctctgac gaagaattac acgatttctt tagaggtatg    720

ggttataatc cttacgaatt tgttgcaggt ttcgatgacg aagaccatat gtctattcac    780
```

-continued

```
agaagattcg ctgatttgtt agaaactgta ttcgacgaaa tctgtgatat caaagctact    840
gcacaaacaa atgatgttga cagaccattc taccctatga tcatattcag aaccccaaaa    900
ggttggactt gccctaagtt tattgatggt aaaaagaccg aaggttcctg gagagcacat    960
caagtcccat tggccagtgc tagagatact gaagaacact tccaagtatt gaagaattgg   1020
ttagaatctt acaagcctga agaattgttc gatgaaaagg gtacattgag accagaagtt   1080
accgagttta tgcctaaggg tgacttgaga attggtgcta atccaaacgc aaatggtggt   1140
agaatcagag aagatttgaa attgcctgtt ttggatgact acaaagtcaa ggaagtagaa   1200
gaatttggtc atggttgggg tcaattggaa gcaactagaa gattaggtgt ttacacaaga   1260
gacatcatta agttaaaccc agattccttt agaatattcg gtcctgatga aactgctagt   1320
aatagattgc aagcagccta tgaagttaca aacaaacaat gggacaatgg ttacttgtct   1380
tcattagtcg atgaacatat ggctgtcacc ggtcaagtaa ctgaacaatt atcagaacac   1440
caaatggaag gttttattga aggttacgtt ttgacaggta gacatggtat atggtccagt   1500
tacgaatctt tcgttcatgt catcgattca atgttgaatc aacacgctaa gtggttagaa   1560
gcaactgtta gagaaattcc atggagaaag cctatatctt cagttaactt gttagtctcc   1620
agtcatgtat ggagacaaga ccataatggt ttttctcacc aagatccagg tgttgtctca   1680
gttttgttga acaaaacttt taataacgac catgtcattg gtatctattt cgcaaccgat   1740
gccaatatgt tgttagccat tggtgaaaaa gcatataaat ctactaacaa gataaatgct   1800
ataatcgcag gtaaacaacc agctgcaacc tggttgtcat tagatgaagc aagagccgaa   1860
ttaactaaag gtgccgctga atggaagtgg gcctccaccg ctaaaaataa cgacgaaact   1920
gaaatagttt tagcaagtgt tggtgacgtc ccaactcaag aaataatggc agccgctgac   1980
aaattgaagg gttacggtat taagtttaaa gtagttaacg tcgtagattt gttatcttta   2040
caaaacccaa aggaaaacaa cgaagcattg tcagacgaag agtttactga attattcacc   2100
gccgataagc ctgtattgat ggcatatcat tcctacgcca gagaagttaa gggtttgttg   2160
ttcgatagac caaacaacgc taacttcaat attcacggtt atcaagaaca aggttcaacc   2220
actacacctt tcgatatggt tagagttaac gatatcgaca gatacgaatt gacagctgaa   2280
gcattgagaa tgttagatgc cgacaagtac gctgatgaca ttaaaaagtt agaagatttc   2340
agacaagaag cattccaata tgccgttgat aacggtcatg atcacccaga ctacacagat   2400
tgggtttggt ctggtgtcaa aaccgataag cctggtgcag ttacagccac cgcagccact   2460
gctggtgaca atgaataa                                                 2478
```

<210> SEQ ID NO 73
<211> LENGTH: 825
<212> TYPE: PRT
<213> ORGANISM: Scardovia inopinata

<400> SEQUENCE: 73

```
Met Thr Ser Pro Val Ile Gly Thr Pro Trp Lys Lys Leu Asp Arg Pro
1               5                   10                  15

Val Thr Asp Glu Ala Leu Glu Gly Val Asp Lys Tyr Trp Arg Ala Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Phe Gly His Ile Asn Arg
```

```
65                  70                  75                  80

Leu Ile Ala Asp His Gln Gln Asn Thr Val Phe Ile Met Gly Pro Gly
                85                  90                  95

His Gly Gly Pro Ala Gly Thr Ser Gln Ser Tyr Leu Asp Gly Thr Tyr
            100                 105                 110

Thr Glu Tyr Tyr Pro Lys Ile Thr Asn Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Ala Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ala Arg Ile Ser Asp Glu Glu Leu His Asp Phe Phe Arg Gly Met
225                 230                 235                 240

Gly Tyr Asn Pro Tyr Glu Phe Val Ala Gly Phe Asp Asp Glu Asp His
                245                 250                 255

Met Ser Ile His Arg Arg Phe Ala Asp Leu Leu Glu Thr Val Phe Asp
            260                 265                 270

Glu Ile Cys Asp Ile Lys Ala Thr Ala Gln Thr Asn Asp Val Asp Arg
        275                 280                 285

Pro Phe Tyr Pro Met Ile Ile Phe Arg Thr Pro Lys Gly Trp Thr Cys
    290                 295                 300

Pro Lys Phe Ile Asp Gly Lys Lys Thr Glu Gly Ser Trp Arg Ala His
305                 310                 315                 320

Gln Val Pro Leu Ala Ser Ala Arg Asp Thr Glu Glu His Phe Gln Val
                325                 330                 335

Leu Lys Asn Trp Leu Glu Ser Tyr Lys Pro Glu Glu Leu Phe Asp Glu
            340                 345                 350

Lys Gly Thr Leu Arg Pro Glu Val Thr Glu Phe Met Pro Lys Gly Asp
        355                 360                 365

Leu Arg Ile Gly Ala Asn Pro Asn Ala Asn Gly Gly Arg Ile Arg Glu
    370                 375                 380

Asp Leu Lys Leu Pro Val Leu Asp Asp Tyr Lys Val Lys Glu Val Glu
385                 390                 395                 400

Glu Phe Gly His Gly Trp Gly Gln Leu Glu Ala Thr Arg Arg Leu Gly
                405                 410                 415

Val Tyr Thr Arg Asp Ile Ile Lys Leu Asn Pro Asp Ser Phe Arg Ile
            420                 425                 430

Phe Gly Pro Asp Glu Thr Ala Ser Asn Arg Leu Gln Ala Ala Tyr Glu
        435                 440                 445

Val Thr Asn Lys Gln Trp Asp Asn Gly Tyr Leu Ser Ser Leu Val Asp
    450                 455                 460

Glu His Met Ala Val Thr Gly Gln Val Thr Glu Gln Leu Ser Glu His
465                 470                 475                 480

Gln Met Glu Gly Phe Ile Glu Gly Tyr Val Leu Thr Gly Arg His Gly
                485                 490                 495
```

```
Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
        515                 520                 525

Arg Lys Pro Ile Ser Ser Val Asn Leu Leu Val Ser Ser His Val Trp
    530                 535                 540

Arg Gln Asp His Asn Gly Phe Ser His Gln Asp Pro Gly Val Val Ser
545                 550                 555                 560

Val Leu Leu Asn Lys Thr Phe Asn Asn Asp His Val Ile Gly Ile Tyr
                565                 570                 575

Phe Ala Thr Asp Ala Asn Met Leu Leu Ala Ile Gly Glu Lys Ala Tyr
            580                 585                 590

Lys Ser Thr Asn Lys Ile Asn Ala Ile Ile Ala Gly Lys Gln Pro Ala
        595                 600                 605

Ala Thr Trp Leu Ser Leu Asp Glu Ala Arg Ala Glu Leu Thr Lys Gly
    610                 615                 620

Ala Ala Glu Trp Lys Trp Ala Ser Thr Ala Lys Asn Asn Asp Glu Thr
625                 630                 635                 640

Glu Ile Val Leu Ala Ser Val Gly Asp Val Pro Thr Gln Glu Ile Met
                645                 650                 655

Ala Ala Ala Asp Lys Leu Lys Gly Tyr Gly Ile Lys Phe Lys Val Val
            660                 665                 670

Asn Val Val Asp Leu Leu Ser Leu Gln Asn Pro Lys Glu Asn Asn Glu
        675                 680                 685

Ala Leu Ser Asp Glu Glu Phe Thr Glu Leu Phe Thr Ala Asp Lys Pro
    690                 695                 700

Val Leu Met Ala Tyr His Ser Tyr Ala Arg Glu Val Lys Gly Leu Leu
705                 710                 715                 720

Phe Asp Arg Pro Asn Asn Ala Asn Phe Asn Ile His Gly Tyr Gln Glu
                725                 730                 735

Gln Gly Ser Thr Thr Thr Pro Phe Asp Met Val Arg Val Asn Asp Ile
            740                 745                 750

Asp Arg Tyr Glu Leu Thr Ala Glu Ala Leu Arg Met Leu Asp Ala Asp
        755                 760                 765

Lys Tyr Ala Asp Asp Ile Lys Lys Leu Glu Asp Phe Arg Gln Glu Ala
    770                 775                 780

Phe Gln Tyr Ala Val Asp Asn Gly His Asp His Pro Asp Tyr Thr Asp
785                 790                 795                 800

Trp Val Trp Ser Gly Val Lys Thr Asp Lys Pro Gly Ala Val Thr Ala
                805                 810                 815

Thr Ala Ala Thr Ala Gly Asp Asn Glu
            820                 825
```

<210> SEQ ID NO 74
<211> LENGTH: 2469
<212> TYPE: DNA
<213> ORGANISM: Schizosaccharomyces japonicus

<400> SEQUENCE: 74

```
atgaagttcg aagccaccaa agaatttatg aacgaatcca gaacagaagc cgcaaaagcc      60

gacccatcac cattacaatc ccacttacca gctactttgg atacattgca agttcatttg     120

ttgaaagact atgtacctga agatgacttg gttacattaa agaatttcca aagagtatgt     180

aactacatcg ctgcagccat gattttcttg tgcgataacg ttttgttaga aaacaaatta     240
```

```
acatctgacc atattaagcc aagattgtta ggtcattggg gtacttgtcc tgccttggct    300
ttagcatact cccattgcaa cagaatcatc agtaagtaca atttggatat gttatttgtt    360
actggtccag gtcacggtgc ccctgctatt ttggctgcat tatacatcga aggttcttta    420
caagcatatt acccacaata cggtcataac atgcaaggtt tgcacagatt gatcaccaaa    480
ttttctgtca ctggtggttt cccatcacat gtcaatgccg aagtacctgg tgctatacac    540
gaaggtggtg aattgggtta tgcattatct gtatcatacg gtgccgtttt ggatagacca    600
aatttgattg ttgcctgtgt tgtcggtgac ggtgaagctg aaaccggtcc tactgccgct    660
tcttggcatt gccacaaatt catagatcca gcagaatcag gtgccgtcat acctatcttg    720
aatttgaatg gttttaagat ctcagaaaga acagtatatg gttgtatgga tagaagagaa    780
ttgtctgctt tgttttctgg tttcggttac caagtagttt tcgtagatta cagaactgct    840
gatgacgtta atagagatat ggcagccgct atggactggt gtgttgaaat catacatgaa    900
atacaagatg cagccagagc aggtacacca ataatcaaac caagatggcc tatgattata    960
ttgcacaccc caaagggttg gggttgccct aaaactttgc atggtaaacc attagaaggt   1020
acttttagag cacatcaagt tcctttgaaa aatgctaaga ctgatgcaga agaattgggt   1080
caattagaaa actggttgaa gtcttaccat atagaagatt tcatcgacaa gtcaaacggt   1140
ttgccattaa agggtttgat tgaacactta ccacctagag taaaaagaat gggtcaaaag   1200
actgatgcta ataacgactt ccaaccatta tgtgttcctg attggaacga cttttctatc   1260
gatagaggta ttttggaatc tgctacctca attgttggta aatacttgga tagagtctta   1320
caagcaaacc caaagacttt gagattattt tcccctgatg aattagccag taacaaattg   1380
gacggtgttt tagaacattc aaacagaaca ttgcaaaccg atgccatatc cgcttggagt   1440
agaggtagag taacagaagt tttgtctgaa catatgtgcc aaggtttcat gcaaggttat   1500
accttaactg gtagaaccgc tatttttcca tcctacgaag cattcttgcc tatcataact   1560
tctatgacag ttcaatacac caagttcttg aagatggcat tagaaactaa gtggcatggt   1620
agagtcggtt ccttaaacta cgtaactaca agtacatggg ctagacaaga acataatggt   1680
ttttctcacc aatcaccaag attcataacc actatgttgt cctttaagcc tacattaacc   1740
agagtttatt tcccacctga tacaaactgt ttcttgtcta ctatcgcaca ttgcttatct   1800
tcagacaatg gtgttaactt gatggtctcc agtaaaaatc caggtccttc ctggttaagt   1860
agagaagaag ctgaagaaca ttgtgtcgca ggtgcctctg tatggaagtt cgcatcaact   1920
gatggtggtt tagatccaga cgtcgtatta gttggtatcg gtaacgaaat catgttcgaa   1980
gtcatagctg cagcctctat cttggctcat gatttgccaa aattgagaat tagagttgtc   2040
aacatcacag atttgatgat cttagccgac aatcatccac actccatgag tgaaatcgag   2100
tttaatgctt tattcactcc taacagacat gtccacttca attatcatgg ttacgtaatg   2160
gatttgcaat ctttgttatt ttcaagaatc gacgcatcta gagtttcaat ggaaggttat   2220
tgtgaagaag gtacaaccac tacaccattc aatatgatga ttgcaaacag aacttctaga   2280
taccatgttg ccatggctgc agtcgctggt gcaacatgta accctgaagt tgctatgaat   2340
tgccacaaat tgatatcaaa ctacaagcat agattgactc aaattaaaca ctatatatac   2400
gaaaacggtg ttgatccaga aggtactttt gatatccctg acaatttgac aaagggtcaa   2460
gtcatttaa                                                           2469
```

<210> SEQ ID NO 75

<211> LENGTH: 822
<212> TYPE: PRT
<213> ORGANISM: Schizosaccharomyces japonicus

<400> SEQUENCE: 75

```
Met Lys Phe Glu Ala Thr Lys Glu Phe Met Asn Glu Ser Arg Thr Glu
1               5                   10                  15

Ala Ala Lys Ala Asp Pro Ser Pro Leu Gln Ser His Leu Pro Ala Thr
            20                  25                  30

Leu Asp Thr Leu Gln Val His Leu Leu Lys Asp Tyr Val Pro Glu Asp
        35                  40                  45

Asp Leu Val Thr Leu Lys Asn Phe Gln Arg Val Cys Asn Tyr Ile Ala
    50                  55                  60

Ala Ala Met Ile Phe Leu Cys Asp Asn Val Leu Leu Glu Asn Lys Leu
65                  70                  75                  80

Thr Ser Asp His Ile Lys Pro Arg Leu Leu Gly His Trp Gly Thr Cys
                85                  90                  95

Pro Ala Leu Ala Leu Ala Tyr Ser His Cys Asn Arg Ile Ile Ser Lys
            100                 105                 110

Tyr Asn Leu Asp Met Leu Phe Val Thr Gly Pro Gly His Gly Ala Pro
        115                 120                 125

Ala Ile Leu Ala Ala Leu Tyr Ile Glu Gly Ser Leu Gln Ala Tyr Tyr
    130                 135                 140

Pro Gln Tyr Gly His Asn Met Gln Gly Leu His Arg Leu Ile Thr Lys
145                 150                 155                 160

Phe Ser Val Thr Gly Gly Phe Pro Ser His Val Asn Ala Glu Val Pro
                165                 170                 175

Gly Ala Ile His Glu Gly Gly Glu Leu Gly Tyr Ala Leu Ser Val Ser
            180                 185                 190

Tyr Gly Ala Val Leu Asp Arg Pro Asn Leu Ile Val Ala Cys Val Val
        195                 200                 205

Gly Asp Gly Glu Ala Glu Thr Gly Pro Thr Ala Ala Ser Trp His Cys
    210                 215                 220

His Lys Phe Ile Asp Pro Ala Glu Ser Gly Ala Val Ile Pro Ile Leu
225                 230                 235                 240

Asn Leu Asn Gly Phe Lys Ile Ser Glu Arg Thr Val Tyr Gly Cys Met
                245                 250                 255

Asp Arg Arg Glu Leu Ser Ala Leu Phe Ser Gly Phe Gly Tyr Gln Val
            260                 265                 270

Val Phe Val Asp Tyr Arg Thr Ala Asp Asp Val Asn Arg Asp Met Ala
        275                 280                 285

Ala Ala Met Asp Trp Cys Val Glu Ile Ile His Glu Ile Gln Asp Ala
    290                 295                 300

Ala Arg Ala Gly Thr Pro Ile Ile Lys Pro Arg Trp Pro Met Ile Ile
305                 310                 315                 320

Leu His Thr Pro Lys Gly Trp Gly Cys Pro Lys Thr Leu His Gly Lys
                325                 330                 335

Pro Leu Glu Gly Thr Phe Arg Ala His Gln Val Pro Leu Lys Asn Ala
            340                 345                 350

Lys Thr Asp Ala Glu Glu Leu Gly Gln Leu Glu Asn Trp Leu Lys Ser
        355                 360                 365

Tyr His Ile Glu Asp Phe Ile Asp Lys Ser Asn Gly Leu Pro Leu Lys
    370                 375                 380

Gly Leu Ile Glu His Leu Pro Pro Arg Val Lys Arg Met Gly Gln Lys
```

-continued

```
385                 390                 395                 400

Thr Asp Ala Asn Asn Asp Phe Gln Pro Leu Cys Val Pro Asp Trp Asn
                405                 410                 415

Asp Phe Ser Ile Asp Arg Gly Ile Leu Glu Ser Ala Thr Ser Ile Val
            420                 425                 430

Gly Lys Tyr Leu Asp Arg Val Leu Gln Ala Asn Pro Lys Thr Leu Arg
        435                 440                 445

Leu Phe Ser Pro Asp Glu Leu Ala Ser Asn Lys Leu Asp Gly Val Leu
    450                 455                 460

Glu His Ser Asn Arg Thr Leu Gln Thr Asp Ala Ile Ser Ala Trp Ser
465                 470                 475                 480

Arg Gly Arg Val Thr Glu Val Leu Ser Glu His Met Cys Gln Gly Phe
                485                 490                 495

Met Gln Gly Tyr Thr Leu Thr Gly Arg Thr Ala Ile Phe Pro Ser Tyr
            500                 505                 510

Glu Ala Phe Leu Pro Ile Ile Thr Ser Met Thr Val Gln Tyr Thr Lys
        515                 520                 525

Phe Leu Lys Met Ala Leu Glu Thr Lys Trp His Gly Arg Val Gly Ser
    530                 535                 540

Leu Asn Tyr Val Thr Thr Ser Thr Trp Ala Arg Gln Glu His Asn Gly
545                 550                 555                 560

Phe Ser His Gln Ser Pro Arg Phe Ile Thr Thr Met Leu Ser Phe Lys
                565                 570                 575

Pro Thr Leu Thr Arg Val Tyr Phe Pro Pro Asp Thr Asn Cys Phe Leu
            580                 585                 590

Ser Thr Ile Ala His Cys Leu Ser Ser Asp Asn Gly Val Asn Leu Met
        595                 600                 605

Val Ser Ser Lys Asn Pro Gly Pro Ser Trp Leu Ser Arg Glu Glu Ala
    610                 615                 620

Glu Glu His Cys Val Ala Gly Ala Ser Val Trp Lys Phe Ala Ser Thr
625                 630                 635                 640

Asp Gly Gly Leu Asp Pro Asp Val Val Leu Val Gly Ile Gly Asn Glu
                645                 650                 655

Ile Met Phe Glu Val Ile Ala Ala Ala Ser Ile Leu Ala His Asp Leu
            660                 665                 670

Pro Lys Leu Arg Ile Arg Val Val Asn Ile Thr Asp Leu Met Ile Leu
        675                 680                 685

Ala Asp Asn His Pro His Ser Met Ser Glu Ile Glu Phe Asn Ala Leu
    690                 695                 700

Phe Thr Pro Asn Arg His Val His Phe Asn Tyr His Gly Tyr Val Met
705                 710                 715                 720

Asp Leu Gln Ser Leu Leu Phe Ser Arg Ile Asp Ala Ser Arg Val Ser
                725                 730                 735

Met Glu Gly Tyr Cys Glu Glu Gly Thr Thr Thr Thr Pro Phe Asn Met
            740                 745                 750

Met Ile Ala Asn Arg Thr Ser Arg Tyr His Val Ala Met Ala Ala Val
        755                 760                 765

Ala Gly Ala Thr Cys Asn Pro Glu Val Ala Met Asn Cys His Lys Leu
    770                 775                 780

Ile Ser Asn Tyr Lys His Arg Leu Thr Gln Ile Lys His Tyr Ile Tyr
785                 790                 795                 800

Glu Asn Gly Val Asp Pro Glu Gly Thr Phe Asp Ile Pro Asp Asn Leu
                805                 810                 815
```

Thr Lys Gly Gln Val Ile
820

<210> SEQ ID NO 76
<211> LENGTH: 2430
<212> TYPE: DNA
<213> ORGANISM: Trichoder mareesei

<400> SEQUENCE: 76
atgccaggtg aagtcataga ccaaccaaac cctcctccat taacatccca cttgccagat 60
accatagaag aattagcagt aaagcctagt aaagctccat tgtctaattt ggatttggtt 120
tctttgagag aatttcaaag agctgcatgt tatatagctt ccgcaatgat cttcttaaag 180
gataacgtat tgttggacag agaattgaga tttgaagatg ttaagcctag attgttaggt 240
cattggggta cttgcccagg tttgatattg atctggtcac acttaaattt gttaattaga 300
gattcttcac aagacatgtt gttcgttata ggtcctggtc atggtgcacc agccgcttta 360
gcctgtttgt ggttagaagg ttctttggaa agattttacc ctgataagta cagaacagac 420
aaggaaggtt tgcataattt gataacaaaa ttttctgttc caaccggttt cccttctcat 480
ataaacccag aaactcctgg ttgtatccac gaaggtggtg aattgggtta tgccttagct 540
gtctcatttg gtgctgtaat ggataagcct gacttgatag ttccatgcgt tgtcggtgac 600
ggtgaagcag aaacaggtcc aaccgcagcc gcttggcatt caatcaaata cttagatcct 660
gctgaatccg gtgcagttat cccaattttg cacgtcaacg gttttaagat atctgaaaga 720
actatcttcg gttgtatgga taacacagaa ttggttttgt tattctctgg ttatggttac 780
gaagtttgca tcgtcgaaaa tttggatgct attgacactg aattgcatac agccttattt 840
tgggctttga gtgaaattaa aagaatacaa ggtgcagcca gatctggtaa ccctattacc 900
aagccaagat ggcctatgat tatattgaga actcctaaag gttggaccgg tccaagaact 960
gttgatgaca agatcattga aggttctttc catgcacacc aagtaccagt tacaaaagcc 1020
aataaggatg aaggtcattt gagaatttta caagattggt tgaagagtta cgacgttaga 1080
ggtttgttac cagatggtaa accttctggt gactttttgg acattttacc acctgatcct 1140
cataaaagat taggtcaatc taagttggct tacgactgtc atcaaccatt ggatttgcct 1200
gactggagac cacactcagt tgataaattt gaagaagcct ccagtatgca acaatccggt 1260
aaattcttgg atgtagttgc tagacaaaac atgaagactt ttagaatttt ctctccagat 1320
gaattagaat caaataagtt atccgcagta ttggatcatt cttcaagaaa cttccaatgg 1380
gaccaatatt ctagagcaca aggtggtaga gttatagaaa tcttgtccga acactgttgc 1440
caaggtttct tgcaaggtta tactttgaca ggtagaactg ctatttttcc ttcttacgaa 1500
tcattcttag gtatcatcca tacaatgatg atacaatact ccaaattcag taagatatct 1560
agaaaattgc catggagagg tgacttgtct tctattaatt acatcgaaac ctctacttgg 1620
gcaagacaag aacataatgg tttttcacac caaaacccat ccttcatagg tgctgtcttg 1680
aatttgaaag cagaaatcgc cagagtatac ttgccacctg atgcaaactg tttcttgtct 1740
actttgcatc actgcttgca atccaaaaat tacgtcaact tgatgatagg tagtaagcaa 1800
ccaacccctg tatacttgtc tgctgaagat gcacaaagac attgtgaaga cggtgccagt 1860
atatggagat gggcttctac ccatgatggt gaacaccctg acgtcgtatt agttggtatc 1920
ggtgtcgaag taacttttga agtcattaaa gctgcacaat tgttatctag attagctcca 1980
aatttgagag ttagagttgt caacgtcaca gatttgttag tattacctca tgaaagtcat 2040

```
cacccacacg ctttggactc taaagcattt gaagatatgt tcacattgga caagccagtc   2100

tgcttcaatt atcattcata cgctaccgaa ttacaaggtt tgttatttgg tagacctgca   2160

ttgcacagaa tgtcagttga aggttataaa gaagaaggtt ccactacaac cccattcgat   2220

atgatgttgg taaacactgt ttcaagattc catgttgcct ccagagcttt gaaggccgct   2280

gcagcccaaa acgatgaagt caaggaaaac ttaagtgcat tgttagccaa ggtagatgac   2340

gaaatgaagt ctgttaagga ttacatcgaa caatggggta aagttgaccc agatgacatc   2400

tatgaattgg atttcttgaa gaaagactaa                                    2430


<210> SEQ ID NO 77
<211> LENGTH: 809
<212> TYPE: PRT
<213> ORGANISM: Trichoder mareesei

<400> SEQUENCE: 77

Met Pro Gly Glu Val Ile Asp Gln Pro Asn Pro Pro Pro Leu Thr Ser
1               5                   10                  15

His Leu Pro Asp Thr Ile Glu Glu Leu Ala Val Lys Pro Ser Lys Ala
            20                  25                  30

Pro Leu Ser Asn Leu Asp Leu Val Ser Leu Arg Glu Phe Gln Arg Ala
        35                  40                  45

Ala Cys Tyr Ile Ala Ser Ala Met Ile Phe Leu Lys Asp Asn Val Leu
    50                  55                  60

Leu Asp Arg Glu Leu Arg Phe Glu Asp Val Lys Pro Arg Leu Leu Gly
65                  70                  75                  80

His Trp Gly Thr Cys Pro Gly Leu Ile Leu Ile Trp Ser His Leu Asn
                85                  90                  95

Leu Leu Ile Arg Asp Ser Ser Gln Asp Met Leu Phe Val Ile Gly Pro
            100                 105                 110

Gly His Gly Ala Pro Ala Ala Leu Ala Cys Leu Trp Leu Glu Gly Ser
        115                 120                 125

Leu Glu Arg Phe Tyr Pro Asp Lys Tyr Arg Thr Asp Lys Glu Gly Leu
    130                 135                 140

His Asn Leu Ile Thr Lys Phe Ser Val Pro Thr Gly Phe Pro Ser His
145                 150                 155                 160

Ile Asn Pro Glu Thr Pro Gly Cys Ile His Glu Gly Gly Glu Leu Gly
                165                 170                 175

Tyr Ala Leu Ala Val Ser Phe Gly Ala Val Met Asp Lys Pro Asp Leu
            180                 185                 190

Ile Val Pro Cys Val Val Gly Asp Gly Glu Ala Glu Thr Gly Pro Thr
        195                 200                 205

Ala Ala Ala Trp His Ser Ile Lys Tyr Leu Asp Pro Ala Glu Ser Gly
    210                 215                 220

Ala Val Ile Pro Ile Leu His Val Asn Gly Phe Lys Ile Ser Glu Arg
225                 230                 235                 240

Thr Ile Phe Gly Cys Met Asp Asn Thr Glu Leu Val Leu Leu Phe Ser
                245                 250                 255

Gly Tyr Gly Tyr Glu Val Cys Ile Val Glu Asn Leu Asp Ala Ile Asp
            260                 265                 270

Thr Glu Leu His Thr Ala Leu Phe Trp Ala Leu Ser Glu Ile Lys Arg
        275                 280                 285

Ile Gln Gly Ala Ala Arg Ser Gly Asn Pro Ile Thr Lys Pro Arg Trp
    290                 295                 300
```

-continued

```
Pro Met Ile Ile Leu Arg Thr Pro Lys Gly Trp Thr Gly Pro Arg Thr
305                 310                 315                 320

Val Asp Asp Lys Ile Ile Glu Gly Ser Phe His Ala His Gln Val Pro
                325                 330                 335

Val Thr Lys Ala Asn Lys Asp Glu Gly His Leu Arg Ile Leu Gln Asp
            340                 345                 350

Trp Leu Lys Ser Tyr Asp Val Arg Gly Leu Leu Pro Asp Gly Lys Pro
        355                 360                 365

Ser Gly Asp Phe Leu Asp Ile Leu Pro Pro Asp Pro His Lys Arg Leu
    370                 375                 380

Gly Gln Ser Lys Leu Ala Tyr Asp Cys His Gln Pro Leu Asp Leu Pro
385                 390                 395                 400

Asp Trp Arg Pro His Ser Val Asp Lys Phe Glu Glu Ala Ser Ser Met
                405                 410                 415

Gln Gln Ser Gly Lys Phe Leu Asp Val Val Ala Arg Gln Asn Met Lys
            420                 425                 430

Thr Phe Arg Ile Phe Ser Pro Asp Glu Leu Glu Ser Asn Lys Leu Ser
        435                 440                 445

Ala Val Leu Asp His Ser Ser Arg Asn Phe Gln Trp Asp Gln Tyr Ser
    450                 455                 460

Arg Ala Gln Gly Gly Arg Val Ile Glu Ile Leu Ser Glu His Cys Cys
465                 470                 475                 480

Gln Gly Phe Leu Gln Gly Tyr Thr Leu Thr Gly Arg Thr Ala Ile Phe
                485                 490                 495

Pro Ser Tyr Glu Ser Phe Leu Gly Ile Ile His Thr Met Met Ile Gln
            500                 505                 510

Tyr Ser Lys Phe Ser Lys Ile Ser Arg Lys Leu Pro Trp Arg Gly Asp
        515                 520                 525

Leu Ser Ser Ile Asn Tyr Ile Glu Thr Ser Thr Trp Ala Arg Gln Glu
    530                 535                 540

His Asn Gly Phe Ser His Gln Asn Pro Ser Phe Ile Gly Ala Val Leu
545                 550                 555                 560

Asn Leu Lys Ala Glu Ile Ala Arg Val Tyr Leu Pro Pro Asp Ala Asn
                565                 570                 575

Cys Phe Leu Ser Thr Leu His His Cys Leu Gln Ser Lys Asn Tyr Val
            580                 585                 590

Asn Leu Met Ile Gly Ser Lys Gln Pro Thr Pro Val Tyr Leu Ser Ala
        595                 600                 605

Glu Asp Ala Gln Arg His Cys Glu Asp Gly Ala Ser Ile Trp Arg Trp
    610                 615                 620

Ala Ser Thr His Asp Gly Glu His Pro Asp Val Val Leu Val Gly Ile
625                 630                 635                 640

Gly Val Glu Val Thr Phe Glu Val Ile Lys Ala Ala Gln Leu Leu Ser
                645                 650                 655

Arg Leu Ala Pro Asn Leu Arg Val Arg Val Val Asn Val Thr Asp Leu
            660                 665                 670

Leu Val Leu Pro His Glu Ser His His Pro His Ala Leu Asp Ser Lys
        675                 680                 685

Ala Phe Glu Asp Met Phe Thr Leu Asp Lys Pro Val Cys Phe Asn Tyr
    690                 695                 700

His Ser Tyr Ala Thr Glu Leu Gln Gly Leu Leu Phe Gly Arg Pro Ala
705                 710                 715                 720
```

-continued

```
Leu His Arg Met Ser Val Glu Gly Tyr Lys Glu Glu Gly Ser Thr Thr
                725                 730                 735

Thr Pro Phe Asp Met Met Leu Val Asn Thr Val Ser Arg Phe His Val
            740                 745                 750

Ala Ser Arg Ala Leu Lys Ala Ala Ala Ala Gln Asn Asp Glu Val Lys
        755                 760                 765

Glu Asn Leu Ser Ala Leu Leu Ala Lys Val Asp Asp Glu Met Lys Ser
    770                 775                 780

Val Lys Asp Tyr Ile Glu Gln Trp Gly Lys Val Asp Pro Asp Asp Ile
785                 790                 795                 800

Tyr Glu Leu Asp Phe Leu Lys Lys Asp
                805
```